(12) United States Patent
Li et al.

(10) Patent No.: US 8,101,184 B2
(45) Date of Patent: Jan. 24, 2012

(54) TREATMENT METHODS USING DKK-1 ANTIBODIES

(75) Inventors: Ji Li, Thousand Oaks, CA (US); Wenyan Shen, Wayne, PA (US); Hsieng Sen Lu, Westlake Village, CA (US); William Gleason Richards, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 275 days.

(21) Appl. No.: 12/603,303

(22) Filed: Oct. 21, 2009

(65) Prior Publication Data
US 2010/0040619 A1 Feb. 18, 2010

Related U.S. Application Data

(62) Division of application No. 11/197,665, filed on Aug. 4, 2005, now Pat. No. 7,709,611.

(60) Provisional application No. 60/598,791, filed on Aug. 4, 2004.

(51) Int. Cl.
*A61K 39/00* (2006.01)
*A61K 39/395* (2006.01)

(52) U.S. Cl. ............... 424/158.1; 424/130.1; 424/133.1; 424/141.1; 424/152.1

(58) Field of Classification Search .................. None
See application file for complete search history.

(56) References Cited

U.S. PATENT DOCUMENTS

| | | | |
|---|---|---|---|
| 5,168,050 A | 12/1992 | Hammonds, Jr. et al. |
| 5,525,486 A | 6/1996 | Honjo et al. |
| 5,608,039 A | 3/1997 | Pastan et al. |
| 6,344,541 B1 | 2/2002 | Bass et al. |
| 6,767,996 B1 | 7/2004 | Gorman et al. |
| 6,844,422 B1 | 1/2005 | Niehrs et al. |
| 7,057,017 B2 | 6/2006 | McCarthy |
| 7,138,508 B2 | 11/2006 | Niehrs et al. |
| 7,308,364 B2 | 12/2007 | Shaughnessy |
| 7,371,736 B2 | 5/2008 | Shaughnessy et al. |
| 7,416,849 B2 | 8/2008 | Allen et al. |
| 7,446,181 B2 | 11/2008 | McCarthy |
| 7,459,437 B2 | 12/2008 | Shaughnessy et al. |
| 7,485,460 B2 | 2/2009 | Prockop et al. |
| 2003/0027151 A1 | 2/2003 | Warman et al. |
| 2003/0068312 A1 | 4/2003 | McCarthy |
| 2003/0165501 A1 | 9/2003 | DeAlmeida et al. |
| 2003/0232364 A1 | 12/2003 | Shaughnessy |
| 2004/0009523 A1 | 1/2004 | Shaughnessy et al. |
| 2004/0038860 A1 | 2/2004 | Allen et al. |
| 2004/0137489 A1 | 7/2004 | Shaughnessy et al. |
| 2004/0221326 A1 | 11/2004 | Babij et al. |
| 2004/0234515 A9 | 11/2004 | McCarthy |
| 2004/0244069 A1 | 12/2004 | Askew et al. |
| 2005/0069915 A1 | 3/2005 | McCarthy |
| 2005/0070699 A1 | 3/2005 | Allen et al. |
| 2005/0079173 A1 | 4/2005 | Niehrs et al. |
| 2005/0084494 A1 | 4/2005 | Prockop et al. |
| 2005/0112630 A1 | 5/2005 | Shaughnessy et al. |
| 2006/0019895 A1 | 1/2006 | Shaughnessy |
| 2006/0051808 A1 | 3/2006 | McCarthy |
| 2006/0294605 A1 | 12/2006 | McCarthy |
| 2007/0066558 A1 | 3/2007 | Shaughnessy |
| 2007/0077244 A1 | 4/2007 | Niehrs et al. |
| 2007/0128187 A1 | 6/2007 | Allen et al. |
| 2008/0085281 A1 | 4/2008 | Prockop |
| 2008/0234139 A1 | 9/2008 | Shaughnessy |
| 2008/0267950 A1 | 10/2008 | Shaughnessy |
| 2008/0293578 A1 | 11/2008 | Shaughnessy |
| 2009/0023905 A1 | 1/2009 | Askew et al. |
| 2009/0092992 A1 | 4/2009 | McCarthy |

FOREIGN PATENT DOCUMENTS

| | | |
|---|---|---|
| WO | WO 98/27932 | 7/1998 |
| WO | WO 98/46755 A1 | 10/1998 |
| WO | WO 99/03990 | 1/1999 |
| WO | WO 99/06549 | 2/1999 |
| WO | WO 99/11287 A1 | 3/1999 |
| WO | WO 99/14328 | 3/1999 |
| WO | WO 99/22000 A1 | 5/1999 |
| WO | WO 99/31236 | 6/1999 |
| WO | WO 99/46281 | 9/1999 |
| WO | WO 00/12708 | 3/2000 |
| WO | WO 00/18914 | 3/2000 |
| WO | WO 00/52047 | 9/2000 |
| WO | WO 00/53756 | 9/2000 |
| WO | WO 00/78961 A1 | 12/2000 |
| WO | WO 01/04311 A1 | 1/2001 |
| WO | WO 01/16318 A2 | 3/2001 |
| WO | WO 01/38528 A1 | 5/2001 |
| WO | WO 01/40466 A2 | 6/2001 |
| WO | WO 01/54477 A2 | 8/2001 |
| WO | WO 01/57188 A2 | 8/2001 |
| WO | WO 01/57190 A2 | 8/2001 |

(Continued)

OTHER PUBLICATIONS

U.S. Appl. No. 09/009,802, filed Jan. 20, 1998, McCarthy.
U.S. Appl. No. 10/653,913, filed Sep. 4, 2003, Warman et al.
Aravind, L. and Koonin, E.V., "A colipase fold in the carboxy-terminal domain of the Wnt antagonists-the Dickkopfs," *Curr. Biol.*, 8(14):R477-8 (1998).
Attwood, "The babel of bioinformatics," *Science* 290:471-473, 2000.
Austin, T.W. et al., "A role for the Wnt gene family in hematopoiesis: Expansion of multilineage progenitor cells," Blood 89(10):3624-3635 (1997).
Bafico, A. et al., "Novel mechanism of Wnt signalling inhibition mediated by Dickkopf-1 interaction with LRP6/Arrow," *Nat Cell Biol* 3:683-686, 2001.

(Continued)

*Primary Examiner* — Sharon Wen
(74) *Attorney, Agent, or Firm* — Randolph N. Mohr

(57) ABSTRACT

The present invention provides antibodies and immunologically functional fragments thereof that specifically bind Dkk-1 polypeptides. The subject antibodies and fragments bind with high affinity to a conformational epitope located in the carboxy region of the Dkk-1 protein. Methods for preparing such antibodies or fragments thereof as well as physiologically acceptable compositions containing the antibodies or fragments are also provided. Use of the antibodies and fragments to treat various diseases including bone disorders, inflammatory diseases, neurological diseases, ocular diseases, renal diseases, pulmonary diseases and skin diseases are also disclosed.

34 Claims, 4 Drawing Sheets

FOREIGN PATENT DOCUMENTS

| | | |
|---|---|---|
| WO | WO 01/68848 A2 | 9/2001 |
| WO | WO 02/16553 A3 | 2/2002 |
| WO | WO 02/066509 A2 | 8/2002 |
| WO | WO 02/092000 A2 | 11/2002 |
| WO | WO 02/092015 A2 | 11/2002 |
| WO | WO 02/092764 A2 | 11/2002 |
| WO | WO 2005/033343 A2 | 4/2005 |
| WO | WO 2005/049640 A2 | 6/2005 |
| WO | WO 2006/105343 | 10/2006 |

OTHER PUBLICATIONS

Bendig, "Humanization of rodent monoclonal antibodies by CDR grafting," *Methods: A Companion to Methods in Enzymology*, 8:83-93, 1995.

Boyden L.M. et al., "High bone density due to a mutation in LDL-receptor-related protein S," *N Engl J Med* 346(20):1513-1521, 2002.

Fedi, P. et al., "Isolation and biochemical characterization of the human Dkk-1 homologue, a novel inhibitor of mammalian Wnt signaling," *J. Biol. Chem.*, 274(27):19465-19472 (1999).

Glinka, A. et al., "Dickkopf-1 is a member of a new family of secreted proteins and functions in head induction," *Nature*, 391:357-362 (1998).

Gong et al., "LDL receptor-related protein 5 (LRP5) affects bone accrual and eye development," *Cell* 107:513-523, 2001.

Kazanskaya et al., "The role of *Xenopus dickkopf1* in prechordal plate specification and neural patterning," *Development* 127:4981-4992, 2000.

Krupnick, V.E. et al., "Functional and structural diversity of the human Dickkopf gene family," *Gene*, 238(2):301-313 (1999).

Li et al., "Second cysteine-rich domain of Dckkopf-2 activates canonical Wnt signaling pathway via LRP-6 independently of disheveled," *J Biol Chem* 277(8):5977-5981, 2002.

Little et al., "A mutation in the LDL receptor-related protein 5 gene results in the autosomal dominant high-bone mass trait," *Am J Hum Genet* 70:11-19, 2002.

Mao & Niehrs, "Kremen2 modulates Dickkopf2 activity during Wnt/LRP6 signaling," *Gene*, 302:179-183 (2003).

Mao et al., "Kremen proteins are Dickkopf receptors that regulate Wnt/β-catenin signaling," *Nature* 417:664-667, 2002.

Mao et al., "LDL-receptor-related protein 6 is a receptor for Dickkopf proteins," *Nature* 411:321-325, 2001.

Mao et al., "Low-density lipoprotein receptor-related protein-5 binds to axin and regulates the canonical Wnt signaling pathway," *Mol Cell* 7:801-809, 2001.

Monaghan, A.P. et al., "Dickkopf genes are co-ordinately expressed in mesodermal lineages," *Mech. Dev.*, 87(1-2):45-56 (1999).

Mukhopadhyay et al., "*Dickkopf1* is required for embryonic head induction and limb morphogenesis in the mouse," *Dev Cell* 1:423-434, 2001.

Nusse, "Making head or tail of Dickkopf," *Nature* 411:255-256, 2001.

Padlan et al., "Structure of an antibody-antigen complex: crystal structure of the HyHEL-10 Fab-lysozyme complex," *Proc Natl Acad Sci USA* 86:5938-5942, 1989.

Patel and Karsenty, "Regulation of bone formation and vision by LRP5," *N Engl J Med* 346(20):1572-1574, 2002.

Rudikoff et al., "Single amino acid substitution altering antigen-binding specificity," *Proc Natl Acad Sci USA* 79:1979-1983, 1982.

Seménov et al., "Head inducer Dickkopf-1 is a ligand for Wnt coreceptor LRP6," *Curr Biol* 11:951-961, 2001.

Skolnick and Fetrow, "From genes to protein structure and function: novel applications of computational approaches in the genomic era," *Trends in Biotech* 18:34-39, 2000.

Tian et al., "The role of the Wnt-signaling antagonist DKK1 in the development of osteolytic lesions in multiple myeloma," *N Engl J Med* 349(26):2483-2494, 2003.

Wu et al., *Curr Biol* 10:1611-1614, 2000.

Zorn, "Wnt signalling: antagonistic Dickkopfs," *Curr Biol* 11:R592-R595, 2001.

Tamura, et al., Structural correlates of an anticarcinoma antibody: identification of specificity-determining residues (SDRs) and development of a minimally immunogenic antibody variant by retention of SDRs only, J. Immunol, vol. 164 pp. 1432-1441 (2000).

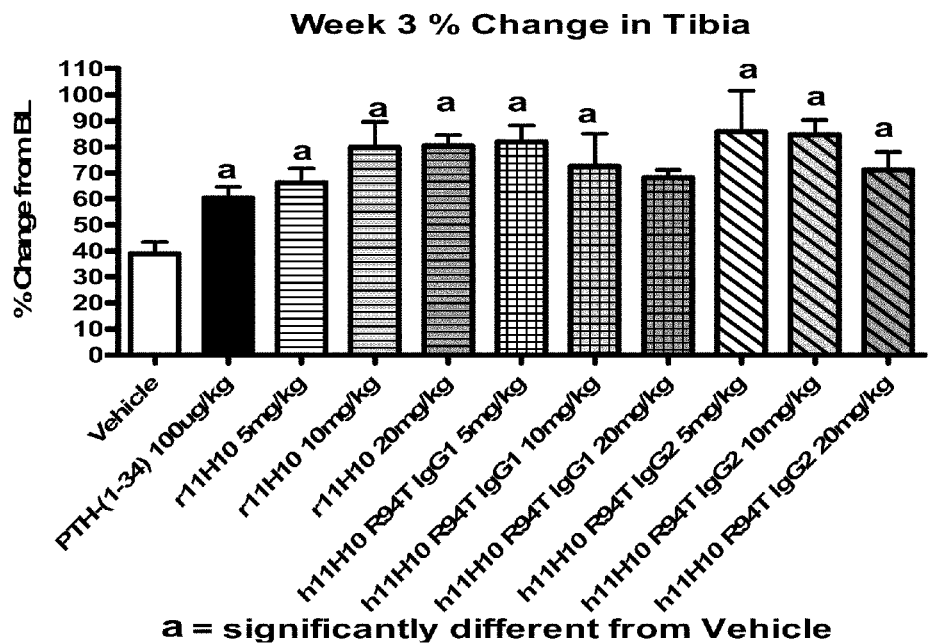
FIG. 4: Percent change in BMD in mice treated with h11H10 R94T

TREATMENT METHODS USING DKK-1 ANTIBODIES

CROSS-REFERENCE TO RELATED APPLICATIONS

This application is a divisional application of U.S. application Ser. No. 11/197,665, filed Aug. 4, 2005, now U.S. Pat. No. 7,709,611, which claims the benefit of U.S. Provisional Application No. 60/598,791, filed Aug. 4, 2004, each of which is incorporated herein by reference in its entirety for all purposes.

REFERENCE TO THE SEQUENCE LISTING

The present application is being filed along with a Sequence Listing in electronic format. The Sequence Listing is provided as a file entitled A-941-US-DIV_Seq_US_ST25.txt, created Oct. 20, 2009, which is 263 KB in size. The information in the electronic format of the Sequence Listing is incorporated herein by reference in its entirety.

FIELD OF THE INVENTION

The invention relates to selective binding agents for dickkopf-1 (Dkk-1) protein, and more particularly, to antibodies and antigen binding domains and CDR regions that mediate selective binding to an epitope located in the carboxyl half of the Dkk-1 protein.

BACKGROUND OF THE INVENTION

Living bone tissue exhibits a dynamic equilibrium between deposition and resorption of bone. These processes are mediated primarily by two cell types: osteoblasts, which secrete molecules that comprise the organic matrix of bone, and osteoclasts, which mediate the dissolution of the bone matrix and solubilization of bone salts. In young individuals with growing bone, the rate of bone deposition exceeds the rate of bone resorption, while in older individuals the rate of resorption may exceed deposition leading to net loss of bone mass. The latter situation can lead to increased risk of bone fracture and slow or incomplete repair of broken bones. Understanding the molecular mechanisms that underlie these processes is critical to the development of therapeutics for the treatment of bone diseases. Human genetics has played a major role in the elucidation of these mechanisms and has enabled the identification of multiple factors involved in both catabolic and anabolic bone activity (Janssens and Van Hul, *Hum Mol Gen*, 11(20):2385-93, 2002; Ralston, *J Clin Endocrin Metab.* 87(6):2460-66, 2002).

Dickkopf-1 (Dkk-1) is a member of the dickkopf family of proteins that have been shown to be negative regulators of the canonical Wnt-signaling pathway, which has a central role in bone development and formation (see, for example, Glinka et al., *Nature* 391:357-62 (1998); Fedi et al., *J Biol Chem* 274 (27):19465-72 (1999); Zorn, *Curr Biol* 11:R592-95 (2001); and Krupnik et al., *Gene* 238: 301-13 (1999)). Dkk-1 inhibits Wnt signaling through its interaction with the Wnt co-receptors LRP5 or LRP6 and the kremen proteins (see, for example, Bafico et al., *Nature Cell Biol* 3:683 (2001); Mao et al., *Nature* 411(17):321 (2001); Mao et al., *Nature* 417:664 (2002); and Semënov et al., *Curr Biol* 11:951-61 (2001). By binding LRP5 (LRP6) and kremen proteins, Dkk-1 prevents LRP5 or LRP6 from associating with members of the Wnt pathway and thus prevents Wnt-mediated signal transduction, which in turn results in the inhibition of bone formation.

LRP5 is a key protein in regulating bone mass (see, for example, Gong et al., *Cell* 107:513-23 (2001); Patel, *N Eng J Med* 346(20):1572 (2002)). An autosomal recessive disorder characterized by low bone mass (osteoporosis-pseudoglioma syndrome, or "OPPG") has been identified as being caused by loss-of-function mutations in LRP5 (Gong et al., 2001). In addition, gain-of-function mutations in LRP5 have been shown to result in autosomal dominant high bone mass in humans (Little et al., *Am J Human Genetics.* 70(1):11-19, 2002). The same mutations in LRP5 that result in high bone mass can interfere with the ability of Dkk-1 to inhibit LRP5 signaling (see, for example, Boyden et al., *N Eng J Med.* 346(20):1513-1521, 2002). Thus, Dkk-1 is appropriately characterized as being a negative regulator of bone deposition.

In view of the involvement of Dkk-1 in the regulation of bone formation and its role in various other diseases that are associated with bone loss (e.g., cancer and diabetes), there is a need for improved anti-Dkk-1 antibodies for therapeutic use and for other purposes.

BRIEF SUMMARY OF THE INVENTION

A variety of binding agents are provided that selectively bind Dkk-1. The agents may also block or reduce binding between Dkk-1 and LRP5 and/or LRP6, thereby stimulating at least one activity associated with Wnt signaling. The agents can be an antibody or an immunologically functional fragment thereof and thus include antibodies with a naturally occurring structure, as well as polypeptides that have an antigen binding domain (e.g., a domain antibody). The antibodies and fragments can be used to treat a variety of different diseases including preventing or treating conditions relating to loss of bone mass or to stimulate production of new bone, as well as various non-bone related disorders. Nucleic acids molecules, vectors, and host cells useful in the production of the antibodies and selective binding agents are also provided.

Some of the antibodies and immunologically functional fragments that are provided include
(a) one or more light chain (LC) complementary determining regions (CDRs) selected from the group consisting of:
(i) a LC CDR1 with at least 80% sequence identity to SEQ ID NO:70;
(ii) a LC CDR2 with at least 80% sequence identity to SEQ ID NO:72; and
(iii) a LC CDR3 with at least 80% sequence identity to SEQ ID NO:74;
(b) one or more heavy chain (HC) CDRs selected from the group consisting of
(i) a HC CDR1 with at least 80% sequence identity to SEQ ID NO:76;
(ii) a HC CDR2 with at least 80% sequence identity to SEQ ID NO:78; and
(iii) a HC CDR3 with at least 80% sequence identity to SEQ ID NO:80;
or
(c) one or more LC CDRs of (a) and one or more HC CDRs of (b).

Such antibodies or fragments can specifically bind a Dkk-1 polypeptide. Certain antibodies or fragments include one, two, three, four, five or all six of the forgoing CDRs.

The light chain and heavy chains of other antibodies or fragments are as described above but have at least 90% sequence identity to the foregoing sequences. Still other antibodies or fragments thereof are ones having a light chain in which CDR1 has the amino acid sequence as set forth in SEQ ID NO:70, CDR2 has the amino acid sequence as set forth in SEQ ID NO:72 and/or CDR3 has the amino acid sequence as set forth in SEQ ID NO:74. Some antibodies and fragments may also have a heavy chain in which CDR1 has the amino acid sequence as set forth in SEQ ID NO:76, CDR2 has the amino acid sequence as set forth in SEQ ID NO:78 and/or HC CDR3 has the amino acid sequence as set forth in SEQ ID NO:80. Certain antibodies or fragments include a light chain CDR3 with the amino acid sequence of SEQ ID NO:74 and/or a heavy chain CDR3 with the amino acid sequence of SEQ ID NO:80.

Certain other antibodies and immunologically functional fragments that are provided include (a) a light chain variable region (VL) having at least 80% sequence identity with SEQ ID NO:84, 28 or 32; (b) a heavy chain variable region (VH) having at least 80% sequence identity with SEQ ID NO:91, 36, 40, 44, 48, 52, 56, 60, 64 or 68; or (c) a VL of (a) and a VH of (b).

Other antibodies or fragments are similar in structure but the VL has at least 90% sequence identity with SEQ ID NO:84, 28 or 32; and the VH has at least 90% sequence identity with SEQ ID NO:91, 36, 40, 44, 48, 52, 56, 60, 64 or 68. In certain antibodies or fragments, the VL has at least 95% sequence identity with SEQ ID NO:84, 28 or 32; and the VH has at least 95% sequence identity with SEQ ID NO:91, 36, 40, 44, 48, 52, 56, 60, 64, or 68. Still other antibodies or fragments are ones that include a VL that has the amino acid sequence of SEQ ID NO:84, 28 or 32, and/or a VH that has the amino acid sequence of SEQ ID NO91, 36, 40, 44, 48, 52, 56, 60, 64 or 68.

Some antibodies or fragments include a light chain that comprises or consists of the amino acid sequence of SEQ ID NO:82, 26, or 30 and/or a heavy chain that comprises or consists of the amino acid sequence of SEQ ID NO:89, 34, 38, 42, 46, 50, 54, 58, 62, or 66.

Also included are isolated antibodies or an immunologically functional fragments thereof that specifically bind a mature human Dkk-1 protein consisting of amino acids 32-266 of SEQ ID NO:2, wherein said antibody binds to an epitope comprising two loops, said loops being formed by disulfide bonds between amino acids 220 and 237 of SEQ ID NO:2 and between cysteine residues 245 and 263 of SEQ ID NO:2.

Other antibodies or fragments that are disclosed compete with an antibody such as those described above for specific binding to a Dkk-1 polypeptide. For example, some antibodies and fragments compete with an antibody that consists of two identical heavy chains and two identical light chains, wherein the heavy chains consist of amino acids 20-465 of SEQ ID NO:12 and said light chains consist of amino acids 21-234 of SEQ ID NO:10.

The various antibodies and fragments that are provided may include a single light and/or heavy chain or a single variable light domain and/or a single variable heavy domain. Other antibodies and fragments include two light and/or two heavy chains. In those instances in which the antibody or fragment includes two light and/or heavy chains, the two light chains in some instances are identical to one another; likewise, the two heavy chains in some instances are identical. The antibodies that are provided may include, for example, monoclonal antibodies, a human antibody, a chimeric antibody, or a humanized antibody. The immunologically functional fragments may include, but are not limited to, a scFv, a Fab, a Fab', a (Fab')$_2$, or a domain antibody. In some instances, the antibody or fragment dissociates from a Dkk-1 polypeptide with a k$_d$ (k$_{off}$) of $5 \times 10^{-4}$ s$^{-1}$ or less.

Pharmaceutical compositions that include any of the foregoing antibodies and immunologically active fragments are also provided. Such compositions typically also include a buffer, a pharmaceutically acceptable diluent, a carrier, a solubilizer, an emulsifier or a preservative. The use of the foregoing antibodies and immunologically active fragments in the preparation of a pharmaceutical composition or medicament is also described.

A variety of nucleic acids encoding the foregoing antibodies are also provided. Some nucleic acids, for instance, encode (a) a light chain CDR with the amino acid sequence as set forth in SEQ ID NO:70, 72 and/or 74; and/or (b) a heavy chain CDR with the amino acid sequence as set forth in SEQ ID NO:76, 78 and/or 80, such that the encoded CDR(s) encode an antibody or an immunologically functional fragment thereof that can specifically bind a Dkk-1 polypeptide. Certain other nucleic acids comprise or consist of a sequence that encodes a variable light region (VL) and/or a variable heavy region (VH) of an antibody or immunologically active fragment, wherein the VL has at least 80%, 90% or 95% sequence identity with SEQ ID NO:84, 28 or 32 and the VH has at least 80% 90%, or 95% sequence identity with SEQ ID NO:91, 36, 40, 44, 48, 52, 56, 60, 64 or 68. Some of the nucleic acids include a sequence that encodes a VL that comprises or consists of SEQ ID NO:84, 28 or 32 and/or a sequence that encodes a VH that comprises or consists of SEQ ID NO:91, 36, 40, 44, 48, 52, 56, 60, 64 or 68. Still other nucleic acids include sequences that encode both a VL or VH with the foregoing sequence characteristics. Expression vectors comprising the foregoing nucleic acids are also disclosed herein, as are cells (e.g., CHO cells) that comprise such expression vectors. Methods of producing an antibody or an immunologically active fragment thereof by culturing cells that contain such expression vectors are also described.

In another aspect, the use of the foregoing antibodies or immunologically functional fragments in the treatment of a variety of diseases is disclosed. Certain methods, for instance, involve administering to a patient in need thereof an effective amount of an antibody or immunologically active fragment as described herein to treat arthritis, diseases responsive to stem cell renewal, inflammatory diseases, neurological diseases, ocular diseases, renal diseases, pulmonary diseases, and skin diseases. Some treatment methods involve treating rheumatoid arthritis, psoriatic arthritis or osteoarthritis. Certain antibodies and fragments are used to treat a disease that: (a) is responsive to stem cell renewal and is selected from the group consisting of diabetes, chronic heart failure and diseases of the muscle; (b) is an inflammatory disease selected from the group consisting of Crohn's disease, colitis, and inflammatory bowel disease; (c) is a neurological disease selected from the group consisting of Alzheimer's disease, Parkinson's disease, and Huntington's disease; (d) is an ocular disease selected from the group consisting of macular degeneration and retinopathies; (e) is a renal disease selected from the group consisting of end stage renal disease, chronic renal disease, glomerulonephritis, tubulointerstitial nephritis, and IgA nephropathy; (f) is a pulmonary disease selected from the group consisting of chronic obstructive pulmonary disease, idiopathic pulmonary fibrosis, and cystic fibrosis; or (g) is a skin disease resulting from chemotherapy-induced damage to the intestinal epithelium.

Further provided herein are methods of treating or preventing loss of bone mass comprising administering to a patient in need thereof a therapeutically effective amount of an antibody or immunologically functional fragment thereof as described herein (e.g., an antibody or immunologically functional fragment that comprises at least one light chain CDR selected from the group consisting of amino acids 44-54 of SEQ ID NO:10, amino acids 70-76 of SEQ ID NO:10 and amino acids 109-117 of SEQ ID NO:10, and/or at least one heavy chain CDR selected from the group consisting of amino acids 50-54 of SEQ ID NO:12, amino acids 69-85 of SEQ ID NO:12 and amino acids 118-128 of SEQ ID NO:12). In one aspect of this embodiment, the patient is one who suffers from cancer that metastasizes to bone, and in another aspect, the patient is one who suffers from multiple myeloma. In yet another aspect, the patient is selected from patients who have osteoporosis, osteopenia, Paget's disease, periodontitis, rheumatoid arthritis, and bone loss due to immobilization.

Methods of inducing increased bone mass are also disclosed. Such methods involve administering to a patient in need thereof a therapeutically effective amount of an antibody or immunologically functional fragment thereof as disclosed herein (e.g., an antibody or immunologically functional fragment that includes at least one light chain CDR selected from the group consisting of amino acids 44-54 of SEQ ID NO:10, amino acids 70-76 of SEQ ID NO:10 and amino acids 109-117 of SEQ ID NO:10, and/or at least one heavy chain CDR selected from the group consisting of amino acids 50-54 of SEQ ID NO:12, amino acids 69-85 of SEQ ID NO:12 and amino acids 118-128 of SEQ ID NO:12). In one aspect, the patient suffers from cancer that metastasizes to bone, and in another aspect, the patient suffers from multiple myeloma. In yet another aspect, the patient is selected from those who have osteoporosis, osteopenia, Paget's disease, periodontitis, rheumatoid arthritis, psoriatic arthritis, ankylosing spondylitis and bone loss due to immobilization. In an additional aspect of this method, the patient is a bone graft recipient or one who suffers from a bone fracture.

Provided also is a method of inducing Wnt activity in a patient in need thereof comprising administering to the patient a therapeutically effective amount of an antibody or immunologically functional fragment thereof as described herein (e.g., at least one light chain CDR selected from the group consisting of amino acids 44-54 of SEQ ID NO:10, amino acids 70-76 of SEQ ID NO:10 and amino acids 109-117 of SEQ ID NO:10, and/or at least one heavy chain CDR selected from the group consisting of amino acids 50-54 of SEQ ID NO:12, amino acids 69-85 of SEQ ID NO:12 and amino acids 118-128 of SEQ ID NO:12).

BRIEF DESCRIPTION OF THE FIGURES

FIG. 2A is a plot of Trabecular Number at different dosage levels of rat 11H10 (5, 10 or 20 mg/kg) in both old mice (8.5 months old) and young mice (6-weeks old) versus vehicle (negative control) and PTH (positive control). FIG. 2B is a plot of endosteal perimeter at different dosage levels of rat 11H10 (5, 10 or 20 mg/kg) in old mice (8.5 months old) versus vehicle (negative control) and PTH (positive control).

FIG. 3A shows the change in BMD in the tibia at day 28 relative to baseline. FIG. 3B shows the change is BMD in the lumbar at day 28 relative to baseline.

FIG. 4 is a plot of percent change in BMD in young mice three weeks after being administered 11H10 RT IgG1 or 11H10 RT IgG2 relative to rat 11H10 or PTH.

DETAILED DESCRIPTION OF THE INVENTION

I. Definitions

Figure 1:
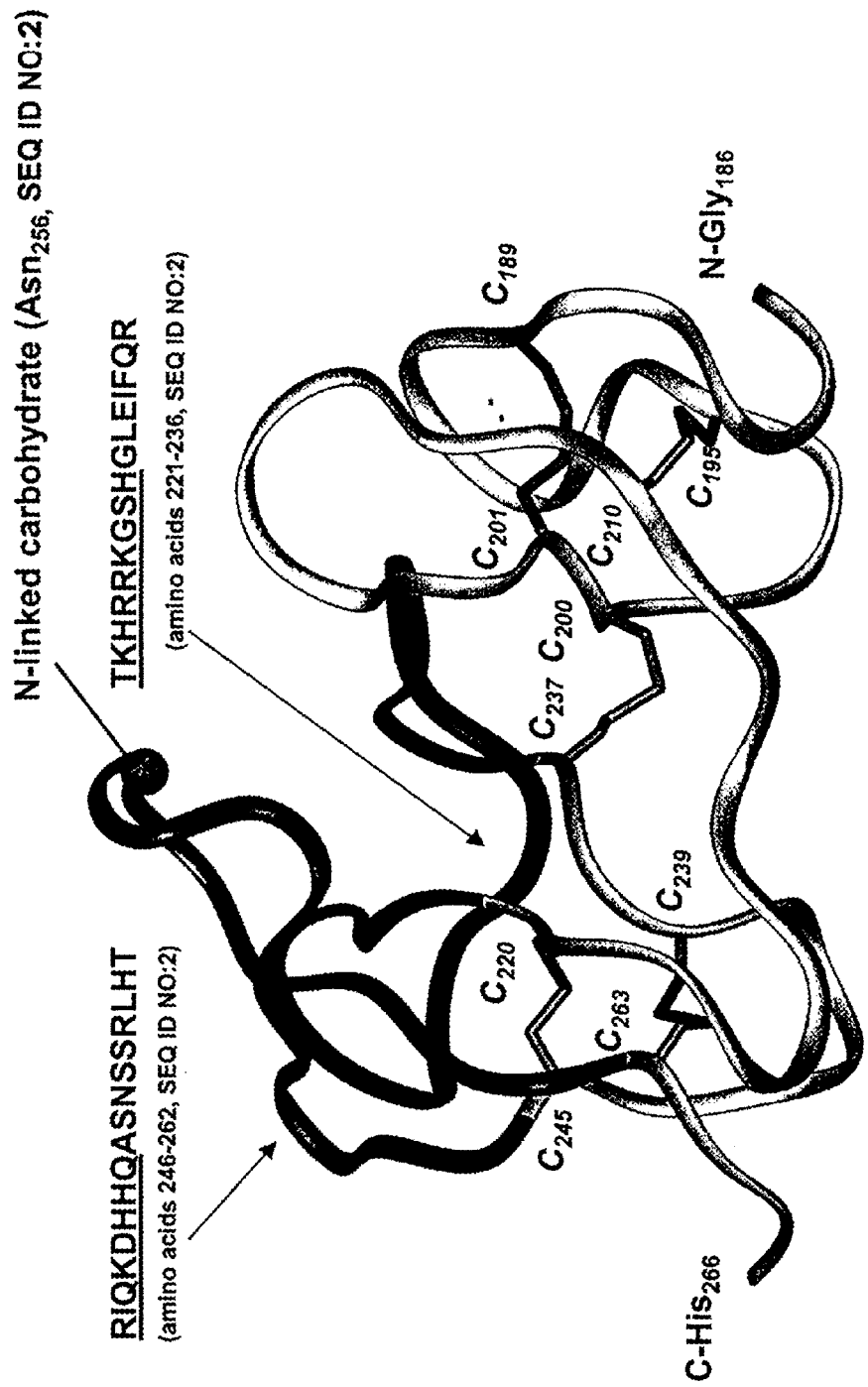
FIG. 1 shows a ribbon diagram depicting the three-dimensional structure of a segment of human Dkk-1 located near the carboxy terminus of the protein. All of the amino acid numbers indicated in the figure correspond to the amino acid sequence of SEQ ID NO:2. The two peptide sequences depicted in the figure represent regions that are important for the 11H10 monoclonal antibody to specifically bind to this protein. The amino acids that are underlined are believed to play an important role for binding of the antibody to the Dkk-1 protein. The loops comprising the epitope are shaded, one of the two epitope loops being shaded slightly darker than the other loop. The very light colored portions of the ribbon diagram represent parts of the polypeptide that are believed to play a lesser role in the binding interaction between 11H10 to human Dkk-1.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

The following terms utilized in this disclosure, unless otherwise indicated, will be understood to have the following meanings:

"Dkk-1" as used herein includes, for example, rat, murine and human native forms of Dkk-1. Exemplary nucleotide sequences encoding human and murine Dkk-1 proteins are shown, respectively, in SEQ ID NOS:1 and 3; the corresponding amino acid sequences are shown, respectively, in SEQ ID NOS:2 and 4. The human Dkk-1 protein (SEQ ID NO:2) has a leader sequence consisting of amino acids 1-31 of SEQ ID NO:2. An exemplary rat Dkk-1 protein sequence is listed in GenBank Accession XP_219804. The term also includes variants of such native sequences that are immunologically cross-reactive with these native proteins. These proteins can inhibit the interaction between LRP5 or LRP6 with Wnt. An exemplary nucleotide sequence encoding human LRP5 is given in SEQ ID NO:5, and the corresponding amino acid sequence is shown in SEQ ID NO:6. An exemplary nucleotide sequence encoding human LRP6 is given in SEQ ID NO:7, and the corresponding amino acid sequence is shown in SEQ ID NO:8. The term can also refer to a fragment of a native or variant form of Dkk-1 that contains an epitope to which an antibody can specifically bind.

The term "polynucleotide" or "nucleic acid" means single-stranded or double-stranded polymers. The nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate. The term includes both single and double stranded forms.

The term "oligonucleotide" means a polynucleotide comprising 200 or fewer nucleotides. In some embodiments, oligonucleotides are 10 to 60 bases in length. In other embodiments, oligonucleotides are 12, 13, 14, 15, 16, 17, 18, 19, or 20 to 40 nucleotides in length. Oligonucleotides may be single stranded or double stranded, e.g., for use in the construction of a mutant gene. Oligonucleotides of the invention may be sense or antisense oligonucleotides. An oligonucleotide of the invention can include a label, including a radiolabel, a fluorescent label, a hapten or an antigenic label, for detection assays. Oligonucleotides of the invention may be used, for example, as PCR primers, cloning primers or hybridization probes.

An "isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty other proteins or portions thereof, or may include operably linked regulatory sequences that control expression of the coding region of the recited nucleic acid sequences, and/or may include vector sequences.

Unless specified otherwise, the left-hand end of any single-stranded polynucleotide sequence discussed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences"; sequence regions on the DNA strand having the same sequence as the RNA transcript that are 3' to the 3' end of the RNA transcript are referred to as "downstream sequences".

The term "control sequence" refers to a polynucleotide sequence that can affect the expression and processing of coding sequences to which it is ligated. The nature of such control sequences may depend upon the host organism. In particular embodiments, control sequences for prokaryotes may include a promoter, a ribosomal binding site, and a transcription termination sequence. For example, control sequences for eukaryotes may include promoters comprising one or a plurality of recognition sites for transcription factors, transcription enhancer sequences, and transcription termination sequence. "Control sequences" according to the invention can include leader sequences and/or fusion partner sequences.

The term "vector" means any molecule or entity (e.g., nucleic acid, plasmid, bacteriophage or virus) used to transfer protein coding information into a host cell.

The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct may include, but is not limited to, sequences that affect or control transcription, translation, and, if introns are present, affect RNA splicing of a coding region operably linked thereto.

As used herein, "operably linked" means that the components to which the term is applied are in a relationship that allows them to carry out their inherent functions under suitable conditions. For example, a control sequence in a vector that is "operably linked" to a protein coding sequence is ligated thereto so that expression of the protein coding sequence is achieved under conditions compatible with the transcriptional activity of the control sequences.

The term "host cell" means a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present.

The term "transduction" means the transfer of genes from one bacterium to another, usually by bacteriophage. "Transduction" also refers to the acquisition and transfer of eukaryotic cellular sequences by retroviruses.

The term "transfection" means the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, Virology 52:456; Sambrook et al., 2001, Molecular Cloning: A Laboratory Manual, Id.; Davis et al., 1986, Basic Methods in Molecular Biology, Elsevier; and Chu et al., 1981, Gene 13:197. Such techniques can be used to introduce one or more exogenous DNA moieties into suitable host cells.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA may recombine with that of the cell by physically integrating into a chromosome of the cell, or may be maintained transiently as an episomal element without being replicated, or may replicate independently as a plasmid. A cell is considered to have been "stably transformed" when the transforming DNA is replicated with the division of the cell.

The terms "polypeptide" or "protein" means a macromolecule having the amino acid sequence of a native protein, that is, a protein produced by a naturally-occurring and non-recombinant cell, or produced by a genetically-engineered or recombinant cell, and comprise molecules having the amino acid sequence of the native protein, or molecules having deletions from, additions to, and/or substitutions of one or more amino acids of the native sequence. The terms "polypeptide" and "protein" specifically encompass anti-Dkk-1 antibodies, or sequences that have deletions from, additions to, and/or substitutions of one or more amino acid of anti-Dkk-1 antibody. The term "polypeptide fragment" refers to a polypeptide that has an amino-terminal deletion, a carboxyl-terminal deletion, and/or an internal deletion as compared with the full-length native protein. Such fragments may also contain modified amino acids as compared with the native protein. In certain embodiments, fragments are about 5 to 500 amino acids long. For example, fragments may be at least 5, 6, 8, 10, 14, 20, 50, 70, 100, 110, 150, 200, 250, 300, 350, 400, or 450 amino acids long. Useful polypeptide fragments for this invention include immunologically functional fragments of antibodies, including binding domains. In the case of anti-Dkk-1 antibody, useful fragments include but are not limited to a CDR region, a variable domain of a heavy or light chain, a portion of an antibody chain or just its variable region including two CDRs, and the like.

The term "isolated protein" referred to herein means that a subject protein (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or noncovalent interaction) with a polypeptide with which it is not associated in nature, or (6) does not occur in nature. Genomic DNA, cDNA, mRNA or other RNA, of synthetic origin, or any combination thereof may encode such an isolated protein. Preferably, the isolated protein is substantially free from proteins or polypeptides or other contaminants that are found in its natural environment that would interfere with its therapeutic, diagnostic, prophylactic, research or other use.

A "variant" of a polypeptide (e.g., an antibody) comprises an amino acid sequence wherein one or more amino acid residues are inserted into, deleted from and/or substituted into the amino acid sequence relative to another polypeptide sequence. Variants of the invention include fusion proteins.

A "derivative" of a polypeptide is a polypeptide (e.g., an antibody) that has been chemically modified in some manner distinct from insertion, deletion, or substitution variants, e.g., via conjugation to another chemical moiety.

The term "antibody" refers to an intact immunoglobulin of any isotype, or a fragment thereof that can compete with the intact antibody for specific binding to the target antigen, and includes chimeric, humanized, fully human, and bispecific antibodies. An intact antibody generally will comprise at least two full-length heavy chains and two full-length light chains, but in some instances may include fewer chains such as antibodies naturally occurring in camelids which may comprise only heavy chains. Antibodies according to the invention may be derived solely from a single source, or may be "chimeric," that is, different portions of the antibody may be derived from two different antibodies. For example, the CDR regions may be derived from a rat or murine source, while the framework region of the V region are derived from a different animal source, such as a human. The antibodies or binding fragments of the invention may be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof, examples of which are described below.

The term "light chain" includes a full-length light chain and fragments thereof having sufficient variable region sequence to confer binding specificity. A full-length light chain includes a variable region domain, $V_L$, and a constant region domain, $C_L$. The variable region domain of the light chain is at the amino-terminus of the polypeptide. Light chains according to the invention include kappa chains and lambda chains.

The term "heavy chain" includes a full-length heavy chain and fragments thereof having sufficient variable region sequence to confer binding specificity. A full-length heavy chain includes a variable region domain, $V_H$, and three constant region domains, $C_H1$, $C_H2$, and $C_H3$. The $V_H$ domain is at the amino-terminus of the polypeptide, and the $C_H$ domains are at the carboxyl-terminus, with the $C_H3$ being closest to the —COOH end. Heavy chains according to the invention may be of any isotype, including IgG (including IgG1, IgG2, IgG3 and IgG4 subtypes), IgA (including $IgA_1$ and $IgA_2$ subtypes), IgM and IgE.

The term "immunologically functional fragment" (or simply "fragment") of an immunoglobulin chain, as used herein, refers to a portion of an antibody light chain or heavy chain that lacks at least some of the amino acids present in a full-length chain but which is capable of binding specifically to an antigen. Such fragments are biologically active in that they bind specifically to the target antigen and can compete with intact antibodies for specific binding to a given epitope. In one aspect of the invention, such a fragment will retain at least one CDR present in the full-length light or heavy chain, and in some embodiments will comprise a single heavy chain and/or light chain or portion thereof. These biologically active fragments may be produced by recombinant DNA techniques, or may be produced by enzymatic or chemical cleavage of intact antibodies. Immunologically functional immunoglobulin fragments of the invention include, but are not limited to, Fab, Fab', $F(ab')_2$, Fv, domain antibodies and single-chain antibodies, and may be derived from any mammalian source, including but not limited to human, mouse, rat, camelid or rabbit. It is contemplated further that a functional portion of the inventive antibodies, for example, one or more CDRs, could be covalently bound to a second protein or to a small molecule to create a therapeutic agent directed to a particular target in the body, possessing bifunctional therapeutic properties, or having a prolonged serum half-life.

A "Fab fragment" is comprised of one light chain and the CHI and variable regions of one heavy chain. The heavy chain of a Fab molecule cannot form a disulfide bond with another heavy chain molecule.

An "Fc" region contains two heavy chain fragments comprising the $C_H1$ and $C_H2$ domains of an antibody. The two heavy chain fragments are held together by two or more disulfide bonds and by hydrophobic interactions of the CH3 domains.

A "Fab' fragment" contains one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a $F(ab')_2$ molecule.

A "$F(ab')_2$ fragment" contains two light chains and two heavy chains containing a portion of the constant region between the $C_H1$ and $C_H2$ domains, such that an interchain disulfide bond is formed between the two heavy chains. A $F(ab')_2$ fragment thus is composed of two Fab' fragments that are held together by a disulfide bond between the two heavy chains.

The "Fv region" comprises the variable regions from both the heavy and light chains, but lacks the constant regions.

"Single-chain antibodies" are Fv molecules in which the heavy and light chain variable regions have been connected by a flexible linker to form a single polypeptide chain, which forms an antigen-binding region. Single chain antibodies are discussed in detail in International Patent Application Publication No. WO 88/01649 and U.S. Pat. Nos. 4,946,778 and 5,260,203, the disclosures of which are incorporated by reference.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen binding sites. In some instances, the two binding sites have the same antigen specificities. However, bivalent antibodies may be bispecific (see below).

A "multispecific antibody" is one that targets more than one antigen or epitope.

A "bispecific," "dual-specific" or "bifunctional" antibody is a hybrid antibody having two different antigen binding sites. Bispecific antibodies are a species of multispecific antibody and may be produced by a variety of methods including, but not limited to, fusion of hybridomas or linking of Fab' fragments. See, e.g., Songsivilai & Lachmann (1990), *Clin. Exp. Immunol.* 79:315-321; Kostelny et al. (1992), *J. Immunol.* 148:1547-1553. The two binding sites of a bispecific antibody will bind to two different epitopes, which may reside on the same or different protein targets.

The term "neutralizing antibody" refers to an antibody that binds to a ligand, prevents binding of the ligand to its binding partner and interrupts the biological response that otherwise would result from the ligand binding to its binding partner. In assessing the binding and specificity of an antibody or immunologically functional fragment thereof, an antibody or fragment will substantially inhibit binding of a ligand to its binding partner when an excess of antibody reduces the quantity of binding partner bound to the ligand by at least about 20%, 30%, 40%, 50%, 60%, 70%, 80%, 85%, 90%, 95%, 97%, 99% or more (as measured in an in vitro competitive binding assay). In the case of antibodies to Dkk-1, a neutralizing antibody will diminish the ability of Dkk-1 to bind LRP5 or LRP6, thereby inducing a measurable increase in Wnt activity.

The term "compete" when used in the context of antibodies that compete for the same epitope means competition between antibodies is determined by an assay in which the antibody or immunologically functional fragment under test prevents or inhibits specific binding of a reference antibody to a common antigen (e.g., Dkk-1 or a fragment thereof). Numerous types of competitive binding assays can be used, for example: solid phase direct or indirect radioimmunoassay (RIA), solid phase direct or indirect enzyme immunoassay (EIA), sandwich competition assay (see, e.g., Stahli et al. (1983) Methods in Enzymology 9:242-253); solid phase direct biotin-avidin EIA (see, e.g., Kirkland et al., (1986) J. Immunol. 137:3614-3619) solid phase direct labeled assay, solid phase direct labeled sandwich assay (see, e.g., Harlow and Lane (1988) Antibodies, A Laboratory Manual, Cold Spring Harbor Press); solid phase direct label RIA using 1-125 label (see, e.g., Morel et al. (1988) Molec. Immunol. 25:7-15); solid phase direct biotin-avidin EIA (see, e.g., Cheung, et al. (1990) Virology 176:546-552); and direct labeled RIA (Moldenhauer et al. (1990) Scand. J. Immunol. 32:77-82). Typically, such an assay involves the use of purified antigen bound to a solid surface or cells bearing either of these, an unlabelled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Additional details regarding methods for determining competitive binding are provided in the examples herein. Usually, when a competing antibody is present in excess, it will inhibit specific binding of a reference antibody to a common antigen by at least 40%, 45%, 50%, 55%, 60%, 65%, 70% or 75%. In some instance, binding is inhibited by at least 80%, 85%, 90%, 95%, or 97% or more.

The term "antigen" refers to a molecule or a portion of a molecule capable of being bound by a selective binding agent, such as an antibody, and additionally capable of being used in an animal to produce antibodies capable of binding to that antigen. An antigen may possess one or more epitopes that are capable of interacting with different antibodies.

The term "epitope" includes any determinant capable of specifically binding to an immunoglobulin or to a T-cell receptor. An epitope is a region of an antigen that is bound by an antibody that specifically targets that antigen, and when the antigen is a protein, includes specific amino acids that directly contact the antibody. Most often, epitopes reside on proteins, but in some instances may reside on other kinds of molecules, such as nucleic acids. Epitope determinants may include chemically active surface groupings of molecules such as amino acids, sugar side chains, phosphoryl or sulfonyl groups, and may have specific three dimensional structural characteristics, and/or specific charge characteristics. Generally, antibodies specific for a particular target antigen will preferentially recognize an epitope on the target antigen in a complex mixture of proteins and/or macromolecules.

An antibody of the invention is said to "specifically bind" its target antigen when the dissociation constant ($K_d$) is $\leq 10^{-8}$ M. The antibody specifically binds antigen with "high affinity" when the $K_d$ is $\leq 5 \times 10^{-9}$ M, and with "very high affinity" when the $K_d$ is $\leq 5 \times 10^{-10}$ M. In one embodiment of the invention, the antibody has a $K_d$ of $\leq 10^{-9}$ M and an off-rate of about $1 \times 10^{-4}$/sec. In one embodiment of the invention, the off-rate is $<1 \times 10^{-5}$. In other embodiments of the invention, the antibodies will bind to human Dkk-1 with a $K_d$ of between about $10^{-8}$ M and $10^{-10}$ M, and in yet another embodiment it will bind with a $K_d \leq 2 \times 10^{-10}$.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) must be addressed by a particular mathematical model or computer program (i.e., an "algorithm"). Methods that can be used to calculate the identity of the aligned nucleic acids or polypeptides include those described in *Computational Molecular Biology*, (Lesk, A. M., ed.), 1988, New York: Oxford University Press; *Biocomputing Informatics and Genome Projects*, (Smith, D. W., ed.), 1993, New York: Academic Press; *Computer Analysis of Sequence Data, Part I*, (Griffin, A. M., and Griffin, H. G., eds.), 1994, New Jersey: Humana Press; von Heinje, G., 1987, *Sequence Analysis in Molecular Biology*, New York: Academic Press; Sequence Analysis Primer, (Gribskov, M. and Devereux, J., eds.), 1991, New York: M. Stockton Press; and Carillo et al., 1988, *SIAM J. Applied Math.* 48: 1073.

In calculating percent identity, the sequences being compared are aligned in a way that gives the largest match between the sequences. The computer program used to determine percent identity is the GCG program package, which includes GAP (Devereux et al., 1984, *Nucl Acid Res* 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see Dayhoff et al., 1978, *Atlas of Protein Sequence and Structure* 5:345-352 for the PAM 250 comparison matrix; Henikoff et al., 1992, *Proc. Natl. Acad. Sci. USA* 89: 10915-10919 for the BLOSUM 62 comparison matrix) is also used by the algorithm.

Recommended parameters for determining percent identity for polypeptides or nucleotide sequences using the GAP program are the following:

Algorithm: Needleman et al., 1970, *J. Mol. Biol.* 48:443-453;
Comparison matrix: BLOSUM 62 from Henikoff et al., 1992, supra;
Gap Penalty: 12 (but with no penalty for end gaps)
Gap Length Penalty: 4
Threshold of Similarity: 0

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 contiguous amino acids of the target polypeptide.

As used herein, "substantially pure" means that the described species of molecule is the predominant species present, that is, on a molar basis it is more abundant than any other individual species in the same mixture. In certain embodiments, a substantially pure molecule is a composition wherein the object species comprises at least 50% (on a molar basis) of all macromolecular species present. In other embodiments, a substantially pure composition will comprise at least 80%, 85%, 90%, 95%, or 99% of all macromolecular species present in the composition. In other embodiments, the object species is purified to essential homogeneity wherein contaminating species cannot be detected in the composition by conventional detection methods and thus the composition consists of a single detectable macromolecular species.

The term "osteopenia" refers to a patient with bone loss of at least one standard deviation compared with a standard patient considered to have normal bone mineral density (BMD). For present purposes, the measurement is determined by Dual Energy X-ray Absorptiometry (DEXA) and the patient's BMD is compared with an age and gender-matched standard (Z score). In determining osteopenia, BMD measurements may be taken of one or more bones.

The term "therapeutically effective amount" refers to the amount of an anti-Dkk-1 antibody determined to produce a therapeutic response in a mammal. Such therapeutically effective amounts are readily ascertained by one of ordinary skill in the art.

"Amino acid" includes its normal meaning in the art. The twenty naturally-occurring amino acids and their abbreviations follow conventional usage. See *Immunology—A Synthesis*, 2nd Edition, (E. S. Golub and D. R. Gren, eds.), Sinauer Associates: Sunderland, Mass. (1991), incorporated herein by reference for any purpose. Stereoisomers (e.g., D-amino acids) of the twenty conventional amino acids, unnatural amino acids such as α-, α-disubstituted amino acids, N-alkyl amino acids, and other unconventional amino acids may also be suitable components for polypeptides of the invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

II. Overview

The present invention provides novel compositions comprising antibodies and antigen-binding sites of immunoglobulins specific for Dkk-1 (e.g., a polypeptide consisting of amino acids 32 to 266 of SEQ ID NO:2 or a polypeptide consisting of amino acids 32 to 272 of SEQ ID NO:4). Some of these antibodies and antibody fragments can cross-react with Dkk-1 from several mammalian sources, including rat, mouse and human Dkk-1. Some of the antibodies and fragments have higher affinity for Dkk-1 from one species than another (e.g., some antibodies and fragments have higher affinity for human Dkk-1 as compared to rat or murine Dkk-1; other antibodies have higher affinity for rat or murine Dkk-1 as compared to human Dkk-1). The invention also provides novel neutralizing antibodies, including chimeric, humanized and human antibodies, as well as antibodies and immunologically functional fragments thereof, that bind a conformational epitope in human Dkk-1. Nucleic acids encoding the antibodies and fragments are also disclosed, as well as methods for expressing the antibodies using these nucleic acids. In another aspect, the invention relates to molecules (e.g., immunologically functional fragments and polypeptides) that are capable of exhibiting immunological binding properties of antibody antigen-binding sites.

The antibodies and immunologically functional fragments that are disclosed herein have a variety of utilities. Some of the antibodies and fragments, for instance, are useful in specific binding assays, affinity purification of Dkk-1 or its ligands and in screening assays to identify other antagonists of Dkk-1 activity. Certain of the antibodies can be used to treat various diseases that are associated with the activity of Dkk-1. Some antibodies and fragments can thus be used in a variety of treatments related to bone such as increasing bone mineral density, synthesis of new bone, treatment of systemic bone loss (e.g., bone erosions), bone repair, and treatments for various forms of arthritis. Some antibodies can also be used to increase osteoclast activity and induce bone resorption. Certain of the antibodies and fragments that are disclosed, however, can be used to treat a variety of diverse diseases that are unrelated to bone diseases. As described in greater detail below, examples of such diseases include those in which it is desirable to promote stem cell renewal (e.g., diabetes and diseases of the muscle), inflammatory diseases (e.g., Crohn's and inflammatory bowel disease), neurological diseases, ocular diseases, renal diseases, and various skin disorders.

III. Antibodies and Immunologically Functional Fragments

A variety of selective binding agents useful for regulating the activity of Dkk-1 are provided. These agents include, for instance, antibodies and immunologically functional fragments thereof that contain an antigen binding domain (e.g., single chain antibodies, domain antibodies, immunoadhesions, and polypeptides with an antigen binding region) and specifically bind to a Dkk-1 polypeptide (e.g., a human, rat and/or murine Dkk-1 polypeptide). Some of the agents, for example, are useful in inhibiting the binding of Dkk-1 to LRP5 and/or LRP6, and can thus be used to stimulate one or more activities associated with Wnt signaling.

A. Naturally Occurring Antibody Structure

Some of the binding agents that are provided have the structure typically associated with naturally occurring antibodies. The structural units of these antibodies typically comprise one or more tetramers, each composed of two identical couplets of polypeptide chains, though some species of mammals also produce antibodies having only a single heavy chain. In a typical antibody, each pair or couplet includes one full-length "light" chain (in certain embodiments, about 25 kDa) and one full-length "heavy" chain (in certain embodiments, about 50-70 kDa). Each individual immunoglobulin chain is composed of several "immunoglobulin domains," each consisting of roughly 90 to 110 amino acids and expressing a characteristic folding pattern. These domains are the basic units of which antibody polypeptides are composed. The amino-terminal portion of each chain typically includes a variable domain that is responsible for antigen recognition. The carboxy-terminal portion is more conserved evolutionarily than the other end of the chain and is referred to as the "constant region" or "C region." Human light chains generally are classified as kappa and lambda light chains, and each of these contains one variable domain and one constant domain. Heavy chains are typically classified as mu, delta, gamma, alpha, or epsilon chains, and these define the antibody's isotype as IgM, IgD, IgG, IgA, and IgE, respectively. IgG has several subtypes, including, but not limited to, $IgG_1$, $IgG_2$, $IgG_3$, and $IgG_4$. IgM subtypes include $IgM_1$ and $IgM_2$. IgA subtypes include $IgA_1$ and $IgA_2$. In humans, the IgA and IgD isotypes contain four heavy chains and four light chains; the IgG and IgE isotypes contain two heavy chains and two light chains; and the IgM isotype contains five heavy chains and five light chains. The heavy chain C region typically comprises one or more domains that may be responsible for effector function. The number of heavy chain constant region domains will depend on the isotype. IgG heavy chains, for example, each contain three C region domains known as $C_H1$, $C_H2$ and $C_H3$. The antibodies that are provided can have any of these isotypes and subtypes. In certain embodiments of the invention, the anti-Dkk-1 antibody is of the IgG1, $IgG_2$ or $IgG_4$ subtype.

In full-length light and heavy chains, the variable and constant regions are joined by a "J" region of about 12 or more amino acids, with the heavy chain also including a "D" region of about 10 more amino acids. See, e.g., *Fundamental Immunology*, 2nd ed., Ch. 7 (Paul, W., ed.) 1989, New York: Raven Press (hereby incorporated by reference in its entirety for all purposes). The variable regions of each light/heavy chain pair typically form the antigen binding site.

Variable regions of immunoglobulin chains generally exhibit the same overall structure, comprising relatively conserved framework regions (FR) joined by three hypervariable regions, more often called "complementarity determining regions" or CDRs. The CDRs from the two chains of each heavy chain/light chain pair mentioned above typically are aligned by the framework regions to form a structure that binds specifically with a specific epitope on the target protein (e.g., Dkk-1). From N-terminal to C-terminal, naturally-occurring light and heavy chain variable regions both typically conform with the following order of these elements: FR1, CDR1, FR2, CDR2, FR3, CDR3 and FR4. A numbering system has been devised for assigning numbers to amino acids that occupy positions in each of these domains. This numbering system is defined in *Kabat Sequences of Proteins of Immunological Interest* (1987 and 1991, National Institutes of Health, Bethesda, Md.), or Chothia & Lesk, 1987, *J. Mol. Biol.* 196: 901-917; Chothia et al., 1989, *Nature* 342: 878-883.

Specific examples of some of the full length light and heavy chains of the antibodies that are provided and their corresponding nucleotide and amino acid sequences are summarized in Table 1.

TABLE 1

Light and Heavy Chains

| Internal Designation | Abbrev. Name | Chain Type | NT Sequence (SEQ ID NO:) | AA Sequence (SEQ ID NO:) |
|---|---|---|---|---|
| 11H10 | L1 | Light | 81 | 82 |
| 11H10CR | L2 | Light | 25 | 26 |
| 11H10A1D | L3 | Light | 29 | 30 |
| 11H10 | H1 | Heavy | 88 | 89 |
| 11H10 RT IgG1 | H2 | Heavy | 33 | 34 |
| 11H10 ATT IgG1 | H3 | Heavy | 37 | 38 |
| 11H10 RT IgG2 | H4 | Heavy | 41 | 42 |
| 11H10 LT IgG2 | H5 | Heavy | 45 | 46 |
| 11H10 SKLT IgG2 | H6 | Heavy | 49 | 50 |
| 11H10 D3A IgG2 | H7 | Heavy | 53 | 54 |
| 11H10 D23A IgG2 | H8 | Heavy | 57 | 58 |
| 11H10 D32A IgG2 | H9 | Heavy | 61 | 62 |
| 11H10 D89A IgG2 | H10 | Heavy | 65 | 66 |

Each of the light chains listed in Table 1 can be combined with any of the heavy chains shown in Table 1 to form an antibody. Examples of such combinations include L1 combined with H1-H10, or L2 combined with H1-H110 and L3 combined with H1-H110 (i.e., L1H1, L1H2, L1H3, L1H4, L1H5, L1H6, L1H7, L1H8, L1H9, L11H10, L2H1, L2H2, L2H3, L2H4, L2H5, L2H6, L2H7, L2H8, L2H9, L2H10, L3H1, L3H2, L3H3, L3H4, L3H5, L3H6, L3H7, L3H8, L3H9, and L3H10. In some instances, the antibodies include at least one heavy chain and one light chain from those listed in Table 1. In other instances, the antibodies contain two identical light chains and two identical heavy chains. As an example, an antibody or immunologically functional fragment may include two L1 light chains and two H1 heavy chains, or two L2 light chains and two H3 heavy chains, or two L2 light chains and two H4 heavy chains or two L2 and two H5 heavy chains and other similar combinations of pairs of light chains and pairs of heavy chains as listed in Table 1.

As a specific example of such antibodies, in one embodiment, the anti-Dkk-1 antibody is a monoclonal antibody derived from rats. Exemplary antibodies capable of binding to the aforementioned conformational epitope are the monoclonal antibodies 11H10 and 1F11 (see, examples below), each of which comprises a light chain and a heavy chain. The complete light chain of 11H10 is encoded by the nucleotide sequence shown in SEQ ID NO:9, and the complete heavy chain of 11H10 by the nucleotide sequence shown in SEQ ID NO:11. The corresponding light and heavy chain amino acid sequences of 11H10 are shown, respectively, in SEQ ID NOS: 10 and 12. Residues 1-20 of SEQ ID NO:10 and residues 1-19 of SEQ ID NO:12 correspond to the signal sequences of these the light and heavy chains of 11H10, respectively. The amino acid sequence of the light chain without the signal sequence is shown in SEQ ID NO:82; the amino acid sequence of the heavy chain lacking the signal sequence is shown in SEQ ID NO:89.

Thus, in one aspect of the foregoing embodiment, the heavy chain may consist of amino acids 20-465 of SEQ ID NO:12 (i.e., H1, corresponding to SEQ ID NO:89), and in another aspect of this embodiment, the light chain may consist of amino acids 21-234 of SEQ ID NO:10 (i.e., L1, corresponding to SEQ ID NO:82). In yet another aspect of this embodiment, the antibody comprises both a heavy chain consisting of amino acids 20-465 of SEQ ID NO:12 and a light chain consisting of amino acids 21-234 of SEQ ID NO:10. In some instances, the antibody consists of two identical heavy chains each consisting of amino acids 20-465 of SEQ ID NO:12 and two identical light chains each consisting of amino acids 21-234 of SEQ ID NO:10. Another specific example is an antibody that includes the light chain L2 (SEQ ID NO:26) and the heavy chain H2 (SEQ ID NO:34). The coding sequences for these light and heavy chains are presented respectively, in SEQ ID NOS:25 and 33. These antibodies may include two identical heavy and light chains. The other heavy chain and light chains listed in Table 1 can be combined in a similar fashion.

Other antibodies that are provided are variants of antibodies formed by combination of the heavy and light chains shown in Table 1 and comprise light and/or heavy chains that each have at least 70%, 75%, 80%, 85%, 90%, 95%, 97% or 99% identity to the amino acid sequences of these chains. In some instances, such antibodies include at least one heavy chain and one light chain, whereas in other instances the such variant forms contain two identical light chains and two identical heavy chains.

B. Variable Domains of Antibodies

Also provided are antibodies that comprise a light chain variable region selected from the group consisting of VL 1, VL2, VL3 and/or a heavy chain variable region selected from the group consisting of VH1-VH10 as shown in Table 2 below, and immunologically functional fragments, derivatives, muteins and variants of these light chain and heavy chain variable regions.

Antibodies of this type can generally be designated by the formula "VLxVHy," where "x" is the number of the light chain variable region and "y" corresponds to the number of the heavy chain variable region as listed in Table 2. In general, x and y are each 1 or 2.

TABLE 2

| | | Variable Regions | | |
|---|---|---|---|---|
| Internal Designation | Abbrev. Name | Chain Type | NT Sequence (SEQ ID NO:) | AA Sequence (SEQ ID NO:) |
| 11H10 | VL1 | Light | 83 | 84 |
| 11H10 CR | VL2 | Light | 27 | 28 |
| 11H10 A1D | VL3 | Light | 31 | 32 |
| 11H10 | VH1 | Heavy | 90 | 91 |
| 11H10 RT IgG1 | VH2 | Heavy | 35 | 36 |
| 11H10 ATT IgG1 | VH3 | Heavy | 39 | 40 |
| 11H10 RT IgG2 | VH4 | Heavy | 43 | 44 |
| 11H10 LT IgG2 | VH5 | Heavy | 47 | 48 |
| 11H10 SKLT IgG2 | VH6 | Heavy | 51 | 52 |
| 11H10 D3A IgG2 | VH7 | Heavy | 55 | 56 |

TABLE 2-continued

| | | Variable Regions | | |
|---|---|---|---|---|
| Internal Designation | Abbrev. Name | Chain Type | NT Sequence (SEQ ID NO:) | AA Sequence (SEQ ID NO:) |
| 11H10 D23A IgG2 | VH8 | Heavy | 59 | 60 |
| 11H10 D32A IgG2 | VH9 | Heavy | 63 | 64 |
| 11H10 D89A IgG2 | VH10 | Heavy | 67 | 68 |

Thus, VL2VH1 refers to an antibody with a light chain variable region domain comprising the amino acid sequence of VL2 and a heavy chain variable region comprising the amino acid sequence of VH1. The antibodies that are provided thus include, but are not limited to, those having the following form: VL1VH1, VL1VH2, VL1VH3, VL1VH4, VL1VH5, VL1VH6, VL1VH7, VL1VH8, VL1VH9, VL1VH10, VL2VH1, VL2VH2, VL2VH3, VL2VH4, VL2VH5, VL2VH6, VL2VH7, VL2VH8, VL2VH9, VL2VH10, VL3VH1, VL3VH2, VL3VH3, VL3VH4, VL3VH5, VL3VH6, VL3VH7, VL3VH8, VL3VH9, and VL3VH10. In some instances, the foregoing antibodies include two light chain variable region domains and two heavy chain variable region domains (e.g. $VL1_2VH1_2$ etc.)

As a specific example of such antibodies, certain antibodies or immunologically functional fragments thereof comprise the variable region of the light chain or the variable region of the heavy chain of 11H10, wherein the light chain variable region consists of amino acids 21-127 of SEQ ID NO:10 (i.e., VL1, corresponding to SEQ ID NO:84) and the heavy chain variable region consists of amino acids 20-139 of SEQ ID NO:12 (i.e., VH1, corresponding to SEQ ID NO:91). In one aspect of this embodiment, the antibody consists of two identical heavy chains and two identical light chains.

Also provided, for instance, is an antibody comprising a light chain variable region that consists of amino acids 21-127 of SEQ ID NO:10 or an antigen-binding or an immunologically functional fragment thereof and further comprising a heavy chain variable region that consists of amino acids 20-139 of SEQ ID NO:12.

Certain antibodies comprise a light chain variable domain comprising a sequence of amino acids that differs from the sequence of a light chain variable domain selected from L1, L2 or L3 at only 1, 2, 3, 4, 5, 6, 7, 8, 9, 10, 11, 12, 13, 14 or 15 amino acid residues, wherein each such sequence difference is independently either a deletion, insertion or substitution of one amino acid. The light chain variable region in some antibodies comprises a sequence of amino acids that has at least 70%, 75%, 80%, 85%, 90%, 95%, 97% or 99% sequence identity to the amino acid sequences of the light chain variable region of VL 1, VL2 or VL3.

Some antibodies that are provided comprise a heavy chain variable domain comprising a sequence of amino acids that differs from the sequence of a heavy chain variable domain selected from H1-H10 at only 1, 2, 3, 4, 5, 6, 7, 8, 9, 10, 11, 12, 13, 14 or 15 amino acid residues, wherein each such sequence difference is independently either a deletion, insertion or substitution of one amino acid. The heavy chain variable region in some antibodies comprises a sequence of amino acids that has at least 70%, 75%, 80%, 85%, 90%, 95%, 97% or 99% sequence identity to the amino acid sequences of the heavy chain variable region of VH1, VH2, VH3, VH4, VH5, VH6, VH7, VH8, VH9, VH10. Still other antibodies or immunologically functional fragments include variant forms of a variant light chain and a variant heavy chain as just described.

C. CDRs of Antibodies

Complementarity determining regions (CDRs) and framework regions (FR) of a given antibody may be identified using the system described by Kabat et al. in Sequences of Proteins of Immunological Interest, 5th Ed., US Dept. of Health and Human Services, PHS, NIH, NIH Publication no. 91-3242, 1991. Certain antibodies that are disclosed herein comprise one or more amino acid sequences that are identical to or have substantial sequence identity to the amino acid sequences of one or more of the CDRs as summarized in Table 3.

TABLE 3

CDRs

| Chain | CDR | NT Sequence (SEQ ID NO:) | AA Sequence |
|---|---|---|---|
| Light | CDR1 | 69 or 85 | LASEDIYSDLA (SEQ ID NO: 70) |
| Light | CDR2 | 71 or 86 | NANSLQN (SEQ ID NO: 72) |
| Light | CDR3 | 73 or 87 | QQYNNYPPT (SEQ ID NO: 74) |
| Heavy | CDR1 | 75 or 92 | DYAMA (SEQ ID NO: 76) |
| Heavy | CDR2 | 77 or 93 | TIIYDGSSTYYRDSVKG (SEQ ID NO: 78) |
| Heavy | CDR3 | 79 or 94 | GLGIATDYFDY (SEQ ID NO: 80) |

The antibodies and immunological functional fragments that are provided can include one, two, three, four, five or all six of the CDRs listed above. Some antibodies or fragments include both the light chain CDR3 and the heavy chain CDR3. Certain antibodies have variant forms of the CDRs listed in Table 3, with one or more (i.e., 2, 3, 4, 5 or 6) of the CDRs each having at least 80%, 85%, 90% or 95% sequence identity to a CDR sequence listed in Table 3. For example, the antibody or fragment can include both a light chain CDR3 and a heavy chain CDR3 that each have at least 80%, 85%, 90% or 95% sequence identity to the light chain CDR3 sequence and the heavy chain CDR3, respectively, listed in Table 3. The CDR sequences of some of the antibodies that are provided may also differ from the CDR sequences listed in Table 3 such that the amino acid sequence for any given CDR differs from the sequence listed in Table 3 by no more than 1, 2, 3, 4 or 5 amino acid residues. Differences from the listed sequences usually are conservative substitutions (see below).

As a specific example, the antibodies and immunologically functional fragments that are provided may comprise one or more of the following CDR sequences from the 11H10 light chain:

CDR1: amino acids 44-54 of SEQ ID NO:10, which also corresponds to SEQ ID NO:70 (encoded by nucleotides 130-162 of SEQ ID NO:9 (SEQ ID NO:85) or SEQ ID NO:69);

CDR2: amino acids 70-76 of SEQ ID NO:10, which also corresponds to SEQ ID NO:72 (encoded by nucleotides 208-228 of SEQ ID NO:9 (SEQ ID NO:86) or SEQ ID NO:71);

CDR3: amino acids 109-117 of SEQ ID NO:10, which also corresponds to SEQ ID NO:74 (encoded by nucleotides 325-351 of SEQ ID NO:9 (SEQ ID NO:87) or SEQ ID NO:73);

Additional antibodies and immunologically functional immunoglobulin fragments of the invention may comprise one or more of the following CDR sequences from the 11H10 heavy chain:

CDR1: amino acids 50-54 of SEQ ID NO:12, which also corresponds with SEQ ID NO:76 (encoded by nucleotides 148-162 of SEQ ID NO:11 (SEQ ID NO:92) or SEQ ID NO:75);

CDR2: amino acids 69-85 of SEQ ID NO:12, which also corresponds with SEQ ID NO:78 (encoded by nucleotides 205-255 of SEQ ID NO:11 (SEQ ID NO:93) or SEQ ID NO:77);

CDR3: and amino acids 118-128 of SEQ ID NO:12, which also corresponds with SEQ ID NO:80 (encoded by nucleotides 352-384 of SEQ ID NO:11 (SEQ ID NO:94) or SEQ ID NO:79).

Polypeptides comprising one or more of the light or heavy chain CDRs may be produced by using a suitable vector to express the polypeptides in a suitable host cell as described in greater detail below.

The heavy and light chain variable regions and the CDRs that are disclosed in Table 2 and 3 can be used to prepare any of the various types of immunologically functional fragments that are known in the art including, but not limited to, domain antibodies, Fab fragments, Fab' fragments, F(ab')$_2$ fragments, Fv fragments, single-chain antibodies and scFvs.

D. Antibodies and Binding Epitopes

When an antibody is said to bind an epitope within specified residues, such as Dkk-1, for example, what is meant is that the antibody specifically binds to a polypeptide consisting of the specified residues (e.g., a specified segment of Dkk-1). Such an antibody does not necessarily contact every residue within Dkk-1. Nor does every single amino acid substitution or deletion within Dkk-1 necessarily significantly affect binding affinity. Epitope specificity of an antibody can be determined in variety of ways. One approach, for example, involves testing a collection of overlapping peptides of about 15 amino acids spanning the sequence of Dkk-1 and differing in increments of a small number of amino acids (e.g., 3 amino acids). The peptides are immobilized within the wells of a microtiter dish. Immobilization can be effected by biotinylating one terminus of the peptides. Optionally, different samples of the same peptide can be biotinylated at the N and C terminus and immobilized in separate wells for purposes of comparison. This is useful for identifying end-specific antibodies. Optionally, additional peptides can be included terminating at a particular amino acid of interest. This approach is useful for identifying end-specific antibodies to internal fragments of Dkk-1. An antibody or immunologically functional fragment is screened for specific binding to each of the various peptides. The epitope is defined as occurring with a segment of amino acids that is common to all peptides to which the antibody shows specific binding. Details regarding a specific approach for defining an epitope is set forth in Example 6.

Antibodies and functional fragments thereof that bind to a conformational epitope that is located in the carboxy-terminal portion of Dkk-1 (see FIG. 1) are also provided. The carboxy-terminus of Dkk-1 contains several cysteine residues that form a cluster of disulfide bonds which create several loops. The invention provides antibodies that bind to two of these loops, thereby neutralizing the ability of Dkk-1 to suppress Wnt activity. Exemplary antibodies capable of binding to the aforementioned conformational epitope are the monoclonal antibodies 11H10 and 1F11, each of which comprises a light chain and a heavy chain. The complete light chain of 11H10 is encoded by the nucleotide sequence shown in SEQ ID NO:9, and the complete heavy chain of 11H10 by the nucleotide sequence shown in SEQ ID NO:11. The corresponding light and heavy chain amino acid sequences of 11H10 (including signal sequences) are shown, respectively, in SEQ ID NOS:10 and 12. The mature forms without the signal sequences correspond to SEQ ID NOS: 82 and 89.

The epitope comprising these two loops is formed by disulfide bonds between cysteine residues 220 and 237 of SEQ ID NO:2 and between cysteine residues 245 and 263 of SEQ ID NO:2. The body of the two loops that form the epitope thus includes amino acids 221-236 and 246-262 of SEQ ID NO:2. Segments within this loop that are involved in binding include amino acids 221-229 of SEQ ID NO:2 and amino acids 246-253 of SEQ ID NO:2. Thus, certain antibodies and fragments that are provided herein specifically bind to the foregoing region(s). Some of the antibodies and fragments, for instance, bind to a peptide comprising or consisting of amino acids 221 to 262 of SEQ ID NO:2.

In one aspect of the invention, peptides comprising or consisting of amino acids 221-229 and/or 246-253 of SEQ ID NO:2 are provided. Other peptides comprise or consist of amino acids 221-236 and/or 246-262 of SEQ ID NO:2. Still other peptides that are provided comprise or consist of the region from 221 to 262 of SEQ ID NO:2 or amino acids 221-253 of SEQ ID NO:2. Such peptides are shorter than the full-length protein sequence of a native Dkk-1 (e.g., the peptides may include one or more of the forgoing regions and be 8, 9, 10, 11, 12, 13, 14, 15, 20, 21, 22, 23, 24, 25, 30, 40, 50, 75, 100, 150, or 200 amino acids in length). These peptides may be fused to another peptide to increase immunogenicity and thus be in the form of a fusion protein.

E. Competing Antibodies

Antibodies and immunologically functional fragments thereof that compete with one the exemplified antibodies or functional fragments for specific binding to Dkk-1 are also provided. Such antibodies and fragments may also bind to the same epitope as one of the exemplified antibodies. Antibodies and fragments that compete with or bind to the same epitope as the exemplified antibody or fragment are expected to show similar functional properties. The exemplified antibodies and fragment include those described above, including those with the heavy and light chains, variable region domains and CDRs listed in Tables 1-3. Competing antibodies or immunologically functional fragments can include those that bind to the epitope described in the section on antibodies and epitopes above.

As a specific example, some competing antibodies or fragments include those that specifically bind a Dkk-1 protein consisting of amino acids 32 to 266 of SEQ ID NO:2 or amino acids 32 to 272 of SEQ ID NO:4 and can prevent or reduce the binding to human Dkk-1 of an antibody that consists of two identical heavy chains and two identical light chains, wherein said heavy chains consist of amino acids 20-465 of SEQ ID NO:12 and said light chains consist of amino acids 21-234 of SEQ ID NO:10. Other competing antibodies prevent or reduce the binding to human Dkk-1 of an antibody that consists of two identical heavy chains and two identical light chains such as those listed in Table 1.

F. Monoclonal Antibodies

The antibodies that are provided include monoclonal antibodies that bind to Dkk-1. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 41, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

In some instances, a hybridoma cell line is produced by immunizing an animal (e.g., a transgenic animal having human immunoglobulin sequences) with a Dkk-1 immunogen; harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that binds a Dkk-1 polypeptide. Such hybridoma cell lines, and anti-Dkk-1 monoclonal antibodies produced by them, are encompassed by the present invention.

Monoclonal antibodies secreted by a hybridoma cell line can be purified using any technique known in the art. Hybridomas or mAbs may be further screened to identify mAbs with particular properties, such as the ability to block a Wnt induced activity. Examples of such screens are provided in the examples below.

G. Chimeric and Humanized Antibodies

Chimeric and humanized antibodies based upon the foregoing sequences are also provided. Monoclonal antibodies for use as therapeutic agents may be modified in various ways prior to use. One example is a "chimeric" antibody, which is an antibody composed of protein segments from different antibodies that are covalently joined to produce functional immunoglobulin light or heavy chains or immunologically functional portions thereof. Generally, a portion of the heavy chain and/or light chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. For methods relating to chimeric antibodies, see, for example, U.S. Pat. No. 4,816,567; and Morrison et al., *Proc. Natl. Acad. Sci. USA* 81:6851-6855 (1985), which are hereby incorporated by reference. CDR grafting is described, for example, in U.S. Pat. Nos. 6,180,370, 5,693,762, 5,693,761, 5,585,089, and 5,530,101, which are all hereby incorporated by reference for all purposes.

Generally, the goal of making a chimeric antibody is to create a chimera in which the number of amino acids from the intended patient species is maximized. One example is the "CDR-grafted" antibody, in which the antibody comprises one or more complementarity determining regions (CDRs) from a particular species or belonging to a particular antibody class or subclass, while the remainder of the antibody chain(s) is/are identical with or homologous to a corresponding sequence in antibodies derived from another species or belonging to another antibody class or subclass. For use in humans, the V region or selected CDRs from a rodent antibody often are grafted into a human antibody, replacing the naturally-occurring V regions or CDRs of the human antibody.

One useful type of chimeric antibody is a "humanized" antibody. Generally, a humanized antibody is produced from a monoclonal antibody raised initially in a non-human animal. Certain amino acid residues in this monoclonal antibody, typically from non-antigen recognizing portions of the antibody, are modified to be homologous to corresponding residues in a human antibody of corresponding isotype. Humanization can be performed, for example, using various methods by substituting at least a portion of a rodent variable region for the corresponding regions of a human antibody (see, e.g., U.S. Pat. Nos. 5,585,089, and 5,693,762; Jones et al., 1986,

*Nature* 321:522-25; Riechmann et al., 1988, *Nature* 332:323-27; Verhoeyen et al., 1988, *Science* 239:1534-36).

In one aspect of the invention, the CDRs of the light and heavy chain variable regions of the antibodies provided herein (see Table 3) are grafted to framework regions (FRs) from antibodies from the same, or a different, phylogenetic species. For example, the CDRs of the light and heavy chain variable regions of the 11H10 antibody can be grafted to consensus human FRs. To create consensus human FRs, FRs from several human heavy chain or light chain amino acid sequences may be aligned to identify a consensus amino acid sequence. In other embodiments, the FRs of the 11H10 antibody heavy chain or light chain are replaced with the FRs from a different heavy chain or light chain. In one aspect of the invention, rare amino acids in the FRs of the heavy and light chains of anti-Dkk-1 antibody are not replaced, while the rest of the FR amino acids are replaced. A "rare amino acid" is a specific amino acid that is in a position in which this particular amino acid is not usually found in an FR. Alternatively, the grafted variable regions from the 11H10 antibody may be used with a constant region that is different from the constant region of 11H10. In other embodiments of the invention, the grafted variable regions are part of a single chain Fv antibody.

In certain embodiments, constant regions from species other than human can be used along with the human variable region(s) to produce hybrid antibodies.

H. Fully Human Antibodies

Fully human antibodies are also provided. Methods are available for making fully human antibodies specific for a given antigen without exposing human beings to the antigen ("fully human antibodies"). One means for implementing the production of fully human antibodies is the "humanization" of the mouse humoral immune system. Introduction of human immunoglobulin (Ig) loci into mice in which the endogenous Ig genes have been inactivated is one means of producing fully human monoclonal antibodies (MAbs) in mouse, an animal that can be immunized with any desirable antigen. Using fully human antibodies can minimize the immunogenic and allergic responses that can sometimes be caused by administering mouse or mouse-derivatized Mabs to humans as therapeutic agents.

Fully human antibodies can be produced by immunizing transgenic animals (usually mice) that are capable of producing a repertoire of human antibodies in the absence of endogenous immunoglobulin production. Antigens for this purpose typically have six or more contiguous amino acids, and optionally are conjugated to a carrier, such as a hapten. See, for example, Jakobovits et al., 1993, *Proc. Natl. Acad. Sci. USA* 90:2551-2555; Jakobovits et al., 1993, *Nature* 362:255-258; and Bruggermann et al., 1993, *Year in Immunol.* 7:33. In one example of such a method, transgenic animals are produced by incapacitating the endogenous mouse immunoglobulin loci encoding the mouse heavy and light immunoglobulin chains therein, and inserting into the mouse genome large fragments of human genome DNA containing loci that encode human heavy and light chain proteins. Partially modified animals, which have less than the full complement of human immunoglobulin loci, are then cross-bred to obtain an animal having all of the desired immune system modifications. When administered an immunogen, these transgenic animals produce antibodies that are immunospecific for the immunogen but have human rather than murine amino acid sequences, including the variable regions. For further details of such methods, see, for example, WO96/33735 and WO94/02602, which are hereby incorporated by reference. Additional methods relating to transgenic mice for making human antibodies are described in U.S. Pat. Nos. 5,545,807; 6,713,610; 6,673,986; 6,162,963; 5,545,807; 6,300,129; 6,255,458; 5,877,397; 5,874,299 and 5,545,806; in PCT publications WO91/10741, WO90/04036, and in EP 546073B1 and EP 546073A1, all of which are hereby incorporated by reference in their entirety for all purposes.

The transgenic mice described above, referred to herein as "HuMab" mice, contain a human immunoglobulin gene minilocus that encodes unrearranged human heavy ($\mu$ and $\gamma$) and $\kappa$ light chain immunoglobulin sequences, together with targeted mutations that inactivate the endogenous $\mu$ and $\kappa$ chain loci (Lonberg et al., 1994, *Nature* 368: 856-859). Accordingly, the mice exhibit reduced expression of mouse IgM or $\kappa$ and in response to immunization, and the introduced human heavy and light chain transgenes undergo class switching and somatic mutation to generate high affinity human IgG $\kappa$ monoclonal antibodies (Lonberg et al., supra.; Lonberg and Huszar, 1995, *Intern. Rev. Immunol.*, 13: 65-93; Harding and Lonberg, 1995, *Ann. N.Y. Acad. Sci* 764: 536-546). The preparation of HuMab mice is described in detail in Taylor et al., 1992, *Nucleic Acids Research*, 20: 6287-6295; Chen et al., 1993, *International Immunology* 5: 647-656; Tuaillon et al., 1994, *J. Immunol.* 152: 2912-2920; Lonberg et al., 1994, *Nature* 368: 856-859; Lonberg, 1994, *Handbook of Exp. Pharmacology* 113: 49-101; Taylor et al., 1994, *International Immunology* 6: 579-591; Lonberg and Huszar, 1995, *Intern. Rev. Immunol.* 13: 65-93; Harding and Lonberg, 1995, *Ann. N.Y. Acad. Sci.* 764: 536-546; Fishwild et al., 1996, *Nature Biotechnology* 14: 845-851; the foregoing references are hereby incorporated by reference in their entirety for all purposes. See further U.S. Pat. Nos. 5,545,806; 5,569,825; 5,625,126; 5,633,425; 5,789,650; 5,877,397; 5,661,016; 5,814,318; 5,874,299; and 5,770,429; as well as U.S. Pat. No. 5,545,807; International Publication Nos. WO 93/1227; WO 92/22646; and WO 92/03918, the disclosures of all of which are hereby incorporated by reference in their entirety for all purposes. Technologies utilized for producing human antibodies in these transgenic mice are disclosed also in WO 98/24893, and Mendez et al., 1997, *Nature Genetics* 15: 146-156, which are hereby incorporated by reference. For example, the HCo7 and HCo12 transgenic mice strains can be used to generate human anti-Dkk-1 antibodies.

Using hybridoma technology, antigen-specific human MAbs with the desired specificity can be produced and selected from the transgenic mice such as those described above. Such antibodies may be cloned and expressed using a suitable vector and host cell, or the antibodies can be harvested from cultured hybridoma cells.

Fully human antibodies can also be derived from phage-display libraries (as disclosed in Hoogenboom et a, 1991, *J. Mol. Biol.* 227:381; and Marks et al., 1991, *J. Mol. Biol.* 222:581). Phage display techniques mimic immune selection through the display of antibody repertoires on the surface of filamentous bacteriophage, and subsequent selection of phage by their binding to an antigen of choice. One such technique is described in PCT Publication No. WO99/10494 (hereby incorporated by reference), which describes the isolation of high affinity and functional agonistic antibodies for MPL- and msk-receptors using such an approach.

I. Bispecific or Bifunctional Antibodies

The antibodies that are provided also include bispecific and bifunctional antibodies that include one or more CDRs or one or more variable regions as described above. A bispecific or bifunctional antibody in some instances is an artificial hybrid antibody having two different heavy/light chain pairs and two different binding sites. Bispecific antibodies may be produced by a variety of methods including, but not limited to, fusion of hybridomas or linking of Fab' fragments. See, e.g., Songsivilai & Lachmann, 1990, *Clin. Exp. Immunol.* 79: 315-321; Kostelny et al., 1992, *J. Immunol.* 148: 1547-1553.

J. Various Other Forms

Some of the antibodies or immunologically functional fragments that are provided are variant forms of the antibodies and fragments disclosed above (e.g., those having the sequences listed in Tables 1-3). For instance, some of the antibodies or fragments are ones having one or more conservative amino acid substitutions in one or more of the heavy or light chains, variable regions or CDRs listed in Tables 1-3.

Naturally-occurring amino acids may be divided into classes based on common side chain properties:
1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Non-conservative substitutions may involve the exchange of a member of one of the above classes for a member from another class. Such substituted residues may be introduced into regions of the antibody that are homologous with human antibodies, or into the non-homologous regions of the molecule.

In making such changes, according to certain embodiments, the hydropathic index of amino acids may be considered. The hydropathic profile of a protein is calculated by assigning each amino acid a numerical value ("hydropathy index") and then repetitively averaging these values along the peptide chain. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic profile in conferring interactive biological function on a protein is understood in the art (see, for example, Kyte et al., 1982, *J. Mol. Biol.* 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In some aspects of the invention, those which are within ±1 are included, and in other aspects of the invention, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigen-binding or immunogenicity, that is, with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in other embodiments, those which are within ±1 are included, and in still other embodiments, those within ±0.5 are included. In some instances, one may also identify epitopes from primary amino acid sequences on the basis of hydrophilicity. These regions are also referred to as "epitopic core regions."

Exemplary conservative amino acid substitutions are set forth in Table 4.

TABLE 4

Amino Acid Substitutions

| Original Residues | Exemplary Substitutions |
|---|---|
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala, Phe, Norleucine |
| Leu | Norleucine, Ile, Val, Met, Ala, Phe |
| Lys | Arg, Gln, Asn, 1,4 Diamine-butyric Acid |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala, Norleucine |

A skilled artisan will be able to determine suitable variants of polypeptides as set forth herein using well-known techniques. One skilled in the art may identify suitable areas of the molecule that may be changed without destroying activity by targeting regions not believed to be important for activity. The skilled artisan also will be able to identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. These variants can then be screened using assays for Dkk-1 neutralizing activity, (see examples below) thus yielding information regarding which amino acids can be changed and which must not be changed. In other words, based on information gathered from such routine experiments, one skilled in the art can readily determine the amino acid positions where further substitutions should be avoided either alone or in combination with other mutations.

A number of scientific publications have been devoted to the prediction of secondary structure. See Moult, 1996, *Curr. Op. in Biotech.* 7:422-427; Chou et al., 1974, *Biochemistry* 13:222-245; Chou et al., 1974, *Biochemistry* 113:211-222; Chou et al., 1978, *Adv. Enzymol. Relat. Areas Mol. Biol.* 47:45-148; Chou et al., 1979, Ann. Rev. Biochem. 47:251-276; and Chou et al., 1979, *Biophys. J.* 26:367-384. Moreover, computer programs are currently available to assist with predicting secondary structure. One method of predicting secondary structure is based upon homology modeling. For example, two polypeptides or proteins that have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., 1999, *Nucl. Acid. Res.* 27:244-247. It has been suggested (Brenner et al., 1997, *Curr. Op. Struct. Biol.* 7:369-376) that there are a limited number of folds in a given polypeptide or protein and that once a critical number of structures have been resolved, structural prediction will become dramatically more accurate.

Additional methods of predicting secondary structure include "threading" (Jones, 1997, *Curr. Opin. Struct. Biol.* 7:377-87; Sippl et al., 1996, *Structure* 4:15-19), "profile analysis" (Bowie et al., 1991, *Science* 253:164-170; Gribskov et al., 1990, *Meth. Enzym.* 183:146-159; Gribskov et al., 1987, *Proc. Nat. Acad. Sci.* 84:4355-4358), and "evolutionary linkage" (See Holm, 1999, supra; and Brenner, 1997, supra).

In some embodiments of the invention, amino acid substitutions are made that: (1) reduce susceptibility to proteolysis, (2) reduce susceptibility to oxidation, (3) alter binding affinity for forming protein complexes, (4) alter ligand or antigen binding affinities, and/or (4) confer or modify other physicochemical or functional properties on such polypeptides. For example, single or multiple amino acid substitutions (in certain embodiments, conservative amino acid substitutions) may be made in the naturally-occurring sequence. Substitutions can be made in that portion of the antibody that lies outside the domain(s) forming intermolecular contacts). In such embodiments, conservative amino acid substitutions can be used that do not substantially change the structural characteristics of the parent sequence (e.g., one or more replacement amino acids that do not disrupt the secondary structure that characterizes the parent or native antibody). Examples of art-recognized polypeptide secondary and tertiary structures are described in *Proteins, Structures and Molecular Principles* (Creighton, Ed.), 1984, W. H. New York: Freeman and Company; *Introduction to Protein Structure* (Branden and Tooze, eds.), 1991, New York: Garland Publishing; and Thornton et al., 1991, *Nature* 354: 105, which are each incorporated herein by reference.

The invention also encompasses glycosylation variants of the inventive antibodies wherein the number and/or type of glycosylation site(s) has been altered compared to the amino acid sequences of the parent polypeptide. In certain embodiments, antibody protein variants comprise a greater or a lesser number of N-linked glycosylation sites than the native antibody. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate or alter this sequence will prevent addition of an N-linked carbohydrate chain present in the native polypeptide. For example, the glycosylation can be reduced by the deletion of an Asn or by substituting the Asn with a different amino acid. In other embodiments, one or more new N-linked sites are created. Antibodies typically have a N-linked glycosylation site in the Fc region. For example, the 11H10 antibody described herein has an N-linked glycosylation site at amino acid 315 (SEQ ID NO:12).

Additional preferred antibody variants include cysteine variants wherein one or more cysteine residues in the parent or native amino acid sequence are deleted from or substituted with another amino acid (e.g., serine). Cysteine variants are useful, inter alia when antibodies must be refolded into a biologically active conformation. Cysteine variants may have fewer cysteine residues than the native antibody, and typically have an even number to minimize interactions resulting from unpaired cysteines.

The heavy and light chains, variable regions domains and CDRs that are disclosed can be used to prepare polypeptides that contain an antigen binding region that can specifically bind to a Dkk-1 polypeptide. For example, one or more of the CDRs listed in Table 3 can be incorporated into a molecule (e.g., a polypeptide) covalently or noncovalently to make an immunoadhesin. An immunoadhesin may incorporate the CDR(s) as part of a larger polypeptide chain, may covalently link the CDR(s) to another polypeptide chain, or may incorporate the CDR(s) noncovalently. The CDR(s) enable the immunoadhesin to bind specifically to a particular antigen of interest (e.g., a Dkk-1 polypeptide or epitope thereof).

Mimetics (e.g., peptide mimetics" or "peptidomimetics") based upon the variable region domains and CDRs that are described herein are also provided. These analogs can be peptides, non-peptides or combinations of peptide and non-peptide regions. Fauchere, 1986, *Adv. Drug Res.* 15: 29; Veber and Freidinger, 1985, *TINS* p. 392; and Evans et al., 1987, *J. Med. Chem.* 30: 1229, which are incorporated herein by reference for any purpose. Peptide mimetics that are structurally similar to therapeutically useful peptides may be used to produce a similar therapeutic or prophylactic effect. Such compounds are often developed with the aid of computerized molecular modeling. Generally, peptidomimetics of the invention are proteins that are structurally similar to an antibody displaying a desired biological activity, such as here the ability to specifically bind Dkk-1, but have one or more peptide linkages optionally replaced by a linkage selected from: —$CH_2NH$—, —$CH_2S$—, —$CH_2$—$CH_2$—, —CH=CH-(cis and trans), —COCH$_2$—, —CH(OH)CH$_2$—, and —CH$_2$SO—, by methods well known in the art. Systematic substitution of one or more amino acids of a consensus sequence with a D-amino acid of the same type (e.g., D-lysine in place of L-lysine) may be used in certain embodiments of the invention to generate more stable proteins. In addition, constrained peptides comprising a consensus sequence or a substantially identical consensus sequence variation may be generated by methods known in the art (Rizo and Gierasch, 1992, *Ann. Rev. Biochem.* 61: 387), incorporated herein by reference), for example, by adding internal cysteine residues capable of forming intramolecular disulfide bridges which cyclize the peptide.

Derivatives of the antibodies and immunologically functional fragments that are described herein are also provided. The derivatized antibody or fragment may comprise any molecule or substance that imparts a desired property to the antibody or fragment, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin)), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly(n-vinyl pyurrolidone), polyethylene glycols, propropylene glycol homopolymers, polypropylene oxide/ethylene oxide co-polymers, polyoxyethylated polyols and polyvinyl alcohols.

Other derivatives include covalent or aggregative conjugates of anti-Dkk-1 antibodies, or fragments thereof, with other proteins or polypeptides, such as by expression of recombinant fusion proteins comprising heterologous polypeptides fused to the N-terminus or C-terminus of an anti-Dkk-1 antibody polypeptide. For example, the conjugated peptide may be a heterologous signal (or leader) polypeptide, e.g., the yeast alpha-factor leader, or a peptide such as an epitope tag. Anti-Dkk-1 antibody-containing fusion proteins can comprise peptides added to facilitate purification or identification of the anti-Dkk-1 antibody (e.g., poly-His). An anti-Dkk-1 antibody polypeptide also can be linked to the FLAG peptide as described in Hopp et al., *Bio/Technology* 6:1204, 1988, and U.S. Pat. No. 5,011,912. The FLAG peptide is highly antigenic and provides an epitope reversibly bound by a specific monoclonal antibody (mAb), enabling rapid assay and facile purification of expressed recombinant protein. Reagents useful for preparing fusion proteins in which the FLAG peptide is fused to a given polypeptide are commercially available (Sigma, St. Louis, Mo.).

Oligomers that contain one or more anti-Dkk-1 antibody polypeptides may be employed as Dkk-1 antagonists. Oligomers may be in the form of covalently-linked or non-covalently-linked dimers, trimers, or higher oligomers. Oligomers comprising two or more anti-Dkk-1 antibody polypeptides are contemplated for use, with one example being a homodimer. Other oligomers include heterodimers, homotrimers, heterotrimers, homotetramers, heterotetramers, etc.

One embodiment is directed to oligomers comprising multiple anti-Dkk-1 antibody polypeptides joined via covalent or non-covalent interactions between peptide moieties fused to the anti-Dkk-1 antibody polypeptides. Such peptides may be peptide linkers (spacers), or peptides that have the property of promoting oligomerization. Leucine zippers and certain polypeptides derived from antibodies are among the peptides that can promote oligomerization of anti-Dkk-1 antibody polypeptides attached thereto, as described in more detail below.

In particular embodiments, the oligomers comprise from two to four anti-Dkk-1 antibody polypeptides. The anti-Dkk-1 antibody moieties of the oligomer may be in any of the forms described above, e.g., variants or fragments. Preferably, the oligomers comprise anti-Dkk-1 antibody polypeptides that have Dkk-1 binding activity.

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, PNAS USA 88:10535; Bym et al., 1990, Nature 344:677; and Hollenbaugh et al., 1992 "Construction of Immunoglobulin Fusion Proteins", in *Current Protocols in Immunology*, Suppl. 4, pages 10.19.1-10.19.11.

One embodiment of the present invention is directed to a dimer comprising two fusion proteins created by fusing a Dkk-1 binding fragment of an anti-Dkk-1 antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 and U.S. Pat. Nos. 5,426,048 and 5,262,522 (each of which is hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., 1994, EMBO J. 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

In other embodiments, the variable portion of the heavy and/or light chains of an anti-Dkk-1 antibody such as disclosed herein may be substituted for the variable portion of an antibody heavy and/or light chain.

Alternatively, the oligomer is a fusion protein comprising multiple anti-Dkk-1 antibody polypeptides, with or without peptide linkers (spacer peptides). Among the suitable peptide linkers are those described in U.S. Pat. Nos. 4,751,180 and 4,935,233.

Another method for preparing oligomeric anti-Dkk-1 antibody derivatives involves use of a leucine zipper. Leucine zipper domains are peptides that promote oligomerization of the proteins in which they are found. Leucine zippers were originally identified in several DNA-binding proteins (Landschulz et al., 1988, Science 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, FEBS Letters 344: 191, hereby incorporated by reference. The use of a modified leucine zipper that allows for stable trimerization of a heterologous protein fused thereto is described in Fanslow et al., 1994, Semin. Immunol. 6:267-78. In one approach, recombinant fusion proteins comprising an anti-Dkk-1 antibody fragment or derivative fused to a leucine zipper peptide are expressed in suitable host cells, and the soluble oligomeric anti-Dkk-1 antibody fragments or derivatives that form are recovered from the culture supernatant.

Some antibodies that are provided have a binding affinity ($K_a$) for Dkk-1 of at least $10^4$ or $10^5$/M×seconds measured, for instance, as described in the examples below. Other antibodies have a $k_a$ of at least $10^6$, $10^7$, $10^8$ or $10^9$/M×seconds. Certain antibodies that are provided have a low disassociation rate. Some antibodies, for instance, have a $K_{off}$ of $1\times10^{-4}$ s$^{-1}$, $1\times10^{-5}$ s$^{-1}$ or lower. In another embodiment, the $K_{off}$ is the same as an antibody having the following combinations of variable region domains VL1VH1, VL1VH2, VL1VH3, VL1VH4, VL1VH5, VL1VH6, VL1VH7, VL1VH8, VL1VH9, VL1VH10, VL2VH1, VL2VH2, VL2VH3, VL2VH4, VL2VH5, VL2VH6, VL2VH7, VL2VH8, VL2VH9, VL2VH10, VL3VH1, VL3VH2, VL3VH3, VL3VH4, VL3VH5, VL3VH6, VL3VH7, VL3VH8, VL3VH9, VL3VH10.

In another aspect, the present invention provides an anti-Dkk-1 antibody having a half-life of at least one day in vitro or in vivo (e.g., when administered to a human subject). In one embodiment, the antibody has a half-life of at least three days. In another embodiment, the antibody or portion thereof has a half-life of four days or longer. In another embodiment, the antibody or portion thereof has a half-life of eight days or longer. In another embodiment, the antibody or antigen-binding portion thereof is derivatized or modified such that it has a longer half-life as compared to the underivatized or unmodified antibody. In another embodiment, the antibody contains point mutations to increase serum half life, such as described in WO 00/09560, published Feb. 24, 2000, incorporated by reference.

IV. Nucleic Acids

Nucleic acids that encode one or both chains of an antibody of the invention, or a fragment, derivative, mutein, or variant thereof, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing are also provided. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids).

Nucleic acids that encode the epitope to which certain of the antibodies provided herein bind are also provided. Thus, some nucleic acids encode amino acids 221-229 and/or 246-253 of SEQ ID NO:2 are included, as are nucleic acids that encode amino acids 221-236 and/or 246-262 of SEQ ID NO:2 and those that encode amino acids 221 to 262 of SEQ ID NO:2 or amino acids 221-253 of SEQ ID NO:2. Nucleic acids encoding fusion proteins that include these peptides are also provided.

DNA encoding antibody polypeptides (e.g., heavy or light chain, variable domain only, or full length) may be isolated from B-cells of mice that have been immunized with Dkk-1 or an immunogenic fragment thereof. The DNA may be isolated by conventional procedures such as polymerase chain reaction (PCR). Phage display is another example of a known technique whereby derivatives of antibodies may be prepared. In one approach, polypeptides that are components of an antibody of interest are expressed in any suitable recombinant expression system, and the expressed polypeptides are allowed to assemble to form antibody molecules.

Exemplary nucleic acids that encode the light and heavy chains, variable regions and CDRs of the antibodies and immunologically functional fragments that are provided are listed in Tables 1-3 above. Due to the degeneracy of the genetic code, each of the polypeptide sequences listed in Tables 1-3 is also encoded by a large number of other nucleic acid sequences besides those listed in Tables 1-3. The present invention provides each degenerate nucleotide sequence encoding each antibody of the invention.

The invention further provides nucleic acids that hybridize to other nucleic acids (e.g., nucleic acids comprising a nucleotide sequence listed in Tables 1-3) under particular hybridization conditions. Methods for hybridizing nucleic acids are well-known in the art. See, e.g., Current Protocols in Molecular Biology, John Wiley & Sons, N.Y. (1989), 6.3.1-6.3.6. As defined herein, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65, 70, 75, 80, 85, 90, 95, 98 or 99% identical to each other typically remain hybridized to each other.

The basic parameters affecting the choice of hybridization conditions and guidance for devising suitable conditions are set forth by, for example, Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the DNA.

Changes can be introduced by mutation into a nucleic acid, thereby leading to changes in the amino acid sequence of a polypeptide (e.g., an antibody or antibody derivative of the invention) that it encodes. Mutations can be introduced using any technique known in the art. In one embodiment, one or more particular amino acid residues are changed using, for example, a site-directed mutagenesis protocol. In another embodiment, one or more randomly selected residues is changed using, for example, a random mutagenesis protocol. However it is made, a mutant polypeptide can be expressed and screened for a desired property.

Mutations can be introduced into a nucleic acid without significantly altering the biological activity of a polypeptide that it encodes. For example, one can make nucleotide substitutions leading to amino acid substitutions at non-essential amino acid residues. Alternatively, one or more mutations can be introduced into a nucleic acid that selectively change the biological activity of a polypeptide that it encodes. For example, the mutation can quantitatively or qualitatively change the biological activity. Examples of quantitative changes include increasing, reducing or eliminating the activity. Examples of qualitative changes include changing the antigen specificity of an antibody.

In another aspect, the present invention provides nucleic acid molecules that are suitable for use as primers or hybridization probes for the detection of nucleic acid sequences of the invention. A nucleic acid molecule of the invention can comprise only a portion of a nucleic acid sequence encoding a full-length polypeptide of the invention, for example, a fragment that can be used as a probe or primer or a fragment encoding an active portion (e.g., a Dkk-1 binding portion) of a polypeptide of the invention.

Probes based on the sequence of a nucleic acid of the invention can be used to detect the nucleic acid or similar nucleic acids, for example, transcripts encoding a polypeptide of the invention. The probe can comprise a label group, e.g., a radioisotope, a fluorescent compound, an enzyme, or an enzyme co-factor. Such probes can be used to identify a cell that expresses the polypeptide.

In another aspect, the present invention provides vectors comprising a nucleic acid encoding a polypeptide of the invention or a portion thereof (e.g., a fragment containing one or more CDRs or one or more variable region domains). Examples of vectors include, but are not limited to, plasmids, viral vectors, non-episomal mammalian vectors and expression vectors, for example, recombinant expression vectors. The recombinant expression vectors of the invention can comprise a nucleic acid of the invention in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see Voss et al., 1986, Trends Biochem. Sci. 11:287, Maniatis et al., 1987, Science 236:1237, incorporated by reference herein in their entireties), and those that direct inducible expression of a nucleotide sequence in response to particular treatment or condition (e.g., the metallothionin promoter in mammalian cells and the tet-responsive and/or streptomycin responsive promoter in both prokaryotic and eukaryotic systems (see id.). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

In another aspect, the present invention provides host cells into which a recombinant expression vector of the invention has been introduced. A host cell can be any prokaryotic cell (for example, *E. coli*) or eukaryotic cell (for example, yeast, insect, or mammalian cells (e.g., CHO cells)). Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

V. Preparation of Antibodies

The non-human antibodies that are provided can be, for example, derived from any antibody-producing animal, such as mouse, rat, rabbit, goat, donkey, or non-human primate (such as monkey (e.g., cynomologous or rhesus monkey) or ape (e.g., chimpanzee)). Non-human antibodies can be used, for instance, in in vitro cell culture and cell-culture based applications, or any other application where an immune response to the antibody does not occur or is insignificant, can be prevented, is not a concern, or is desired. In certain embodiments of the invention, the antibodies may be produced by immunizing with full-length Dkk-1 or with the carboxy-terminal half of Dkk-1. Alternatively, the certain non-human antibodies may be raised by immunizing with amino acids 221-236 and/or amino acids 246-262 of SEQ ID NO:2, which are segments of human Dkk-1 that form part of the epitope to which certain antibodies provided herein bind (e.g., the 11H10, see FIG. 1). The antibodies may be polyclonal, monoclonal, or may be synthesized in host cells by expressing recombinant DNA.

Fully human antibodies may be prepared as described above by immunizing transgenic animals containing human immunoglobulin loci or by selecting a phage display library that is expressing a repertoire of human antibodies.

The monoclonal antibodies (mAbs) of the invention can be produced by a variety of techniques, including conventional monoclonal antibody methodology, e.g., the standard somatic cell hybridization technique of Kohler and Milstein, 1975, *Nature* 256: 495. Alternatively, other techniques for producing monoclonal antibodies can be employed, for example, the viral or oncogenic transformation of B-lymphocytes. One suitable animal system for preparing hybridomas is the murine system, which is a very well established procedure. Immunization protocols and techniques for isolation of immunized splenocytes for fusion are known in the art. For such procedures, B cells from immunized mice are fused with a suitable immortalized fusion partner, such as a murine myeloma cell line. If desired, rats or other mammals besides can be immunized instead of mice and B cells from such animals can be fused with the murine myeloma cell line to form hybridomas. Alternatively, a myeloma cell line from a source other than mouse may be used. Fusion procedures for making hybridomas also are well known.

The single chain antibodies that are provided may be formed by linking heavy and light chain variable domain (Fv region) fragments (see, e.g., Table 2) via an amino acid bridge (short peptide linker), resulting in a single polypeptide chain. Such single-chain Fvs (scFvs) may be prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, Prot. Eng. 10:423; Kortt et al., 2001, Biomol. Eng. 18:95-108). By combining different $V_L$ and $V_H$-comprising polypeptides, one can form multimeric scFvs that bind to different epitopes (Kriangkum et al., 2001, Biomol. Eng. 18:31-40). Techniques developed for the production of single chain antibodies include those described in U.S. Pat. No. 4,946,778; Bird, 1988, Science 242:423; Huston et al., 1988, Proc. Natl. Acad. Sci. USA 85:5879; Ward et al., 1989, Nature 334:544, de Graaf et al., 2002, Methods Mol Biol. 178:379-87. Single chain antibodies derived from antibodies provided herein include, but are not limited to scFvs comprising the variable domain combinations: VL1VH1, VL1VH2, VL1VH3, VL1VH4, VL1VH5, VL1VH6, VL1VH7, VL1VH8, VL1VH9, VL1VH10, VL2VH1, VL2VH2, VL2VH3, VL2VH4, VL2VH5, VL2VH6, VL2VH7, VL2VH8, VL2VH9, VL2VH10, VL3VH1, VL3VH2, VL3VH3, VL3VH4, VL3VH5, VL3VH6, VL3VH7, VL3VH8, VL3VH9, VL3VH10.

Antibodies provided herein that are of one subclass can be changed to antibodies from a different subclass using subclass switching methods. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See, e.g., Lantto et al., 2002, Methods Mol. Biol. 178:303-16.

Accordingly, the antibodies that are provided include those comprising, for example, the following variable domain combinations: VL1VH1, VL1VH2, VL1VH3, VL1VH4, VL1VH5, VL1VH6, VL1VH7, VL1VH8, VL1VH9, VL1VH10, VL2VH1, VL2VH2, VL2VH3, VL2VH4, VL2VH5, VL2VH6, VL2VH7, VL2VH8, VL2VH9, VL2VH10, VL3VH1, VL3VH2, VL3VH3, VL3VH4, VL3VH5, VL3VH6, VL3VH7, VL3VH8, VL3VH9, VL3VH10 having a desired isotype (for example, IgA, IgG1, IgG2, IgG3, IgG4, IgM, IgE, and IgD) as well as Fab or F(ab')$_2$ fragments thereof. Moreover, if an IgG4 is desired, it may also be desired to introduce a point mutation (CPSCP->CPPCP) in the hinge region as described in Bloom et al., 1997, Protein Science 6:407, incorporated by reference herein) to alleviate a tendency to form intra-H chain disulfide bonds that can lead to heterogeneity in the IgG4 antibodies.

Moreover, techniques for deriving antibodies having different properties (i.e., varying affinities for the antigen to which they bind) are also known. One such technique, referred to as chain shuffling, involves displaying immunoglobulin variable domain gene repertoires on the surface of filamentous bacteriophage, often referred to as phage display. Chain shuffling has been used to prepare high affinity antibodies to the hapten 2-phenyloxazol-5-one, as described by Marks et al., 1992, BioTechnology, 10:779.

Conservative modifications may be made to the heavy and light chains described in Table 1 (and corresponding modifications to the encoding nucleic acids) to produce an anti-Dkk-1 antibody having functional and biochemical characteristics. Methods for achieving such modifications are described above.

Antibodies and functional fragments thereof according to the invention may be further modified in various ways. For example, if they are to be used for therapeutic purposes, they may be conjugated with polyethylene glycol (pegylated) to prolong the serum half-life or to enhance protein delivery. Alternatively, the V region of the subject antibodies or fragments thereof may be fused with the Fc region of a different antibody molecule. The Fc region used for this purpose may be modified so that it does not bind complement, thus reducing the likelihood of inducing cell lysis in the patient when the fusion protein is used as a therapeutic agent. In addition, the subject antibodies or functional fragments thereof may be conjugated with human serum albumin to enhance the serum half-life of the antibody or fragment thereof. Another useful fusion partner for the inventive antibodies or fragments thereof is transthyretin (TTR). TTR has the capacity to form a tetramer, thus an antibody-TTR fusion protein can form a multivalent antibody which may increase its binding avidity.

Alternatively, substantial modifications in the functional and/or biochemical characteristics of the antibodies and fragments described herein may be achieved by creating substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulkiness of the side chain. A "conservative amino acid substitution" may involve a substitution of a native amino acid residue with a normative residue that has little or no effect on the polarity or charge of the amino acid residue at that position. Furthermore, any native residue in the polypeptide may also be substituted with alanine, as has been previously described for alanine scanning mutagenesis.

Amino acid substitutions (whether conservative or non-conservative) of the subject antibodies can be implemented by those skilled in the art by applying routine techniques. Amino acid substitutions can be used to identify important residues of the antibodies provided herein, or to increase or decrease the affinity of these antibodies for human Dkk-1 or for modifying the binding affinity of other anti-Dkk-1 antibodies described herein.

VI. Expression of Anti-Dkk-1 Antibodies

The anti-Dkk-1 antibodies and immunological functional fragments can be prepared by any of a number of conventional techniques. For example, anti-Dkk-1 antibodies may be produced by recombinant expression systems, using any technique known in the art. See, for example, Monoclonal Antibodies, Hybridomas: A New Dimension in Biological Analyses, Kennet et al. (eds.) Plenum Press, New York (1980): and Antibodies: A Laboratory Manual, Harlow and Lane (eds.), Cold Spring Harbor Laboratory Press, Cold Spring Harbor, N.Y. (1988).

Antibodies of the present invention can be expressed in hybridoma cell lines or in cell lines other than hybridomas. Expression constructs encoding the antibodies can be used to transform a mammalian, insect or microbial host cell. Transformation can be performed using any known method for introducing polynucleotides into a host cell, including, for example packaging the polynucleotide in a virus or bacteriophage and transducing a host cell with the construct by transfection procedures known in the art, as exemplified by U.S. Pat. Nos. 4,399,216, 4,912,040, 4,740,461, and 4,959,455 (which patents are hereby incorporated herein by reference for any purpose). The optimal transformation procedure used will depend upon which type of host cell is being transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, mixing nucleic acid with positively-charged lipids, and direct microinjection of the DNA into nuclei.

Recombinant expression constructs of the invention typically comprise a nucleic acid molecule encoding a polypeptide comprising one or more of the following: a heavy chain constant region (e.g., $C_H1$, $C_H2$ and/or $C_H3$); a heavy chain variable region; a light chain constant region; a light chain variable region; one or more CDRs of the light or heavy chain of the anti-Dkk-1 antibody. These nucleic acid sequences are inserted into an appropriate expression vector using standard ligation techniques. In one embodiment, the 11H10 heavy or light chain constant region is appended to the C-terminus of the Dkk-1-specific heavy or light chain variable region and is ligated into an expression vector. The vector is typically selected to be functional in the particular host cell employed (i.e., the vector is compatible with the host cell machinery, permitting amplification and/or expression of the gene can occur). In some embodiments, vectors are used that employ protein-fragment complementation assays using protein reporters, such as dihydrofolate reductase (see, for example, U.S. Pat. No. 6,270,964, which is hereby incorporated by reference). Suitable expression vectors can be purchased, for example, from Invitrogen Life Technologies or BD Biosciences (formerly "Clontech"). Other useful vectors for cloning and expressing the antibodies and fragments of the invention include those described in Bianchi and McGrew, *Biotech Biotechnol Bioeng* 84(4):439-44 (2003), which is hereby incorporated by reference. Additional suitable expression vectors are discussed, for example, in *Methods Enzymol*, vol. 185 (D. V. Goeddel, ed.), 1990, New York: Academic Press, which is hereby incorporated by reference.

Typically, expression vectors used in any of the host cells contain sequences for plasmid or virus maintenance and for cloning and expression of exogenous nucleotide sequences. Such sequences, collectively referred to as "flanking sequences" typically include one or more of the following operatively linked nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element.

Optionally, the vector may contain a "tag"-encoding sequence, that is, an oligonucleotide molecule located at the 5' or 3' end of the coding sequence, the oligonucleotide sequence encoding polyHis (such as hexaHis), or another "tag" for which commercially available antibodies exist, such as FLAG®, HA (hemaglutinin from influenza virus), or myc. The tag is typically fused to the antibody protein upon expression, and can serve as a means for affinity purification of the antibody from the host cell. Affinity purification can be accomplished, for example, by column chromatography using antibodies against the tag as an affinity matrix. Optionally, the tag can subsequently be removed from the purified antibody polypeptide by various means such as using certain peptidases for cleavage.

Flanking sequences in the expression vector may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Where all or only a portion of the flanking sequence is known, it may be obtained using PCR and/or by screening a genomic library with a suitable oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to those skilled in the art.

An origin of replication is typically a part of prokaryotic expression vectors, particularly those purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria and various origins (e.g., SV40, polyoma, adenovirus, vesicular stomatitis virus (VSV), or papillomaviruses such as HPV or BPV) are useful for cloning vectors in mammalian cells. Generally, a mammalian origin of replication is not needed for mammalian expression vectors (for example, the SV40 origin is often used only because it contains the early promoter).

The expression and cloning vectors of the present invention will typically contain a promoter that is recognized by the host organism and operably linked to nucleic acid encoding the anti-Dkk-1 antibody or immunologically functional fragment thereof. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continuous gene product production; that is, there is little or no experimental control over gene expression. A large number of promoters, recognized by a variety of potential host cells, are well known. A suitable promoter is operably linked to the DNA encoding anti-Dkk-1 antibody by removing the promoter from the source DNA by restriction enzyme digestion or amplifying the promoter by polymerase chain reaction and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Particular promoters useful in the practice of the recombinant expression vectors of the invention include, but are not limited to: the SV40 early promoter region (Bemoist and Chambon, 1981, *Nature* 290: 304-10); the CMV promoter; the promoter contained in the 3' long terminal repeat of Rous sarcoma virus (Yamamoto, et al., 1980, *Cell* 22: 787-97); the herpes thymidine kinase promoter (Wagner et al., 1981, *Proc. Natl. Acad. Sci. U.S.A.* 78: 1444-45); the regulatory sequences of the metallothionine gene (Brinster et al., 1982, *Nature* 296: 39-42); prokaryotic expression vectors such as the beta-lactamase promoter (Villa-Kamaroff et al., 1978, *Proc. Natl. Acad. Sci. U.S.A.*, 75: 3727-31); or the tac promoter (DeBoer et al., 1983, *Proc. Natl. Acad. Sci. U.S.A.* 80: 21-25). Also available for use are the following animal transcriptional control regions, which exhibit tissue specificity and have been utilized in transgenic animals: the elastase I gene control region that is active in pancreatic acinar cells (Swift et al., 1984, *Cell* 38: 639-46; Ornitz et al., 1986, *Cold Spring Harbor Symp. Quant. Biol.* 50: 399-409; MacDonald, 1987, *Hepatology* 7: 425-515); the insulin gene control region that is active in pancreatic beta cells (Hanahan, 1985, *Nature* 315: 115-22); the mouse mammary tumor virus control region that is active in testicular, breast, lymphoid and mast cells (Leder et al., 1986, *Cell* 45: 485-95); the albumin gene control region that is active in liver (Pinkert et al., 1987, *Genes and Devel.* 1: 268-76); the alpha-feto-protein gene control region that is active in liver (Krumlauf et al., 1985, *Mol. Cell. Biol.* 5: 1639-48; Hammer et al., 1987, *Science* 235: 53-58); the alpha 1-antitrypsin gene control region that is active in the liver (Kelsey et al., 1987, *Genes and Devel.* 1: 161-71); the beta-globin gene control region that is active in myeloid cells (Mogram et al., 1985, *Nature* 315: 338-40; Kollias et al., 1986, *Cell* 46: 89-94); the myelin basic protein gene control region that is active in oligodendrocyte cells in the brain (Readhead et al., 1987, *Cell* 48: 703-12); the myosin light chain-2 gene control region that is active in skeletal muscle (Sani, 1985, *Nature* 314: 283-86); the gonadotropic releasing hormone gene control region that is active in the hypothalamus (Mason et al., 1986, *Science* 234: 1372-78); and most particularly the immunoglobulin gene control region that is active in lymphoid cells (Grosschedl et al., 1984, *Cell* 38: 647-58; Adames et al., 1985, *Nature* 318: 533-38; Alexander et al., 1987, *Mol. Cell Biol.* 7: 1436-44).

An enhancer sequence may be inserted into the vector to increase the transcription in higher eukaryotes of a nucleic acid encoding an anti-Dkk-1 antibody or immunologically functional fragment thereof of the present invention. Enhancers are cis-acting elements of DNA, usually about 10-300 bp in length, that act on promoters to increase transcription. Enhancers are relatively orientation and position independent. They have been found 5' and 3' to the transcription unit. Several enhancer sequences available from mammalian genes are known (e.g., globin, elastase, albumin, alpha-fetoprotein and insulin). An enhancer sequence from a virus also can be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to a nucleic acid molecule, it is typically placed at a site 5' to the promoter.

In expression vectors, a transcription termination sequence is typically located 3' of the end of a polypeptide-coding region and serves to terminate transcription. A transcription termination sequence used for expression in prokaryotic cells typically is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes used in expression vectors encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex media. Examples of selectable markers include the kanamycin resistance gene, the ampicillin resistance gene and the tetracycline resistance gene. A bacterial neomycin resistance gene can also be used for selection in both prokaryotic and eukaryotic host cells.

Other selection genes can be used to amplify the gene that will be expressed. Amplification is a process whereby genes that cannot in single copy be expressed at high enough levels to permit survival and growth of cells under certain selection conditions are reiterated in tandem within the chromosomes of successive generations of recombinant cells. Examples of suitable amplifiable selectable markers for mammalian cells include dihydrofolate reductase (DHFR) and promoterless thymidine kinase. In the use of these markers mammalian cell transformants are placed under selection pressure wherein only the transformants are uniquely adapted to survive by virtue of the selection gene present in the vector. Selection pressure is imposed by culturing the transformed cells under conditions in which the concentration of selection agent in the medium is successively increased, thereby permitting survival of only those cells in which the selection gene has been amplified. Under these circumstances, DNA adjacent to the selection gene, such as DNA encoding an antibody of the invention, is co-amplified with the selection gene. As a result, increased quantities of anti-Dkk-1 polypeptide are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, for example where glycosylation is desired in a eukaryotic host cell expression system, various presequences can be manipulated to improve glycosylation or yield. For example, the peptidase cleavage site of a particular signal peptide can be altered, or pro-sequences added, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated yet active form of the desired polypeptide, if the enzyme cuts at such area within the mature polypeptide.

Where a commercially available expression vector lacks some of the desired flanking sequences as described above, the vector can be modified by individually ligating these sequences into the vector. After the vector has been chosen and modified as desired, a nucleic acid molecule encoding an anti-Dkk-1 antibody or immunologically functional fragment thereof is inserted into the proper site of the vector.

The completed vector containing sequences encoding the inventive antibody or immunologically functional fragment thereof is inserted into a suitable host cell for amplification and/or polypeptide expression. The transformation of an expression vector for an anti-Dkk-1 antibody immunologically functional fragment thereof into a selected host cell may be accomplished by well-known methods including methods such as transfection, infection, calcium chloride, electroporation, microinjection, lipofection, DEAE-dextran method, or other known techniques. The method selected will in part be a function of the type of host cell to be used. These methods and other suitable methods are well known to the skilled artisan.

The transformed host cell, when cultured under appropriate conditions, synthesizes an anti-Dkk-1 antibody or functional fragment thereof that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, many immortalized cell lines available from the American Type Culture Collection (ATCC), such as Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, the best cell line for expressing a particular DNA construct may be selected by testing various cell lines to determine which ones have the highest levels of expression levels and produce antibodies with constitutive Dkk-1 binding properties.

VII. Pharmaceutical Compositions

A. Exemplary Formulations

In certain embodiments, the invention also provides compositions comprising the subject anti-Dkk-1 antibodies or immunologically functional fragments thereof together with one or more of the following: a pharmaceutically acceptable diluent; a carrier; a solubilizer; an emulsifier; a preservative; and/or an adjuvant. Such compositions may contain an effective amount of the anti-Dkk-1 antibody or immunologically functional fragment thereof. Thus, the use of the antibodies and immunologically active fragments that are provided herein in the preparation of a pharmaceutical composition or medicament is also included. Such compositions can be used in the treatment of a variety of diseases such as listed below in the section on exemplary utilities.

Acceptable formulation components for pharmaceutical preparations are nontoxic to recipients at the dosages and concentrations employed. In addition to the antibodies and immunologically functional fragments that are provided, compositions according to the invention may contain components for modifying, maintaining or preserving, for example, the pH, osmolarity, viscosity, clarity, color, isotonicity, odor, sterility, stability, rate of dissolution or release, adsorption or penetration of the composition. Suitable materials for formulating pharmaceutical compositions include, but are not limited to, amino acids (such as glycine, glutamine, asparagine, arginine or lysine); antimicrobials; antioxidants (such as ascorbic acid, sodium sulfite or sodium hydrogen-sulfite); buffers (such as acetate, borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (see *Remington's Pharmaceutical Sciences*, 18$^{th}$ Edition, (A. R. Gennaro, ed.), 1990, Mack Publishing Company), hereby incorporated by reference.

The primary vehicle or carrier in a pharmaceutical composition may be either aqueous or non-aqueous in nature. Suitable vehicles or carriers for such compositions include water for injection, physiological saline solution or artificial cerebrospinal fluid, possibly supplemented with other materials common in compositions for parenteral administration. Neutral buffered saline or saline mixed with serum albumin are further exemplary vehicles. Compositions comprising anti-Dkk-1 antibodies or immunologically functional fragments thereof may be prepared for storage by mixing the selected composition having the desired degree of purity with optional formulation agents in the form of a lyophilized cake or an aqueous solution. Further, the anti-Dkk-1 antibodies or immunologically functional fragments thereof may be formulated as a lyophilizate using appropriate excipients such as sucrose.

Formulation components are present in concentrations that are acceptable to the site of administration. Buffers are advantageously used to maintain the composition at physiological pH or at a slightly lower pH, typically within a pH range of from about 4.0 to about 8.5, or alternatively, between about 5.0 to 8.0. Pharmaceutical compositions can comprise TRIS buffer of about pH 6.5-8.5, or acetate buffer of about pH 4.0-5.5, which may further include sorbitol or a suitable substitute therefor.

A pharmaceutical composition may involve an effective quantity of anti-Dkk-1 antibodies or immunologically functional fragments thereof in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert materials, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions are in the form of sustained- or controlled-delivery formulations. Techniques for formulating a variety of other sustained- or controlled-delivery means, such as liposome carriers, bio-erodible microparticles or porous beads and depot injections can be used (see, for e.g., PCT/US93/00829, which describes the controlled release of porous polymeric microparticles for the delivery of pharmaceutical compositions). Sustained-release preparations may include semipermeable polymer matrices in the form of shaped articles, e.g. films, or microcapsules, polyesters, hydrogels, polylactides (U.S. Pat. No. 3,773,919 and EP 058,481), copolymers of L-glutamic acid and gamma ethyl-L-glutamate (Sidman et al., 1983, *Biopolymers* 22: 547-556), poly (2-hydroxyethyl-methacrylate) (Langer et al., 1981, *J Biomed Mater Res* 15: 167-277) and Langer, 1982, *Chem Tech* 12: 98-105), ethylene vinyl acetate (Langer et al., ibid.) or poly-D(−)-3-hydroxybutyric acid (EP 133,988). Sustained release compositions may also include liposomes, which can be prepared by any of several methods known in the art. See e.g., Eppstein et al., 1985, *Proc. Natl. Acad. Sci. USA* 82: 3688-3692; EP 036,676; EP 088,046 and EP 143,949.

The pharmaceutical composition to be used for in vivo administration typically is sterile. Sterilization may be accomplished by filtration through sterile filtration membranes. If the composition is lyophilized, sterilization may be conducted either prior to or following lyophilization and reconstitution. The composition for parenteral administration may be stored in lyophilized form or in a solution. In certain embodiments, parenteral compositions are placed into a container having a sterile access port, for example, an intravenous solution bag or vial having a stopper pierceable by a hypodermic injection needle, or a sterile pre-filled syringe ready to use for injection.

Once the pharmaceutical composition of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The present invention provides kits for producing a multi-dose or single-dose administration units. For example, kits according to the invention may each contain both a first container having a dried protein and a second container having an aqueous diluent, including for example single and multi-chambered pre-filled syringes (e.g., liquid syringes, lyosyringes or needle-free syringes).

The pharmaceutical compositions of the invention can be delivered parenterally, typically by injection. Injections can be intraocular, intraperitoneal, intraportal, intramuscular, intravenous, intrathecal, intracerebral (intra-parenchymal), intracerebroventricular, intraarterial, intralesional, perilesional or subcutaneous. Eye drops can be used for intraocular administration. In some instances, injections may be localized to the vicinity of a particular bone or bones to which the treatment is targeted. For parenteral administration, the antibodies may be administered in a pyrogen-free, parenterally acceptable aqueous solution comprising the desired anti-Dkk-1 antibodies or immunologically functional fragments thereof in a pharmaceutically acceptable vehicle. A particularly suitable vehicle for parenteral injection is sterile distilled water in which the anti-Dkk-1 antibodies or immunologically functional fragments thereof are formulated as a sterile, isotonic solution, properly preserved.

Pharmaceutical compositions comprising the subject anti-Dkk-1 antibodies and functional fragments thereof may be administered by bolus injection or continuously by infusion, by implantation device, sustained release systems or other means for accomplishing prolonged release. The pharmaceutical composition also can be administered locally via implantation of a membrane, sponge or another appropriate material onto which the desired molecule has been absorbed or encapsulated. Where an implantation device is used, the device may be implanted into any suitable tissue or organ, and delivery of the desired molecule may be via diffusion, timed-release bolus, or continuous release. The preparation may be formulated with agent, such as injectable microspheres, bio-erodible particles, polymeric compounds (such as polylactic acid; polyglycolic acid; or copoly (lactic/glycolic) acid (PLGA), beads or liposomes, that can provide controlled or sustained release of the product which may then be delivered via a depot injection. Formulation with hyaluronic acid has the effect of promoting sustained duration in the circulation.

The subject compositions comprising an anti-Dkk-1 antibody or functional fragment thereof may be formulated for inhalation. In these embodiments, an anti-Dkk-1 antibody is formulated as a dry powder for inhalation, or anti-Dkk-1 antibody inhalation solutions may also be formulated with a propellant for aerosol delivery, such as by nebulization. Pulmonary administration is further described in PCT/US94/001875, which describes pulmonary delivery of chemically modified proteins, and which is hereby incorporated by reference.

Certain pharmaceutical compositions of the invention can be delivered through the digestive tract, such as orally. The subject anti-Dkk-1 antibodies or immunologically functional fragments thereof that are administered in this fashion may be formulated with or without those carriers customarily used in the compounding of solid dosage forms such as tablets and capsules. A capsule may be designed to release the active portion of the formulation at the point in the gastrointestinal tract when bioavailability is maximized and pre-systemic degradation is minimized. Additional agents can be included to facilitate absorption of the anti-Dkk-1 antibody or functional fragment thereof. For oral administration, modified amino acids may be used to confer resistance to digestive enzymes. Diluents, flavorings, low melting point waxes, vegetable oils, lubricants, suspending agents, tablet disintegrating agents, and binders may also be employed.

The subject compositions comprising anti-Dkk-1 antibodies or immunologically functional fragments thereof also may be used ex vivo. In such instances, cells, tissues or organs that have been removed from the patient are exposed to or cultured with the anti-Dkk-1 antibody. The cultured cells may then be implanted back into the patient or a different patient or used for other purposes.

In certain embodiments, anti-Dkk-1 antibodies or immunologically functional fragments thereof can be delivered by implanting certain cells that have been genetically engineered, using methods such as those described herein, to express and secrete the polypeptide. Such cells may be animal or human cells, and may be autologous, heterologous, or xenogenic, or may be immortalized. In order to decrease the chance of an immunological response, the cells may be encapsulated to avoid infiltration of surrounding tissues. Encapsulation materials are typically biocompatible, semi-permeable polymeric enclosures or membranes that allow the release of the protein product(s) but prevent the destruction of the cells by the patient's immune system or by other detrimental factors from the surrounding tissues.

B. Dosage

The pharmaceutical compositions that are provided can be administered for prophylactic and/or therapeutic treatments. An "effective amount" refers generally to an amount that is a sufficient, but non-toxic, amount of the active ingredient (i.e., an anti-Dkk-1 antibody or immunologically functional fragment thereof) to achieve the desired effect, which is a reduction or elimination in the severity and/or frequency of symptoms and/or improvement or remediation of damage. A "therapeutically effective amount" refers to an amount that is sufficient to remedy a disease state or symptoms, or otherwise prevent, hinder, retard or reverse the progression of a disease or any other undesirable symptom. A "prophylactically effective amount" refers to an amount that is effective to prevent, hinder or retard the onset of a disease state or symptom.

In general, toxicity and therapeutic efficacy of the antibody or fragment can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with little or no toxicity. The dosage can vary within this range depending upon the dosage form employed and the route of administration utilized.

The effective amount of a pharmaceutical composition comprising anti-Dkk-1 antibodies or immunologically functional fragments thereof to be employed therapeutically or prophylactically will depend, for example, upon the therapeutic context and objectives. One skilled in the art will appreciate that the appropriate dosage levels for treatment, according to certain embodiments, will thus vary depending, in part, upon the molecule delivered, the indication for which the anti-Dkk-1 antibody is being used, the route of administration, and the size (body weight, body surface or organ size) and/or condition (the age and general health) of the patient. A clinician may titer the dosage and modify the route of administration to obtain the optimal therapeutic effect. Typical dosages range from about 0.1 µg/kg up to about 100 mg/kg or more, depending on the factors mentioned above. In certain embodiments, the dosage may range from 0.1 µg/kg up to about 150 mg/kg; or 1 µg/kg up to about 100 mg/kg; or 5 µg/kg up to about 50 mg/kg.

The dosing frequency will depend upon the pharmacokinetic parameters of the anti-Dkk-1 antibody or immunologically functional fragment thereof in the formulation. For example, a clinician will administer the composition until a dosage is reached that achieves the desired effect. The composition may therefore be administered as a single dose, or as two or more doses (which may or may not contain the same amount of the desired molecule) over time, or as a continuous infusion via an implantation device or catheter. Treatment may be continuous over time or intermittent. Further refinement of the appropriate dosage is routinely made by those of ordinary skill in the art and is within the ambit of tasks routinely performed by them. Appropriate dosages may be ascertained through use of appropriate dose-response data.

To treat a medical disorder characterized by abnormal or excess expression of Dkk-1, a composition comprising the subject anti-Dkk-1 antibodies or immunologically functional fragments thereof may be administered to the patient in an amount and for a time sufficient to induce a sustained improvement in at least one indicator that reflects the severity of the disorder. An improvement is considered "sustained" if the patient exhibits the improvement on at least two occasions separated by at least one to seven days, or in some instances one to six weeks. The appropriate interval will depend to some extent on what disease condition is being treated; it is within the purview of the skilled physician to determine the appropriate interval for determining whether the improvement is sustained. The degree of improvement is determined based on signs or symptoms, and may also employ questionnaires that are administered to the patient, such as quality-of-life questionnaires.

Various indicators that reflect the extent of the patient's illness may be assessed for determining whether the amount and time of the treatment is sufficient. The baseline value for the chosen indicator or indicators is established by examination of the patient prior to administration of the first dose of antibody. Preferably, the baseline examination is done within about 60 days of administering the first dose. If the antibody is being administered to treat acute symptoms, such as for example to treat a broken bone, the first dose is administered as soon as practically possible after the injury has occurred.

Improvement is induced by administering the subject anti-Dkk-1 antibodies or immunologically functional fragments thereof until the patient manifests an improvement over baseline for the chosen indicator or indicators. In treating chronic conditions, this degree of improvement is obtained by repeatedly administering this medicament over a period of at least a month or more, e.g., for one, two, or three months or longer, or indefinitely. A period of one to six weeks, or even a single dose, often is sufficient for treating acute conditions. For injuries or acute conditions, a single dose may be sufficient.

Although the extent of the patient's illness after treatment may appear improved according to one or more indicators, treatment may be continued indefinitely at the same level or at a reduced dose or frequency. Once treatment has been reduced or discontinued, it later may be resumed at the original level if symptoms should reappear.

VIII. Exemplary Utilities for Anti-Dkk-1 Antibodies

A. Detection and Screening

The subject anti-Dkk-1 antibodies and immunologically functional fragments thereof can be used to detect Dkk-1 in biological samples. Such uses allow the identification of cells or tissues that produce the protein or serve as a diagnostic for detecting pathological conditions in which Dkk-1 is overproduced or underproduced.

The antibodies and fragments that are provided can also be used in methods to screen for a molecule that binds to Dkk-1.

A variety of competitive screening methods, for example, can be used. In some methods, a Dkk-1 molecule or fragment thereof to which an anti-Dkk-1 antibody binds, is contacted with an antibody or fragment disclosed herein together with another molecule (i.e., a candidate molecule). A reduction in binding between the antibody or fragment and Dkk-1 is an indication that the molecule binds Dkk-1. Binding of the antibody or fragment can be detected using a variety of methods, e.g., an ELISA. Detection of binding between the anti-Dkk-1 antibody or fragment to Dkk-1 can be simplified by detectably labeling the antibody. In some methods, a molecule that exhibits binding in the initial screen is further analyzed to determine whether it inhibits a Dkk-1 activity (e.g., whether the molecule activates Wnt signaling).

B. Treatment of Bone Related Disorders

In other aspects, certain of the antibodies and immunologically functional fragments that are provided can be used to treat patients with a variety of different diseases including, for example, diseases that are responsive to the inhibition of Dkk-1 activity. These antibodies and fragments can also be used to treat diseases that are responsive to the induction of Wnt signaling. The term "patient" as used herein includes human and animal subjects unless stated otherwise. Examples of such diseases include, but are not limited to, a variety of diseases involving a bone disorder including low bone mass conditions, systemic bone loss, suppressed bone formation and bone erosions. Some of the antibodies and fragments can also be used in bone repair.

Certain of the antibodies or fragments have therapeutic use in stimulating osteoblast activity and increasing bone mineral density or bone mass. These antibodies and fragments are thus useful for treating patients suffering from various medical disorders that involve excessive bone loss or patients who require the formation of new bone even where there may not necessarily be excessive osteoclast activity. Blocking Dkk-1 activity results in osteoblast activation via signaling transmitted by Wnt proteins. Excessive osteoclast activity is associated with numerous osteopenic disorders that can be treated with the antibodies and immunologically functional fragments that are provided, including ostopenia, osteoporosis, periodontitis, Paget's disease, bone loss due to immobilization, lytic bone metastases and arthritis, including rheumatoid arthritis, psoriatic arthritis, ankylosing spondylitis and other conditions that involve bone erosion.

Various other low bone mass conditions can also be treated including a variety of forms of osteoporosis, including but not limited to, glucocorticoid induced osteoporosis, osteoporosis induced after transplantation, osteoporosis associated with chemotherapy (i.e., chemotherapy induced osteoporosis), immobilization induced osteoporosis, osteoporosis due to mechanical unloading, and osteoporosis associated with anticonvulsant use. Additional bone diseases that can be treated with some of the antibodies or fragments include bone disease associated with renal failure and nutritional, gastrointestinal and/or hepatic associated bone diseases.

Different forms of arthritis can also be treated, examples including osteoarthritis and rheumatoid arthritis. The antibodies and fragments can also be used to treat systemic bone loss associated with arthritis (e.g., rheumatoid arthritis). In treating arthritis, patients may benefit by perilesional or intralesional injections of the subject antibodies or fragments thereof. For example, the antibody or fragment thereof can be injected adjacent to or directly into an inflamed joint, thus stimulating repair of damaged bone at the site.

Some cancers are known to increase osteoclast activity and induce bone resorption, such as breast and prostate cancer. Multiple myeloma, which arises in bone marrow, also is associated with bone loss, in part likely due to the increased expression of Dkk-1 by plasma cells, which then suppresses the bone building activity of osteoblasts in the vicinity. Reducing Dkk-1 activity by administering the subject antibodies or immunologically functional fragments thereof can result in an increase in osteoblast activity that serves to counteract the excessive osteoclast activity, thereby reducing the severity of the aforementioned disorders, reducing bone erosion and inducing new bone formation in the patient. Treatment with certain of the anti-Dkk-1-specific antibodies or immunologically functional fragments can induce a significant increase in bone mineral density in a patient suffering from an osteopenic disorder.

Inhibiting Dkk-1 with the antibodies or immunologically functional fragments described herein can also be used in various bone repair applications. For example, certain antibodies and fragments can be useful in retarding wear debris osteolysis associated with artificial joints, accelerating the repair of bone fractures, and enhancing the incorporation of bone grafts into the surrounding living bone into which they have been engrafted.

Anti-Dkk-1 antibodies or immunologically functional fragments thereof can be administered alone or in combination with other therapeutic agents, for example, in combination with cancer therapy agents, with agents that inhibit osteoclast activity or with other agents that enhance osteoblast activity. For example, the inventive antibodies can be administered to cancer patients undergoing radiation therapy or chemotherapy. Chemotherapies used in combination with the inventive antibodies may include anthracyclines, taxol, tamoxifene, doxorubicin, 5-fluorouracil, oxaloplatin, Velcade® ([(1R)-3-methyl-1-[[(2S)-1-oxo-3-phenyl-2-[(pyrazinylcarbonyl)amino]propyl]amino]butyl]boronic acid) and/or other small molecule drugs that are used in treating cancer. Breast cancer patients will benefit from the administration of an aromatase inhibitor concurrently with combination treatments comprising a chemotherapeutic agent and an anti-Dkk-1 antibody or immunologically functional fragment thereof.

Anti-Dkk-1 antibodies and immunologically functional fragments thereof may be used alone for the treatment of the above referenced conditions resulting in loss of bone mass or in combination with a therapeutically effective amount of a bone growth promoting (anabolic) agent or a bone anti-resorptive agent including but not limited to: bone morphogenic factors designated BMP-1 to BMP-12; transforming growth factor-β and TGF-β family members; fibroblast growth factors FGF-1 to FGF-10; interleukin-1 inhibitors (including IL-1ra, antibodies to IL-1 and antibodies to IL-1 receptors); TNFα inhibitors (including etanercept, adalibumab and infliximab); RANK ligand inhibitors (including soluble RANK, osteoprotegerin and antagonistic antibodies that specifically bind RANK or RANK ligand), parathyroid hormone, E series prostaglandins, bisphosphonates and bone-enhancing minerals such as fluoride and calcium. Anabolic agents that can be used in combination with the inventive antibodies and functional fragments thereof include parathyroid hormone and insulin-like growth factor (IGF), wherein the latter agent is preferably complexed with an IGF binding protein. An IL-1 receptor antagonist suitable for such combination treatment is described in WO89/11540 and a suitable soluble TNF receptor-1 is described in WO98/01555. Exemplary RANK ligand antagonists are disclosed, for example, in WO 03/086289, WO 03/002713, U.S. Pat. Nos. 6,740,511 and 6,479,635. All of the aforementioned patents and patent applications are hereby incorporated by reference).

In addition, anti-Dkk-1 antibodies can be administered to patients in combination with antibodies that bind to tumor cells and induce a cytotoxic and/or cytostatic effect on tumor growth. Examples of such antibodies include those that bind to cell surface proteins Her2, CDC20, CDC33, mucin-like glycoprotein and epidermal growth factor receptor (EGFR) present on tumor cells and induce a cytostatic and/or cytotoxic effect on tumor cells displaying these proteins. Examples of such antibodies include HERCEPTIN® for treatment of breast cancer and RITUXAN® for the treatment of non-Hodgkin's lymphoma, and include also antibody-based drugs such as ERBITUX® and AVASTIN®. Also, combination therapy can include as cancer therapy agents polypeptides that selectively induce apoptosis in tumor cells, such as the TNF-related polypeptide TRAIL.

The subject antibodies or immunologically functional fragments thereof can be administered concurrently with other treatments and therapeutic agents being administered for the same condition. "Concurrent administration," as used herein, encompasses treatments that are administered simultaneously or sequentially. Anti-Dkk-1 antibodies or immunologically functional fragments thereof can be administered prophylactically to prevent or mitigate the onset of loss of bone mass by early stage cancer (stages I or II), or can be given to ameliorate an existing condition of loss of bone mass due to metastasis to the bone.

Anti-Dkk-1 antibodies of the invention may be used to prevent and/or treat the growth of tumor cells in bone. Cancer that metastasizes to bone can spread readily as tumor cells stimulate osteoclasts to resorb the internal bone matrix. Treatment with an anti-Dkk-1 antibody or immunologically functional fragment thereof will help maintain bone mineral density at the site of such metastases by stimulating increased osteoblast activity. Any cancer that has potential to metastasize to bone may be prevented or treated with an anti-Dkk-1 antibody administered before or after metastasis has occurred.

Multiple myeloma is an example of a type of cancer that may be prevented and/or treated with an anti-Dkk-1 antibody or antigen binding fragment thereof. Affected patients typically exhibit a loss of bone mass due to increased osteoclast activation in localized regions of the bone. Myeloma cells either directly or indirectly produce RANK ligand, a protein that activates osteoclasts resulting in lysis of the bone surrounding the myeloma cells embedded in bone marrow spaces. The normal osteoclasts adjacent to the myeloma cell in turn produce IL-6, leading to growth and proliferation of myeloma cells. In addition multiple myeloma cells produce Dkk-1 thereby inhibiting osteoblast activity and further promoting bone resorptive activity in this disease. Treatment of an animal with an anti-Dkk-1 antibody or immunologically functional fragment thereof will instigate osteoblast activity, thereby resulting in increased bone mass at the site of the tumors. Such treatment may result in reduction of bone pain, and may block further metastisis to bone by preventing the resorptive activity that releases bone nutrients utilized by the tumor cells. In treating this disease, the anti-Dkk-1 antibody or immunologically functional fragment thereof can be administered concurrently with antagonistic antibodies directed against RANK ligand or antibodies against IL-6.

C. Treatment of Other Disorders

In addition to the foregoing uses related to bone disorders, certain of the antibodies and immunologically functional fragments that are provided can be used to treat other diseases. The role of Dkk-1 in these various diseases is supported in part by its expression in various different tissues. The antibodies and fragments, for example, can be used to treat diseases in which it is desirable to promote stem cell renewal. Such diseases include, but are not limited to, diabetes, chronic heart failure and various diseases of the muscle [e.g., disuse atrophy resulting, for instance, from immobilization or bed-rest); aging frailty (sarcopenia of the elderly); muscular dystrophies; cachexia associated with cancer, AIDS or inflammation; protein-energy malnutrition in renal failure/uremia, and muscle wasting in obesity]. Various inflammatory diseases can also be treated, including, for instance, Crohn's disease, colitis, and inflammatory bowel disease. The antibodies and fragments can also be used in the treatment of various neurological diseases (e.g., Alzheimer's disease, Parkinson's disease, and Huntington's disease). Ocular diseases (e.g., macular degeneration and various retinopathies) can also be treated with certain of the antibodies and fragments. Different renal diseases (e.g., end stage renal disease, chronic renal disease, glomerulonephritis, tubulointerstitial nephritis and IgA nephropathy) can also be treated with some antibodies. Additionally, various pulmonary diseases (e.g., chronic obstructive pulmonary disease, idiopathic pulmonary fibrosis and cystic fibrosis) and various skin disorders, including dermal and epidermal diseases, can also be treated. Examples of skin disorders that can be treated include damaged intestinal epithelium (e.g., chemotherapy induced damage), and other diseases in which it is desirable to stimulate growth and survival of the intestinal epithelium.

IX. Kits

Kits that include an antibody or immunologically functional fragment or a pharmaceutical composition as described herein are also provided. Some kits include such an antibody, fragment or composition in a container (e.g., vial or ampule), and may also include instructions for use of the antibody or fragment in the various detection, screening and therapeutic applications disclosed above. The antibody, fragment or composition can be in various forms, including, for instance, as part of a solution or as a solid (e.g., lyophilized powder). The instructions may include a description of how to prepare (e.g., dissolve or resuspend) the antibody or fragment in an appropriate fluid and/or how to administer the antibody or fragment for the treatment of the diseases described above (e.g., bone disorders such as low bone mass, systemic bone loss, suppressed bone formation and bone erosions; stem cell renewal; inflammatory diseases; neurological diseases; ocular diseases; renal diseases and skin disorders).

The kits may also include various other components, such as buffers, salts, complexing metal ions and other agents described above in the section on pharmaceutical compositions. These components may be included with the antibody or fragment or may be in separate containers. The kits may also include other therapeutic agents for administration with the antibody or fragment. Examples of such agents include, but are not limited to, agents to treat cancers, bone promoting agents and antibodies that bind tumor cells, and other agents listed above.

The following examples are provided solely to illustrate certain aspects of the antibodies, fragments and compositions that are provided herein and thus should not be construed to limit the scope of the claimed invention.

EXAMPLE 1

Generation of Monoclonal Antibodies to Murine Dkk-1 in Mice and Rats

A. Immunization

Recombinant murine Dkk-1 that was used as antigen was cloned from a mouse placenta cDNA library using publicly available sequences (GenBank Accession #AF030433.1). The cloning of human Dkk-1, which was used to test cross-reactivity of anti-mouse Dkk-1 antibodies, was as described in U.S. Pat. No. 6,344,541. To prepare mouse Dkk-1 for use as an antigen, 850 cm$^2$ roller bottles were seeded with 4–5×10$^7$ adherent 293T cells (human embryonic kidney cells, obtained from Cellular and Molecular Technologies) overnight in DMEM with 5% FBS, 1× non-essential amino acids, 1× pen/strep/glut and 1× sodium pyruvate (complete DMEM, GIBCO, Grand Island N.Y.).

Cells were transfected the following day. 675 µl of FuGene6 transfection reagent were diluted into 6.75 ml of serum-free DMEM (Roche Diagnostics) and 112.5 µg of pcDNA3.1 DNA (this plasmid expresses mouse Dkk-1 conjugated to FLAG). After incubation at room temperature for 30 minutes, the DNA mixture was added to each roller bottle (about 30 bottles in all) and incubated in a 5% CO$_2$ incubator. After 24 hours, 100 ml of serum-free DMEM containing 1× non-essential amino acids, 1× pen/strep/glut, 1× sodium pyruvate, 1× insulin-transferrin-selenium supplement (Invitrogen) and 0.5% DMSO were added to each bottle. The medium was harvested and replaced with fresh medium every 48 hours for 14 days. Mouse Dkk-1 was purified from the pooled clarified culture medium.

Mice and rats were immunized as described below by injection with full-length recombinant murine Dkk-1. In some experiments, mice (but not rats) were injected with recombinant muDkk-1 that had been conjugated prior to injection to a PADRE peptide (Epimmune). The conjugation was performed by reacting murine Dkk-1 with a 25-fold molar excess of N-succinimidyl 6-maleimideocaproate (MICA) (Fluka #63177) at room temperature for 3 hours. The maleimide-activated murine Dkk-1 was separated from the untreated MICA by a 8 mm×125 mm column filled with Sephadex G-25. One mg of the maleimide-activated murine Dkk-1 was incubated with 0.5 mg of PADRE peptide (AK-FVAAWTLKAAAC; SEQ ID NO:13) and 0.5 mg of a second PADRE peptide (CAKXVAAWTLKAAA (X=cyclohexyl-alanine); SEQ ID NO:14) at room temperature for 1 hour and then dialyzed against PBS.

Balb/c mice and C57BL/6 mice (Jackson Laboratories) as well as transgenic AGP3 mice (Khare et al., *PNAS* 97: 3370-3375, 2000) were immunized targeting the peripheral draining lymph nodes or the spleen as described below. Lewis rats were immunized only by targeting the spleen.

To target the lymph nodes, injections were given 5 times at 12 spots subcutaneously (6 dorsal, 6 ventral) over 10-13 days using a 1:1 ratio of Dkk-1:adjuvant. The adjuvant used was either complete/incomplete Freund's Adjuvant mixture (Pierce) or RIBI (Corixa). One to three days after the last injection, the peripheral lymph nodes from each injected mouse were harvested and fused to murine SP2/0.Ag14 myeloma cells (ATCC No. CRL 1581) using dielectrophoretic cell fusion, as described below. For injected rats, lymph nodes were removed 13 days after the last antigen injection and the lymphocytes were fused to Y3 Ag 1.2.3 fusion partner cells (ATCC No. CRL 1631), which are derived from rat.

To target the spleen, mice were injected subcutaneously at 2-4 sites using a 1:1 ratio of either muDkk-1:complete Freund's adjuvant or muDkk-1-PADRE:complete Freud's adjuvant. A second immunization was given 2 weeks later using a 1:1 ratio of muDkk:RIBI adjuvant or muDkk-PADRE:RIBI adjuvant at 2 sites subcutaneous and 1 site intraperitoneal. Blood samples were taken 10 days later to be analyzed for anti-mDkk-1 antibody response. The best responders were boosted by intraperitoneal injection with mDkk-1 in PBS. Five days later, the spleens were removed for the preparation of lymphocytes to be fused to murine SP2/0.Ag14 myeloma cells.

B. Lymphocyte Fusion Protocol

Isolated lymphocytes from the lymph nodes or spleens of immunized animals were fused with murine SP2/0.Ag14 or Y3 Ag 1.2.3 rat cells using the following optimized protocol.

Single cell suspensions were prepared from spleen cells or peripheral lymph node (PLN) cells, and filtered through a 100 µm cell strainer into a 50 ml tube, using 30-40 ml serum-free medium. The tubes were centrifuged at 2000 rpm for 5 minutes to collect the cells. To lyse red blood cells (when present), cells were resuspended in 10 ml RBC lysis buffer (8.3 g/L ammonium chloride in 0.01 M TRIS/HCl, pH 7.2), and additional lysis buffer added to a total of 30 mls. Cells were allowed to stand for 2-5 minutes, then were centrifuged at 2000 rpm for 5 minutes. The lysis procedure was repeated if a red color persisted in the pellet. After the lysis step, cells were resuspended in a SF medium, an aliquot removed for counting, then the cells were washed in a total of 50 ml SF medium.

Prior to being used for fusion, these cells were subjected to two rounds of the following "selection" procedure. This selection was performed for the purpose of selecting cells that were resistant to these manipulations and was repeated twice as follows. Selection consisted of subjecting the cells to several steps of the fusion protocol, namely, centrifugation, incubation in ECF fusion buffer (Cytopulse Sciences Cytofusion Medium C, catalogue no. CPS-LCM) and exposure to the current alignment phase of the fusion process. SP2/0.AG 14 myeloma cells that had undergone this selection were designated "SP2/0-ECF-F" cells and the Y3.AG 1.2.3 cells that underwent selection were designated "Y3-ECF-F" cells.

A B cell enrichment step was performed only for mice, except that it was not done when using AGP3 mice. In brief, this step consisted of suspending 10$^7$ spleen or lymph node cells in SF, adding 10 µl of CD 90$^+$ magnetic beads (Miltenyi Biotec Cat# 130-049-101) that had been pre-washed with SF medium, mixing gently and incubating at 4-12° C. for 15 minutes. Next, cells were diluted 1:3 with medium and filtered through a 40 µm strainer. Up to 2×10$^8$ total cells (10$^8$ positive cells) were loaded onto an LS+ Column (Miltenyi Biotec Cat# 130-042-401) and the effluent collected as the CD 90$^-$ fraction.

Prior to performing the fusion, fusion chambers were sterilized with 70% ethanol, then air-dried in a sterile hood. If B cell enrichment was performed, myeloma and CD 90$^-$ cells were combined 1:1 and mixed well in a 50 ml tube. When no B cell enrichment was done, myeloma and splenocytes or PMNs were combined in a 1:2.5 ratio. Serum-free medium was added to 40 ml and the cells centrifuged at 2000 RPM for 5 minutes. Cell pellets were washed twice in 25 ml isoosmolar fusion buffer (ECF). Cells were resuspended in a volume of ECF to give a final concentration of 2×10$^6$ to 1×10$^7$ per ml. Two ml of suspended cells were transferred into the 2 ml fusion chamber, and the cables connected. Sixty V of AC were applied for 30 seconds, followed by 3 successive pulses 1 second apart of 1500 V of DC for 30 microseconds, followed by 60 V of AC for 3 seconds. During this procedure the cells' exposure to isoosmolar fusion buffer; including washes, was kept under 3 hours or less. Post-fusion, the cells always were permitted to sit undisturbed in the fusion chamber at room temperature for 15-45 minutes before proceeding further.

Fused cells were removed from the fusion chamber and resuspended to 1–5×10$^5$ cells/ml in BD Quantum Yield medium (Becton Dickinson) containing 15% low IgG FBS (Gibco), 1×PSG (Gibco), 55 µm β-mercaptoethanol (Gibco), 1×OPI (Sigma) and 5% Origen cloning factor (Igen International). In experiments involving the Y3Ag1.2.3 fusion partner, 1 ng/ml IL-6 was substituted for the Origen cloning factor. Individual wells of 96-well culture plates (Falcon) were seeded with 100 µl of the cells and incubated at 37° C. in 6.5% $CO_2$. Next day, 100 µl of the same medium containing 1×HAT (Sigma) was added to each well and the plates incubated for an additional 7 days, after which the medium was removed and replaced with 200 µl of the same medium. ELISA screening was performed after a total of 10-14 days of incubation.

plates incubated for 1 hour at room temperature. Plates were washed again in PBS, after which 50 µl of ABTS substrate (2,2'-azino-bis(3-ethyl benzthiazoline-6-sulfonic acid; KPL) were added per well. This substrate produces a water soluble green product upon reaction with HRP. The optical density was read using a Spectramax plate reader (Molecular Devices) and data were interpreted using Softmax pro software (Molecular Devices). Table 6 below shows the numbers of ELISA-positive clones obtained from each category of immunized animals. All of the antigen-reactive hybridomas were expanded in cell culture for production and further testing of the antibodies.

TABLE 6

| Antibody | Antigen | Source of lymphocytes | Animals | ELISA-positive | Luciferase assay positive |
|---|---|---|---|---|---|
| mouse mDkk-1 | mDkk-1 | Peripheral lymph nodes | 2 x AGP3 transgenic mice, 2 x Balb/C | 9 | 3 |
| rat mDkk-1 | mDkk-1 | Peripheral lymph nodes | 2 x Lewis rats | 48 | 7 |
| mouse mDkk-1 | PADRE-conjugated-mDkk-1 | Spleen | 2 x C57BL/6 | 78 | 0 |
| mouse mDkk-1 | PADRE-conjugated-mDkk-1 | Peripheral lymph nodes | 3 x C57BL/6 | 593 | 0 |

All fusions were performed in Cytopulse Sciences Cytofusion Medium C Cell (Cat# CPS-LCM). Cell fusion to myeloma cells was accomplished as follows, using the ECM 2001 and Enhancer 400 pulse monitor. The conditions used are shown below in Table 5.

TABLE 5

| Condition | Mouse (SP2/0-ECF-F) | Rat (Y3-ECF-F) |
|---|---|---|
| Alignment: | 60 v, 30 sec | 60 v, 30 sec |
| Membrane breaking: | 1500 V, 30 µs, 3X | 2000 V, 30 µs, 3X |
| Post-fusion pulse: | 60 V, 3 sec | 60 V, 3 sec |

Generally, the fused lymphocytes were frozen directly after fusion for later analysis. For freezing, t-150 flasks were seeded with freshly-fused hybrids at a myeloma cell density of between $1-3 \times 10^5$/ml in fusion media, then incubated overnight at 37° C. The following day, cells were harvested and frozen in a 90% FBS containing 10% DMSO.

EXAMPLE 2

Isolation of Hybridomas Producing Neutralizing Antibodies to Dkk-1

The hybridomas described in Example 1 were screened first using an ELISA assay. Plates were prepared for ELISA by adding 50 µl of a 1-5 µg/ml recombinant muDkk-1 in phosphate-buffered saline (PBS; GIBCO) to each well of a high binding ELISA plate (COSTAR®) for 1 hour. Next, wells were incubated for 1 hour with 200 µl of PBS containing 1% bovine serum albumin (BSA) and 1% goat serum (GIBCO) to block non-specific binding of the hybridoma supernatants. Plates were washed with PBS, 40 µl of hybridoma supernatant were added to each well, then the plates were incubated for one hour. After another PBS wash, 50 µl of a 1:10,000 dilution of goat anti-mu IgG (Fc-specific) which was conjugated to HRP (Pierce) or goat anti-rat IgG H+L conjugated to HRP (Zymed) were added to each well and the A. TCF/Lef-luciferase Assay Several hundred of the hybridomas obtained as described in Example 1 were tested utilizing a TCF/lef-luciferase reporter construct in which luciferase expression is under the control of Wnt. When cells transfected with this construct are exposed to biologically active Wnt, luciferase activity is induced. The Wnt-induced luciferase activity can be suppressed by adding recombinant Dkk-1 protein to the cells that contain this construct. For the present experiments, both Wnt3a and Dkk-1 first were added to the cells in amounts optimized to suppress approximately 80% of the Wnt-dependent luciferase expression. The further addition of an anti-Dkk-1 antibody to these same cells is expected to restore Wnt activity, thus resulting in increased luciferase expression. Supernatants from the hybridomas were thus tested to determine whether they were capable of restoring luciferase expression in cells transfected with the Wnt/luciferase construct. Luciferase activity was quantified as described below.

On day zero, freshly trypsinized 293T cells were plated at $2.5 \times 10^4$ cells/well in fibronectin-coated 96 well plates. The cells were then co-transfected with DNA encoding firefly luciferase and DNA encoding renilla luciferase. On day 1, for each well, 10 ng of TCF/lef-luciferase DNA (TOPflash from Upstate, #21-170) and 1 ng renilla luciferase DNA (pRL-TK; Promega #E2241) in 30 µl of DMEM (minus antibiotics) were mixed with 20 µl of 1:10 Polyfect Transfection Reagent® (Qiagen 301107) and incubated for 10 minutes at room temperature to allow formation of a PolyFect-DNA complex. Following this incubation, 100 µl of growth medium were added to the complex. Then the culture medium was removed from each well and the complex in growth medium was added to the well. The growth medium in the wells was removed three hours later and replaced with conditioned medium.

After three days, the cells were washed once with PBS, and to each well were added 40 µl of the freshly made passive lysis buffer included in the Dual Luciferase kit (Promega #PAE1960). Passive lysis buffer also is available separately from Promega (#E1941). Plates were shaken for 20 minutes at room temperature to induce lysis. Ten µl of lysate per assay were used to perform the Dual Luciferase Assay in 96 well white plates (VWR 62402-980), using Promega #PAE1960 according to the manufacturer's protocol. Using Lmax from Molecular Devices (Luminometer with dual injectors), luminescent signals from firefly and renilla luciferases were both recorded and the ratio of those signals was used to determine the EC50 and to plot dose-response curves. First, the substrate of firefly luciferase was injected into a well with cell lysate and the luminescent signal recorded; then the substrate of renilla luciferase was injected into the same well and the resulting second luminescent signal was recorded. Table 2 above reports the numbers of hybridomas that induced a positive result in this assay, thus indicating that the monoclonals they produced were capable of neutralizing Wnt.

B. Hybridoma Screening Using an ST2 Cell Assay

The stromal cell line ST2 (RIKEN, Cell # RCB0224), derived from mouse bone marrow, was used for further screening of those hybridomas that tested positive in the luciferase assay. In response to Wnt3a signaling, ST2 cells differentiate into osteoblasts which express the osteoblast marker protein alkaline phosphatase (ALP). The induction of ALP by Wnt3a in these cells can be blocked by adding the Wnt inhibitor Dkk-1 to the culture medium. ALP expression can be restored under these conditions by exposing the cells to an agent capable of neutralizing Dkk-1 activity, such as a neutralizing anti-Dkk-1 antibody. Accordingly, the hybridomas were screened for their ability to restore ALP activity to ST2 cells in the presence of Wnt3a.

In preparation for the assay, ST2 cells were cultivated in MEM-α, containing 10% fetal bovine serum, 1× penicillin/streptomycin/glutamine and 1× sodium pyruvate (all these reagents were obtained from GIBCO). Cells were plated at $1\times10^4$ cells/well in 96 well plates with 22 µl of culture medium per well. The cells were incubated overnight for up to 24 hours at 37° C. in a humidified incubator with 5% $CO_2$.

On day zero of the assay, 200 ng of recombinant murine or human Dkk-1 in 20 µl of buffer plus 20 µl of Wnt3a-conditioned medium derived from a murine L-Wnt3a stable cell line were added to each well. The conditioned medium provided a source of Wnt3a. These amounts of these two reagents (that is, Dkk-1 and Wnt3a) were adjusted relative to one another to permit about 10% of the full dynamic range of ALP expression in these cells. Next, each antibody to be tested was titrated in DMEM at 1:2 intervals to determine its ability to restore ALP activity. At the high end of the tested range, each well received 100 µg of antibody per ml. Goat anti-human Dkk-1 polyclonal antibody (R&D Systems, Cat#: AF1096) served as a positive control. Either mock-transfected conditioned media or the ST2 culture medium described above was used as a negative control. After adding antibody or control medium, the plates were incubated at 37° for 72 hours.

On day 3, the media were removed and the cells were rinsed with 0.1 M TRIS (pH 7.4). Next, 150 µl of 0.1% IGEPAL CA-630 (Sigma: Cat. No. I-3021) in glycine buffer was added per well, after which the plates were frozen at −80° C. then thawed. Once thawed, 100 µl of each cell lysate were transferred to fresh 96 well plates to be assayed for ALP. As substrate, 100 µl of 4 mg/ml disodium p-nitrophenol phosphate (Sigma: Cat. No. 104-40) in glycine buffer (0.1 M glycine, 1 mM $MgCl_2$, pH 10.5) was added per well to a final substrate concentration of 2 mg/ml. Upon hydrolysis by ALP, this substrate yields p-nitrophenol, which has a yellow color. Plates were then incubated for 30 minutes at 37 C to permit hydrolysis of the substrate by ALP. After this incubation, the reactions were stopped by adding 50 µl of 0.5 N NaOH per well. Plates were read at 405-410 nM. The ALP assay was normalized using BCA Protein Assay, performed according to the manufacturer's instructions (Pierce Cat #23223, 23224). The normalization (PNP nmol/protein mg) was done to offset cell number variation encountered in each well that could interfere with a true alkaline phosphatase induction determination.

The results of the ALP assay were compared with the positive and negative controls and the results reported in Table 7. The data in Table 7 indicate that of the large number of clones tested, the two expressing the most potent neutralizing activity were 1F11-2 and 11H10, both derived from rat.

TABLE 7

| Source of antibody | Mouse Dkk-1 EC50 (nM) | Human Dkk-1 EC50 (nM) |
|---|---|---|
| Mouse Monoclonal | | |
| 5H6-1 | 2068 | 479 |
| 7D6-1 | 490 | 1465 |
| 7D6-3 | 770 | 533 |
| 10A7-1 | 272 | 1032 |
| 10A7-3 | 276 | 63 |
| Rat Monoclonal | | |
| 1F11-1 | 18.3 | 33.8 |
| 1F11-2 | 24.0 | 25.5 |
| 4A3 | 1113 | 1128 |
| 6D8 | 5908 | 8852 |
| 7H52 | 2706 | 481 |
| 8D11 | 604 | 1567 |
| 8D12 | 1346 | 537 |
| 13F41 | 190 | 1027 |
| 13F42 | 2549 | 2183 |
| 11H10 | 6.1 | 3.5 |
| Goat Polyclonal | | |
| R&D | 57.9 | 14.1 |

In summary, a total of 19,250 hybridomas were screened in the ELISA assay. Of these, 728 bound Dkk-1 in the ELISA assays and 10 were positive in one or both of the neutralization assays (TCR/lef reporter assay or ST2 cell assay). The data in Table 7 indicate that of the positive clones, the 11H10 clone had the best activity. For example, the 11H10 clone had an $EC_{50}$ of 3.5 nM against 8 nm human Dkk-1 and an $EC_{50}$ of 6.1 nM against 8 nm murine Dkk-1.

EXAMPLE 3

Affinity Binding of Monoclonals Against Dkk-1

As noted above, the hybridomas exhibiting the best Dkk-1-neutralizing activity in cell-based assays were the rat-derived 11H10 and 1F11 (see Example 2). The 11H10 antibody is of the $IgG_1$ isotype. This example illustrates that these two antibodies both bind with high affinity to murine, rat and human Dkk-1. Consistent with its better neutralizing activity, the 11H10 clone also had a higher affinity for Dkk-1 in these assays than did 1F11.

Kinetic analyses were performed to study the binding of the 11H10 and 1F11 antibodies to Dkk-1 using BiaCore 2000 (BIACORE, Uppsala, Sweden). Rat Dkk-1 (260 µg/ml), murine Dkk-1 (690 µg/ml) and human Dkk-1 (900 µg/ml) were immobilized on a CM5 chip surface, and various concentrations (0.78 nM to about 100 nM) of the antibodies were injected over the immobilized Dkk-1 surfaces. The binding sensorgrams were analyzed using BIAevaluation 3.2. The data are summarized in Tables 8 and 9 below.

TABLE 8

Binding Kinetics of 1F11 Determined by BiaCore

|  | Rat Dkk-1 | Mouse Dkk-1 | Human Dkk-1 |
|---|---|---|---|
| $k_a$ (1/Ms) | $1.4 \times 10^5$ | $1.2 \times 10^5$ | $1.2 \times 10^5$ |
| $k_d$ (1/s) | $3.1 \times 10^{-4}$ | $3.6 \times 10^{-4}$ | $3.3 \times 10^{-4}$ |
| Kd (M) | $2.2 \times 10^{-9}$ | $2.9 \times 10^{-9}$ | $2.8 \times 10^{-9}$ |

TABLE 9

Binding Kinetics of 11H10 Determined by BiaCore

|  | Rat Dkk-1 | Mouse Dkk-1 | Human Dkk-1 |
|---|---|---|---|
| $k_a$ (1/Ms) | $5.4 \times 10^4$ | $5.4 \times 10^4$ | $5.2 \times 10^4$ |
| $k_d$ (1/s) | $1.54 \times 10^{-5}$ | $<5 \times 10^{-5}$ | $<5 \times 10^{-5}$ |
| $K_d$ (pM) | 290 | <100 | <100 |

It was apparent from the BiaCore results that 11H10 had the higher affinity for Dkk-1, and that its affinity for target exceeded the sensitivity limits of the BiaCore assay. Accordingly, the affinity of binding of 11H10 to Dkk-1 was further assessed by an equilibrium binding analysis using the more sensitive KinExA® 3000 (Sapidyne Instruments Inc., Boise, Id.). For these measurements, Reacti-Gel 6× beads (Pierce, Rockford, Ill.) were pre-coated with either mouse, rat or human Dkk-1 and blocked with BSA. One hundred pM, 300 pM, or 1000 pM of the 11H10 antibody was mixed with various concentrations of human, mouse or rat Dkk-1, ranging in concentration from 1 pM to 50 nM, and equilibrated at room temperature for 8 hours. The mixtures were then passed over the Dkk-1-coated beads. The amount of bead-bound anti-Dkk-1 antibody was quantified using goat anti-rat-IgG antibody labeled with a fluorescent tag (Cy5; Jackson Immuno Research, West Grove, Pa.). The amount of fluorescent signal measured was proportional to the concentration of free anti-Dkk-1 antibody in each reaction mixture at equilibrium. The dissociation equilibrium constant ($K_d$) was obtained from nonlinear regression of the competition curves using a dual-curve one-site homogeneous binding model using the KinExA software. Results of the KinExA assays for 11H10 indicated that the $K_d$ towards human Dkk-1 was $1.3 \times 10^{-10}$ M, and towards mouse and rat Dkk-1 was $1.65 \times 10^{-10}$ M and $5.4 \times 10^{-10}$ M, respectively.

Binding kinetic studies were conducted with several different combinations of the light chain and heavy chains (identical pairs of each chain) listed in Table 1 above. In general these antibodies have $k_a$ values of between $10^4$ and $10^6$/M× seconds, and $k_{off}(k_d)$ values of between $10^{-4}$ and $10^{-5}$ s$^{-1}$.

EXAMPLE 4

In vivo Testing of Hybridoma 11H10

Experiments were conducted to determine whether neutralization of Dkk-1 in a young mouse animal model would cause an increase in bone mineral density (BMD) and in serum osteocalcin, a marker for bone formation.

For these experiments, 11H10 antibody was purified from the medium of cultured 11H10 hybridoma cells. The harvested culture medium was concentrated 12-fold using a Pellicon ultrafiltration device (Amicon) fitted with a 50 kD MWCO screen channel cassette (Millipore). The concentrated medium was filtered though a 0.2 μm pore filter, then bound to Protein G Sepharose (Pharmacia). After washing the Protein G Sepharose with at least four volumes of PBS, the antibody was eluted with IgG Elution buffer (Pierce), then buffered to neutral pH by adding 5% v/v 1M Tris-HCl. Next, the antibody was dialyzed against PBS. The dialysate was filtered through a 0.2 μm filter and tested for endotoxin with 0.06 EU/ml Pyrotell LAL vials (Associates of Cape Cod). Protein concentration in the purified antibody was determined by absorbance at 280 nm using an extinction coefficient of 1.35.

Four week old male BDF-1 mice (APR 233757, Charles River) were injected subcutaneously over a three week period with one of three doses of the purified 11H10 monoclonal antibody (5, 10, or 20 mg/kg), as indicated in Table 10. Five mice were used per group. Negative control mice were injected with vehicle (PBS), and positive control mice were injected with parathyroid hormone (amino acids 1-34), which is known to stimulate increased bone density in these mice (Dempster et al., *Endocrine Reviews* 14(6):690-709 (1993)). One hundred μg/kg of PTH (1-34) in 0.001N HCl, 0.15M NaCl, 2% BSA, pH 8.0 was used per injection. This experiment was repeated a second time exactly as shown in Table 10, but with an additional group of negative control mice which received 20 mg of rat IgG. In addition, these experiments have been repeated with recombinantly expressed 11H10.

TABLE 10

| Group | Dose | Schedule | N |
|---|---|---|---|
| Vehicle | 1xPBS | 3x/wk MWF | 5 |
| PTH Control | PTH B. | 5x/wk M-F | 5 |
| PTH | 100 μg/kg | 5x/wk M-F | 5 |
| 11-H-10 | 5 mg/kg | 3x/wk MWF | 5 |
| 11-H-10 | 10 mg/kg | 3x/wk MWF | 5 |
| 11-H-10 | 20 mg/kg | 3x/wk MWF | 5 |

Blood was collected at baseline (day 0) and at days 3, 5, 7, 14 (retro-orbital), and at day 21 (terminal cardiac puncture) for osteocalcin assays and clinical chemistry panels.

Serum osteocalcin levels were determined using an immunoradiometric assay (IRMA) kit specific for mouse osteocalcin (Immunotopics, Inc. San Clemente, Calif.). Serum samples prior to assay were equilibrated to room temperature and all assays were performed in duplicate. The assays employed two different antibodies to mouse osteocalcin. The first was an affinity purified polyclonal goat antibody that recognizes the mid-region of the C-terminal of the osteocalcin molecule; this antibody was immobilized on plastic beads to be used as a capture reagent. The other antibody was an affinity purified polyclonal antibody that recognizes the amino terminal of the osteocalcin molecule; this antibody was radiolabeled to use for detecting osteocalcin. Mouse serum samples were incubated with an antibody coated bead and the $^{125}$I labeled antibody at room temperature for 18 to 24 hours to permit the osteocalcin to become bound by the immobilized antibody and the radiolabeled antibody to form a labeled bead-bound "sandwich." After incubation, beads were washed twice to remove unbound labeled antibody, counted in a gamma counter, and the counts corrected for background. In these assays, the reactivity of the antibody complex was directly proportional to the amount of mouse osteocalcin in the serum. Concentrations of mouse osteocalcin in the samples were determined directly from a standard curve generated from control osteocalcin provided for this purpose in the kit.

By day 3 and thereafter, all doses of 11H10 had induced an increase in osteocalcin as compared with vehicle-treated mice. The magnitude of increase was dose-dependent. For the 10 mg/kg and 20 mg/kg doses, the magnitude of the increase was statistically significant versus vehicle at the 5 day point, and for the 20 mg/kg dose, remained statistically significant at the 7 day time point. For all doses administered, osteocalcin induction was observed as early as three days after 11H10 treatment had begun and the magnitudes of the observed increases overall were similar to or greater than that observed in the PTH-treated animals.

To assay BMD, whole mouse radiographs were taken at the end of the first, second and third weeks at 56 kvp for 49 seconds using a Faxitron No. 43855A X-ray system (Buffalo Grove, Ill.) and Kodak X-OMAT TL Film (Rochester, N.Y.). The resulting x-ray films were inspected visually for increased in bone density in 10 different bones. No increases were noted in groups treated with vehicle or PTH buffer. However, groups treated with PTH (1-34) or 11H10 exhibited increased density in five or more bones by one week, and in most of the ten bones by the end of week three.

At the end of the three-week injection period, pQCT BMD analysis was conducted on the proximal tibial metaphysis and measured for total, trabecular and cortical density. Total BMD measured by pQTC showed a positive response at the highest dose of 11H10, mostly due to an increase in trabecular BMD. Table 11 presents the BMD measurements obtained in one of the two experiments that were performed. Similar results were obtained in both the experiments. The numbers in Table 11 represent percent change as compared with the vehicle control. The asterisks in Table 11 indicate that there was a statistically significant difference between the 11H10 group and the control group (ANOVA $p<0.05$). Overall, the amount of BMD increase induced by 11H10 was comparable to the amount of increase induced by the PTH (1-34) positive control.

TABLE 11

Bone Mineral Density in 11H10-treated Mice
% Change Compared With Vehicle-injected Mice

| Dose of 11H10 | Total Density (proximal tibial metaphysis) | Trabecular Density (proximal tibial metaphysis) | Cortical Density (proximal tibial metaphysis) |
|---|---|---|---|
| 5 mg/kg | 4.1 | 9.8 | −0.49 |
| 10 mg/kg | 10.2 | 16.8* | 0.59 |
| 20 mg/kg | 12.2* | 19.5* | 4.3 |
| PTH-(1-34) 100 μg/kg | 10.6 | 16.7 | 7.9 |
| PTH Buffer Control | −2.2 | 2.0 | −5.3 |

EXAMPLE 5

In vivo Testing of Various Antibodies

To further access the ability of neutralizing Dkk1 to increase bone mass both young (6-weeks old) and old mice (8.5-month old) were treated with rat 11H10 as described above in Example 4. Mice were analyzed for BMD changes by pQCT and microCT (PCT). For PCT, trabecular architecture and cortical geometry were examined in mouse femurs using an eXplore Locus SP Micro-CT System (GE Healthcare, Waukesha, Wis., USA). Femurs were placed in 2 ml cryo-tubes with a bone density phantom, filled with PBS, and stabilized with gauze. Whole femurs were scanned at 0.5° rotations for 200° (80 kVp, 80 uA) calibrated with the density phantom, and reconstructed to yield images with a voxel size of 18×18×18 μm.

Regions of interest were analyzed for cortical and trabecular morphometric and density parameters (GEHC MicroView software). The central 10% (in length) of the femur diaphysis was analyzed for average endosteal and periosteal perimeters, as well as cortical area and volumetric BMD (threshold=640 mg/cc). Regions of trabecular bone from the distal femur were isolated and analyzed for BMD and stereology parameters, including bone volume fraction (BV/TV), trabecular thickness (Tb.Th), trabecular number (Tb.N), and volumetric BMD (threshold=320 mg/cc). These regions were selected based on the femur length (10% of length) and located proximal to growth plate spongiosa.

Figure 2A:
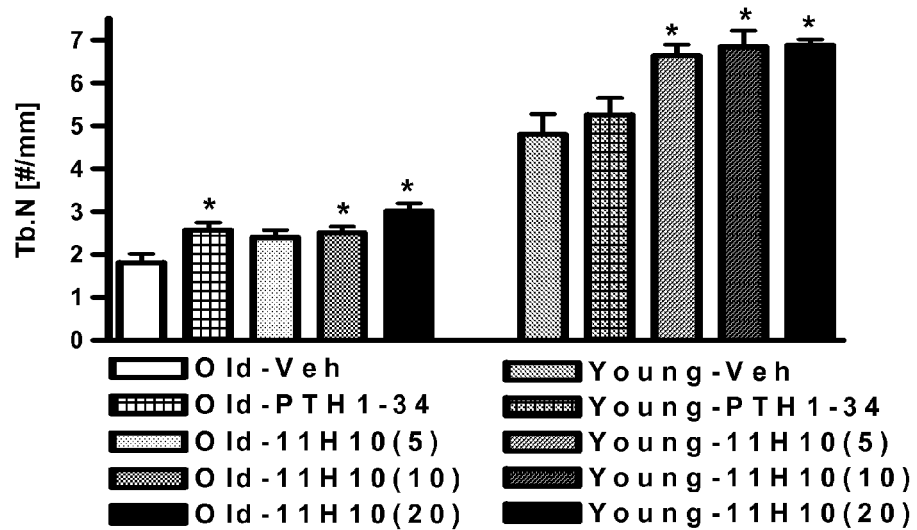
FIGS. 2A and 2B show μCT results for young and old mice treated with rat 11H10.
Figure 2B:
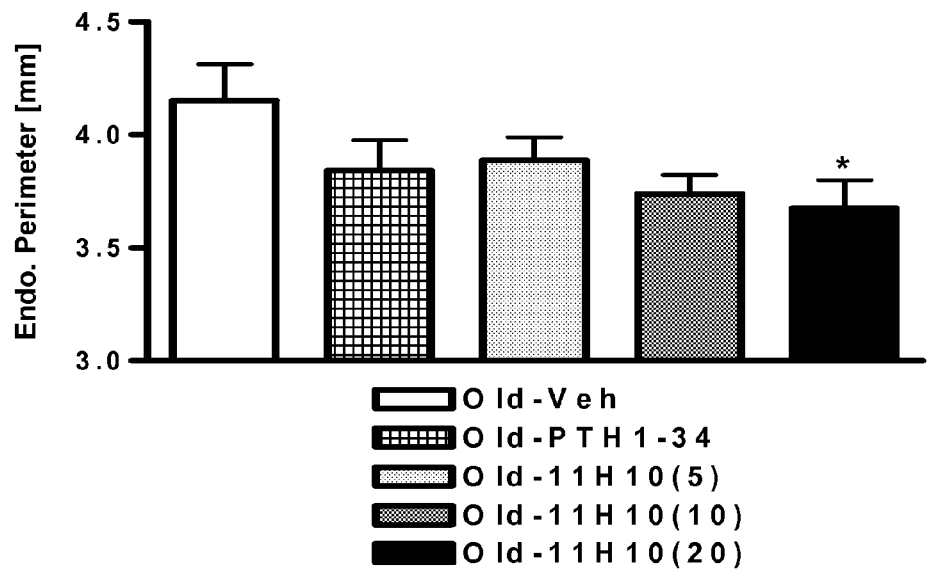

Both pQCT and μCT showed significant changes in BMD in r at 11H10 treated young and old mice. In addition, μCT allowed showed that neutralizing Dkk1 activity with rat 11H10 led to significant increases in trabecular number in both young and old mice (FIG. 2). The highest dose of rat 11H10 in old mice resulted in a decrease in the endosteal perimeter, indicating that rat 11H10 also positively affected cortical bone growth, in addition to cancellous bone.

Figure 3A:
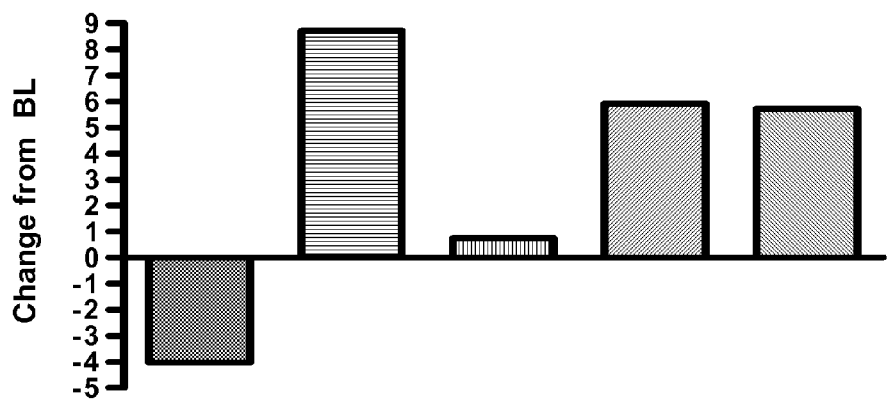
FIGS. 3A and 3B are plots that depict the percent change in BMD in oviarectomized (OVX) mice 28 days after being treated with rat 11H10 (3, 10 or 30 mg/kg) versus vehicle or PTH (100 μg/kg). The mice used were 5 months post OVX.
Figure 3B:
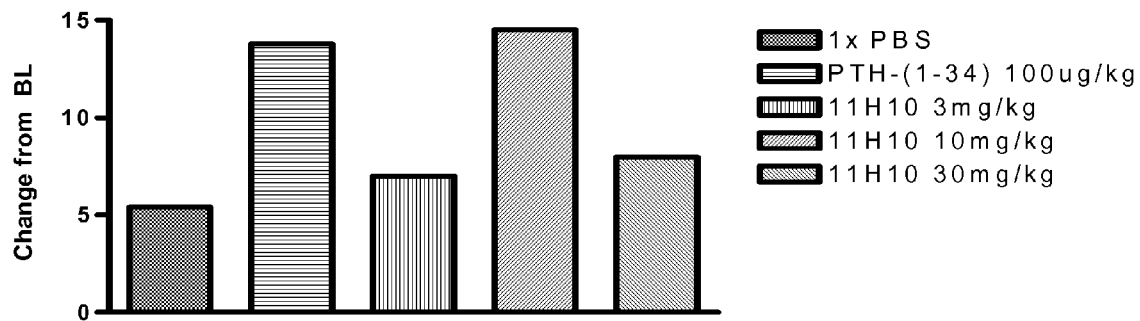

To determine whether Dkk1 neutralization could help restore bone loss due to lack of estrogen, oviarectomized (OVX) mice were treated with rat 11H10 (3, 10, 30 mg/kg twice per week by subcutaneous injection). In this experiment 7 month old CDF-1 mice, 5-months post-OVX, were treated with rat 11H10, PTH (100 μg/Kg) or vehicle. BMD was analyzed by pQCT at baseline, day 7, 14, 21 and 28. The data from day 28 are shown below as percent change from baseline for the tibia and lumbar vertebrae (FIG. 3).

In a separate experiment, the efficacy of the h11H10 RT IgG1 isotype and the h11H10 RT IgG2 isotype (see Tables 1 and 2 for sequences of light and heavy chains and variable regions) was determined in young mice using a protocol similar to that described above with the modification that the h11H10 RT IgG1 isotype and the h11H10 RT IgG2 isotype were compared to rat 11H10 and PTH (FIG. 4). The data indicate that these two antibodies also increased BMD, as determined by DEXA analysis, in mice.

The results of the experiments described above indicate that neutralization of Dkk-1 activity with certain of the antibodies described herein has an anabolic effect on bone formation.

EXAMPLE 6

Characterization of Human Dkk-1 Epitopes that Bind 11H10 Antibody

Human Dkk-1 contains two disulfide-rich domains located near the N-terminus and near the end of the C-terminus, referred to here as the N- and C-terminal disulfide domains. The N-terminal disulfide domain (hereinafter, "disulfide domain 1") contains 55 amino acids residues (amino acids 85-139 of SEQ ID NO:2) and has 10 cysteines forming 5 intramolecular disulfide bonds. The C-terminal disulfide domain (hereinafter, "disulfide domain 2") contains about 75 amino acids (amino acids 189-263 of SEQ ID NO:2) and contains 10 cysteines that form 5 intramolecular disulfide bridges, resulting in the formation of seven loops in the fully-folded protein (see FIG. 1). Disulfide domain 2 of Dkk-1 has been proposed to have a molecular structure similar to the canonical colipase fold, the crystal structure of which has been determined using porcine colipase (Aravind, A. and Koonin, E. V., *Current Biology* 8:R477-479 (1998)). The seven loops in disulfide domain 2 of human Dkk-1 consist of amino acids 190-194, 196-199, 202-209, 211-219, 221-236, 240-244 and 246-262 of SEQ ID NO:2.

Treatment with a reducing agent abolished the ability of Dkk-1 to bind 11H10, thus indicating that the epitope targeted by this antibody was conformational and required the maintenance of at least some of the disulfide bonds in this protein. To characterize this conformational epitope, a strategy was applied that involved fragmenting human Dkk-1 with cyanogen bromide (CNBr) and several different proteases, then testing the resulting fragments to see whether they could still bind to the 11H10 antibody. The resulting data permitted the location of the epitope to be determined. In brief, the peptide digests were incubated with or without the antibody, passed through a 10 K cut-off membrane to trap any peptides that had become bound to the antibody (~150,000 Da), then subjected to HPLC peptide mapping. A reduction in the height of an HPLC peak in a sample exposed to antibody indicated that the peptides in that peak had bound to the antibody and thus formed part of the epitope. The individual HPLC peaks were collected and the peptides identified and mapped by N-terminal sequencing. To determine if the peptides could bind 11H10, they were subjected to real time biospecific interaction assays with a BiaCore work station, using Protein A-trapped anti-Dkk-1 antibody as a biosensor for binding.

All HPLC analyses for these studies were performed using a reverse-phase C5 column (1 mm i.d.×10 cm length). HPLC peptide mapping was performed with a linear gradient from 0.05% trifluoroacetic acid (mobile phase A) to 90% acetonitrile in 0.05% trifluoroacetic acid. Columns were developed over 70 minutes at a flow rate of 0.15 ml/min.

CNBr Digestion

CNBr cleavage of hDkk-1 generated two large fragments, CNBr1 and CNBr2. These represented, respectively, disulfide domain 2 and disulfide domain 1. CNBr1 consisted of two peptides (amino acids 179-206 of SEQ ID NO:2 and amino acids 207-266 of SEQ ID NO:2) held together by disulfide bonds. CNBr2 similarly consisted of two peptides (amino acids 32-122 of SEQ ID NO:2 and amino acids 127-178 of SEQ ID NO:2), also held together by disulfide bonds. The results of BiaCore analysis indicated that 11H10 was capable of binding significantly to CNBr1 but did not bind at all to CNBr2. Thus, it was concluded that 11H10 binds to an epitope located in disulfide domain 2 of Dkk-1.

Trypsin Digestion

Human Dkk-1 was next digested with trypsin, which cleaves after arg and lys. About 200 μg of Dkk-1 at 0.5-1.0 mg/ml were incubated in PBS (pH 7.2) for 20 h at 37° C. with 8 μg of one or the other of these proteases to achieve complete digestion of the Dkk-1.

HPLC chromatography of the trypsin digests yielded multiple peaks. To determine which, if any, of the tryptic fragments retained the ability to bind antibody, the digest was incubated with 11H10 antibody at a 1:2 molar ratio at 0° C. for 2 hours. Antibody and any peptides bound to it were captured on a Microcon membrane (30,000 molecular weight cut-off). Peptides in the flow-through from the Microcon filter were analyzed on HPLC to determine which peaks were reduced or eliminated due to having bound to the antibody. The HPLC results for samples exposed to antibody were compared with control digests that had been subjected to the same procedures without 11H10. As discussed below, none of the fragments generated by trypsin digestion retained the ability to bind 11H10.

Sequence analysis was conducted to identify and map the peptides in the peaks recovered from HPLC after trypsin digestion. Two peaks, Tryp40.5 (retention time 40.5 minutes) (~6-7 kDa) and Tryp45 (~8 kDa), were confirmed to contain sequences that mapped, respectively, to disulfide domain 2 and disulfide domain 1. Neither Tryp40.5 nor Tryp45 bound to 11H10 when tested by Microcon membrane capturing or by BiaCore binding experiments. Tryp40.5 consisted of seven small peptides (6 to 12 amino acids in length) held together by the five disulfide bonds of disulfide domain 2. Three small segments of the sequence of disulfide domain 2 were missing from Tryp40.5 These missing sequences were amino acids 204-208, 223-226 and 247-249 of SEQ ID NO:2). Since Tryp40.5 cannot bind 11H10, it appears that one or more of these three missing peptides must form an essential part of the epitope to which this antibody binds.

Endo Lys C Digestion

Digestion of human Dkk-1 with Endo LysC (cleaves only after lys) also generated several peaks when subjected to HPLC as described above. Only one HPLC fraction, LysC48.7, showed a reduction in peak height when the digest was incubated with antibody prior to HPLC analysis. LysC48.7 consisted of three peptide fragments held together by all five of the disulfide bonds in disulfide domain 2. Sequence analysis indicated that these three peptides consisted of amino acids 183-222, 227-249, and 250-266 of SEQ ID NO:2. The sequence analysis revealed that LysC48.7 lacked only one segment of disulfide domain 2, namely a peptide located at amino acids 223-226 of SEQ ID NO:2. Thus, LysC48.7 was structurally more intact than Tryp40.8, which lacked three segments of disulfide domain 2.

The ability of 11H10 to bind the LysC fractions was determined using the BiaCore binding assay. Only the LysC48.7 fraction showed any binding activity. The LysC48.7 fraction showed a strong on-rate of binding the antibody. However, the off-rate was very fast with the binding quickly diminishing to background levels. These data indicate that the target epitope for 11H10 will not retain binding to the antibody when amino acids 223-226 of SEQ ID NO:2 are clipped out of disulfide domain 2. Therefore, it was concluded that residues 223-226 may come into direct contact with 11H10 when it binds Dkk-1 or that these residues are essential for maintaining the three-dimensional structure that enables the antibody to effectively contact other amino acid residues in the immediate vicinity of amino acids 223-226 in the folded protein.

AspN Digestion

To further delineate the 11H10-binding epitope, hDkk-1 was digested with the protease AspN and the resulting fragments analyzed as described above. Of the major HPLC peaks generated by AspN digestion, three were reduced in height if the digest was pre-exposed to 11H10, indicating that these peptides had bound to the antibody. The peaks that bound antibody were AspN48.7, AspN49.6 and AspN52. Sequence analysis indicated that these three antibody-reactive peaks were derived from disulfide domain 2. AspN48.7 and AspN49.6 were identical in amino acid sequence and each of them consisted of two peptides held together by the five disulfide bonds in disulfide domain 2. The difference in HPLC migration of these two peaks probably was due to the heterogeneity of carbohydrate moieties attached to $Asn_{256}$. These two peptides consisted of amino acids 166-231 and 232-266 of SEQ ID NO:2. AspN52 contained only a single peptide, corresponding to amino acids 166-266 of SEQ ID NO:2. Thus, AspN52 evidently is a partial digestion product whose sequence largely overlaps AspN48.7 and 49.6, though the latter two received an extra clip between $Leu_{231}$ and $Glu_{232}$ relative to AspN52. This clip occurs in the loop that lies between amino acids 221 and 236 of SEQ ID NO:2. All three of these peaks showed significant binding to 11H10 in Microcon capturing experiments and Biacore binding analysis. These data indicate that disrupting the peptide bond between amino acids 231 and 232 of hDkk-1 (SEQ ID NO:2) does not affect the ability of 11H10 to recognize its target epitope.

Analysis of Digestion Results

The above results indicate that 11H10 binds to a non-linear epitope of human Dkk-1 located in disulfide domain 2 of the protein, and that the epitope resides in the two large loops formed by disulfide bonds $Cys_{220}$-$Cys_{245}$, $Cys_{239}$-$Cys_{263}$ and $Cys_{200}$-$Cys_{237}$ of SEQ ID NO:2 (see FIG. 1). As illustrated in FIG. 1, the two loops that form the epitope lie between $Cys_{220}$ and $Cys_{237}$ and between $Cys_{245}$ and $Cys_{263}$, the body of the two loops thus comprising amino acids 221-236 and 246-262 of SEQ ID NO:2. Trypsin digestion of Dkk-1 opened up the $Cys_{220}$/$Cys_{237}$ and $Cys_{245}$/$Cys_{263}$ loops by removing amino acids 223-226 and 247-249. With these two peptides removed, the trypsin digestion products could not bind 11H10. A third peptide (amino acids 204-208 of SEQ ID NO:2) also was deleted by trypsin digestion but was deemed to lie outside the epitope because the other proteases were able to reduce antibody binding without clipping the loop where these amino acids reside. LysC digestion, which drastically reduced antibody binding, also opened up the $Cys_{220}$/$Cys_{237}$ loop by removing amino acids 223-226 of SEQ ID NO:2 and the $Cys_{245}$/$Cys_{263}$ loop by cleaving at a single peptide bond at $Lys_{249}$ (SEQ ID NO:2). Thus, the LysC digestion results again implicated the $Cys_{220}$/$Cys_{237}$ and $Cys_{245}$/$Cys_{263}$ loops for 11H10 binding. AspN digestion clipped at $Glu_{232}$ (SEQ ID NO:2) in the $Cys_{220}$/$Cys_{237}$ loop without reducing antibody binding, thus suggesting that preservation of proper epitope conformation did not require this loop to be absolutely intact. However, this loop clearly is important because, as shown above, the removal of amino acids 223-226 of SEQ ID NO:2 by LysC from this same loop did destroy antibody binding.

According to these analyses, the epitope that binds 11H10 is located in the vicinity of the $Cys_{220}$/$Cys_{237}$ and $Cys_{245}$/$Cys_{263}$ loops in disulfide domain 2, thus amino acids 220-237 and amino acids 245-263 of SEQ ID NO:2 are very important for antibody binding. The loops formed by the other disulfide bonds in this C-terminal domain disulfide cluster do not appear to be involved in recognition by this antibody. The results show also that the disulfide bonds in this domain must be intact to retain the epitope in a configuration that permits antibody binding. Within the epitope, the minimum portions that would appear necessary to retain binding include amino acids 221-229 of SEQ ID NO:2 (this follows from the fact that cleaving at $Glu_{232}$ had no effect on binding) and amino acids 246-253 of SEQ ID NO:2, as structural considerations indicate that $Asn_{256}$ is linked to bulky carbohydrate moieties that can mask the other amino acids in this loop from binding to 11H10.

EXAMPLE 7

The 1F11 Antibody Competes with 11H10 for Binding to Dkk-1

Experiments were conducted to determine whether the 1F11 monoclonal antibody might bind to the same epitope on Dkk-1 as 11H10. This matter was of interest because both of these monoclonal antibodies neutralize the biological activity of Dkk-1. As shown in Table 12 below, 1F11 neutralizes mouse, rat and human Dkk-1 activity in the TCF-lef assay, though not as well as 11H10.

TABLE 12

| Antibody (200 ng/ml) | EC50 (nM) | | |
|---|---|---|---|
| | mouse Dkk-1 | rat Dkk-1 | human Dkk-1 |
| 11H10 | 11.5 | 5.0 | 4.0 |
| 1F11 | 62.6 | 21.2 | 19.5 |

Competition experiments between 11H10 and 1F11 were conducted using the BiaCore 2000, as described above. BiaCore chips onto which either 11H10 or 1F11 had been immobilized were used to capture human Dkk-1. Following the capture step, either 1F11 or 11H10 was injected over the surfaces of the chips to see if further binding to Dkk-1 could be achieved. In these experiments, neither of the antibodies injected over the chips was able to bind to the captured human Dkk-1, that is, 11H10 was not able to bind human Dkk-1 that had been captured by 1F11, nor could 1F11 bind human Dkk-1 that had been captured by 11H10. These data strongly indicate that these two antibodies bind to the same epitope on human Dkk-1, thus suggesting that targeting this particular epitope is a particularly effective means for neutralizing Dkk-1 activity.

Other experiments were conducted to determine if some of the other antibodies including the heavy and light chains listed in Table 1 (identical pairs of heavy and light chains) could compete for the same epitope as recognized by rat 11H10 and 1F11 and were found to do so.

EXAMPLE 8

11H10 Blocks Binding of Dkk-1 to LRP6

To determine if 11H10 was exerting its biological effect by interfering with the interaction of Dkk-1 and LRP6, and by inference LRP5, we established an LRP6 Dkk-1 binding assay utilizing flow cytometry. This assays uses a commercially obtained LRP6-Fc fusion protein (R&D Systems, #1505-LR) and an amino-terminal biotin-tagged human Dkk-1. The biotin-tagged Dkk-1 fusion construct was generated by cloning DNA encoding hDkk-1 so that was expressed fused to the C-terminus of biotin in a mammalian expression construct. This construct was transiently transfected into 293T cells and conditioned medium was collected 48 hours after transfection.

To determine whether 11H10 was capable of interfering with Dkk-1 binding to LRP6, LRP6 was added to the conditioned medium with and without 11H10. Streptavidin beads were then added to this preparation, which allowed the binding of the biotin-Dkk1 fusion protein to the beads. The binding of LRP6 to Dkk-1 was determined by using a FITC-conjugated antibody specific to the Fc portion of the LRP6-Fc fusion construct. LRP6 binding to Dkk-1 was detected by using flow cytometry. A specific binding signal (specific binding is equal to the total signal observed minus the signal observed in the absence of Dkk-1) of 6.46 was detected with LRP6 and Dkk-1. Incubation of Dkk-1 with 11H10 prior to addition of LRP6 reduced this signal to 2.66, which was less than 50% of the specific binding observed without the antibody, thereby indicating that 11H10 interferes with the binding of Dkk-1 to LRP6.

EXAMPLE 9

Cloning the 11H10 Heavy and Light Chain cDNAs

Total RNA was isolated from rat hybridoma 11H10 cells with TRIzol® reagent (Invitrogen) according to the manufacturer's instructions, then further purified using a Qiagen RNeasy® column. A 5' RACE (rapid amplification of cDNA ends) oligonucleotide (5'-CGA CUG GAG CAC GAG GAC ACU GAC AUG GAC UGA AGG AGU AGA AA-3'; SEQ ID NO:15) was ligated to the RNA using the GeneRacer™ Kit (Invitrogen) components and protocol. This oligonucleotide provides two unique priming sites on the 5' ends of the mRNA molecules. First strand cDNA was synthesized from this modified RNA using a random primer with an extension adapter (5'-GGC CGG ATA GGC CTC ACN NNN NNT-3'; SEQ ID NO:16).

Taking advantage of conserved sequences in the rat antibody genes, 5' RACE PCR reactions were performed to amplify those cDNAs coding for the anti-muDkk-1 antibody. To clone the complete light chain of 11H10, a RACE PCR was preformed using the 5' GeneRacer™ primer (5'CGA CTG GAG CAC GAG GAC ACT GA-3'; SEQ ID NO:17) as the forward primer, and using 5'-GCA ACA GTG GTA GGT CGC TTG TGG-3' (SEQ ID NO:18) as the reverse primer. This reverse primer corresponds to nucleotides 74-98 in the rat kappa chain 3' untranslated region. This PCR product was then used as a template for a nested PCR using the 5' GeneRacer™ nested primer (5' GGA CAC TGA CAT GGA CTG AAG GAG TA-3' (SEQ ID NO:19)) as the forward primer and the same reverse primer (SEQ ID NO:18).

The RACE PCR for the variable region of the heavy chains used the GeneRacer™ primer as the forward primer and as the reverse primer used 5'-AGG AGC CAG TGG ATA GAC AGA-3' (SEQ ID NO:20) which corresponds to nucleotides nineteen to thirty nine in the rat IgG constant region. This PCR product was then used as template for a nested PCR using the 5' GeneRacer™ nested primer as the forward primer and the same reverse primer 5'-AGG AGC CAG TGG ATA GAC AGA-3' (SEQ ID NO:20).

The RACE PCR products were then cloned into the cloning vector pCR4-TOPO TA (Invitrogen). The DNA sequences of these clones were determined using pCR4 vector primers flanking the cloning site, dye labeled nucleotides and ABI DNA sequencers. Consensus sequences for the 11H10 light chain and heavy chain variable regions were assembled and used to design 5' PCR primers directed at the amino terminal ends of the coding sequences. These primers also contained contain a SalI restriction site for cloning and a Kozak sequence. The 5' PCR primer designed for the light chain had the following nucleotide sequence: 5'-AAG CTC GAG GTC GAC TAG ACC ACC ATG GGT GTG CCT ACT CAT CTC-3' (SEQ ID NO:21); for the heavy chain, 5'-AAG CTC GAG GTC GAC TAG ACC ACC ATG GAC ATC AGG CTC AGC TTG G-3' (SEQ ID NO:22). These 5' primers were then used with 3' primers directed at the carboxy terminal ends of the coding sequences and containing a NotI restriction site for cloning. The 3' primer for the light chain had the following nucleotide sequence: 5'-AAC CGT TTA AAC GCG GCC GCC TAA CAC TCA TTC CTG TTG A-3' (SEQ ID NO:23); and the 3' primer for the heavy chain, 5'-AAC CGT TTA AAC GCG GCC GCT CAT TTA CCC GGA GAG TGG GAG-3' (SEQ ID NO:24). These primers were used in PCR reactions to amplify the complete coding regions of the 11H10 antibody light and heavy chain genes. Cloned sequences were expressed in CHO cells as described in Bianchi and McGrew, 2003.

Nucleotide sequences encoding the 11H10 complete light and heavy chains are shown in SEQ ID NOS:9 and 11, respectively, and SEQ ID NOS:10 and 12 depict the amino acid sequences. The 11H10 light chain has a leader sequence consisting of amino acids 1-20 (encoded by nucleotides 1-60 of SEQ ID NO:9), thus the mature protein begins at amino acid 21 of SEQ ID NO:10. The light chain variable region of 11H10 is encoded by nucleotides 61-381 of SEQ ID NO:9 (see, also SEQ ID NO:83), which corresponds to amino acids 21-127 of SEQ ID NO:10 (see, also SEQ ID NO:84). The 11H10 light chain CDR1 is encoded by nucleotides 130-162 of SEQ ID NO:9 (see also SEQ ID NO:85), encoding amino acids 44-54 of SEQ ID NO:10 (see also SEQ ID NO:70); the 11H10 light chain CDR2 are residues encoded by 208-228 of SEQ ID NO:9 (see also SEQ ID NO:86), which encode amino acids 70-76 of SEQ ID NO:10 (see also SEQ ID NO:72); and CDR3 of 11H10 is encoded by nucleotides 325-351 of SEQ ID NO:9 (see also SEQ ID NO:87), which encode amino acids 109-117 of SEQ ID NO:10 (see also SEQ ID NO:74).

The 11H10 heavy chain has a leader sequence consisting of amino acids 1-19 (encoded by nucleotides 1-57 of SEQ ID NO:11), thus the mature protein begins at residue 20 of SEQ ID NO:12 and is encoded by nucleotides 58-1395. The heavy chain variable region is encoded by nucleotides 58-417 of SEQ ID NO:11 (see also SEQ ID NO:90), which encode amino acids 20-139 of SEQ ID NO:12 (see also SEQ ID NO:91). The heavy chain CDR1 is encoded by nucleotides 148-162 of SEQ ID NO:11 (see also SEQ ID NO:92), encoding amino acids 50-54 of SEQ ID NO:12 (see also SEQ ID NO:76); the 11H10 heavy chain CDR2 is encoded by nucleotides 205-255 of SEQ ID NO:11 (see also SEQ ID NO:93), which encode amino acids 69-85 of SEQ ID NO:11 (see also SEQ ID NO:78); and the 11H10 heavy chain CDR3 is encoded by nucleotides 352-384 of SEQ ID NO:11 (see also SEQ ID NO:94), encoding amino acids 118-128 of SEQ ID NO:12 (see also SEQ ID NO:80).

****

It is understood that the examples and embodiments described herein are for illustrative purposes only and that various modifications or changes in light thereof will be suggested to persons skilled in the art and are to be included within the spirit and purview of this application and scope of the appended claims. All publications, patents and patent applications cited herein are hereby incorporated by reference in their entirety for all purposes to the same extent as if each individual publication, patent or patent application were specifically and individually indicated to be so incorporated by reference.

We claim:

1. A method of treating a bone fracture in an individual in need thereof, comprising administering to the individual a therapeutically effective amount of an antibody or immunologically functional fragment thereof that comprises:
   (a) the following three light chain (LC) complementary determining regions (CDRs):
      (i) a LC CDR1 comprising the amino acid sequence of SEQ ID NO:70;
      (ii) a LC CDR2 comprising the amino acid sequence of SEQ ID NO:72; and
      (iii) a LC CDR3 comprising the amino acid sequence of SEQ ID NO:74; and
   (b) the following three heavy chain (HC) CDRs:
      (i) a HC CDR1 comprising the amino acid sequence of SEQ ID NO:76;
      (ii) a HC CDR2 comprising the amino acid sequence of SEQ ID NO:78; and
      (iii) a HC CDR3 comprising the amino acid sequence of SEQ ID NO:80,
   wherein the antibody or immunologically functional fragment thereof can specifically bind a Dkk-1 polypeptide consisting of amino acids 32-266 of SEQ ID NO:2 or amino acids 32-272 of SEQ ID NO:4.

2. The method of claim 1, wherein the antibody or immunologically functional fragment dissociates from the Dkk-1 polypeptide with a $k_d$ of $1 \times 10^{-4}$ $s^{-1}$ or less.

3. The method of claim 1, wherein the antibody or immunologically functional fragment is a monoclonal antibody.

4. The method of claim 1, wherein the antibody or immunologically functional fragment is a scFv, a Fab, a Fab' or a (Fab')$_2$.

5. The method of claim 1, wherein the antibody or immunologically functional fragment is a humanized antibody.

6. The method of claim 1, further comprising administering a bone growth promoting agent and/or a bone anti-resorptive agent.

7. The method of claim 6, wherein the bone growth promoting agent or anti-resorptive agent is selected from the group consisting of a bone morphogenic factor, a transforming growth factor-β, a fibroblast growth factor, an interleukin-1 inhibitor, a TNFα inhibitor, a RANK ligand inhibitor, parathyroid hormone, a bisphosphonate and insulin-like growth factor.

8. A method of treating a bone fracture in an individual in need thereof, comprising administering to the individual a therapeutically effective amount of monoclonal antibody or immunologically functional fragment thereof, wherein the monoclonal antibody or fragment
   (a) specifically binds a Dkk-1 protein consisting of amino acids 32-266 of SEQ ID NO:2; and
   (b) binds to an epitope containing two loops, said loops being between cysteine residues 220 and 237 of SEQ ID NO:2 and between cysteine residues 245 and 263 of SEQ ID NO:2.

9. The method of claim 8, wherein the monoclonal antibody or immunologically functional fragment dissociates from the Dkk-1 polypeptide with a $k_d$ of $1\times10^{-4}$ $s^{-1}$ or less.

10. The method of claim 8, wherein the monoclonal antibody or immunologically functional fragment is a scFv, a Fab, a Fab' or a (Fab')$_2$.

11. The method of claim 8, wherein the monoclonal antibody or immunologically functional fragment is a human or humanized antibody.

12. The method of claim 8, further comprising administering a bone growth promoting agent and/or a bone anti-resorptive agent.

13. The method of claim 12, wherein the bone growth promoting agent or anti-resorptive agent is selected from the group consisting of a bone morphogenic factor, a transforming growth factor-β, a fibroblast growth factor, an interleukin-1 inhibitor, a TNFα inhibitor, a RANK ligand inhibitor, parathyroid hormone, a bisphosphonate and insulin-like growth factor.

14. A method of treating a bone fracture in an individual in need thereof, comprising administering to the individual a therapeutically effective amount of an antibody or immunologically functional fragment thereof, wherein the antibody or fragment competes with a reference antibody for specific binding to a Dkk-1 polypeptide consisting of amino acids 32 to 266 of SEQ ID NO:2 or amino acids 32 to 272 of SEQ ID NO:4, and wherein
   (a) the reference antibody consists of two identical heavy chains and two identical light chains;
   (b) the light chains are selected from the group consisting of SEQ ID NO:82, 26 and 30; and
   (c) the heavy chains are selected from the group consisting of SEQ ID NO:89, 34, 38, 42 46, 50, 54, 58, 62 and 66.

15. The method of claim 14, wherein the light chains each consist of the amino acid sequence of SEQ ID NO:82 and the heavy chains each consist of the amino acid sequence of SEQ ID NO:89.

16. The method of claim 14, wherein the antibody or fragment dissociates from the Dkk-1 polypeptide with a $k_d$ of $1\times10^{-4}$ $s^{-1}$ or less.

17. The method of claim 14, wherein the antibody or immunologically functional fragment is a monoclonal antibody.

18. The method of claim 14, wherein the antibody or immunologically functional fragment is a scFv, a Fab, a Fab' or a (Fab')$_2$.

19. The method of claim 14, wherein the antibody or immunologically functional fragment is a human or humanized antibody.

20. The method of claim 14, further comprising administering a bone growth promoting agent and/or a bone anti-resorptive agent.

21. The method of claim 20, wherein the bone growth promoting agent or anti-resorptive agent is selected from the group consisting of a bone morphogenic factor, a transforming growth factor-β, a fibroblast growth factor, an interleukin-1 inhibitor, a TNFα inhibitor, a RANK ligand inhibitor, parathyroid hormone, a bisphosphonate and insulin-like growth factor.

22. method of treating a bone fracture in an individual in need thereof, comprising administering to the individual a therapeutically effective amount of a monoclonal antibody or immunologically functional fragment thereof, wherein the monoclonal antibody or fragment binds to two separated regions located between amino acids 221-262 of SEQ ID NO:2.

23. The method of claim 22, wherein one region is amino acids 221-236 of SEQ ID NO:2 and the second region is amino acids 246-262 of SEQ ID NO:2.

24. The method of claim 22, wherein one region is amino acids 221-229 of SEQ ID NO:2 and the second region is amino acids 246-253 of SEQ ID NO:2.

25. The method of claim 22, wherein the monoclonal antibody or immunologically functional fragment is a scFv, a Fab, a Fab' or a (Fab')$_2$.

26. The method of claim 22, wherein the monoclonal antibody or immunologically functional fragment is a human or humanized antibody.

27. The method of claim 22, further comprising administering a bone growth promoting agent and/or a bone anti-resorptive agent.

28. The method of claim 27, wherein the bone growth promoting agent or anti-resorptive agent is selected from the group consisting of a bone morphogenic factor, a transforming growth factor-β, a fibroblast growth factor, an interleukin-1 inhibitor, a TNFα inhibitor, a RANK ligand inhibitor, parathyroid hormone, a bisphosphonate and insulin-like growth factor.

29. A method of treating a bone fracture in an individual in need thereof, comprising administering to the individual a monoclonal antibody or immunologically functional fragment thereof, wherein the monoclonal antibody or fragment binds to a non-linear epitope of a human Dkk-1 polypeptide consisting of amino acids 32-266 of SEQ ID NO:2, wherein the non-linear epitope is located between amino acids 221 and 262 of SEQ ID NO:2.

30. The method of claim 29, wherein the monoclonal antibody or fragment dissociates from the Dkk-1 polypeptide with a $k_d$ of $1\times10^{-4}$ $s^{-1}$ or less.

31. The method of claim 29, wherein the monoclonal antibody or immunologically functional fragment is a scFv, a Fab, a Fab' or a (Fab')$_2$.

32. The method of claim 29, wherein the monoclonal antibody or immunologically functional fragment is a human or humanized antibody.

33. The method of claim 29, further comprising administering a bone growth promoting agent and/or a bone anti-resorptive agent.

34. The method of claim 33, wherein the bone growth promoting agent or anti-resorptive agent is selected from the group consisting of a bone morphogenic factor, a transforming growth factor-β, a fibroblast growth factor, an interleukin-1 inhibitor, a TNFα inhibitor, a RANK ligand inhibitor, parathyroid hormone, a bisphosphonate and insulin-like growth factor.

* * * * *

SEQUENCE LISTING

```
<160> NUMBER OF SEQ ID NOS: 94

<210> SEQ ID NO 1
<211> LENGTH: 801
<212> TYPE: DNA
<213> ORGANISM: Homo sapiens
<220> FEATURE:
```

```
<221> NAME/KEY: CDS
<222> LOCATION: (1)..(801)

<400> SEQUENCE: 1 atg atg gct ctg ggc gca gcg gga gct acc cgg gtc ttt gtc gcg atg      48
Met Met Ala Leu Gly Ala Ala Gly Ala Thr Arg Val Phe Val Ala Met
1               5                   10                  15 gta gcg gcg gct ctc ggc ggc cac cct ctg ctg gga gtg agc gcc acc      96
Val Ala Ala Ala Leu Gly Gly His Pro Leu Leu Gly Val Ser Ala Thr
            20                  25                  30 ttg aac tcg gtt ctc aat tcc aac gct atc aag aac ctg ccc cca ccg     144
Leu Asn Ser Val Leu Asn Ser Asn Ala Ile Lys Asn Leu Pro Pro Pro
        35                  40                  45 ctg ggc ggc gct gcg ggg cac cca ggc tct gca gtc agc gcc gcg ccg     192
Leu Gly Gly Ala Ala Gly His Pro Gly Ser Ala Val Ser Ala Ala Pro
    50                  55                  60 gga atc ctg tac ccg ggc ggg aat aag tac cag acc att gac aac tac     240
Gly Ile Leu Tyr Pro Gly Gly Asn Lys Tyr Gln Thr Ile Asp Asn Tyr
65                  70                  75                  80 cag ccg tac ccg tgc gca gag gac gag gag tgc gga act gat gag tac     288
Gln Pro Tyr Pro Cys Ala Glu Asp Glu Glu Cys Gly Thr Asp Glu Tyr
                85                  90                  95 tgc gct agt ccc acc cgc gga ggg gac gcg ggc gtg caa atc tgt ctc     336
Cys Ala Ser Pro Thr Arg Gly Gly Asp Ala Gly Val Gln Ile Cys Leu
            100                 105                 110 gcc tgc agg aag cgc cga aaa cgc tgc atg cgt cac gct atg tgc tgc     384
Ala Cys Arg Lys Arg Arg Lys Arg Cys Met Arg His Ala Met Cys Cys
        115                 120                 125 ccc ggg aat tac tgc aaa aat gga ata tgt gtg tct tct gat caa aat     432
Pro Gly Asn Tyr Cys Lys Asn Gly Ile Cys Val Ser Ser Asp Gln Asn
    130                 135                 140 cat ttc cga gga gaa att gag gaa acc atc act gaa agc ttt ggt aat     480
His Phe Arg Gly Glu Ile Glu Glu Thr Ile Thr Glu Ser Phe Gly Asn
145                 150                 155                 160 gat cat agc acc ttg gat ggg tat tcc aga aga acc acc ttg tct tca     528
Asp His Ser Thr Leu Asp Gly Tyr Ser Arg Arg Thr Thr Leu Ser Ser
                165                 170                 175 aaa atg tat cac acc aaa gga caa gaa ggt tct gtt tgt ctc cgg tca     576
Lys Met Tyr His Thr Lys Gly Gln Glu Gly Ser Val Cys Leu Arg Ser
            180                 185                 190 tca gac tgt gcc tca gga ttg tgt tgt gct aga cac ttc tgg tcc aag     624
Ser Asp Cys Ala Ser Gly Leu Cys Cys Ala Arg His Phe Trp Ser Lys
        195                 200                 205 atc tgt aaa cct gtc ctg aaa gaa ggt caa gtg tgt acc aag cat agg     672
Ile Cys Lys Pro Val Leu Lys Glu Gly Gln Val Cys Thr Lys His Arg
    210                 215                 220 aga aaa ggc tct cat gga cta gaa ata ttc cag cgt tgt tac tgt gga     720
Arg Lys Gly Ser His Gly Leu Glu Ile Phe Gln Arg Cys Tyr Cys Gly
225                 230                 235                 240 gaa ggt ctg tct tgc cgg ata cag aaa gat cac cat caa gcc agt aat     768
Glu Gly Leu Ser Cys Arg Ile Gln Lys Asp His His Gln Ala Ser Asn
                245                 250                 255 tct tct agg ctt cac act tgt cag aga cac taa                         801
Ser Ser Arg Leu His Thr Cys Gln Arg His
            260                 265

<210> SEQ ID NO 2
<211> LENGTH: 266
<212> TYPE: PRT
<213> ORGANISM: Homo sapiens

<400> SEQUENCE: 2
```

```
Met Met Ala Leu Gly Ala Ala Gly Ala Thr Arg Val Phe Val Ala Met
1               5                   10                  15

Val Ala Ala Ala Leu Gly Gly His Pro Leu Leu Gly Val Ser Ala Thr
            20                  25                  30

Leu Asn Ser Val Leu Asn Ser Asn Ala Ile Lys Asn Leu Pro Pro
        35                  40                  45

Leu Gly Gly Ala Ala Gly His Pro Gly Ser Ala Val Ser Ala Ala Pro
50                  55                  60

Gly Ile Leu Tyr Pro Gly Gly Asn Lys Tyr Gln Thr Ile Asp Asn Tyr
65                  70                  75                  80

Gln Pro Tyr Pro Cys Ala Glu Asp Glu Glu Cys Gly Thr Asp Glu Tyr
                85                  90                  95

Cys Ala Ser Pro Thr Arg Gly Gly Asp Ala Gly Val Gln Ile Cys Leu
                100                 105                 110

Ala Cys Arg Lys Arg Lys Arg Cys Met Arg His Ala Met Cys Cys
        115                 120                 125

Pro Gly Asn Tyr Cys Lys Asn Gly Ile Cys Val Ser Ser Asp Gln Asn
130                 135                 140

His Phe Arg Gly Glu Ile Glu Glu Thr Ile Thr Glu Ser Phe Gly Asn
145                 150                 155                 160

Asp His Ser Thr Leu Asp Gly Tyr Ser Arg Arg Thr Thr Leu Ser Ser
                165                 170                 175

Lys Met Tyr His Thr Lys Gly Gln Glu Gly Ser Val Cys Leu Arg Ser
                180                 185                 190

Ser Asp Cys Ala Ser Gly Leu Cys Cys Ala Arg His Phe Trp Ser Lys
        195                 200                 205

Ile Cys Lys Pro Val Leu Lys Glu Gly Gln Val Cys Thr Lys His Arg
        210                 215                 220

Arg Lys Gly Ser His Gly Leu Glu Ile Phe Gln Arg Cys Tyr Cys Gly
225                 230                 235                 240

Glu Gly Leu Ser Cys Arg Ile Gln Lys Asp His His Gln Ala Ser Asn
                245                 250                 255

Ser Ser Arg Leu His Thr Cys Gln Arg His
        260                 265

<210> SEQ ID NO 3
<211> LENGTH: 819
<212> TYPE: DNA
<213> ORGANISM: Mouse
<220> FEATURE:
<221> NAME/KEY: CDS
<222> LOCATION: (1)..(819)

<400> SEQUENCE: 3 atg atg gtt gtg tgt gca ccg gca gct gtc cgg ttc ttg gcc gtg ttt       48
Met Met Val Val Cys Ala Pro Ala Ala Val Arg Phe Leu Ala Val Phe
1               5                   10                  15 aca atg atg gct ctc tgc agc ctc cct ctg cta gga gcc agt gcc acc       96
Thr Met Met Ala Leu Cys Ser Leu Pro Leu Leu Gly Ala Ser Ala Thr
            20                  25                  30 ttg aac tca gtt ctc atc aat tcc aac gcg atc aag aac ctg ccc ca       144
Leu Asn Ser Val Leu Ile Asn Ser Asn Ala Ile Lys Asn Leu Pro Pro
        35                  40                  45 ccg ctg ggt ggt gct ggg ggg cag ccg ggc tct gct gtc agt gtg gcg      192
Pro Leu Gly Gly Ala Gly Gly Gln Pro Gly Ser Ala Val Ser Val Ala
50                  55                  60 ccg gga gtt ctc tat gag ggc ggg aac aag tac cag act ctt gac aac      240
Pro Gly Val Leu Tyr Glu Gly Gly Asn Lys Tyr Gln Thr Leu Asp Asn
```

```
Pro Gly Val Leu Tyr Glu Gly Gly Asn Lys Tyr Gln Thr Leu Asp Asn
65                  70                  75                  80 tac cag ccc tac cct tgc gct gaa gat gag gag tgc ggc tct gac gag     288
Tyr Gln Pro Tyr Pro Cys Ala Glu Asp Glu Glu Cys Gly Ser Asp Glu
                85                  90                  95 tac tgc tcc agc ccc agc cgc ggg gca gcc ggc gtc gga ggt gta cag     336
Tyr Cys Ser Ser Pro Ser Arg Gly Ala Ala Gly Val Gly Gly Val Gln
                100                 105                 110 atc tgt ctg gct tgc cga aag cgc agg aag cgc tgc atg acg cac gct     384
Ile Cys Leu Ala Cys Arg Lys Arg Arg Lys Arg Cys Met Thr His Ala
            115                 120                 125 atg tgc tgc ccc ggg aac tac tgc aaa aat gga ata tgc atg ccc tct     432
Met Cys Cys Pro Gly Asn Tyr Cys Lys Asn Gly Ile Cys Met Pro Ser
130                 135                 140 gac cac agc cat ttt cct cga ggg gaa att gag gaa agc atc att gaa     480
Asp His Ser His Phe Pro Arg Gly Glu Ile Glu Glu Ser Ile Ile Glu
145                 150                 155                 160 aac ctt ggt aat gac cac aac gcc gcc gcg ggg gat gga tat ccc aga     528
Asn Leu Gly Asn Asp His Asn Ala Ala Ala Gly Asp Gly Tyr Pro Arg
                165                 170                 175 aga acc aca ctg act tca aaa ata tat cac acc aaa gga caa gaa ggc     576
Arg Thr Thr Leu Thr Ser Lys Ile Tyr His Thr Lys Gly Gln Glu Gly
            180                 185                 190 tcc gtc tgc ctc cga tca tca gac tgt gcc gca ggg ctg tgt tgt gca     624
Ser Val Cys Leu Arg Ser Ser Asp Cys Ala Ala Gly Leu Cys Cys Ala
            195                 200                 205 aga cac ttc tgg tcc aag atc tgt aaa cct gtc ctt aaa gaa ggt cag     672
Arg His Phe Trp Ser Lys Ile Cys Lys Pro Val Leu Lys Glu Gly Gln
210                 215                 220 gtg tgc acc aag cac aaa cgg aaa ggc tcc cac ggg ctg gag ata ttc     720
Val Cys Thr Lys His Lys Arg Lys Gly Ser His Gly Leu Glu Ile Phe
225                 230                 235                 240 cag cgc tgt tac tgc ggg gaa ggc ctg gct tgc agg ata cag aaa gat     768
Gln Arg Cys Tyr Cys Gly Glu Gly Leu Ala Cys Arg Ile Gln Lys Asp
                245                 250                 255 cac cat caa gcc agc aat tct tct agg ctc cac acc tgc cag aga cac     816
His His Gln Ala Ser Asn Ser Ser Arg Leu His Thr Cys Gln Arg His
            260                 265                 270 taa                                                                 819

<210> SEQ ID NO 4
<211> LENGTH: 272
<212> TYPE: PRT
<213> ORGANISM: Mouse

<400> SEQUENCE: 4

Met Met Val Val Cys Ala Pro Ala Ala Val Arg Phe Leu Ala Val Phe
1               5                   10                  15

Thr Met Met Ala Leu Cys Ser Leu Pro Leu Leu Gly Ala Ser Ala Thr
                20                  25                  30

Leu Asn Ser Val Leu Ile Asn Ser Asn Ala Ile Lys Asn Leu Pro Pro
            35                  40                  45

Pro Leu Gly Gly Ala Gly Gly Gln Pro Gly Ser Ala Val Ser Val Ala
50                  55                  60

Pro Gly Val Leu Tyr Glu Gly Gly Asn Lys Tyr Gln Thr Leu Asp Asn
65                  70                  75                  80

Tyr Gln Pro Tyr Pro Cys Ala Glu Asp Glu Glu Cys Gly Ser Asp Glu
                85                  90                  95

Tyr Cys Ser Ser Pro Ser Arg Gly Ala Ala Gly Val Gly Gly Val Gln
```

-continued

```
                    100                 105                 110
Ile Cys Leu Ala Cys Arg Lys Arg Lys Arg Cys Met Thr His Ala
            115                 120                 125
Met Cys Cys Pro Gly Asn Tyr Cys Lys Asn Gly Ile Cys Met Pro Ser
        130                 135                 140
Asp His Ser His Phe Pro Arg Gly Glu Ile Glu Ser Ile Ile Glu
145                 150                 155                 160
Asn Leu Gly Asn Asp His Asn Ala Ala Ala Gly Asp Gly Tyr Pro Arg
                165                 170                 175
Arg Thr Thr Leu Thr Ser Lys Ile Tyr His Thr Lys Gly Gln Glu Gly
            180                 185                 190
Ser Val Cys Leu Arg Ser Ser Asp Cys Ala Ala Gly Leu Cys Cys Ala
            195                 200                 205
Arg His Phe Trp Ser Lys Ile Cys Lys Pro Val Leu Lys Glu Gly Gln
        210                 215                 220
Val Cys Thr Lys His Lys Arg Lys Gly Ser His Gly Leu Glu Ile Phe
225                 230                 235                 240
Gln Arg Cys Tyr Cys Gly Glu Gly Leu Ala Cys Arg Ile Gln Lys Asp
                245                 250                 255
His His Gln Ala Ser Asn Ser Ser Arg Leu His Thr Cys Gln Arg His
            260                 265                 270

<210> SEQ ID NO 5
<211> LENGTH: 4848
<212> TYPE: DNA
<213> ORGANISM: Homo sapiens
<220> FEATURE:
<221> NAME/KEY: CDS
<222> LOCATION: (1)..(4848)

<400> SEQUENCE: 5 atg gag gca gcg ccg ccc ggg ccg ccg tgg ccg ctg ctg ctg ctg ctg     48
Met Glu Ala Ala Pro Pro Gly Pro Pro Trp Pro Leu Leu Leu Leu Leu
1               5                   10                  15 ctg ctg ctg ctg gcg ctg tgc ggc tgc ccg gcc ccc gcc gcg gcc tcg     96
Leu Leu Leu Leu Ala Leu Cys Gly Cys Pro Ala Pro Ala Ala Ala Ser
                20                  25                  30 ccg ctc ctg cta ttt gcc aac cgc cgg gac gta cgg ctg gtg gac gcc    144
Pro Leu Leu Leu Phe Ala Asn Arg Arg Asp Val Arg Leu Val Asp Ala
            35                  40                  45 ggc gga gtc aag ctg gag tcc acc atc gtg gtc agc ggc ctg gag gat    192
Gly Gly Val Lys Leu Glu Ser Thr Ile Val Val Ser Gly Leu Glu Asp
        50                  55                  60 gcg gcc gca gtg gac ttc cag ttt tcc aag gga gcc gtg tac tgg aca    240
Ala Ala Ala Val Asp Phe Gln Phe Ser Lys Gly Ala Val Tyr Trp Thr
65                  70                  75                  80 gac gtg agc gag gag gcc atc aag cag acc tac ctg aac cag acg ggg    288
Asp Val Ser Glu Glu Ala Ile Lys Gln Thr Tyr Leu Asn Gln Thr Gly
                85                  90                  95 gcc gcc gtg cag aac gtg gtc atc tcc ggc ctg gtc tct ccc gac ggc    336
Ala Ala Val Gln Asn Val Val Ile Ser Gly Leu Val Ser Pro Asp Gly
                100                 105                 110 ctc gcc tgc gac tgg gtg ggc aag aag ctg tac tgg acg gac tca gag    384
Leu Ala Cys Asp Trp Val Gly Lys Lys Leu Tyr Trp Thr Asp Ser Glu
            115                 120                 125 acc aac cgc atc gag gtg gcc aac ctc aat ggc aca tcc cgg aag gtg    432
Thr Asn Arg Ile Glu Val Ala Asn Leu Asn Gly Thr Ser Arg Lys Val
        130                 135                 140 ctc ttc tgg cag gac ctt gac cag ccg agg gcc atc gcc ttg gac ccc    480
```

-continued

```
                Leu Phe Trp Gln Asp Leu Asp Gln Pro Arg Ala Ile Ala Leu Asp Pro
                145                 150                 155                 160 gct cac ggg tac atg tac tgg aca gac tgg ggt gag acg ccc cgg att              528
Ala His Gly Tyr Met Tyr Trp Thr Asp Trp Gly Glu Thr Pro Arg Ile
                165                 170                 175 gag cgg gca ggg atg gat ggc agc acc cgg aag atc att gtg gac tcg              576
Glu Arg Ala Gly Met Asp Gly Ser Thr Arg Lys Ile Ile Val Asp Ser
            180                 185                 190 gac att tac tgg ccc aat gga ctg acc atc gac ctg gag gag cag aag              624
Asp Ile Tyr Trp Pro Asn Gly Leu Thr Ile Asp Leu Glu Glu Gln Lys
        195                 200                 205 ctc tac tgg gct gac gcc aag ctc agc ttc atc cac cgt gcc aac ctg              672
Leu Tyr Trp Ala Asp Ala Lys Leu Ser Phe Ile His Arg Ala Asn Leu
    210                 215                 220 gac ggc tcg ttc cgg cag aag gtg gtg gag ggc agc ctg acg cac ccc              720
Asp Gly Ser Phe Arg Gln Lys Val Val Glu Gly Ser Leu Thr His Pro
225                 230                 235                 240 ttc gcc ctg acg ctc tcc ggg gac act ctg tac tgg aca gac tgg cag              768
Phe Ala Leu Thr Leu Ser Gly Asp Thr Leu Tyr Trp Thr Asp Trp Gln
                245                 250                 255 acc cgc tcc atc cat gcc tgc aac aag cgc act ggg ggg aag agg aag              816
Thr Arg Ser Ile His Ala Cys Asn Lys Arg Thr Gly Gly Lys Arg Lys
                260                 265                 270 gag atc ctg agt gcc ctc tac tca ccc atg gac atc cag gtg ctg agc              864
Glu Ile Leu Ser Ala Leu Tyr Ser Pro Met Asp Ile Gln Val Leu Ser
            275                 280                 285 cag gag cgg cag cct ttc ttc cac act cgc tgt gag gag gac aat ggc              912
Gln Glu Arg Gln Pro Phe Phe His Thr Arg Cys Glu Glu Asp Asn Gly
        290                 295                 300 ggc tgc tcc cac ctg tgc ctg ctg tcc cca agc gag cct ttc tac aca              960
Gly Cys Ser His Leu Cys Leu Leu Ser Pro Ser Glu Pro Phe Tyr Thr
305                 310                 315                 320 tgc gcc tgc ccc acg ggt gtg cag ctg cag gac aac ggc agg acg tgt             1008
Cys Ala Cys Pro Thr Gly Val Gln Leu Gln Asp Asn Gly Arg Thr Cys
                325                 330                 335 aag gca gga gcc gag gag gtg ctg ctg ctg gcc cgg cgg acg gac cta             1056
Lys Ala Gly Ala Glu Glu Val Leu Leu Leu Ala Arg Arg Thr Asp Leu
                340                 345                 350 cgg agg atc tcg ctg gac acg ccg gac ttt acc gac atc gtg ctg cag             1104
Arg Arg Ile Ser Leu Asp Thr Pro Asp Phe Thr Asp Ile Val Leu Gln
            355                 360                 365 gtg gac gac atc cgg cac gcc att gcc atc gac tac gac ccg cta gag             1152
Val Asp Asp Ile Arg His Ala Ile Ala Ile Asp Tyr Asp Pro Leu Glu
        370                 375                 380 ggc tat gtc tac tgg aca gat gac gag gtg cgg gcc atc cgc agg gcg             1200
Gly Tyr Val Tyr Trp Thr Asp Asp Glu Val Arg Ala Ile Arg Arg Ala
385                 390                 395                 400 tac ctg gac ggg tct ggg gcg cag acg ctg gtc aac acc gag atc aac             1248
Tyr Leu Asp Gly Ser Gly Ala Gln Thr Leu Val Asn Thr Glu Ile Asn
                405                 410                 415 gac ccc gat ggc atc gcg gtc gac tgg gtg gcc cga aac ctc tac tgg             1296
Asp Pro Asp Gly Ile Ala Val Asp Trp Val Ala Arg Asn Leu Tyr Trp
                420                 425                 430 acc gac acg ggc acg gac cgc atc gag gtg acg cgc ctc aac ggc acc             1344
Thr Asp Thr Gly Thr Asp Arg Ile Glu Val Thr Arg Leu Asn Gly Thr
            435                 440                 445 tcc cgc aag atc ctg gtg tcg gag gac ctg gac gag ccc cga gcc atc             1392
Ser Arg Lys Ile Leu Val Ser Glu Asp Leu Asp Glu Pro Arg Ala Ile
        450                 455                 460 gca ctg cac ccc gtg atg ggc ctc atg tac tgg aca gac tgg gga gag             1440
```

|     |     |     |     |     |     |     |     |     |     |     |     |     |     |      |
|-----|-----|-----|-----|-----|-----|-----|-----|-----|-----|-----|-----|-----|-----|------|
| Ala | Leu | His | Pro | Val | Met | Gly | Leu | Met | Tyr | Trp | Thr | Asp | Trp | Gly Glu |
| 465 |     |     |     |     | 470 |     |     |     | 475 |     |     |     |     | 480 |

| aac | cct | aaa | atc | gag | tgt | gcc | aac | ttg | gat | ggg | cag | gag | cgg | cgt gtg | 1488 |
|-----|-----|-----|-----|-----|-----|-----|-----|-----|-----|-----|-----|-----|-----|---------|------|
| Asn | Pro | Lys | Ile | Glu | Cys | Ala | Asn | Leu | Asp | Gly | Gln | Glu | Arg | Arg Val |      |
|     |     |     |     | 485 |     |     |     |     | 490 |     |     |     | 495 |         |      |

| ctg | gtc | aat | gcc | tcc | ctc | ggg | tgg | ccc | aac | ggc | ctg | gcc | ctg | gac ctg | 1536 |
| Leu | Val | Asn | Ala | Ser | Leu | Gly | Trp | Pro | Asn | Gly | Leu | Ala | Leu | Asp Leu |      |
|     |     | 500 |     |     |     |     | 505 |     |     |     |     | 510 |     |         |      |

| cag | gag | ggg | aag | ctc | tac | tgg | gga | gac | gcc | aag | aca | gac | aag | atc gag | 1584 |
| Gln | Glu | Gly | Lys | Leu | Tyr | Trp | Gly | Asp | Ala | Lys | Thr | Asp | Lys | Ile Glu |      |
|     |     | 515 |     |     |     |     | 520 |     |     |     | 525 |     |     |         |      |

| gtg | atc | aat | gtt | gat | ggg | acg | aag | agg | cgg | acc | ctc | ctg | gag | gac aag | 1632 |
| Val | Ile | Asn | Val | Asp | Gly | Thr | Lys | Arg | Arg | Thr | Leu | Leu | Glu | Asp Lys |      |
| 530 |     |     |     |     | 535 |     |     |     |     | 540 |     |     |     |         |      |

| ctc | ccg | cac | att | ttc | ggg | ttc | acg | ctg | ctg | ggg | gac | ttc | atc | tac tgg | 1680 |
| Leu | Pro | His | Ile | Phe | Gly | Phe | Thr | Leu | Leu | Gly | Asp | Phe | Ile | Tyr Trp |      |
| 545 |     |     |     |     | 550 |     |     |     |     | 555 |     |     |     | 560     |      |

| act | gac | tgg | cag | cgc | cgc | agc | atc | gag | cgg | gtg | cac | aag | gtc | aag gcc | 1728 |
| Thr | Asp | Trp | Gln | Arg | Arg | Ser | Ile | Glu | Arg | Val | His | Lys | Val | Lys Ala |      |
|     |     |     |     | 565 |     |     |     |     | 570 |     |     |     |     | 575     |      |

| agc | cgg | gac | gtc | atc | att | gac | cag | ctg | ccc | gac | ctg | atg | ggg | ctc aaa | 1776 |
| Ser | Arg | Asp | Val | Ile | Ile | Asp | Gln | Leu | Pro | Asp | Leu | Met | Gly | Leu Lys |      |
|     |     |     | 580 |     |     |     |     | 585 |     |     |     |     | 590 |         |      |

| gct | gtg | aat | gtg | gcc | aag | gtc | gtc | gga | acc | aac | ccg | tgt | gcg | gac agg | 1824 |
| Ala | Val | Asn | Val | Ala | Lys | Val | Val | Gly | Thr | Asn | Pro | Cys | Ala | Asp Arg |      |
|     | 595 |     |     |     |     | 600 |     |     |     |     | 605 |     |     |         |      |

| aac | ggg | ggg | tgc | agc | cac | ctg | tgc | ttc | ttc | aca | ccc | cac | gca | acc cgg | 1872 |
| Asn | Gly | Gly | Cys | Ser | His | Leu | Cys | Phe | Phe | Thr | Pro | His | Ala | Thr Arg |      |
|     | 610 |     |     |     |     | 615 |     |     |     |     | 620 |     |     |         |      |

| tgt | ggc | tgc | ccc | atc | ggc | ctg | gag | ctg | ctg | agt | gac | atg | aag | acc tgc | 1920 |
| Cys | Gly | Cys | Pro | Ile | Gly | Leu | Glu | Leu | Leu | Ser | Asp | Met | Lys | Thr Cys |      |
| 625 |     |     |     | 630 |     |     |     |     | 635 |     |     |     |     | 640     |      |

| atc | gtg | cct | gag | gcc | ttc | ttg | gtc | ttc | acc | agc | aga | gcc | gcc | atc cac | 1968 |
| Ile | Val | Pro | Glu | Ala | Phe | Leu | Val | Phe | Thr | Ser | Arg | Ala | Ala | Ile His |      |
|     |     |     |     | 645 |     |     |     |     | 650 |     |     |     |     | 655     |      |

| agg | atc | tcc | ctc | gag | acc | aat | aac | aac | gac | gtg | gcc | atc | ccg | ctc acg | 2016 |
| Arg | Ile | Ser | Leu | Glu | Thr | Asn | Asn | Asn | Asp | Val | Ala | Ile | Pro | Leu Thr |      |
|     |     |     | 660 |     |     |     |     | 665 |     |     |     |     | 670 |         |      |

| ggc | gtc | aag | gag | gcc | tca | gcc | ctg | gac | ttt | gat | gtg | tcc | aac | aac cac | 2064 |
| Gly | Val | Lys | Glu | Ala | Ser | Ala | Leu | Asp | Phe | Asp | Val | Ser | Asn | Asn His |      |
|     |     | 675 |     |     |     |     | 680 |     |     |     |     | 685 |     |         |      |

| atc | tac | tgg | aca | gac | gtc | agc | ctg | aag | acc | atc | agc | cgc | gcc | ttc atg | 2112 |
| Ile | Tyr | Trp | Thr | Asp | Val | Ser | Leu | Lys | Thr | Ile | Ser | Arg | Ala | Phe Met |      |
|     | 690 |     |     |     |     | 695 |     |     |     |     | 700 |     |     |         |      |

| aac | ggg | agc | tcg | gtg | gag | cac | gtg | gtg | gag | ttt | ggc | ctt | gac | tac ccc | 2160 |
| Asn | Gly | Ser | Ser | Val | Glu | His | Val | Val | Glu | Phe | Gly | Leu | Asp | Tyr Pro |      |
| 705 |     |     |     |     | 710 |     |     |     |     | 715 |     |     |     | 720     |      |

| gag | ggc | atg | gcc | gtt | gac | tgg | atg | ggc | aag | aac | ctc | tac | tgg | gcc gac | 2208 |
| Glu | Gly | Met | Ala | Val | Asp | Trp | Met | Gly | Lys | Asn | Leu | Tyr | Trp | Ala Asp |      |
|     |     |     |     | 725 |     |     |     |     | 730 |     |     |     |     | 735     |      |

| act | ggg | acc | aac | aga | atc | gaa | gtg | gcg | cgg | ctg | gac | ggg | cag | ttc cgg | 2256 |
| Thr | Gly | Thr | Asn | Arg | Ile | Glu | Val | Ala | Arg | Leu | Asp | Gly | Gln | Phe Arg |      |
|     |     |     | 740 |     |     |     |     | 745 |     |     |     |     | 750 |         |      |

| caa | gtc | ctc | gtg | tgg | agg | gac | ttg | gac | aac | ccg | agg | tcg | ctg | gcc ctg | 2304 |
| Gln | Val | Leu | Val | Trp | Arg | Asp | Leu | Asp | Asn | Pro | Arg | Ser | Leu | Ala Leu |      |
|     |     |     | 755 |     |     |     |     | 760 |     |     |     |     | 765 |         |      |

| gat | ccc | acc | aag | ggc | tac | atc | tac | tgg | acc | gag | tgg | ggc | ggc | aag ccg | 2352 |
| Asp | Pro | Thr | Lys | Gly | Tyr | Ile | Tyr | Trp | Thr | Glu | Trp | Gly | Gly | Lys Pro |      |
| 770 |     |     |     |     | 775 |     |     |     |     | 780 |     |     |     |         |      |

| agg | atc | gtg | cgg | gcc | ttc | atg | gac | ggg | acc | aac | tgc | atg | acg | ctg gtg | 2400 |

```
            Arg Ile Val Arg Ala Phe Met Asp Gly Thr Asn Cys Met Thr Leu Val
            785                 790                 795                 800 gac aag gtg ggc cgg gcc aac gac ctc acc att gac tac gct gac cag      2448
Asp Lys Val Gly Arg Ala Asn Asp Leu Thr Ile Asp Tyr Ala Asp Gln
            805                 810                 815 cgc ctc tac tgg acc gac ctg gac acc aac atg atc gag tcg tcc aac      2496
Arg Leu Tyr Trp Thr Asp Leu Asp Thr Asn Met Ile Glu Ser Ser Asn
            820                 825                 830 atg ctg ggt cag gag cgg gtc gtg att gcc gac gat ctc ccg cac ccg      2544
Met Leu Gly Gln Glu Arg Val Val Ile Ala Asp Asp Leu Pro His Pro
            835                 840                 845 ttc ggt ctg acg cag tac agc gat tat atc tac tgg aca gac tgg aat      2592
Phe Gly Leu Thr Gln Tyr Ser Asp Tyr Ile Tyr Trp Thr Asp Trp Asn
        850                 855                 860 ctg cac agc att gag cgg gcc gac aag act agc ggc cgg aac cgc acc      2640
Leu His Ser Ile Glu Arg Ala Asp Lys Thr Ser Gly Arg Asn Arg Thr
865                 870                 875                 880 ctc atc cag ggc cac ctg gac ttc gtg atg gac atc ctg gtg ttc cac      2688
Leu Ile Gln Gly His Leu Asp Phe Val Met Asp Ile Leu Val Phe His
                885                 890                 895 tcc tcc cgc cag gat ggc ctc aat gac tgt atg cac aac aac ggg cag      2736
Ser Ser Arg Gln Asp Gly Leu Asn Asp Cys Met His Asn Asn Gly Gln
            900                 905                 910 tgt ggg cag ctg tgc ctt gcc atc ccc ggc ggc cac cgc tgc ggc tgc      2784
Cys Gly Gln Leu Cys Leu Ala Ile Pro Gly Gly His Arg Cys Gly Cys
            915                 920                 925 gcc tca cac tac acc ctg gac ccc agc agc cgc aac tgc agc ccg ccc      2832
Ala Ser His Tyr Thr Leu Asp Pro Ser Ser Arg Asn Cys Ser Pro Pro
        930                 935                 940 acc acc ttc ttg ctg ttc agc cag aaa tct gcc atc agt cgg atg atc      2880
Thr Thr Phe Leu Leu Phe Ser Gln Lys Ser Ala Ile Ser Arg Met Ile
945                 950                 955                 960 ccg gac gac cag cac agc ccg gat ctc atc ctg ccc ctg cat gga ctg      2928
Pro Asp Asp Gln His Ser Pro Asp Leu Ile Leu Pro Leu His Gly Leu
                965                 970                 975 agg aac gtc aaa gcc atc gac tat gac cca ctg gac aag ttc atc tac      2976
Arg Asn Val Lys Ala Ile Asp Tyr Asp Pro Leu Asp Lys Phe Ile Tyr
            980                 985                 990 tgg gtg gat ggg cgc cag aac atc  aag cga gcc aag gac  gac ggg acc    3024
Trp Val Asp Gly Arg Gln Asn Ile  Lys Arg Ala Lys Asp  Asp Gly Thr
                995                 1000                1005 cag ccc ttt gtt ttg acc tct  ctg agc caa ggc caa  aac cca gac        3069
Gln Pro Phe Val Leu Thr Ser  Leu Ser Gln Gly Gln  Asn Pro Asp
    1010                1015                1020 agg cag ccc cac gac ctc agc  atc gac atc tac agc  cgg aca ctg        3114
Arg Gln Pro His Asp Leu Ser  Ile Asp Ile Tyr Ser  Arg Thr Leu
    1025                1030                1035 ttc tgg acg tgc gag gcc acc  aat acc atc aac gtc  cac agg ctg        3159
Phe Trp Thr Cys Glu Ala Thr  Asn Thr Ile Asn Val  His Arg Leu
    1040                1045                1050 agc ggg gaa gcc atg ggg gtg  gtg ctg cgt ggg gac  cgc gac aag        3204
Ser Gly Glu Ala Met Gly Val  Val Leu Arg Gly Asp  Arg Asp Lys
    1055                1060                1065 ccc agg gcc atc gtc gtc aac  gcg gag cga ggg tac  ctg tac ttc        3249
Pro Arg Ala Ile Val Val Asn  Ala Glu Arg Gly Tyr  Leu Tyr Phe
    1070                1075                1080 acc aac atg cag gac cgg gca  gcc aag atc gaa cgc  gca gcc ctg        3294
Thr Asn Met Gln Asp Arg Ala  Ala Lys Ile Glu Arg  Ala Ala Leu
    1085                1090                1095 gac ggc acc gag cgc gag gtc  ctc ttc acc acc ggc  ctc atc cgc        3339
```

|     |     |     |     |     |     |     |     |     |     |     |
| --- | --- | --- | --- | --- | --- | --- | --- | --- | --- | --- |
| Asp | Gly | Thr | Glu | Arg | Glu | Val | Leu | Phe | Thr | Thr | Gly | Leu | Ile | Arg |
|     |     |     |     | 1100 |     |     |     | 1105 |     |     |     | 1110 |     |     |

| cct | gtg | gcc | ctg | gtg | gta | gac | aac | aca | ctg | ggc | aag | ctg | ttc | tgg |     | 3384 |
| Pro | Val | Ala | Leu | Val | Val | Asp | Asn | Thr | Leu | Gly | Lys | Leu | Phe | Trp |     |      |
|     | 1115 |     |     |     | 1120 |     |     |     | 1125 |     |     |     |     |     |     |      |

| gtg | gac | gcg | gac | ctg | aag | cgc | att | gag | agc | tgt | gac | ctg | tca | ggg |     | 3429 |
| Val | Asp | Ala | Asp | Leu | Lys | Arg | Ile | Glu | Ser | Cys | Asp | Leu | Ser | Gly |     |      |
| 1130 |     |     |     | 1135 |     |     |     | 1140 |     |     |     |     |     |     |     |      |

| gcc | aac | cgc | ctg | acc | ctg | gag | gac | gcc | aac | atc | gtg | cag | cct | ctg |     | 3474 |
| Ala | Asn | Arg | Leu | Thr | Leu | Glu | Asp | Ala | Asn | Ile | Val | Gln | Pro | Leu |     |      |
| 1145 |     |     |     | 1150 |     |     |     | 1155 |     |     |     |     |     |     |     |      |

| ggc | ctg | acc | atc | ctt | ggc | aag | cat | ctc | tac | tgg | atc | gac | cgc | cag |     | 3519 |
| Gly | Leu | Thr | Ile | Leu | Gly | Lys | His | Leu | Tyr | Trp | Ile | Asp | Arg | Gln |     |      |
| 1160 |     |     |     | 1165 |     |     |     | 1170 |     |     |     |     |     |     |     |      |

| cag | cag | atg | atc | gag | cgt | gtg | gag | aag | acc | acc | ggg | gac | aag | cgg |     | 3564 |
| Gln | Gln | Met | Ile | Glu | Arg | Val | Glu | Lys | Thr | Thr | Gly | Asp | Lys | Arg |     |      |
| 1175 |     |     |     | 1180 |     |     |     | 1185 |     |     |     |     |     |     |     |      |

| act | cgc | atc | cag | ggc | cgt | gtc | gcc | cac | ctc | act | ggc | atc | cat | gca |     | 3609 |
| Thr | Arg | Ile | Gln | Gly | Arg | Val | Ala | His | Leu | Thr | Gly | Ile | His | Ala |     |      |
| 1190 |     |     |     | 1195 |     |     |     | 1200 |     |     |     |     |     |     |     |      |

| gtg | gag | gaa | gtc | agc | ctg | gag | gag | ttc | tca | gcc | cac | cca | tgt | gcc |     | 3654 |
| Val | Glu | Glu | Val | Ser | Leu | Glu | Glu | Phe | Ser | Ala | His | Pro | Cys | Ala |     |      |
| 1205 |     |     |     | 1210 |     |     |     | 1215 |     |     |     |     |     |     |     |      |

| cgt | gac | aat | ggt | ggc | tgc | tcc | cac | atc | tgt | att | gcc | aag | ggt | gat |     | 3699 |
| Arg | Asp | Asn | Gly | Gly | Cys | Ser | His | Ile | Cys | Ile | Ala | Lys | Gly | Asp |     |      |
| 1220 |     |     |     | 1225 |     |     |     | 1230 |     |     |     |     |     |     |     |      |

| ggg | aca | cca | cgg | tgc | tca | tgc | cca | gtc | cac | ctc | gtc | ctc | ctg | cag |     | 3744 |
| Gly | Thr | Pro | Arg | Cys | Ser | Cys | Pro | Val | His | Leu | Val | Leu | Leu | Gln |     |      |
| 1235 |     |     |     | 1240 |     |     |     | 1245 |     |     |     |     |     |     |     |      |

| aac | ctg | ctg | acc | tgt | gga | gag | ccg | ccc | acc | tgc | tcc | ccg | gac | cag |     | 3789 |
| Asn | Leu | Leu | Thr | Cys | Gly | Glu | Pro | Pro | Thr | Cys | Ser | Pro | Asp | Gln |     |      |
| 1250 |     |     |     | 1255 |     |     |     | 1260 |     |     |     |     |     |     |     |      |

| ttt | gca | tgt | gcc | aca | ggg | gag | atc | gac | tgt | atc | ccc | ggg | gcc | tgg |     | 3834 |
| Phe | Ala | Cys | Ala | Thr | Gly | Glu | Ile | Asp | Cys | Ile | Pro | Gly | Ala | Trp |     |      |
| 1265 |     |     |     | 1270 |     |     |     | 1275 |     |     |     |     |     |     |     |      |

| cgc | tgt | gac | ggc | ttt | ccc | gag | tgc | gat | gac | cag | agc | gac | gag | gag |     | 3879 |
| Arg | Cys | Asp | Gly | Phe | Pro | Glu | Cys | Asp | Asp | Gln | Ser | Asp | Glu | Glu |     |      |
| 1280 |     |     |     | 1285 |     |     |     | 1290 |     |     |     |     |     |     |     |      |

| ggc | tgc | ccc | gtg | tgc | tcc | gcc | gcc | cag | ttc | ccc | tgc | gcg | cgg | ggt |     | 3924 |
| Gly | Cys | Pro | Val | Cys | Ser | Ala | Ala | Gln | Phe | Pro | Cys | Ala | Arg | Gly |     |      |
| 1295 |     |     |     | 1300 |     |     |     | 1305 |     |     |     |     |     |     |     |      |

| cag | tgt | gtg | gac | ctg | cgc | ctg | cgc | tgc | gac | ggc | gag | gca | gac | tgt |     | 3969 |
| Gln | Cys | Val | Asp | Leu | Arg | Leu | Arg | Cys | Asp | Gly | Glu | Ala | Asp | Cys |     |      |
| 1310 |     |     |     | 1315 |     |     |     | 1320 |     |     |     |     |     |     |     |      |

| cag | gac | cgc | tca | gac | gag | gcg | gac | tgt | gac | gcc | atc | tgc | ctg | ccc |     | 4014 |
| Gln | Asp | Arg | Ser | Asp | Glu | Ala | Asp | Cys | Asp | Ala | Ile | Cys | Leu | Pro |     |      |
| 1325 |     |     |     | 1330 |     |     |     | 1335 |     |     |     |     |     |     |     |      |

| aac | cag | ttc | cgg | tgt | gcg | agc | ggc | cag | tgt | gtc | ctc | atc | aaa | cag |     | 4059 |
| Asn | Gln | Phe | Arg | Cys | Ala | Ser | Gly | Gln | Cys | Val | Leu | Ile | Lys | Gln |     |      |
| 1340 |     |     |     | 1345 |     |     |     | 1350 |     |     |     |     |     |     |     |      |

| cag | tgc | gac | tcc | ttc | ccc | gac | tgt | atc | gac | ggc | tcc | gac | gag | ctc |     | 4104 |
| Gln | Cys | Asp | Ser | Phe | Pro | Asp | Cys | Ile | Asp | Gly | Ser | Asp | Glu | Leu |     |      |
| 1355 |     |     |     | 1360 |     |     |     | 1365 |     |     |     |     |     |     |     |      |

| atg | tgt | gaa | atc | acc | aag | ccg | ccc | tca | gac | gac | agc | ccg | gcc | cac |     | 4149 |
| Met | Cys | Glu | Ile | Thr | Lys | Pro | Pro | Ser | Asp | Asp | Ser | Pro | Ala | His |     |      |
| 1370 |     |     |     | 1375 |     |     |     | 1380 |     |     |     |     |     |     |     |      |

| agc | agt | gcc | atc | ggg | ccc | gtc | att | ggc | atc | atc | ctc | tct | ctc | ttc |     | 4194 |
| Ser | Ser | Ala | Ile | Gly | Pro | Val | Ile | Gly | Ile | Ile | Leu | Ser | Leu | Phe |     |      |
| 1385 |     |     |     | 1390 |     |     |     | 1395 |     |     |     |     |     |     |     |      |

| gtc | atg | ggt | ggt | gtc | tat | ttt | gtg | tgc | cag | cgc | gtg | gtg | tgc | cag |     | 4239 |

|     |     |     |     |     |     |     |     |     |     |     |     |     |     |     |      |
|---|---|---|---|---|---|---|---|---|---|---|---|---|---|---|---|
| Val | Met | Gly | Gly | Val | Tyr | Phe | Val | Cys | Gln | Arg | Val | Val | Cys | Gln |      |
|     | 1400 |     |     |     | 1405 |     |     |     | 1410 |     |     |     |     |     |      |
| cgc | tat | gcg | ggg | gcc | aac | ggg | ccc | ttc | ccg | cac | gag | tat | gtc | agc | 4284 |
| Arg | Tyr | Ala | Gly | Ala | Asn | Gly | Pro | Phe | Pro | His | Glu | Tyr | Val | Ser |      |
|     | 1415 |     |     |     | 1420 |     |     |     | 1425 |     |     |     |     |     |      |
| ggg | acc | ccg | cac | gtg | ccc | ctc | aat | ttc | ata | gcc | ccg | ggc | ggt | tcc | 4329 |
| Gly | Thr | Pro | His | Val | Pro | Leu | Asn | Phe | Ile | Ala | Pro | Gly | Gly | Ser |      |
|     | 1430 |     |     |     | 1435 |     |     |     | 1440 |     |     |     |     |     |      |
| cag | cat | ggc | ccc | ttc | aca | ggc | atc | gca | tgc | gga | aag | tcc | atg | atg | 4374 |
| Gln | His | Gly | Pro | Phe | Thr | Gly | Ile | Ala | Cys | Gly | Lys | Ser | Met | Met |      |
|     | 1445 |     |     |     | 1450 |     |     |     | 1455 |     |     |     |     |     |      |
| agc | tcc | gtg | agc | ctg | atg | ggc | ggc | cgg | ggc | ggg | gtg | ccc | ctc | tac | 4419 |
| Ser | Ser | Val | Ser | Leu | Met | Gly | Gly | Arg | Gly | Gly | Val | Pro | Leu | Tyr |      |
|     | 1460 |     |     |     | 1465 |     |     |     | 1470 |     |     |     |     |     |      |
| gac | cgg | aac | cac | gtc | aca | ggg | gcc | tcg | tcc | agc | agc | tcg | tcc | agc | 4464 |
| Asp | Arg | Asn | His | Val | Thr | Gly | Ala | Ser | Ser | Ser | Ser | Ser | Ser | Ser |      |
|     | 1475 |     |     |     | 1480 |     |     |     | 1485 |     |     |     |     |     |      |
| acg | aag | gcc | acg | ctg | tac | ccg | ccg | atc | ctg | aac | ccg | ccg | ccc | tcc | 4509 |
| Thr | Lys | Ala | Thr | Leu | Tyr | Pro | Pro | Ile | Leu | Asn | Pro | Pro | Pro | Ser |      |
|     | 1490 |     |     |     | 1495 |     |     |     | 1500 |     |     |     |     |     |      |
| ccg | gcc | acg | gac | ccc | tcc | ctg | tac | aac | atg | gac | atg | ttc | tac | tct | 4554 |
| Pro | Ala | Thr | Asp | Pro | Ser | Leu | Tyr | Asn | Met | Asp | Met | Phe | Tyr | Ser |      |
|     | 1505 |     |     |     | 1510 |     |     |     | 1515 |     |     |     |     |     |      |
| tca | aac | att | ccg | gcc | act | gtg | aga | ccg | tac | agg | ccc | tac | atc | att | 4599 |
| Ser | Asn | Ile | Pro | Ala | Thr | Val | Arg | Pro | Tyr | Arg | Pro | Tyr | Ile | Ile |      |
|     | 1520 |     |     |     | 1525 |     |     |     | 1530 |     |     |     |     |     |      |
| cga | gga | atg | gcg | ccc | ccg | acg | acg | ccc | tgc | agc | acc | gac | gtg | tgt | 4644 |
| Arg | Gly | Met | Ala | Pro | Pro | Thr | Thr | Pro | Cys | Ser | Thr | Asp | Val | Cys |      |
|     | 1535 |     |     |     | 1540 |     |     |     | 1545 |     |     |     |     |     |      |
| gac | agc | gac | tac | agc | gcc | agc | cgc | tgg | aag | gcc | agc | aag | tac | tac | 4689 |
| Asp | Ser | Asp | Tyr | Ser | Ala | Ser | Arg | Trp | Lys | Ala | Ser | Lys | Tyr | Tyr |      |
|     | 1550 |     |     |     | 1555 |     |     |     | 1560 |     |     |     |     |     |      |
| ctg | gat | ttg | aac | tcg | gac | tca | gac | ccc | tat | cca | ccc | cca | ccc | acg | 4734 |
| Leu | Asp | Leu | Asn | Ser | Asp | Ser | Asp | Pro | Tyr | Pro | Pro | Pro | Pro | Thr |      |
|     | 1565 |     |     |     | 1570 |     |     |     | 1575 |     |     |     |     |     |      |
| ccc | cac | agc | cag | tac | ctg | tcg | gcg | gag | gac | agc | tgc | ccg | ccc | tcg | 4779 |
| Pro | His | Ser | Gln | Tyr | Leu | Ser | Ala | Glu | Asp | Ser | Cys | Pro | Pro | Ser |      |
|     | 1580 |     |     |     | 1585 |     |     |     | 1590 |     |     |     |     |     |      |
| ccc | gcc | acc | gag | agg | agc | tac | ttc | cat | ctc | ttc | ccg | ccc | cct | ccg | 4824 |
| Pro | Ala | Thr | Glu | Arg | Ser | Tyr | Phe | His | Leu | Phe | Pro | Pro | Pro | Pro |      |
|     | 1595 |     |     |     | 1600 |     |     |     | 1605 |     |     |     |     |     |      |
| tcc | ccc | tgc | acg | gac | tca | tcc | tga |     |     |     |     |     |     |     | 4848 |
| Ser | Pro | Cys | Thr | Asp | Ser | Ser |     |     |     |     |     |     |     |     |      |
|     | 1610 |     |     |     | 1615 |     |     |     |     |     |     |     |     |     |      |

<210> SEQ ID NO 6
<211> LENGTH: 1615
<212> TYPE: PRT
<213> ORGANISM: Homo sapiens

<400> SEQUENCE: 6

Met Glu Ala Ala Pro Gly Pro Pro Trp Pro Leu Leu Leu Leu Leu
1               5                   10                  15

Leu Leu Leu Leu Ala Leu Cys Gly Cys Pro Ala Pro Ala Ala Ser
                20                  25                  30

Pro Leu Leu Leu Phe Ala Asn Arg Arg Asp Val Arg Leu Val Asp Ala
                35                  40                  45

Gly Gly Val Lys Leu Glu Ser Thr Ile Val Ser Gly Leu Glu Asp
        50                  55                  60

Ala Ala Ala Val Asp Phe Gln Phe Ser Lys Gly Ala Val Tyr Trp Thr

```
            65                  70                  75                  80
Asp Val Ser Glu Glu Ala Ile Lys Gln Thr Tyr Leu Asn Gln Thr Gly
                    85                  90                  95

Ala Ala Val Gln Asn Val Val Ile Ser Gly Leu Val Ser Pro Asp Gly
                    100                 105                 110

Leu Ala Cys Asp Trp Val Gly Lys Leu Tyr Trp Thr Asp Ser Glu
                    115                 120                 125

Thr Asn Arg Ile Glu Val Ala Asn Leu Asn Gly Thr Ser Arg Lys Val
                    130                 135                 140

Leu Phe Trp Gln Asp Leu Asp Gln Pro Arg Ala Ile Ala Leu Asp Pro
145                 150                 155                 160

Ala His Gly Tyr Met Tyr Trp Thr Asp Trp Gly Thr Pro Arg Ile
                    165                 170                 175

Glu Arg Ala Gly Met Asp Gly Ser Thr Arg Lys Ile Ile Val Asp Ser
                    180                 185                 190

Asp Ile Tyr Trp Pro Asn Gly Leu Thr Ile Asp Leu Glu Glu Gln Lys
                    195                 200                 205

Leu Tyr Trp Ala Asp Ala Lys Leu Ser Phe Ile His Arg Ala Asn Leu
                    210                 215                 220

Asp Gly Ser Phe Arg Gln Lys Val Val Glu Gly Ser Leu Thr His Pro
225                 230                 235                 240

Phe Ala Leu Thr Leu Ser Gly Asp Thr Leu Tyr Trp Thr Asp Trp Gln
                    245                 250                 255

Thr Arg Ser Ile His Ala Cys Asn Lys Arg Thr Gly Gly Lys Arg Lys
                    260                 265                 270

Glu Ile Leu Ser Ala Leu Tyr Ser Pro Met Asp Ile Gln Val Leu Ser
                    275                 280                 285

Gln Glu Arg Gln Pro Phe Phe His Thr Arg Cys Glu Glu Asp Asn Gly
                    290                 295                 300

Gly Cys Ser His Leu Cys Leu Leu Ser Pro Ser Glu Pro Phe Tyr Thr
305                 310                 315                 320

Cys Ala Cys Pro Thr Gly Val Gln Leu Gln Asp Asn Gly Arg Thr Cys
                    325                 330                 335

Lys Ala Gly Ala Glu Glu Val Leu Leu Leu Ala Arg Arg Thr Asp Leu
                    340                 345                 350

Arg Arg Ile Ser Leu Asp Thr Pro Asp Phe Thr Asp Ile Val Leu Gln
                    355                 360                 365

Val Asp Asp Ile Arg His Ala Ile Ala Ile Asp Tyr Asp Pro Leu Glu
370                 375                 380

Gly Tyr Val Tyr Trp Thr Asp Asp Glu Val Arg Ala Ile Arg Arg Ala
385                 390                 395                 400

Tyr Leu Asp Gly Ser Gly Ala Gln Thr Leu Val Asn Thr Glu Ile Asn
                    405                 410                 415

Asp Pro Asp Gly Ile Ala Val Asp Trp Val Ala Arg Asn Leu Tyr Trp
                    420                 425                 430

Thr Asp Thr Gly Thr Asp Arg Ile Glu Val Thr Arg Leu Asn Gly Thr
                    435                 440                 445

Ser Arg Lys Ile Leu Val Ser Glu Asp Leu Asp Glu Pro Arg Ala Ile
                    450                 455                 460

Ala Leu His Pro Val Met Gly Leu Met Tyr Trp Thr Asp Trp Gly Glu
465                 470                 475                 480

Asn Pro Lys Ile Glu Cys Ala Asn Leu Asp Gly Gln Glu Arg Arg Val
                    485                 490                 495
```

```
Leu Val Asn Ala Ser Leu Gly Trp Pro Asn Gly Leu Ala Leu Asp Leu
            500                 505                 510

Gln Glu Gly Lys Leu Tyr Trp Gly Asp Ala Lys Thr Asp Lys Ile Glu
            515                 520                 525

Val Ile Asn Val Asp Gly Thr Lys Arg Arg Thr Leu Leu Glu Asp Lys
        530                 535                 540

Leu Pro His Ile Phe Gly Phe Thr Leu Leu Gly Asp Phe Ile Tyr Trp
545                 550                 555                 560

Thr Asp Trp Gln Arg Arg Ser Ile Glu Arg Val His Lys Val Lys Ala
                565                 570                 575

Ser Arg Asp Val Ile Ile Asp Gln Leu Pro Asp Leu Met Gly Leu Lys
            580                 585                 590

Ala Val Asn Val Ala Lys Val Val Gly Thr Asn Pro Cys Ala Asp Arg
        595                 600                 605

Asn Gly Gly Cys Ser His Leu Cys Phe Phe Thr Pro His Ala Thr Arg
        610                 615                 620

Cys Gly Cys Pro Ile Gly Leu Glu Leu Leu Ser Asp Met Lys Thr Cys
625                 630                 635                 640

Ile Val Pro Glu Ala Phe Leu Val Phe Thr Ser Arg Ala Ala Ile His
                645                 650                 655

Arg Ile Ser Leu Glu Thr Asn Asn Asn Asp Val Ala Ile Pro Leu Thr
            660                 665                 670

Gly Val Lys Glu Ala Ser Ala Leu Asp Phe Asp Val Ser Asn Asn His
        675                 680                 685

Ile Tyr Trp Thr Asp Val Ser Leu Lys Thr Ile Ser Arg Ala Phe Met
        690                 695                 700

Asn Gly Ser Ser Val Glu His Val Val Glu Phe Gly Leu Asp Tyr Pro
705                 710                 715                 720

Glu Gly Met Ala Val Asp Trp Met Gly Lys Asn Leu Tyr Trp Ala Asp
                725                 730                 735

Thr Gly Thr Asn Arg Ile Glu Val Ala Arg Leu Asp Gly Gln Phe Arg
            740                 745                 750

Gln Val Leu Val Trp Arg Asp Leu Asp Asn Pro Arg Ser Leu Ala Leu
        755                 760                 765

Asp Pro Thr Lys Gly Tyr Ile Tyr Trp Thr Glu Trp Gly Gly Lys Pro
770                 775                 780

Arg Ile Val Arg Ala Phe Met Asp Gly Thr Asn Cys Met Thr Leu Val
785                 790                 795                 800

Asp Lys Val Gly Arg Ala Asn Asp Leu Thr Ile Asp Tyr Ala Asp Gln
            805                 810                 815

Arg Leu Tyr Trp Thr Asp Leu Asp Thr Asn Met Ile Glu Ser Ser Asn
                820                 825                 830

Met Leu Gly Gln Glu Arg Val Val Ile Ala Asp Asp Leu Pro His Pro
        835                 840                 845

Phe Gly Leu Thr Gln Tyr Ser Asp Tyr Ile Tyr Trp Thr Asp Trp Asn
850                 855                 860

Leu His Ser Ile Glu Arg Ala Asp Lys Thr Ser Gly Arg Asn Arg Thr
865                 870                 875                 880

Leu Ile Gln Gly His Leu Asp Phe Val Met Asp Ile Leu Val Phe His
                885                 890                 895

Ser Ser Arg Gln Asp Gly Leu Asn Asp Cys Met His Asn Asn Gly Gln
            900                 905                 910

Cys Gly Gln Leu Cys Leu Ala Ile Pro Gly Gly His Arg Cys Gly Cys
        915                 920                 925
```

```
Ala Ser His Tyr Thr Leu Asp Pro Ser Ser Arg Asn Cys Ser Pro Pro
        930                 935                 940

Thr Thr Phe Leu Leu Phe Ser Gln Lys Ser Ala Ile Ser Arg Met Ile
945                 950                 955                 960

Pro Asp Asp Gln His Ser Pro Asp Leu Ile Leu Pro Leu His Gly Leu
                965                 970                 975

Arg Asn Val Lys Ala Ile Asp Tyr Asp Pro Leu Asp Lys Phe Ile Tyr
            980                 985                 990

Trp Val Asp Gly Arg Gln Asn Ile Lys Arg Ala Lys Asp Asp Gly Thr
        995                 1000                1005

Gln Pro Phe Val Leu Thr Ser Leu Ser Gln Gly Gln Asn Pro Asp
    1010                1015                1020

Arg Gln Pro His Asp Leu Ser Ile Asp Ile Tyr Ser Arg Thr Leu
    1025                1030                1035

Phe Trp Thr Cys Glu Ala Thr Asn Thr Ile Asn Val His Arg Leu
    1040                1045                1050

Ser Gly Glu Ala Met Gly Val Val Leu Arg Gly Asp Arg Asp Lys
    1055                1060                1065

Pro Arg Ala Ile Val Val Asn Ala Glu Arg Gly Tyr Leu Tyr Phe
    1070                1075                1080

Thr Asn Met Gln Asp Arg Ala Ala Lys Ile Glu Arg Ala Ala Leu
    1085                1090                1095

Asp Gly Thr Glu Arg Glu Val Leu Phe Thr Thr Gly Leu Ile Arg
    1100                1105                1110

Pro Val Ala Leu Val Val Asp Asn Thr Leu Gly Lys Leu Phe Trp
    1115                1120                1125

Val Asp Ala Asp Leu Lys Arg Ile Glu Ser Cys Asp Leu Ser Gly
    1130                1135                1140

Ala Asn Arg Leu Thr Leu Glu Asp Ala Asn Ile Val Gln Pro Leu
    1145                1150                1155

Gly Leu Thr Ile Leu Gly Lys His Leu Tyr Trp Ile Asp Arg Gln
    1160                1165                1170

Gln Gln Met Ile Glu Arg Val Glu Lys Thr Thr Gly Asp Lys Arg
    1175                1180                1185

Thr Arg Ile Gln Gly Arg Val Ala His Leu Thr Gly Ile His Ala
    1190                1195                1200

Val Glu Glu Val Ser Leu Glu Glu Phe Ser Ala His Pro Cys Ala
    1205                1210                1215

Arg Asp Asn Gly Gly Cys Ser His Ile Cys Ile Ala Lys Gly Asp
    1220                1225                1230

Gly Thr Pro Arg Cys Ser Cys Pro Val His Leu Val Leu Leu Gln
    1235                1240                1245

Asn Leu Leu Thr Cys Gly Glu Pro Pro Thr Cys Ser Pro Asp Gln
    1250                1255                1260

Phe Ala Cys Ala Thr Gly Glu Ile Asp Cys Ile Pro Gly Ala Trp
    1265                1270                1275

Arg Cys Asp Gly Phe Pro Glu Cys Asp Asp Gln Ser Asp Glu Glu
    1280                1285                1290

Gly Cys Pro Val Cys Ser Ala Ala Gln Phe Pro Cys Ala Arg Gly
    1295                1300                1305

Gln Cys Val Asp Leu Arg Leu Arg Cys Asp Gly Glu Ala Asp Cys
    1310                1315                1320

Gln Asp Arg Ser Asp Glu Ala Asp Cys Asp Ala Ile Cys Leu Pro
```

```
                   1325               1330                1335

Asn Gln  Phe Arg Cys Ala Ser  Gly Gln Cys Val Leu  Ile Lys Gln
    1340                 1345                 1350

Gln Cys  Asp Ser Phe Pro Asp  Cys Ile Asp Gly Ser  Asp Glu Leu
    1355                 1360                 1365

Met Cys  Glu Ile Thr Lys Pro  Pro Ser Asp Asp Ser  Pro Ala His
    1370                 1375                 1380

Ser Ser  Ala Ile Gly Pro Val  Ile Gly Ile Ile Leu  Ser Leu Phe
    1385                 1390                 1395

Val Met  Gly Gly Val Tyr Phe  Val Cys Gln Arg Val  Val Cys Gln
    1400                 1405                 1410

Arg Tyr  Ala Gly Ala Asn Gly  Pro Phe Pro His Glu  Tyr Val Ser
    1415                 1420                 1425

Gly Thr  Pro His Val Pro Leu  Asn Phe Ile Ala Pro  Gly Gly Ser
    1430                 1435                 1440

Gln His  Gly Pro Phe Thr Gly  Ile Ala Cys Gly Lys  Ser Met Met
    1445                 1450                 1455

Ser Ser  Val Ser Leu Met Gly  Gly Arg Gly Gly Val  Pro Leu Tyr
    1460                 1465                 1470

Asp Arg  Asn His Val Thr Gly  Ala Ser Ser Ser Ser  Ser Ser Ser
    1475                 1480                 1485

Thr Lys  Ala Thr Leu Tyr Pro  Pro Ile Leu Asn Pro  Pro Pro Ser
    1490                 1495                 1500

Pro Ala  Thr Asp Pro Ser Leu  Tyr Asn Met Asp Met  Phe Tyr Ser
    1505                 1510                 1515

Ser Asn  Ile Pro Ala Thr Val  Arg Pro Tyr Arg Pro  Tyr Ile Ile
    1520                 1525                 1530

Arg Gly  Met Ala Pro Pro Thr  Thr Pro Cys Ser Thr  Asp Val Cys
    1535                 1540                 1545

Asp Ser  Asp Tyr Ser Ala Ser  Arg Trp Lys Ala Ser  Lys Tyr Tyr
    1550                 1555                 1560

Leu Asp  Leu Asn Ser Asp Ser  Asp Pro Tyr Pro Pro  Pro Pro Thr
    1565                 1570                 1575

Pro His  Ser Gln Tyr Leu Ser  Ala Glu Asp Ser Cys  Pro Pro Ser
    1580                 1585                 1590

Pro Ala  Thr Glu Arg Ser Tyr  Phe His Leu Phe Pro  Pro Pro Pro
    1595                 1600                 1605

Ser Pro  Cys Thr Asp Ser Ser
    1610                 1615

<210> SEQ ID NO 7
<211> LENGTH: 4842
<212> TYPE: DNA
<213> ORGANISM: Homo sapiens
<220> FEATURE:
<221> NAME/KEY: CDS
<222> LOCATION: (1)..(4842)

<400> SEQUENCE: 7 atg ggg gcc gtc ctg agg agc ctc ctg gcc tgc agc ttc tgt gtg ctc    48
Met Gly Ala Val Leu Arg Ser Leu Leu Ala Cys Ser Phe Cys Val Leu
1               5                   10                  15 ctg aga gcg gcc cct ttg ttg ctt tat gca aac aga cgg gac ttg cga    96
Leu Arg Ala Ala Pro Leu Leu Leu Tyr Ala Asn Arg Arg Asp Leu Arg
            20                  25                  30 ttg gtt gat gct aca aat ggc aaa gag aat gct acg att gta gtt gga   144
Leu Val Asp Ala Thr Asn Gly Lys Glu Asn Ala Thr Ile Val Val Gly
```

```
                  35                  40                  45
ggc ttg gag gat gca gct gcg gtg gac ttt gtg ttt agt cat ggc ttg      192
Gly Leu Glu Asp Ala Ala Ala Val Asp Phe Val Phe Ser His Gly Leu
 50                  55                  60 ata tac tgg agt gat gtc agc gaa gaa gcc att aaa cga aca gaa ttt      240
Ile Tyr Trp Ser Asp Val Ser Glu Glu Ala Ile Lys Arg Thr Glu Phe
 65                  70                  75                  80 aac aaa act gag agt gtg cag aat gtt gtt gtt tct gga tta ttg tcc      288
Asn Lys Thr Glu Ser Val Gln Asn Val Val Val Ser Gly Leu Leu Ser
                     85                  90                  95 ccc gat ggg ctg gca tgt gat tgg ctt gga gaa aaa ttg tac tgg aca      336
Pro Asp Gly Leu Ala Cys Asp Trp Leu Gly Glu Lys Leu Tyr Trp Thr
            100                 105                 110 gat tct gaa act aat cgg att gaa gtt tct aat tta gat gga tct tta      384
Asp Ser Glu Thr Asn Arg Ile Glu Val Ser Asn Leu Asp Gly Ser Leu
            115                 120                 125 cga aaa gtt tta ttt tgg caa gag ttg gat caa ccc aga gct att gcc      432
Arg Lys Val Leu Phe Trp Gln Glu Leu Asp Gln Pro Arg Ala Ile Ala
130                 135                 140 tta gat cct tca agt ggg ttc atg tac tgg aca gac tgg gga gaa gtg      480
Leu Asp Pro Ser Ser Gly Phe Met Tyr Trp Thr Asp Trp Gly Glu Val
145                 150                 155                 160 cca aag ata gaa cgt gct gga atg gat ggt tca agt cgc ttc att ata      528
Pro Lys Ile Glu Arg Ala Gly Met Asp Gly Ser Ser Arg Phe Ile Ile
                165                 170                 175 ata aac agt gaa att tac tgg cca aat gga ctg act ttg gat tat gaa      576
Ile Asn Ser Glu Ile Tyr Trp Pro Asn Gly Leu Thr Leu Asp Tyr Glu
            180                 185                 190 gaa caa aag ctt tat tgg gca gat gca aaa ctt aat ttc atc cac aaa      624
Glu Gln Lys Leu Tyr Trp Ala Asp Ala Lys Leu Asn Phe Ile His Lys
            195                 200                 205 tca aat ctg gat gga aca aat cgg cag gca gtg gtt aaa ggt tcc ctt      672
Ser Asn Leu Asp Gly Thr Asn Arg Gln Ala Val Val Lys Gly Ser Leu
210                 215                 220 cca cat cct ttt gcc ttg acg tta ttt gag gac ata ttg tac tgg act      720
Pro His Pro Phe Ala Leu Thr Leu Phe Glu Asp Ile Leu Tyr Trp Thr
225                 230                 235                 240 gac tgg agc aca cac tcc att ttg gct tgc aac aag tat act ggt gag      768
Asp Trp Ser Thr His Ser Ile Leu Ala Cys Asn Lys Tyr Thr Gly Glu
                245                 250                 255 ggt ctg cgt gaa atc cat tct gac atc ttc tct ccc atg gat ata cat      816
Gly Leu Arg Glu Ile His Ser Asp Ile Phe Ser Pro Met Asp Ile His
            260                 265                 270 gcc ttc agc caa cag agg cag cca aat gcc aca aat cca tgt gga att      864
Ala Phe Ser Gln Gln Arg Gln Pro Asn Ala Thr Asn Pro Cys Gly Ile
            275                 280                 285 gac aat ggg ggt tgt tcc cat ttg tgt ttg atg tct cca gtc aag cct      912
Asp Asn Gly Gly Cys Ser His Leu Cys Leu Met Ser Pro Val Lys Pro
290                 295                 300 ttt tat cag tgt gct tgc ccc act ggg gtc aaa ctc ctg gag aat gga      960
Phe Tyr Gln Cys Ala Cys Pro Thr Gly Val Lys Leu Leu Glu Asn Gly
305                 310                 315                 320 aaa acc tgc aaa gat ggt gcc aca gaa tta ttg ctt tta gct cga agg     1008
Lys Thr Cys Lys Asp Gly Ala Thr Glu Leu Leu Leu Leu Ala Arg Arg
                325                 330                 335 aca gac ttg aga cgc att tct ttg gat aca cca gat ttt aca gac att     1056
Thr Asp Leu Arg Arg Ile Ser Leu Asp Thr Pro Asp Phe Thr Asp Ile
            340                 345                 350 gtt ctg cag tta gaa gac atc cgt cat gcc att gcc ata gat tac gat     1104
Val Leu Gln Leu Glu Asp Ile Arg His Ala Ile Ala Ile Asp Tyr Asp
```

-continued

```
              355                 360                 365
cct gtg gaa ggc tac atc tac tgg act gat gat gaa gtg agg gcc ata      1152
Pro Val Glu Gly Tyr Ile Tyr Trp Thr Asp Asp Glu Val Arg Ala Ile
370                 375                 380 cgc cgt tca ttt ata gat gga tct ggc agt cag ttt gtg gtc act gct      1200
Arg Arg Ser Phe Ile Asp Gly Ser Gly Ser Gln Phe Val Val Thr Ala
385                 390                 395                 400 caa att gcc cat cct gat ggt att gct gtg gac tgg gtt gca cga aat      1248
Gln Ile Ala His Pro Asp Gly Ile Ala Val Asp Trp Val Ala Arg Asn
            405                 410                 415 ctt tat tgg aca gac act ggc act gat cga ata gaa gtg aca agg ctc      1296
Leu Tyr Trp Thr Asp Thr Gly Thr Asp Arg Ile Glu Val Thr Arg Leu
        420                 425                 430 aat ggg acc atg agg aag atc ttg att tca gag gac tta gag gaa ccc      1344
Asn Gly Thr Met Arg Lys Ile Leu Ile Ser Glu Asp Leu Glu Glu Pro
    435                 440                 445 cgg gct att gtg tta gat ccc atg gtt ggg tac atg tat tgg act gac      1392
Arg Ala Ile Val Leu Asp Pro Met Val Gly Tyr Met Tyr Trp Thr Asp
450                 455                 460 tgg gga gaa att ccg aaa att gag cga gca gct ctg gat ggt tct gac      1440
Trp Gly Glu Ile Pro Lys Ile Glu Arg Ala Ala Leu Asp Gly Ser Asp
465                 470                 475                 480 cgt gta gta ttg gtt aac act tct ctt ggt tgg cca aat ggt tta gcc      1488
Arg Val Val Leu Val Asn Thr Ser Leu Gly Trp Pro Asn Gly Leu Ala
            485                 490                 495 ttg gat tat gat gaa ggc aaa ata tac tgg gga gat gcc aaa aca gac      1536
Leu Asp Tyr Asp Glu Gly Lys Ile Tyr Trp Gly Asp Ala Lys Thr Asp
        500                 505                 510 aag att gag gtt atg aat act gat ggc act ggg aga cga gta cta gtg      1584
Lys Ile Glu Val Met Asn Thr Asp Gly Thr Gly Arg Arg Val Leu Val
    515                 520                 525 gaa gac aaa att cct cac ata ttt gga ttt act ttg ttg ggt gac tat      1632
Glu Asp Lys Ile Pro His Ile Phe Gly Phe Thr Leu Leu Gly Asp Tyr
530                 535                 540 gtt tac tgg act gac tgg cag agg cgt agc att gaa aga gtt cat aaa      1680
Val Tyr Trp Thr Asp Trp Gln Arg Arg Ser Ile Glu Arg Val His Lys
545                 550                 555                 560 cga agt gca gag agg gaa gtg atc ata gat cag ctg cct gac ctc atg      1728
Arg Ser Ala Glu Arg Glu Val Ile Ile Asp Gln Leu Pro Asp Leu Met
            565                 570                 575 ggc cta aag gct aca aat gtt cat cga gtg att ggt tcc aac ccc tgt      1776
Gly Leu Lys Ala Thr Asn Val His Arg Val Ile Gly Ser Asn Pro Cys
        580                 585                 590 gct gag gaa aac ggg gga tgt agc cat ctc tgc ctc tat aga cct cag      1824
Ala Glu Glu Asn Gly Gly Cys Ser His Leu Cys Leu Tyr Arg Pro Gln
    595                 600                 605 ggc ctt cgc tgt gct tgc cct att ggc ttt gaa ctc atc agt gac atg      1872
Gly Leu Arg Cys Ala Cys Pro Ile Gly Phe Glu Leu Ile Ser Asp Met
610                 615                 620 aag acc tgc att gtc cca gag gct ttc ctt ttg ttt tca cgg aga gca      1920
Lys Thr Cys Ile Val Pro Glu Ala Phe Leu Leu Phe Ser Arg Arg Ala
625                 630                 635                 640 gat atc aga cga att tct ctg gaa aca aac aat aat aat gtg gct att      1968
Asp Ile Arg Arg Ile Ser Leu Glu Thr Asn Asn Asn Asn Val Ala Ile
            645                 650                 655 cca ctc act ggt gtc aaa gaa gct tct gct ttg gat ttt gat gtg aca      2016
Pro Leu Thr Gly Val Lys Glu Ala Ser Ala Leu Asp Phe Asp Val Thr
        660                 665                 670 gac aac cga att tat tgg act gat ata tca ctc aag acc atc agc aga      2064
Asp Asn Arg Ile Tyr Trp Thr Asp Ile Ser Leu Lys Thr Ile Ser Arg
```

```
                  675                 680                 685
gcc ttt atg aat ggc agt gca ctg gaa cat gtg gta gaa ttc ggc tta    2112
Ala Phe Met Asn Gly Ser Ala Leu Glu His Val Val Glu Phe Gly Leu
            690                 695                 700 gat tat cca gaa ggc atg gca gta gac tgg ctt ggg aag aac ttg tac    2160
Asp Tyr Pro Glu Gly Met Ala Val Asp Trp Leu Gly Lys Asn Leu Tyr
705                 710                 715                 720 tgg gca gac aca gga acg aat cga att gag gtg tca aag ttg gat ggg    2208
Trp Ala Asp Thr Gly Thr Asn Arg Ile Glu Val Ser Lys Leu Asp Gly
                        725                 730                 735 cag cac cga caa gtt ttg gtg tgg aaa gac cta gat agt ccc aga gct    2256
Gln His Arg Gln Val Leu Val Trp Lys Asp Leu Asp Ser Pro Arg Ala
                740                 745                 750 ctc gcg ttg gac cct gcc gaa gga ttt atg tat tgg act gaa tgg ggt    2304
Leu Ala Leu Asp Pro Ala Glu Gly Phe Met Tyr Trp Thr Glu Trp Gly
            755                 760                 765 gga aaa cct aag ata gac aga gct gca atg gat gga agt gaa cgt act    2352
Gly Lys Pro Lys Ile Asp Arg Ala Ala Met Asp Gly Ser Glu Arg Thr
770                 775                 780 acc tta gtt cca aat gtg ggg cgg gca aac ggc cta act att gat tat    2400
Thr Leu Val Pro Asn Val Gly Arg Ala Asn Gly Leu Thr Ile Asp Tyr
785                 790                 795                 800 gct aaa agg agg ctt tat tgg aca gac ctg gac acc aac tta ata gaa    2448
Ala Lys Arg Arg Leu Tyr Trp Thr Asp Leu Asp Thr Asn Leu Ile Glu
                    805                 810                 815 tct tca aat atg ctt ggg ctc aac cgt gaa gtt ata gca gat gac ttg    2496
Ser Ser Asn Met Leu Gly Leu Asn Arg Glu Val Ile Ala Asp Asp Leu
                820                 825                 830 cct cat cct ttt ggc tta act cag tac caa gat tat atc tac tgg acg    2544
Pro His Pro Phe Gly Leu Thr Gln Tyr Gln Asp Tyr Ile Tyr Trp Thr
            835                 840                 845 gac tgg agc cga cgc agc att gag cgt gcc aac aaa acc agt ggc caa    2592
Asp Trp Ser Arg Arg Ser Ile Glu Arg Ala Asn Lys Thr Ser Gly Gln
850                 855                 860 aac cgc acc atc att cag ggc cat ttg gat tat gtg atg gac atc ctc    2640
Asn Arg Thr Ile Ile Gln Gly His Leu Asp Tyr Val Met Asp Ile Leu
865                 870                 875                 880 gtc ttt cac tca tct cga cag tca ggg tgg aat gaa tgt gct tcc agc    2688
Val Phe His Ser Ser Arg Gln Ser Gly Trp Asn Glu Cys Ala Ser Ser
                    885                 890                 895 aat ggg cac tgc tcc cac ctc tgc ttg gct gtg cca gtt ggg ggt ttt    2736
Asn Gly His Cys Ser His Leu Cys Leu Ala Val Pro Val Gly Gly Phe
                900                 905                 910 gtt tgt gga tgc cct gcc cac tac tct ctt aat gct gac aac agg act    2784
Val Cys Gly Cys Pro Ala His Tyr Ser Leu Asn Ala Asp Asn Arg Thr
            915                 920                 925 tgt agt gct cct acg act ttc ctg ctc ttc agt caa aag agt gcc atc    2832
Cys Ser Ala Pro Thr Thr Phe Leu Leu Phe Ser Gln Lys Ser Ala Ile
930                 935                 940 aac cgc atg gtg att gat gaa caa cag agc ccc gac atc atc ctt ccc    2880
Asn Arg Met Val Ile Asp Glu Gln Gln Ser Pro Asp Ile Ile Leu Pro
945                 950                 955                 960 atc cac agc ctt cgg aat gtc cgg gcc att gac tat gac cca ctg gac    2928
Ile His Ser Leu Arg Asn Val Arg Ala Ile Asp Tyr Asp Pro Leu Asp
                    965                 970                 975 aag caa ctc tat tgg att gac tca cga caa aac atg atc cga aag gca    2976
Lys Gln Leu Tyr Trp Ile Asp Ser Arg Gln Asn Met Ile Arg Lys Ala
                980                 985                 990 caa gaa gat ggc agc cag ggc ttt act gtg gtt gtg agc tca gtt ccg    3024
Gln Glu Asp Gly Ser Gln Gly Phe Thr Val Val Val Ser Ser Val Pro
```

```
                                995                      1000                       1005
agt  cag  aac  ctg  gaa  ata  caa  ccc  tat  gac  ctc  agc  att  gat  att        3069
Ser  Gln  Asn  Leu  Glu  Ile  Gln  Pro  Tyr  Asp  Leu  Ser  Ile  Asp  Ile
     1010                     1015                      1020 tac  agc  cgc  tac  atc  tac  tgg  act  tgt  gag  gct  acc  aat  gtc  att        3114
Tyr  Ser  Arg  Tyr  Ile  Tyr  Trp  Thr  Cys  Glu  Ala  Thr  Asn  Val  Ile
     1025                     1030                      1035 aat  gtg  aca  aga  tta  gat  ggg  aga  tca  gtt  gga  gtg  gtg  ctg  aaa        3159
Asn  Val  Thr  Arg  Leu  Asp  Gly  Arg  Ser  Val  Gly  Val  Val  Leu  Lys
     1040                     1045                      1050 ggc  gag  cag  gac  aga  cct  cga  gcc  att  gtg  gta  aac  cca  gag  aaa        3204
Gly  Glu  Gln  Asp  Arg  Pro  Arg  Ala  Ile  Val  Val  Asn  Pro  Glu  Lys
     1055                     1060                      1065 ggg  tat  atg  tat  ttt  acc  aat  ctt  cag  gaa  agg  tct  cct  aaa  att        3249
Gly  Tyr  Met  Tyr  Phe  Thr  Asn  Leu  Gln  Glu  Arg  Ser  Pro  Lys  Ile
     1070                     1075                      1080 gaa  cgg  gct  gct  ttg  gat  ggg  aca  gaa  cgg  gag  gtc  ctc  ttt  ttc        3294
Glu  Arg  Ala  Ala  Leu  Asp  Gly  Thr  Glu  Arg  Glu  Val  Leu  Phe  Phe
     1085                     1090                      1095 agt  ggc  tta  agt  aaa  cca  att  gct  tta  gcc  ctt  gat  agc  agg  ctg        3339
Ser  Gly  Leu  Ser  Lys  Pro  Ile  Ala  Leu  Ala  Leu  Asp  Ser  Arg  Leu
     1100                     1105                      1110 ggc  aag  ctc  ttt  tgg  gct  gat  tca  gat  ctc  cgg  cga  att  gaa  agc        3384
Gly  Lys  Leu  Phe  Trp  Ala  Asp  Ser  Asp  Leu  Arg  Arg  Ile  Glu  Ser
     1115                     1120                      1125 agt  gat  ctc  tca  ggt  gct  aac  cgg  ata  gta  tta  gaa  gac  tcc  aat        3429
Ser  Asp  Leu  Ser  Gly  Ala  Asn  Arg  Ile  Val  Leu  Glu  Asp  Ser  Asn
     1130                     1135                      1140 atc  ttg  cag  cct  gtg  gga  ctt  act  gtg  ttt  gaa  aac  tgg  ctc  tat        3474
Ile  Leu  Gln  Pro  Val  Gly  Leu  Thr  Val  Phe  Glu  Asn  Trp  Leu  Tyr
     1145                     1150                      1155 tgg  att  gat  aaa  cag  cag  caa  atg  att  gaa  aaa  att  gac  atg  aca        3519
Trp  Ile  Asp  Lys  Gln  Gln  Gln  Met  Ile  Glu  Lys  Ile  Asp  Met  Thr
     1160                     1165                      1170 ggt  cga  gag  ggt  aga  acc  aaa  gtc  caa  gct  cga  att  gcc  cag  ctt        3564
Gly  Arg  Glu  Gly  Arg  Thr  Lys  Val  Gln  Ala  Arg  Ile  Ala  Gln  Leu
     1175                     1180                      1185 agt  gac  att  cat  gca  gta  aag  gag  ctg  aac  ctt  caa  gaa  tac  aga        3609
Ser  Asp  Ile  His  Ala  Val  Lys  Glu  Leu  Asn  Leu  Gln  Glu  Tyr  Arg
     1190                     1195                      1200 cag  cac  cct  tgt  gct  cag  gat  aat  ggt  ggc  tgt  tca  cat  att  tgt        3654
Gln  His  Pro  Cys  Ala  Gln  Asp  Asn  Gly  Gly  Cys  Ser  His  Ile  Cys
     1205                     1210                      1215 ctt  gta  aag  ggg  gat  ggt  act  aca  agg  tgt  tct  tgc  ccc  atg  cac        3699
Leu  Val  Lys  Gly  Asp  Gly  Thr  Thr  Arg  Cys  Ser  Cys  Pro  Met  His
     1220                     1225                      1230 ctg  gtt  cta  ctt  caa  gat  gag  cta  tca  tgt  gga  gaa  cct  cca  aca        3744
Leu  Val  Leu  Leu  Gln  Asp  Glu  Leu  Ser  Cys  Gly  Glu  Pro  Pro  Thr
     1235                     1240                      1245 tgt  tct  cct  cag  cag  ttt  act  tgt  ttc  acg  ggg  gaa  att  gac  tgt        3789
Cys  Ser  Pro  Gln  Gln  Phe  Thr  Cys  Phe  Thr  Gly  Glu  Ile  Asp  Cys
     1250                     1255                      1260 atc  cct  gtg  gct  tgg  cgg  tgc  gat  ggg  ttt  act  gaa  tgt  gaa  gac        3834
Ile  Pro  Val  Ala  Trp  Arg  Cys  Asp  Gly  Phe  Thr  Glu  Cys  Glu  Asp
     1265                     1270                      1275 cac  agt  gat  gaa  ctc  aat  tgt  cct  gta  tgc  tca  gag  tcc  cag  ttc        3879
His  Ser  Asp  Glu  Leu  Asn  Cys  Pro  Val  Cys  Ser  Glu  Ser  Gln  Phe
     1280                     1285                      1290 cag  tgt  gcc  agt  ggg  cag  tgt  att  gat  ggt  gcc  ctc  cga  tgc  aat        3924
Gln  Cys  Ala  Ser  Gly  Gln  Cys  Ile  Asp  Gly  Ala  Leu  Arg  Cys  Asn
```

```
                    1295                1300                1305 gga gat gca aac tgc cag gac aaa tca gat gag aag aac tgt gaa   3969
Gly Asp Ala Asn Cys Gln Asp Lys Ser Asp Glu Lys Asn Cys Glu
1310                1315                1320 gtg ctt tgt tta att gat cag ttc cgc tgt gcc aat ggt cag tgc   4014
Val Leu Cys Leu Ile Asp Gln Phe Arg Cys Ala Asn Gly Gln Cys
1325                1330                1335 att gga aag cac aag aag tgt gat cat aat gtg gat tgc agt gac   4059
Ile Gly Lys His Lys Lys Cys Asp His Asn Val Asp Cys Ser Asp
1340                1345                1350 aag tca gat gaa ctg gat tgt tat ccg act gaa gaa cca gca cca   4104
Lys Ser Asp Glu Leu Asp Cys Tyr Pro Thr Glu Glu Pro Ala Pro
1355                1360                1365 cag gcc acc aat aca gtt ggt tct gtt att ggc gta att gtc acc   4149
Gln Ala Thr Asn Thr Val Gly Ser Val Ile Gly Val Ile Val Thr
1370                1375                1380 att ttt gtg tct gga act gta tac ttt atc tgc cag agg atg ttg   4194
Ile Phe Val Ser Gly Thr Val Tyr Phe Ile Cys Gln Arg Met Leu
1385                1390                1395 tgt cca cgt atg aag gga gat ggg gaa act atg act aat gac tat   4239
Cys Pro Arg Met Lys Gly Asp Gly Glu Thr Met Thr Asn Asp Tyr
1400                1405                1410 gta gtt cat gga cca gct tct gtg cct ctt ggt tat gtg cca cac   4284
Val Val His Gly Pro Ala Ser Val Pro Leu Gly Tyr Val Pro His
1415                1420                1425 cca agt tct ttg tca gga tct ctt cca gga atg tct cga ggt aaa   4329
Pro Ser Ser Leu Ser Gly Ser Leu Pro Gly Met Ser Arg Gly Lys
1430                1435                1440 tca atg atc agc tcc ctc agt atc atg ggg gga agc agt gga ccc   4374
Ser Met Ile Ser Ser Leu Ser Ile Met Gly Gly Ser Ser Gly Pro
1445                1450                1455 ccc tat gac cga gcc cat gtt aca gga gca tca tca agt agt tct   4419
Pro Tyr Asp Arg Ala His Val Thr Gly Ala Ser Ser Ser Ser Ser
1460                1465                1470 tca agc acc aaa ggc act tac ttc cct gca att ttg aac cct cca   4464
Ser Ser Thr Lys Gly Thr Tyr Phe Pro Ala Ile Leu Asn Pro Pro
1475                1480                1485 cca tcc cca gcc aca gag cga tca cat tac act atg gaa ttt gga   4509
Pro Ser Pro Ala Thr Glu Arg Ser His Tyr Thr Met Glu Phe Gly
1490                1495                1500 tat tct tca aac agt cct tcc act cat agg tca tac agc tac agg   4554
Tyr Ser Ser Asn Ser Pro Ser Thr His Arg Ser Tyr Ser Tyr Arg
1505                1510                1515 cca tat agc tac cgg cac ttt gca ccc ccc acc aca ccc tgc agc   4599
Pro Tyr Ser Tyr Arg His Phe Ala Pro Pro Thr Thr Pro Cys Ser
1520                1525                1530 aca gat gtt tgt gac agt gac tat gct cct agt cgg aga atg acc   4644
Thr Asp Val Cys Asp Ser Asp Tyr Ala Pro Ser Arg Arg Met Thr
1535                1540                1545 tca gtg gca aca gcc aag ggc tat acc agt gac ttg aac tat gat   4689
Ser Val Ala Thr Ala Lys Gly Tyr Thr Ser Asp Leu Asn Tyr Asp
1550                1555                1560 tca gaa cct gtg ccc cca cct ccc aca ccc cga agc caa tac ttg   4734
Ser Glu Pro Val Pro Pro Pro Thr Pro Arg Ser Gln Tyr Leu
1565                1570                1575 tca gca gag gag aac tat gaa agc tgc cca cct tct cca tac aca   4779
Ser Ala Glu Glu Asn Tyr Glu Ser Cys Pro Pro Ser Pro Tyr Thr
1580                1585                1590 gag agg agc tat tct cat cac ctc tac cca ccg cca ccc tct ccc   4824
Glu Arg Ser Tyr Ser His His Leu Tyr Pro Pro Pro Ser Pro
```

```
                  1595                1600                1605
tgt   aca   gac   tcc   tcc   tga                                              4842
Cys   Thr   Asp   Ser   Ser
            1610
```

<210> SEQ ID NO 8
<211> LENGTH: 1613
<212> TYPE: PRT
<213> ORGANISM: Homo sapiens

<400> SEQUENCE: 8

Met Gly Ala Val Leu Arg Ser Leu Leu Ala Cys Ser Phe Cys Val Leu
1               5                   10                  15

Leu Arg Ala Ala Pro Leu Leu Leu Tyr Ala Asn Arg Arg Asp Leu Arg
            20                  25                  30

Leu Val Asp Ala Thr Asn Gly Lys Glu Asn Ala Thr Ile Val Val Gly
        35                  40                  45

Gly Leu Glu Asp Ala Ala Ala Val Asp Phe Val Phe Ser His Gly Leu
    50                  55                  60

Ile Tyr Trp Ser Asp Val Ser Glu Glu Ala Ile Lys Arg Thr Glu Phe
65                  70                  75                  80

Asn Lys Thr Glu Ser Val Gln Asn Val Val Val Ser Gly Leu Leu Ser
                85                  90                  95

Pro Asp Gly Leu Ala Cys Asp Trp Leu Gly Glu Lys Leu Tyr Trp Thr
            100                 105                 110

Asp Ser Glu Thr Asn Arg Ile Glu Val Ser Asn Leu Asp Gly Ser Leu
        115                 120                 125

Arg Lys Val Leu Phe Trp Gln Glu Leu Asp Gln Pro Arg Ala Ile Ala
    130                 135                 140

Leu Asp Pro Ser Ser Gly Phe Met Tyr Trp Thr Asp Trp Gly Glu Val
145                 150                 155                 160

Pro Lys Ile Glu Arg Ala Gly Met Asp Gly Ser Ser Arg Phe Ile Ile
                165                 170                 175

Ile Asn Ser Glu Ile Tyr Trp Pro Asn Gly Leu Thr Leu Asp Tyr Glu
            180                 185                 190

Glu Gln Lys Leu Tyr Trp Ala Asp Ala Lys Leu Asn Phe Ile His Lys
        195                 200                 205

Ser Asn Leu Asp Gly Thr Asn Arg Gln Ala Val Val Lys Gly Ser Leu
    210                 215                 220

Pro His Pro Phe Ala Leu Thr Leu Phe Glu Asp Ile Leu Tyr Trp Thr
225                 230                 235                 240

Asp Trp Ser Thr His Ser Ile Leu Ala Cys Asn Lys Tyr Thr Gly Glu
                245                 250                 255

Gly Leu Arg Glu Ile His Ser Asp Ile Phe Ser Pro Met Asp Ile His
            260                 265                 270

Ala Phe Ser Gln Gln Arg Gln Pro Asn Ala Thr Asn Pro Cys Gly Ile
        275                 280                 285

Asp Asn Gly Gly Cys Ser His Leu Cys Leu Met Ser Pro Val Lys Pro
    290                 295                 300

Phe Tyr Gln Cys Ala Cys Pro Thr Gly Val Lys Leu Leu Glu Asn Gly
305                 310                 315                 320

Lys Thr Cys Lys Asp Gly Ala Thr Glu Leu Leu Leu Leu Ala Arg Arg
                325                 330                 335

Thr Asp Leu Arg Arg Ile Ser Leu Asp Thr Pro Asp Phe Thr Asp Ile
            340                 345                 350

```
Val Leu Gln Leu Glu Asp Ile Arg His Ala Ile Ala Ile Asp Tyr Asp
    355                 360                 365

Pro Val Glu Gly Tyr Ile Tyr Trp Thr Asp Asp Glu Val Arg Ala Ile
370                 375                 380

Arg Arg Ser Phe Ile Asp Gly Ser Gly Ser Gln Phe Val Val Thr Ala
385                 390                 395                 400

Gln Ile Ala His Pro Asp Gly Ile Ala Val Asp Trp Val Ala Arg Asn
                405                 410                 415

Leu Tyr Trp Thr Asp Thr Gly Thr Asp Arg Ile Glu Val Thr Arg Leu
                420                 425                 430

Asn Gly Thr Met Arg Lys Ile Leu Ile Ser Glu Asp Leu Glu Glu Pro
                435                 440                 445

Arg Ala Ile Val Leu Asp Pro Met Val Gly Tyr Met Tyr Trp Thr Asp
450                 455                 460

Trp Gly Glu Ile Pro Lys Ile Glu Arg Ala Ala Leu Asp Gly Ser Asp
465                 470                 475                 480

Arg Val Val Leu Val Asn Thr Ser Leu Gly Trp Pro Asn Gly Leu Ala
                485                 490                 495

Leu Asp Tyr Asp Glu Gly Lys Ile Tyr Trp Gly Asp Ala Lys Thr Asp
                500                 505                 510

Lys Ile Glu Val Met Asn Thr Asp Gly Thr Gly Arg Arg Val Leu Val
                515                 520                 525

Glu Asp Lys Ile Pro His Ile Phe Gly Phe Thr Leu Leu Gly Asp Tyr
530                 535                 540

Val Tyr Trp Thr Asp Trp Gln Arg Arg Ser Ile Glu Arg Val His Lys
545                 550                 555                 560

Arg Ser Ala Glu Arg Glu Val Ile Ile Asp Gln Leu Pro Asp Leu Met
                565                 570                 575

Gly Leu Lys Ala Thr Asn Val His Arg Val Ile Gly Ser Asn Pro Cys
                580                 585                 590

Ala Glu Glu Asn Gly Gly Cys Ser His Leu Cys Leu Tyr Arg Pro Gln
                595                 600                 605

Gly Leu Arg Cys Ala Cys Pro Ile Gly Phe Glu Leu Ile Ser Asp Met
610                 615                 620

Lys Thr Cys Ile Val Pro Glu Ala Phe Leu Leu Phe Ser Arg Arg Ala
625                 630                 635                 640

Asp Ile Arg Arg Ile Ser Leu Glu Thr Asn Asn Asn Asn Val Ala Ile
                645                 650                 655

Pro Leu Thr Gly Val Lys Glu Ala Ser Ala Leu Asp Phe Asp Val Thr
                660                 665                 670

Asp Asn Arg Ile Tyr Trp Thr Asp Ile Ser Leu Lys Thr Ile Ser Arg
                675                 680                 685

Ala Phe Met Asn Gly Ser Ala Leu Glu His Val Val Glu Phe Gly Leu
690                 695                 700

Asp Tyr Pro Glu Gly Met Ala Val Asp Trp Leu Gly Lys Asn Leu Tyr
705                 710                 715                 720

Trp Ala Asp Thr Gly Thr Asn Arg Ile Glu Val Ser Lys Leu Asp Gly
                725                 730                 735

Gln His Arg Gln Val Leu Val Trp Lys Asp Leu Asp Ser Pro Arg Ala
                740                 745                 750

Leu Ala Leu Asp Pro Ala Glu Gly Phe Met Tyr Trp Thr Glu Trp Gly
                755                 760                 765

Gly Lys Pro Lys Ile Asp Arg Ala Ala Met Asp Gly Ser Glu Arg Thr
770                 775                 780
```

```
Thr Leu Val Pro Asn Val Gly Arg Ala Asn Gly Leu Thr Ile Asp Tyr
785                 790                 795                 800

Ala Lys Arg Arg Leu Tyr Trp Thr Asp Leu Asp Thr Asn Leu Ile Glu
            805                 810                 815

Ser Ser Asn Met Leu Gly Leu Asn Arg Glu Val Ile Ala Asp Asp Leu
        820                 825                 830

Pro His Pro Phe Gly Leu Thr Gln Tyr Gln Asp Tyr Ile Tyr Trp Thr
    835                 840                 845

Asp Trp Ser Arg Arg Ser Ile Glu Arg Ala Asn Lys Thr Ser Gly Gln
850                 855                 860

Asn Arg Thr Ile Ile Gln Gly His Leu Asp Tyr Val Met Asp Ile Leu
865                 870                 875                 880

Val Phe His Ser Ser Arg Gln Ser Gly Trp Asn Glu Cys Ala Ser Ser
            885                 890                 895

Asn Gly His Cys Ser His Leu Cys Leu Ala Val Pro Val Gly Gly Phe
        900                 905                 910

Val Cys Gly Cys Pro Ala His Tyr Ser Leu Asn Ala Asp Asn Arg Thr
    915                 920                 925

Cys Ser Ala Pro Thr Thr Phe Leu Leu Phe Ser Gln Lys Ser Ala Ile
930                 935                 940

Asn Arg Met Val Ile Asp Glu Gln Gln Ser Pro Asp Ile Ile Leu Pro
945                 950                 955                 960

Ile His Ser Leu Arg Asn Val Arg Ala Ile Asp Tyr Asp Pro Leu Asp
            965                 970                 975

Lys Gln Leu Tyr Trp Ile Asp Ser Arg Gln Asn Met Ile Arg Lys Ala
        980                 985                 990

Gln Glu Asp Gly Ser Gln Gly Phe Thr Val Val Ser Ser Val Pro
    995                 1000                1005

Ser Gln Asn Leu Glu Ile Gln Pro Tyr Asp Leu Ser Ile Asp Ile
    1010                1015                1020

Tyr Ser Arg Tyr Ile Tyr Trp Thr Cys Glu Ala Thr Asn Val Ile
    1025                1030                1035

Asn Val Thr Arg Leu Asp Gly Arg Ser Val Gly Val Val Leu Lys
    1040                1045                1050

Gly Glu Gln Asp Arg Pro Arg Ala Ile Val Val Asn Pro Glu Lys
    1055                1060                1065

Gly Tyr Met Tyr Phe Thr Asn Leu Gln Glu Arg Ser Pro Lys Ile
    1070                1075                1080

Glu Arg Ala Ala Leu Asp Gly Thr Glu Arg Glu Val Leu Phe Phe
    1085                1090                1095

Ser Gly Leu Ser Lys Pro Ile Ala Leu Ala Leu Asp Ser Arg Leu
    1100                1105                1110

Gly Lys Leu Phe Trp Ala Asp Ser Asp Leu Arg Arg Ile Glu Ser
    1115                1120                1125

Ser Asp Leu Ser Gly Ala Asn Arg Ile Val Leu Glu Asp Ser Asn
    1130                1135                1140

Ile Leu Gln Pro Val Gly Leu Thr Val Phe Glu Asn Trp Leu Tyr
    1145                1150                1155

Trp Ile Asp Lys Gln Gln Gln Met Ile Glu Lys Ile Asp Met Thr
    1160                1165                1170

Gly Arg Glu Gly Arg Thr Lys Val Gln Ala Arg Ile Ala Gln Leu
    1175                1180                1185

Ser Asp Ile His Ala Val Lys Glu Leu Asn Leu Gln Glu Tyr Arg
```

```
            1190               1195               1200

Gln His Pro Cys Ala Gln Asp Asn Gly Gly Cys Ser His Ile Cys
    1205               1210               1215

Leu Val Lys Gly Asp Gly Thr Thr Arg Cys Ser Cys Pro Met His
    1220               1225               1230

Leu Val Leu Leu Gln Asp Glu Leu Ser Cys Gly Glu Pro Pro Thr
    1235               1240               1245

Cys Ser Pro Gln Gln Phe Thr Cys Phe Thr Gly Glu Ile Asp Cys
    1250               1255               1260

Ile Pro Val Ala Trp Arg Cys Asp Gly Phe Thr Glu Cys Glu Asp
    1265               1270               1275

His Ser Asp Glu Leu Asn Cys Pro Val Cys Ser Glu Ser Gln Phe
    1280               1285               1290

Gln Cys Ala Ser Gly Gln Cys Ile Asp Gly Ala Leu Arg Cys Asn
    1295               1300               1305

Gly Asp Ala Asn Cys Gln Asp Lys Ser Asp Glu Lys Asn Cys Glu
    1310               1315               1320

Val Leu Cys Leu Ile Asp Gln Phe Arg Cys Ala Asn Gly Gln Cys
    1325               1330               1335

Ile Gly Lys His Lys Lys Cys Asp His Asn Val Asp Cys Ser Asp
    1340               1345               1350

Lys Ser Asp Glu Leu Asp Cys Tyr Pro Thr Glu Glu Pro Ala Pro
    1355               1360               1365

Gln Ala Thr Asn Thr Val Gly Ser Val Ile Gly Val Ile Val Thr
    1370               1375               1380

Ile Phe Val Ser Gly Thr Val Tyr Phe Ile Cys Gln Arg Met Leu
    1385               1390               1395

Cys Pro Arg Met Lys Gly Asp Gly Glu Thr Met Thr Asn Asp Tyr
    1400               1405               1410

Val Val His Gly Pro Ala Ser Val Pro Leu Gly Tyr Val Pro His
    1415               1420               1425

Pro Ser Ser Leu Ser Gly Ser Leu Pro Gly Met Ser Arg Gly Lys
    1430               1435               1440

Ser Met Ile Ser Ser Leu Ser Ile Met Gly Gly Ser Ser Gly Pro
    1445               1450               1455

Pro Tyr Asp Arg Ala His Val Thr Gly Ala Ser Ser Ser Ser Ser
    1460               1465               1470

Ser Ser Thr Lys Gly Thr Tyr Phe Pro Ala Ile Leu Asn Pro Pro
    1475               1480               1485

Pro Ser Pro Ala Thr Glu Arg Ser His Tyr Thr Met Glu Phe Gly
    1490               1495               1500

Tyr Ser Ser Asn Ser Pro Ser Thr His Arg Ser Tyr Ser Tyr Arg
    1505               1510               1515

Pro Tyr Ser Tyr Arg His Phe Ala Pro Pro Thr Thr Pro Cys Ser
    1520               1525               1530

Thr Asp Val Cys Asp Ser Asp Tyr Ala Pro Ser Arg Arg Met Thr
    1535               1540               1545

Ser Val Ala Thr Ala Lys Gly Tyr Thr Ser Asp Leu Asn Tyr Asp
    1550               1555               1560

Ser Glu Pro Val Pro Pro Pro Thr Pro Arg Ser Gln Tyr Leu
    1565               1570               1575

Ser Ala Glu Glu Asn Tyr Glu Ser Cys Pro Pro Ser Pro Tyr Thr
    1580               1585               1590
```

Glu Arg Ser Tyr Ser His His Leu Tyr Pro Pro Pro Ser Pro
1595                1600                1605

Cys Thr Asp Ser Ser
    1610

<210> SEQ ID NO 9
<211> LENGTH: 702
<212> TYPE: DNA
<213> ORGANISM: Rat
<220> FEATURE:
<221> NAME/KEY: CDS
<222> LOCATION: (1)..(702)

<400> SEQUENCE: 9

```
atg ggt gtg cct act cat ctc ctg ggt ttg ttg ctg ctc tgg att aca       48
Met Gly Val Pro Thr His Leu Leu Gly Leu Leu Leu Leu Trp Ile Thr
1               5                   10                  15 cat gcc ata tgt gat atc cgg atg aca cag tct cca gct tcc ctg tct       96
His Ala Ile Cys Asp Ile Arg Met Thr Gln Ser Pro Ala Ser Leu Ser
            20                  25                  30 gca tct ctg gga gaa act gtc aac atc gaa tgt cta gca agt gag gac      144
Ala Ser Leu Gly Glu Thr Val Asn Ile Glu Cys Leu Ala Ser Glu Asp
        35                  40                  45 att tac agt gat tta gca tgg tat cag cag aag cca ggg aaa tct cct      192
Ile Tyr Ser Asp Leu Ala Trp Tyr Gln Gln Lys Pro Gly Lys Ser Pro
    50                  55                  60 cag ctc ctg atc tat aat gca aat agc ttg caa aat ggg gtc cct tca      240
Gln Leu Leu Ile Tyr Asn Ala Asn Ser Leu Gln Asn Gly Val Pro Ser
65                  70                  75                  80 cgg ttt agt ggc agt gga tct ggc aca cag tat tct cta aaa ata aac      288
Arg Phe Ser Gly Ser Gly Ser Gly Thr Gln Tyr Ser Leu Lys Ile Asn
                85                  90                  95 agc ctg caa tct gaa gat gtc gcg act tat ttc tgt caa caa tat aac      336
Ser Leu Gln Ser Glu Asp Val Ala Thr Tyr Phe Cys Gln Gln Tyr Asn
            100                 105                 110 aat tat cct ccg acg ttc ggt gga ggc acc aag ctg gaa ttg aaa cgg      384
Asn Tyr Pro Pro Thr Phe Gly Gly Gly Thr Lys Leu Glu Leu Lys Arg
        115                 120                 125 gct gat gct gca cca act gta tct atc ttc cca cca tcc acg gaa cag      432
Ala Asp Ala Ala Pro Thr Val Ser Ile Phe Pro Pro Ser Thr Glu Gln
    130                 135                 140 tta gca act gga ggt gcc tca gtc gtg tgc ctc atg aac aac ttc tat      480
Leu Ala Thr Gly Gly Ala Ser Val Val Cys Leu Met Asn Asn Phe Tyr
145                 150                 155                 160 ccc aga gac atc agt gtc aag tgg aag att gat ggc act gaa cga cga      528
Pro Arg Asp Ile Ser Val Lys Trp Lys Ile Asp Gly Thr Glu Arg Arg
                165                 170                 175 gat ggt gtc ctg gac agt gtt act gat cag gac agc aaa gac agc acg      576
Asp Gly Val Leu Asp Ser Val Thr Asp Gln Asp Ser Lys Asp Ser Thr
            180                 185                 190 tac agc atg agc agc acc ctc tcg ttg acc aag gct gac tat gaa agt      624
Tyr Ser Met Ser Ser Thr Leu Ser Leu Thr Lys Ala Asp Tyr Glu Ser
        195                 200                 205 cat aac ctc tat acc tgt gag gtt gtt cat aag aca tca tcc tca ccc      672
His Asn Leu Tyr Thr Cys Glu Val Val His Lys Thr Ser Ser Ser Pro
    210                 215                 220 gtc gtc aag agc ttc aac agg aat gag tgt                              702
Val Val Lys Ser Phe Asn Arg Asn Glu Cys
225                 230
```

<210> SEQ ID NO 10
<211> LENGTH: 234

<212> TYPE: PRT
<213> ORGANISM: Rat

<400> SEQUENCE: 10

```
Met Gly Val Pro Thr His Leu Gly Leu Leu Leu Trp Ile Thr
1               5                   10                  15

His Ala Ile Cys Asp Ile Arg Met Thr Gln Ser Pro Ala Ser Leu Ser
            20                  25                  30

Ala Ser Leu Gly Glu Thr Val Asn Ile Glu Cys Leu Ala Ser Glu Asp
        35                  40                  45

Ile Tyr Ser Asp Leu Ala Trp Tyr Gln Gln Lys Pro Gly Lys Ser Pro
    50                  55                  60

Gln Leu Leu Ile Tyr Asn Ala Asn Ser Leu Gln Asn Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Ser Glu Asp Val Ala Thr Tyr Phe Cys Gln Gln Tyr Asn
            100                 105                 110

Asn Tyr Pro Pro Thr Phe Gly Gly Gly Thr Lys Leu Glu Leu Lys Arg
        115                 120                 125

Ala Asp Ala Ala Pro Thr Val Ser Ile Phe Pro Pro Ser Thr Glu Gln
    130                 135                 140

Leu Ala Thr Gly Gly Ala Ser Val Val Cys Leu Met Asn Asn Phe Tyr
145                 150                 155                 160

Pro Arg Asp Ile Ser Val Lys Trp Lys Ile Asp Gly Thr Glu Arg Arg
                165                 170                 175

Asp Gly Val Leu Asp Ser Val Thr Asp Gln Asp Ser Lys Asp Ser Thr
            180                 185                 190

Tyr Ser Met Ser Ser Thr Leu Ser Leu Thr Lys Ala Asp Tyr Glu Ser
        195                 200                 205

His Asn Leu Tyr Thr Cys Glu Val Val His Lys Thr Ser Ser Ser Pro
    210                 215                 220

Val Val Lys Ser Phe Asn Arg Asn Glu Cys
225                 230
```

<210> SEQ ID NO 11
<211> LENGTH: 1395
<212> TYPE: DNA
<213> ORGANISM: Rat
<220> FEATURE:
<221> NAME/KEY: CDS
<222> LOCATION: (1)..(1395)

<400> SEQUENCE: 11

```
atg gac atc agg ctc agc ttg gct ttc ctt gtc ctt ttc ata aaa ggt    48
Met Asp Ile Arg Leu Ser Leu Ala Phe Leu Val Leu Phe Ile Lys Gly
1               5                   10                  15 gtc cag tgt gag gta cag ctg gtg gag tct ggc gga gga ttg gta cag    96
Val Gln Cys Glu Val Gln Leu Val Glu Ser Gly Gly Gly Leu Val Gln
            20                  25                  30 cct gca aac tcc ctg aaa ctc tcc tgt gca gcc tca gga ttc act ttc   144
Pro Ala Asn Ser Leu Lys Leu Ser Cys Ala Ala Ser Gly Phe Thr Phe
        35                  40                  45 agt gac tat gcc atg gcc tgg gtc cgc cag tct cca aag aag ggt ctg   192
Ser Asp Tyr Ala Met Ala Trp Val Arg Gln Ser Pro Lys Lys Gly Leu
    50                  55                  60 gag tgg gtc gca acc att att tat gat ggt agt agc act tac tat cga   240
Glu Trp Val Ala Thr Ile Ile Tyr Asp Gly Ser Ser Thr Tyr Tyr Arg
65                  70                  75                  80
```

|       |       |       |       |       |       |       |       |       |       |       |       |       |       |       |       |       |
|-------|-------|-------|-------|-------|-------|-------|-------|-------|-------|-------|-------|-------|-------|-------|-------|-------|
| gac | tcc | gtg | aag | ggc | cga | ttc | act | atc | tcc | aga | gat | aat | gca | aaa | agc | 288 |
| Asp | Ser | Val | Lys | Gly | Arg | Phe | Thr | Ile | Ser | Arg | Asp | Asn | Ala | Lys | Ser | |
| | | | 85 | | | | | 90 | | | | | 95 | | | |
| acc | cta | tac | ctg | caa | atg | gac | agt | ctg | agg | tct | gag | gac | acg | gcc | act | 336 |
| Thr | Leu | Tyr | Leu | Gln | Met | Asp | Ser | Leu | Arg | Ser | Glu | Asp | Thr | Ala | Thr | |
| | | | 100 | | | | | 105 | | | | | 110 | | | |
| tat | tac | tgt | gca | aca | ggt | ctg | ggt | ata | gct | acg | gac | tac | ttt | gat | tac | 384 |
| Tyr | Tyr | Cys | Ala | Thr | Gly | Leu | Gly | Ile | Ala | Thr | Asp | Tyr | Phe | Asp | Tyr | |
| | | 115 | | | | | 120 | | | | | 125 | | | | |
| tgg | ggc | caa | gga | gtc | ctg | gtc | aca | gtc | tcc | tca | gct | gaa | aca | aca | gcc | 432 |
| Trp | Gly | Gln | Gly | Val | Leu | Val | Thr | Val | Ser | Ser | Ala | Glu | Thr | Thr | Ala | |
| | 130 | | | | | 135 | | | | | 140 | | | | | |
| cca | tct | gtc | tat | cca | ctg | gct | cct | gga | act | gct | ctc | aaa | agt | aac | tcc | 480 |
| Pro | Ser | Val | Tyr | Pro | Leu | Ala | Pro | Gly | Thr | Ala | Leu | Lys | Ser | Asn | Ser | |
| 145 | | | | 150 | | | | | 155 | | | | | 160 | | |
| atg | gtg | acc | ctg | gga | tgc | ctg | gtc | aag | ggc | tat | ttc | cct | gag | cca | gtc | 528 |
| Met | Val | Thr | Leu | Gly | Cys | Leu | Val | Lys | Gly | Tyr | Phe | Pro | Glu | Pro | Val | |
| | | | 165 | | | | | 170 | | | | | 175 | | | |
| acc | gtg | acc | tgg | aac | tct | gga | gcc | ctg | tcc | agc | ggt | gtg | cac | acc | ttc | 576 |
| Thr | Val | Thr | Trp | Asn | Ser | Gly | Ala | Leu | Ser | Ser | Gly | Val | His | Thr | Phe | |
| | | | 180 | | | | | 185 | | | | | 190 | | | |
| cca | gct | gtc | ctg | cag | tct | ggg | ctc | tac | act | ctc | acc | agc | tca | gtg | act | 624 |
| Pro | Ala | Val | Leu | Gln | Ser | Gly | Leu | Tyr | Thr | Leu | Thr | Ser | Ser | Val | Thr | |
| | | 195 | | | | | 200 | | | | | 205 | | | | |
| gta | ccc | tcc | agc | acc | tgg | ccc | agc | cag | acc | gtc | acc | tgc | aac | gta | gcc | 672 |
| Val | Pro | Ser | Ser | Thr | Trp | Pro | Ser | Gln | Thr | Val | Thr | Cys | Asn | Val | Ala | |
| | 210 | | | | | 215 | | | | | 220 | | | | | |
| cac | ccg | gcc | agc | agc | acc | aag | gtg | gac | aag | aaa | att | gtg | ccc | aga | aac | 720 |
| His | Pro | Ala | Ser | Ser | Thr | Lys | Val | Asp | Lys | Lys | Ile | Val | Pro | Arg | Asn | |
| 225 | | | | 230 | | | | | 235 | | | | | 240 | | |
| tgt | gga | ggt | gat | tgc | aag | cct | tgt | ata | tgt | aca | ggc | tca | gaa | gta | tca | 768 |
| Cys | Gly | Gly | Asp | Cys | Lys | Pro | Cys | Ile | Cys | Thr | Gly | Ser | Glu | Val | Ser | |
| | | | 245 | | | | | 250 | | | | | 255 | | | |
| tct | gtc | ttc | atc | ttc | ccc | cca | aag | ccc | aaa | gat | gtg | ctc | acc | atc | act | 816 |
| Ser | Val | Phe | Ile | Phe | Pro | Pro | Lys | Pro | Lys | Asp | Val | Leu | Thr | Ile | Thr | |
| | | | 260 | | | | | 265 | | | | | 270 | | | |
| ctg | act | cct | aag | gtc | acg | tgt | gtt | gtg | gta | gac | att | agc | cag | gac | gat | 864 |
| Leu | Thr | Pro | Lys | Val | Thr | Cys | Val | Val | Val | Asp | Ile | Ser | Gln | Asp | Asp | |
| | | 275 | | | | | 280 | | | | | 285 | | | | |
| ccc | gag | gtc | cat | ttc | agc | tgg | ttt | gta | gat | gac | gtg | gaa | gtc | cac | aca | 912 |
| Pro | Glu | Val | His | Phe | Ser | Trp | Phe | Val | Asp | Asp | Val | Glu | Val | His | Thr | |
| | 290 | | | | | 295 | | | | | 300 | | | | | |
| gct | cag | act | cga | cca | cca | gag | gag | cag | ttc | aac | agc | act | ttc | cgc | tca | 960 |
| Ala | Gln | Thr | Arg | Pro | Pro | Glu | Glu | Gln | Phe | Asn | Ser | Thr | Phe | Arg | Ser | |
| 305 | | | | 310 | | | | | 315 | | | | | 320 | | |
| gtc | agt | gaa | ctc | ccc | atc | ctg | cac | cag | gac | tgg | ctc | aat | ggc | agg | acg | 1008 |
| Val | Ser | Glu | Leu | Pro | Ile | Leu | His | Gln | Asp | Trp | Leu | Asn | Gly | Arg | Thr | |
| | | | 325 | | | | | 330 | | | | | 335 | | | |
| ttc | aga | tgc | aag | gtc | acc | agt | gca | gct | ttc | cca | tcc | ccc | atc | gag | aaa | 1056 |
| Phe | Arg | Cys | Lys | Val | Thr | Ser | Ala | Ala | Phe | Pro | Ser | Pro | Ile | Glu | Lys | |
| | | 340 | | | | | 345 | | | | | 350 | | | | |
| acc | atc | tcc | aaa | ccc | gaa | ggc | aga | aca | caa | gtt | ccg | cat | gta | tac | acc | 1104 |
| Thr | Ile | Ser | Lys | Pro | Glu | Gly | Arg | Thr | Gln | Val | Pro | His | Val | Tyr | Thr | |
| | | | 355 | | | | | 360 | | | | | 365 | | | |
| atg | tca | cct | acc | aag | gaa | gag | atg | acc | cag | aat | gaa | gtc | agt | atc | acc | 1152 |
| Met | Ser | Pro | Thr | Lys | Glu | Glu | Met | Thr | Gln | Asn | Glu | Val | Ser | Ile | Thr | |
| | | 370 | | | | | 375 | | | | | 380 | | | | |
| tgc | atg | gta | aaa | ggc | ttc | tat | ccc | cca | gac | att | tat | gtg | gag | tgg | cag | 1200 |
| Cys | Met | Val | Lys | Gly | Phe | Tyr | Pro | Pro | Asp | Ile | Tyr | Val | Glu | Trp | Gln | |
| 385 | | | | 390 | | | | | 395 | | | | | 400 | | |

-continued

```
atg aac ggg cag cca cag gaa aac tac aag aac act cca cct acg atg    1248
Met Asn Gly Gln Pro Gln Glu Asn Tyr Lys Asn Thr Pro Pro Thr Met
        405                 410                 415 gac aca gat ggg agt tac ttc ctc tac agc aag ctc aat gtg aag aag    1296
Asp Thr Asp Gly Ser Tyr Phe Leu Tyr Ser Lys Leu Asn Val Lys Lys
        420                 425                 430 gaa aaa tgg cag cag gga aac acg ttc acg tgt tct gtg ctg cat gaa    1344
Glu Lys Trp Gln Gln Gly Asn Thr Phe Thr Cys Ser Val Leu His Glu
        435                 440                 445 ggc ctg cac aac cac cat act gag aag agt ctc tcc cac tct ccg ggt    1392
Gly Leu His Asn His His Thr Glu Lys Ser Leu Ser His Ser Pro Gly
    450                 455                 460 aaa                                                                 1395
Lys
465

<210> SEQ ID NO 12
<211> LENGTH: 465
<212> TYPE: PRT
<213> ORGANISM: Rat

<400> SEQUENCE: 12

Met Asp Ile Arg Leu Ser Leu Ala Phe Leu Val Leu Phe Ile Lys Gly
1               5                   10                  15

Val Gln Cys Glu Val Gln Leu Val Glu Ser Gly Gly Gly Leu Val Gln
            20                  25                  30

Pro Ala Asn Ser Leu Lys Leu Ser Cys Ala Ala Ser Gly Phe Thr Phe
        35                  40                  45

Ser Asp Tyr Ala Met Ala Trp Val Arg Gln Ser Pro Lys Lys Gly Leu
    50                  55                  60

Glu Trp Val Ala Thr Ile Ile Tyr Asp Gly Ser Ser Thr Tyr Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asp Ser Leu Arg Ser Glu Asp Thr Ala Thr
            100                 105                 110

Tyr Tyr Cys Ala Thr Gly Leu Gly Ile Ala Thr Asp Tyr Phe Asp Tyr
        115                 120                 125

Trp Gly Gln Gly Val Leu Val Thr Val Ser Ser Ala Glu Thr Thr Ala
    130                 135                 140

Pro Ser Val Tyr Pro Leu Ala Pro Gly Thr Ala Leu Lys Ser Asn Ser
145                 150                 155                 160

Met Val Thr Leu Gly Cys Leu Val Lys Gly Tyr Phe Pro Glu Pro Val
                165                 170                 175

Thr Val Thr Trp Asn Ser Gly Ala Leu Ser Ser Gly Val His Thr Phe
            180                 185                 190

Pro Ala Val Leu Gln Ser Gly Leu Tyr Thr Leu Thr Ser Ser Val Thr
        195                 200                 205

Val Pro Ser Ser Thr Trp Pro Ser Gln Thr Val Thr Cys Asn Val Ala
    210                 215                 220

His Pro Ala Ser Ser Thr Lys Val Asp Lys Lys Ile Val Pro Arg Asn
225                 230                 235                 240

Cys Gly Gly Asp Cys Lys Pro Cys Ile Cys Thr Gly Ser Glu Val Ser
                245                 250                 255

Ser Val Phe Ile Phe Pro Pro Lys Pro Lys Asp Val Leu Thr Ile Thr
            260                 265                 270
```

```
Leu Thr Pro Lys Val Thr Cys Val Val Asp Ile Ser Gln Asp Asp
        275                 280                 285

Pro Glu Val His Phe Ser Trp Phe Val Asp Asp Val Glu Val His Thr
    290                 295                 300

Ala Gln Thr Arg Pro Pro Glu Glu Gln Phe Asn Ser Thr Phe Arg Ser
305                 310                 315                 320

Val Ser Glu Leu Pro Ile Leu His Gln Asp Trp Leu Asn Gly Arg Thr
                325                 330                 335

Phe Arg Cys Lys Val Thr Ser Ala Ala Phe Pro Ser Pro Ile Glu Lys
            340                 345                 350

Thr Ile Ser Lys Pro Glu Gly Arg Thr Gln Val Pro His Val Tyr Thr
        355                 360                 365

Met Ser Pro Thr Lys Glu Glu Met Thr Gln Asn Glu Val Ser Ile Thr
370                 375                 380

Cys Met Val Lys Gly Phe Tyr Pro Pro Asp Ile Tyr Val Glu Trp Gln
385                 390                 395                 400

Met Asn Gly Gln Pro Gln Glu Asn Tyr Lys Asn Thr Pro Pro Thr Met
                405                 410                 415

Asp Thr Asp Gly Ser Tyr Phe Leu Tyr Ser Lys Leu Asn Val Lys Lys
            420                 425                 430

Glu Lys Trp Gln Gln Gly Asn Thr Phe Thr Cys Ser Val Leu His Glu
        435                 440                 445

Gly Leu His Asn His His Thr Glu Lys Ser Leu Ser His Ser Pro Gly
    450                 455                 460

Lys
465

<210> SEQ ID NO 13
<211> LENGTH: 14
<212> TYPE: PRT
<213> ORGANISM: Artificial
<220> FEATURE:
<223> OTHER INFORMATION: PADRE peptide

<400> SEQUENCE: 13

Ala Lys Phe Val Ala Ala Trp Thr Leu Lys Ala Ala Ala Cys
1               5                   10

<210> SEQ ID NO 14
<211> LENGTH: 14
<212> TYPE: PRT
<213> ORGANISM: Artificial
<220> FEATURE:
<223> OTHER INFORMATION: PADRE peptide
<220> FEATURE:
<221> NAME/KEY: MISC_FEATURE
<222> LOCATION: (4)..(4)
<223> OTHER INFORMATION: X = cyclohexyl-alanine

<400> SEQUENCE: 14

Cys Ala Lys Xaa Val Ala Ala Trp Thr Leu Lys Ala Ala Ala
1               5                   10

<210> SEQ ID NO 15
<211> LENGTH: 44
<212> TYPE: RNA
<213> ORGANISM: Artificial
<220> FEATURE:
<223> OTHER INFORMATION: RACE oligonucleotide

<400> SEQUENCE: 15
cgacuggagc acgaggacac ugacauggac ugaaggagua gaaa                    44
```

-continued

<210> SEQ ID NO 16
<211> LENGTH: 24
<212> TYPE: DNA
<213> ORGANISM: Artificial
<220> FEATURE:
<223> OTHER INFORMATION: RACE oligonucleotide
<220> FEATURE:
<221> NAME/KEY: misc_feature
<222> LOCATION: (18)..(23)
<223> OTHER INFORMATION: N=any nucleotide

<400> SEQUENCE: 16
ggccggatag gcctcacnnn nnnt                                              24

<210> SEQ ID NO 17
<211> LENGTH: 23
<212> TYPE: DNA
<213> ORGANISM: Artificial
<220> FEATURE:
<223> OTHER INFORMATION: PCR primer

<400> SEQUENCE: 17
cgactggagc acgaggacac tga                                              23

<210> SEQ ID NO 18
<211> LENGTH: 24
<212> TYPE: DNA
<213> ORGANISM: Artificial
<220> FEATURE:
<223> OTHER INFORMATION: PCR primer

<400> SEQUENCE: 18
gcaacagtgg taggtcgctt gtgg                                             24

<210> SEQ ID NO 19
<211> LENGTH: 26
<212> TYPE: DNA
<213> ORGANISM: Artificial
<220> FEATURE:
<223> OTHER INFORMATION: PCR primer

<400> SEQUENCE: 19
ggacactgac atggactgaa ggagta                                           26

<210> SEQ ID NO 20
<211> LENGTH: 21
<212> TYPE: DNA
<213> ORGANISM: Artificial
<220> FEATURE:
<223> OTHER INFORMATION: PCR primer

<400> SEQUENCE: 20
aggagccagt ggatagacag a                                                21

<210> SEQ ID NO 21
<211> LENGTH: 45
<212> TYPE: DNA
<213> ORGANISM: Artificial
<220> FEATURE:
<223> OTHER INFORMATION: PCR primer

<400> SEQUENCE: 21
aagctcgagg tcgactagac caccatgggt gtgcctactc atctc                      45

<210> SEQ ID NO 22
<211> LENGTH: 46

```
<212> TYPE: DNA
<213> ORGANISM: Artificial
<220> FEATURE:
<223> OTHER INFORMATION: PCR primer

<400> SEQUENCE: 22
aagctcgagg tcgactagac caccatggac atcaggctca gcttgg                    46

<210> SEQ ID NO 23
<211> LENGTH: 40
<212> TYPE: DNA
<213> ORGANISM: Artificial
<220> FEATURE:
<223> OTHER INFORMATION: PCR primer

<400> SEQUENCE: 23
aaccgtttaa acgcggccgc ctaacactca ttcctgttga                           40

<210> SEQ ID NO 24
<211> LENGTH: 42
<212> TYPE: DNA
<213> ORGANISM: Artificial
<220> FEATURE:
<223> OTHER INFORMATION: PCR primer

<400> SEQUENCE: 24
aaccgtttaa acgcggccgc tcatttaccc ggagagtggg ag                        42

<210> SEQ ID NO 25
<211> LENGTH: 642
<212> TYPE: DNA
<213> ORGANISM: Artificial Sequence
<220> FEATURE:
<223> OTHER INFORMATION: Chimera
<220> FEATURE:
<221> NAME/KEY: CDS
<222> LOCATION: (1)..(642)

<400> SEQUENCE: 25
```

| | | | | | | | | | | | | | | | | |
|---|---|---|---|---|---|---|---|---|---|---|---|---|---|---|---|---|
| gct | att | cga | atg | acc | caa | tcc | ccc | ttt | tct | ctt | tcc | gcc | tca | gtt | gga | 48 |
| Ala | Ile | Arg | Met | Thr | Gln | Ser | Pro | Phe | Ser | Leu | Ser | Ala | Ser | Val | Gly | |
| 1 | | | | 5 | | | | | 10 | | | | | 15 | | |
| gat | cgc | gta | acc | ata | acc | tgc | ctg | gca | tca | gaa | gac | att | tac | agc | gac | 96 |
| Asp | Arg | Val | Thr | Ile | Thr | Cys | Leu | Ala | Ser | Glu | Asp | Ile | Tyr | Ser | Asp | |
| | | | 20 | | | | | 25 | | | | | 30 | | | |
| ctt | gca | tgg | tat | caa | caa | aaa | ccc | gcc | aaa | gct | ccc | aaa | ctt | ttc | atc | 144 |
| Leu | Ala | Trp | Tyr | Gln | Gln | Lys | Pro | Ala | Lys | Ala | Pro | Lys | Leu | Phe | Ile | |
| | | | 35 | | | | | 40 | | | | | 45 | | | |
| tat | aac | gcc | aat | agc | ctc | cag | aac | ggt | gtt | cca | tcc | aga | ttt | agc | ggc | 192 |
| Tyr | Asn | Ala | Asn | Ser | Leu | Gln | Asn | Gly | Val | Pro | Ser | Arg | Phe | Ser | Gly | |
| | 50 | | | | | 55 | | | | | 60 | | | | | |
| tca | gga | tcc | ggc | aca | gac | tac | aca | ctc | act | att | tca | tca | ctg | caa | ccc | 240 |
| Ser | Gly | Ser | Gly | Thr | Asp | Tyr | Thr | Leu | Thr | Ile | Ser | Ser | Leu | Gln | Pro | |
| 65 | | | | | 70 | | | | | 75 | | | | | 80 | |
| gaa | gac | ttc | gcc | aca | tac | tac | tgc | caa | caa | tac | aat | aac | tac | ccc | ccc | 288 |
| Glu | Asp | Phe | Ala | Thr | Tyr | Tyr | Cys | Gln | Gln | Tyr | Asn | Asn | Tyr | Pro | Pro | |
| | | | 85 | | | | | 90 | | | | | 95 | | | |
| aca | ttc | ggc | ggc | ggc | act | aaa | gtc | gaa | att | aaa | cgt | acg | gtg | gct | gca | 336 |
| Thr | Phe | Gly | Gly | Gly | Thr | Lys | Val | Glu | Ile | Lys | Arg | Thr | Val | Ala | Ala | |
| | | | 100 | | | | | 105 | | | | | 110 | | | |
| cca | tct | gtc | ttc | atc | ttc | ccg | cca | tct | gat | gag | cag | ttg | aaa | tct | gga | 384 |
| Pro | Ser | Val | Phe | Ile | Phe | Pro | Pro | Ser | Asp | Glu | Gln | Leu | Lys | Ser | Gly | |
| | | | 115 | | | | | 120 | | | | | 125 | | | |
| act | gcc | tct | gtt | gtg | tgc | ctg | ctg | aat | aac | ttc | tat | ccc | aga | gag | gcc | 432 |
| Thr | Ala | Ser | Val | Val | Cys | Leu | Leu | Asn | Asn | Phe | Tyr | Pro | Arg | Glu | Ala | |

```
                        130                 135                 140
aaa gta cag tgg aag gtg gat aac gcc ctc caa tcg ggt aac tcc cag        480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc        528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac        576
Ser Thr Leu Thr Leu Ser Lys Ala Asp Tyr Glu Lys His Lys Val Tyr
            180                 185                 190 gcc tgc gaa gtc acc cat cag ggc ctg agc tcg ccc gtc aca aag agc        624
Ala Cys Glu Val Thr His Gln Gly Leu Ser Ser Pro Val Thr Lys Ser
        195                 200                 205 ttc aac agg gga gag tgt                                                 642
Phe Asn Arg Gly Glu Cys
    210

<210> SEQ ID NO 26
<211> LENGTH: 214
<212> TYPE: PRT
<213> ORGANISM: Artificial Sequence
<220> FEATURE:
<223> OTHER INFORMATION: Synthetic Construct

<400> SEQUENCE: 26

Ala Ile Arg Met Thr Gln Ser Pro Phe Ser Leu Ser Ala Ser Val Gly
1               5                   10                  15

Asp Arg Val Thr Ile Thr Cys Leu Ala Ser Glu Asp Ile Tyr Ser Asp
            20                  25                  30

Leu Ala Trp Tyr Gln Gln Lys Pro Ala Lys Ala Pro Lys Leu Phe Ile
        35                  40                  45

Tyr Asn Ala Asn Ser Leu Gln Asn Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Asn Asn Tyr Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 27
<211> LENGTH: 321
<212> TYPE: DNA
<213> ORGANISM: Artificial Sequence
<220> FEATURE:
```

<223> OTHER INFORMATION: Chimera
<220> FEATURE:
<221> NAME/KEY: CDS
<222> LOCATION: (1)..(321)

<400> SEQUENCE: 27

```
gct att cga atg acc caa tcc ccc ttt tct ctt tcc gcc tca gtt gga       48
Ala Ile Arg Met Thr Gln Ser Pro Phe Ser Leu Ser Ala Ser Val Gly
1               5                   10                  15 gat cgc gta acc ata acc tgc ctg gca tca gaa gac att tac agc gac       96
Asp Arg Val Thr Ile Thr Cys Leu Ala Ser Glu Asp Ile Tyr Ser Asp
            20                  25                  30 ctt gca tgg tat caa caa aaa ccc gcc aaa gct ccc aaa ctt ttc atc      144
Leu Ala Trp Tyr Gln Gln Lys Pro Ala Lys Ala Pro Lys Leu Phe Ile
        35                  40                  45 tat aac gcc aat agc ctc cag aac ggt gtt cca tcc aga ttt agc ggc      192
Tyr Asn Ala Asn Ser Leu Gln Asn Gly Val Pro Ser Arg Phe Ser Gly
    50                  55                  60 tca gga tcc ggc aca gac tac aca ctc act att tca tca ctg caa ccc      240
Ser Gly Ser Gly Thr Asp Tyr Thr Leu Thr Ile Ser Ser Leu Gln Pro
65                  70                  75                  80 gaa gac ttc gcc aca tac tac tgc caa caa tac aat aac tac ccc ccc      288
Glu Asp Phe Ala Thr Tyr Tyr Cys Gln Gln Tyr Asn Asn Tyr Pro Pro
                85                  90                  95 aca ttc ggc ggc ggc act aaa gtc gaa att aaa                          321
Thr Phe Gly Gly Gly Thr Lys Val Glu Ile Lys
                100                 105
```

<210> SEQ ID NO 28
<211> LENGTH: 107
<212> TYPE: PRT
<213> ORGANISM: Artificial Sequence
<220> FEATURE:
<223> OTHER INFORMATION: Synthetic Construct

<400> SEQUENCE: 28

```
Ala Ile Arg Met Thr Gln Ser Pro Phe Ser Leu Ser Ala Ser Val Gly
1               5                   10                  15

Asp Arg Val Thr Ile Thr Cys Leu Ala Ser Glu Asp Ile Tyr Ser Asp
            20                  25                  30

Leu Ala Trp Tyr Gln Gln Lys Pro Ala Lys Ala Pro Lys Leu Phe Ile
        35                  40                  45

Tyr Asn Ala Asn Ser Leu Gln Asn Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Asn Asn Tyr Pro Pro
                85                  90                  95

Thr Phe Gly Gly Gly Thr Lys Val Glu Ile Lys
                100                 105
```

<210> SEQ ID NO 29
<211> LENGTH: 642
<212> TYPE: DNA
<213> ORGANISM: Artificial Sequence
<220> FEATURE:
<223> OTHER INFORMATION: Chimera
<220> FEATURE:
<221> NAME/KEY: CDS
<222> LOCATION: (1)..(642)

<400> SEQUENCE: 29

```
gat att cga atg acc caa tcc ccc ttt tct ctt tcc gcc tca gtt gga       48
```

```
Asp Ile Arg Met Thr Gln Ser Pro Phe Ser Leu Ser Ala Ser Val Gly
1               5                   10                  15 gat cgc gta acc ata acc tgc ctg gca tca gaa gac att tac agc gac    96
Asp Arg Val Thr Ile Thr Cys Leu Ala Ser Glu Asp Ile Tyr Ser Asp
            20                  25                  30 ctt gca tgg tat caa caa aaa ccc gcc aaa gct ccc aaa ctt ttc atc    144
Leu Ala Trp Tyr Gln Gln Lys Pro Ala Lys Ala Pro Lys Leu Phe Ile
        35                  40                  45 tat aac gcc aat agc ctc cag aac ggt gtt cca tcc aga ttt agc ggc    192
Tyr Asn Ala Asn Ser Leu Gln Asn Gly Val Pro Ser Arg Phe Ser Gly
    50                  55                  60 tca gga tcc ggc aca gac tac aca ctc act att tca tca ctg caa ccc    240
Ser Gly Ser Gly Thr Asp Tyr Thr Leu Thr Ile Ser Ser Leu Gln Pro
65                  70                  75                  80 gaa gac ttc gcc aca tac tac tgc caa caa tac aat aac tac ccc ccc    288
Glu Asp Phe Ala Thr Tyr Tyr Cys Gln Gln Tyr Asn Asn Tyr Pro Pro
                85                  90                  95 aca ttc ggc ggc ggc act aaa gtc gaa att aaa cgt acg gtg gct gca    336
Thr Phe Gly Gly Gly Thr Lys Val Glu Ile Lys Arg Thr Val Ala Ala
            100                 105                 110 cca tct gtc ttc atc ttc ccg cca tct gat gag cag ttg aaa tct gga    384
Pro Ser Val Phe Ile Phe Pro Pro Ser Asp Glu Gln Leu Lys Ser Gly
        115                 120                 125 act gcc tct gtt gtg tgc ctg ctg aat aac ttc tat ccc aga gag gcc    432
Thr Ala Ser Val Val Cys Leu Leu Asn Asn Phe Tyr Pro Arg Glu Ala
    130                 135                 140 aaa gta cag tgg aag gtg gat aac gcc ctc caa tcg ggt aac tcc cag    480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc    528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac    576
Ser Thr Leu Thr Leu Ser Lys Ala Asp Tyr Glu Lys His Lys Val Tyr
            180                 185                 190 gcc tgc gaa gtc acc cat cag ggc ctg agc tcg ccc gtc aca aag agc    624
Ala Cys Glu Val Thr His Gln Gly Leu Ser Ser Pro Val Thr Lys Ser
        195                 200                 205 ttc aac agg gga gag tgt                                            642
Phe Asn Arg Gly Glu Cys
        210

<210> SEQ ID NO 30
<211> LENGTH: 214
<212> TYPE: PRT
<213> ORGANISM: Artificial Sequence
<220> FEATURE:
<223> OTHER INFORMATION: Synthetic Construct

<400> SEQUENCE: 30

Asp Ile Arg Met Thr Gln Ser Pro Phe Ser Leu Ser Ala Ser Val Gly
1               5                   10                  15

Asp Arg Val Thr Ile Thr Cys Leu Ala Ser Glu Asp Ile Tyr Ser Asp
            20                  25                  30

Leu Ala Trp Tyr Gln Gln Lys Pro Ala Lys Ala Pro Lys Leu Phe Ile
        35                  40                  45

Tyr Asn Ala Asn Ser Leu Gln Asn Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80
```

```
Glu Asp Phe Ala Thr Tyr Tyr Cys Gln Gln Tyr Asn Asn Tyr Pro Pro
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 31
<211> LENGTH: 321
<212> TYPE: DNA
<213> ORGANISM: Artificial Sequence
<220> FEATURE:
<223> OTHER INFORMATION: Chimera
<220> FEATURE:
<221> NAME/KEY: CDS
<222> LOCATION: (1)..(321)

<400> SEQUENCE: 31 gat att cga atg acc caa tcc ccc ttt tct ctt tcc gcc tca gtt gga    48
Asp Ile Arg Met Thr Gln Ser Pro Phe Ser Leu Ser Ala Ser Val Gly
1               5                   10                  15 gat cgc gta acc ata acc tgc ctg gca tca gaa gac att tac agc gac    96
Asp Arg Val Thr Ile Thr Cys Leu Ala Ser Glu Asp Ile Tyr Ser Asp
            20                  25                  30 ctt gca tgg tat caa caa aaa ccc gcc aaa gct ccc aaa ctt ttc atc   144
Leu Ala Trp Tyr Gln Gln Lys Pro Ala Lys Ala Pro Lys Leu Phe Ile
        35                  40                  45 tat aac gcc aat agc ctc cag aac ggt gtt cca tcc aga ttt agc ggc   192
Tyr Asn Ala Asn Ser Leu Gln Asn Gly Val Pro Ser Arg Phe Ser Gly
    50                  55                  60 tca gga tcc ggc aca gac tac aca ctc act att tca tca ctg caa ccc   240
Ser Gly Ser Gly Thr Asp Tyr Thr Leu Thr Ile Ser Ser Leu Gln Pro
65                  70                  75                  80 gaa gac ttc gcc aca tac tac tgc caa caa tac aat aac tac ccc ccc   288
Glu Asp Phe Ala Thr Tyr Tyr Cys Gln Gln Tyr Asn Asn Tyr Pro Pro
                85                  90                  95 aca ttc ggc ggc ggc act aaa gtc gaa att aaa                       321
Thr Phe Gly Gly Gly Thr Lys Val Glu Ile Lys
            100                 105

<210> SEQ ID NO 32
<211> LENGTH: 107
<212> TYPE: PRT
<213> ORGANISM: Artificial Sequence
<220> FEATURE:
<223> OTHER INFORMATION: Synthetic Construct

<400> SEQUENCE: 32

Asp Ile Arg Met Thr Gln Ser Pro Phe Ser Leu Ser Ala Ser Val Gly
1               5                   10                  15
```

```
Asp Arg Val Thr Ile Thr Cys Leu Ala Ser Glu Asp Ile Tyr Ser Asp
         20                  25                  30

Leu Ala Trp Tyr Gln Gln Lys Pro Ala Lys Ala Pro Lys Leu Phe Ile
     35                  40                  45

Tyr Asn Ala Asn Ser Leu Gln Asn Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Tyr Asn Asn Tyr Pro Pro
                 85                  90                  95

Thr Phe Gly Gly Gly Thr Lys Val Glu Ile Lys
                100                 105

<210> SEQ ID NO 33
<211> LENGTH: 1350
<212> TYPE: DNA
<213> ORGANISM: Artificial Sequence
<220> FEATURE:
<223> OTHER INFORMATION: Chimera
<220> FEATURE:
<221> NAME/KEY: CDS
<222> LOCATION: (1)..(1350)

<400> SEQUENCE: 33 gaa gta cag ttg gtc gaa agt ggg ggg gga gtt gta caa cct gga cga        48
Glu Val Gln Leu Val Glu Ser Gly Gly Gly Val Val Gln Pro Gly Arg
  1               5                  10                  15 tca ctt aga ctt tct tgc gct gca agc gga ttt aca ttt tca gat tac        96
Ser Leu Arg Leu Ser Cys Ala Ala Ser Gly Phe Thr Phe Ser Asp Tyr
             20                  25                  30 gcc atg gca tgg gtt cga caa gct cct ggg aaa gga ttg gaa tgg gta       144
Ala Met Ala Trp Val Arg Gln Ala Pro Gly Lys Gly Leu Glu Trp Val
         35                  40                  45 gca aca att att tac gat gga tct tca aca tat tat cgc gac tct gtc       192
Ala Thr Ile Ile Tyr Asp Gly Ser Ser Thr Tyr Tyr Arg Asp Ser Val
     50                  55                  60 aaa gga cga ttt aca atc tca cga gat aac tct aag aat acc ctt tac       240
Lys Gly Arg Phe Thr Ile Ser Arg Asp Asn Ser Lys Asn Thr Leu Tyr
 65                  70                  75                  80 ctt caa atg aat tca ctg aga gca gaa gat acg gct gtt tat tat tgt       288
Leu Gln Met Asn Ser Leu Arg Ala Glu Asp Thr Ala Val Tyr Tyr Cys
                 85                  90                  95 gca acc gga ctt gga att gcg act gat tat ttt gat tat tgg ggc cag       336
Ala Thr Gly Leu Gly Ile Ala Thr Asp Tyr Phe Asp Tyr Trp Gly Gln
            100                 105                 110 gga aca ttg gta acc gtc tct agt gcc tcc acc aag ggc cca tcg gtc       384
Gly Thr Leu Val Thr Val Ser Ser Ala Ser Thr Lys Gly Pro Ser Val
        115                 120                 125 ttc ccc ctg gca ccc tcc tcc aag agc acc tct ggg ggc aca gcg gcc       432
Phe Pro Leu Ala Pro Ser Ser Lys Ser Thr Ser Gly Gly Thr Ala Ala
    130                 135                 140 ctg ggc tgc ctg gtc aag gac tac ttc ccc gaa ccg gtg acg gtg tcg       480
Leu Gly Cys Leu Val Lys Asp Tyr Phe Pro Glu Pro Val Thr Val Ser
145                 150                 155                 160 tgg aac tca ggc gcc ctg acc agc ggc gtg cac acc ttc ccg gct gtc       528
Trp Asn Ser Gly Ala Leu Thr Ser Gly Val His Thr Phe Pro Ala Val
                165                 170                 175 cta cag tcc tca gga ctc tac tcc ctc agc agc gtg gtg acc gtg ccc       576
Leu Gln Ser Ser Gly Leu Tyr Ser Leu Ser Ser Val Val Thr Val Pro
            180                 185                 190
```

```
tcc agc agc ttg ggc acc cag acc tac atc tgc aac gtg aat cac aag      624
Ser Ser Ser Leu Gly Thr Gln Thr Tyr Ile Cys Asn Val Asn His Lys
            195                 200                 205 ccc agc aac acc aag gtg gac aag aaa gtt gag ccc aaa tct tgt gac      672
Pro Ser Asn Thr Lys Val Asp Lys Lys Val Glu Pro Lys Ser Cys Asp
    210                 215                 220 aaa act cac aca tgc cca ccg tgc cca gca cct gaa ctc ctg ggg gga      720
Lys Thr His Thr Cys Pro Pro Cys Pro Ala Pro Glu Leu Leu Gly Gly
225                 230                 235                 240 ccg tca gtc ttc ctc ttc ccc cca aaa ccc aag gac acc ctc atg atc      768
Pro Ser Val Phe Leu Phe Pro Pro Lys Pro Lys Asp Thr Leu Met Ile
            245                 250                 255 tcc cgg acc cct gag gtc aca tgc gtg gtg gtg gac gtg agc cac gaa      816
Ser Arg Thr Pro Glu Val Thr Cys Val Val Val Asp Val Ser His Glu
    260                 265                 270 gac cct gag gtc aag ttc aac tgg tac gtg gac ggc gtg gag gtg cat      864
Asp Pro Glu Val Lys Phe Asn Trp Tyr Val Asp Gly Val Glu Val His
275                 280                 285 aat gcc aag aca aag ccg cgg gag gag cag tac aac agc acg tac cgt      912
Asn Ala Lys Thr Lys Pro Arg Glu Glu Gln Tyr Asn Ser Thr Tyr Arg
            290                 295                 300 gtg gtc agc gtc ctc acc gtc ctg cac cag gac tgg ctg aat ggc aag      960
Val Val Ser Val Leu Thr Val Leu His Gln Asp Trp Leu Asn Gly Lys
305                 310                 315                 320 gag tac aag tgc aag gtc tcc aac aaa gcc ctc cca gcc ccc atc gag     1008
Glu Tyr Lys Cys Lys Val Ser Asn Lys Ala Leu Pro Ala Pro Ile Glu
            325                 330                 335 aaa acc atc tcc aaa gcc aaa ggg cag ccc cga gaa cca cag gtg tac     1056
Lys Thr Ile Ser Lys Ala Lys Gly Gln Pro Arg Glu Pro Gln Val Tyr
    340                 345                 350 acc ctg ccc cca tcc cgg gat gag ctg acc aag aac cag gtc agc ctg     1104
Thr Leu Pro Pro Ser Arg Asp Glu Leu Thr Lys Asn Gln Val Ser Leu
            355                 360                 365 acc tgc ctg gtc aaa ggc ttc tat ccc agc gac atc gcc gtg gag tgg     1152
Thr Cys Leu Val Lys Gly Phe Tyr Pro Ser Asp Ile Ala Val Glu Trp
370                 375                 380 gag agc aat ggg cag ccg gag aac aac tac aag acc acg cct ccc gtg     1200
Glu Ser Asn Gly Gln Pro Glu Asn Asn Tyr Lys Thr Thr Pro Pro Val
            385                 390                 395             400 ctg gac tcc gac ggc tcc ttc ttc ctc tat agc aag ctc acc gtg gac     1248
Leu Asp Ser Asp Gly Ser Phe Phe Leu Tyr Ser Lys Leu Thr Val Asp
                    405                 410                 415 aag agc agg tgg cag cag ggg aac gtc ttc tca tgc tcc gtg atg cat     1296
Lys Ser Arg Trp Gln Gln Gly Asn Val Phe Ser Cys Ser Val Met His
            420                 425                 430 gag gct ctg cac aac cac tac acg cag aag agc ctc tcc ctg tct ccg     1344
Glu Ala Leu His Asn His Tyr Thr Gln Lys Ser Leu Ser Leu Ser Pro
    435                 440                 445 ggt aaa                                                              1350
Gly Lys
    450

<210> SEQ ID NO 34
<211> LENGTH: 450
<212> TYPE: PRT
<213> ORGANISM: Artificial Sequence
<220> FEATURE:
<223> OTHER INFORMATION: Synthetic Construct

<400> SEQUENCE: 34

Glu Val Gln Leu Val Glu Ser Gly Gly Gly Val Val Gln Pro Gly Arg
1               5                   10                  15
```

```
Ser Leu Arg Leu Ser Cys Ala Ala Ser Gly Phe Thr Phe Ser Asp Tyr
            20                  25                  30

Ala Met Ala Trp Val Arg Gln Ala Pro Gly Lys Gly Leu Glu Trp Val
        35                  40                  45

Ala Thr Ile Ile Tyr Asp Gly Ser Ser Thr Tyr Tyr Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Gly Leu Gly Ile Ala Thr Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
```

Gly Lys
    450

<210> SEQ ID NO 35
<211> LENGTH: 360
<212> TYPE: DNA
<213> ORGANISM: Artificial Sequence
<220> FEATURE:
<223> OTHER INFORMATION: Chimera
<220> FEATURE:
<221> NAME/KEY: CDS
<222> LOCATION: (1)..(360)

<400> SEQUENCE: 35

```
gaa gta cag ttg gtc gaa agt ggg ggg gga gtt gta caa cct gga cga       48
Glu Val Gln Leu Val Glu Ser Gly Gly Gly Val Val Gln Pro Gly Arg
1               5                   10                  15 tca ctt aga ctt tct tgc gct gca agc gga ttt aca ttt tca gat tac       96
Ser Leu Arg Leu Ser Cys Ala Ala Ser Gly Phe Thr Phe Ser Asp Tyr
            20                  25                  30 gcc atg gca tgg gtt cga caa gct cct ggg aaa gga ttg gaa tgg gta      144
Ala Met Ala Trp Val Arg Gln Ala Pro Gly Lys Gly Leu Glu Trp Val
        35                  40                  45 gca aca att att tac gat gga tct tca aca tat tat cgc gac tct gtc      192
Ala Thr Ile Ile Tyr Asp Gly Ser Ser Thr Tyr Tyr Arg Asp Ser Val
    50                  55                  60 aaa gga cga ttt aca atc tca cga gat aac tct aag aat acc ctt tac      240
Lys Gly Arg Phe Thr Ile Ser Arg Asp Asn Ser Lys Asn Thr Leu Tyr
65                  70                  75                  80 ctt caa atg aat tca ctg aga gca gaa gat acg gct gtt tat tat tgt      288
Leu Gln Met Asn Ser Leu Arg Ala Glu Asp Thr Ala Val Tyr Tyr Cys
                85                  90                  95 gca acc gga ctt gga att gcg act gat tat ttt gat tat tgg ggc cag      336
Ala Thr Gly Leu Gly Ile Ala Thr Asp Tyr Phe Asp Tyr Trp Gly Gln
            100                 105                 110 gga aca ttg gta acc gtc tct agt                                      360
Gly Thr Leu Val Thr Val Ser Ser
        115                 120
```

<210> SEQ ID NO 36
<211> LENGTH: 120
<212> TYPE: PRT
<213> ORGANISM: Artificial Sequence
<220> FEATURE:
<223> OTHER INFORMATION: Synthetic Construct

<400> SEQUENCE: 36

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Ala Met Ala Trp Val Arg Gln Ala Pro Gly Lys Gly Leu Glu Trp Val
        35                  40                  45

Ala Thr Ile Ile Tyr Asp Gly Ser Ser Thr Tyr Tyr Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Gly Leu Gly Ile Ala Thr Asp Tyr Phe Asp Tyr Trp Gly Gln
            100                 105                 110

```
Gly Thr Leu Val Thr Val Ser Ser
        115                 120

<210> SEQ ID NO 37
<211> LENGTH: 1350
<212> TYPE: DNA
<213> ORGANISM: Artificial Sequence
<220> FEATURE:
<223> OTHER INFORMATION: Chimera
<220> FEATURE:
<221> NAME/KEY: CDS
<222> LOCATION: (1)..(1350)

<400> SEQUENCE: 37 gaa gta cag ttg gtc gaa agt ggg ggg gga gtt gta caa cct gga cga      48
Glu Val Gln Leu Val Glu Ser Gly Gly Gly Val Val Gln Pro Gly Arg
1               5                   10                  15 tca ctt aga ctt tct tgc gct gca agc gga ttt aca ttt tca gat tac      96
Ser Leu Arg Leu Ser Cys Ala Ala Ser Gly Phe Thr Phe Ser Asp Tyr
            20                  25                  30 gcc atg gca tgg gtt cga caa gct cct ggg aaa gga ttg gaa tgg gta     144
Ala Met Ala Trp Val Arg Gln Ala Pro Gly Lys Gly Leu Glu Trp Val
        35                  40                  45 gca aca att att tac gat gga tct tca aca tat tat cgc gac tct gtc     192
Ala Thr Ile Ile Tyr Asp Gly Ser Ser Thr Tyr Tyr Arg Asp Ser Val
    50                  55                  60 aaa gga cga ttt aca atc tca cga gat aac gct aag aat acc ctt tac     240
Lys Gly Arg Phe Thr Ile Ser Arg Asp Asn Ala Lys Asn Thr Leu Tyr
65                  70                  75                  80 ctt caa atg aat tca ctg aga gca gaa gat acg gct aca tat tat tgt     288
Leu Gln Met Asn Ser Leu Arg Ala Glu Asp Thr Ala Thr Tyr Tyr Cys
                85                  90                  95 gca acc gga ctt gga att gcg act gat tat ttt gat tat tgg ggc cag     336
Ala Thr Gly Leu Gly Ile Ala Thr Asp Tyr Phe Asp Tyr Trp Gly Gln
            100                 105                 110 gga aca ttg gta acc gtc tct agt gcc tcc acc aag ggc cca tcg gtc     384
Gly Thr Leu Val Thr Val Ser Ser Ala Ser Thr Lys Gly Pro Ser Val
        115                 120                 125 ttc ccc ctg gca ccc tcc tcc aag agc acc tct ggg ggc aca gcg gcc     432
Phe Pro Leu Ala Pro Ser Ser Lys Ser Thr Ser Gly Gly Thr Ala Ala
    130                 135                 140 ctg ggc tgc ctg gtc aag gac tac ttc ccc gaa ccg gtg acg gtg tcg     480
Leu Gly Cys Leu Val Lys Asp Tyr Phe Pro Glu Pro Val Thr Val Ser
145                 150                 155                 160 tgg aac tca ggc gcc ctg acc agc ggc gtg cac acc ttc ccg gct gtc     528
Trp Asn Ser Gly Ala Leu Thr Ser Gly Val His Thr Phe Pro Ala Val
                165                 170                 175 cta cag tcc tca gga ctc tac tcc ctc agc agc gtg gtg acc gtg ccc     576
Leu Gln Ser Ser Gly Leu Tyr Ser Leu Ser Ser Val Val Thr Val Pro
            180                 185                 190 tcc agc agc ttg ggc acc cag acc tac atc tgc aac gtg aat cac aag     624
Ser Ser Ser Leu Gly Thr Gln Thr Tyr Ile Cys Asn Val Asn His Lys
        195                 200                 205 ccc agc aac acc aag gtg gac aag aaa gtt gag ccc aaa tct tgt gac     672
Pro Ser Asn Thr Lys Val Asp Lys Lys Val Glu Pro Lys Ser Cys Asp
    210                 215                 220 aaa act cac aca tgc cca ccg tgc cca gca cct gaa ctc ctg ggg gga     720
Lys Thr His Thr Cys Pro Pro Cys Pro Ala Pro Glu Leu Leu Gly Gly
225                 230                 235                 240 ccg tca gtc ttc ctc ttc ccc cca aaa ccc aag gac acc ctc atg atc     768
Pro Ser Val Phe Leu Phe Pro Pro Lys Pro Lys Asp Thr Leu Met Ile
                245                 250                 255
```

```
tcc cgg acc cct gag gtc aca tgc gtg gtg gtg gac gtg agc cac gaa      816
Ser Arg Thr Pro Glu Val Thr Cys Val Val Val Asp Val Ser His Glu
            260                 265                 270 gac cct gag gtc aag ttc aac tgg tac gtg gac ggc gtg gag gtg cat      864
Asp Pro Glu Val Lys Phe Asn Trp Tyr Val Asp Gly Val Glu Val His
        275                 280                 285 aat gcc aag aca aag ccg cgg gag gag cag tac aac agc acg tac cgt      912
Asn Ala Lys Thr Lys Pro Arg Glu Glu Gln Tyr Asn Ser Thr Tyr Arg
    290                 295                 300 gtg gtc agc gtc ctc acc gtc ctg cac cag gac tgg ctg aat ggc aag      960
Val Val Ser Val Leu Thr Val Leu His Gln Asp Trp Leu Asn Gly Lys
305                 310                 315                 320 gag tac aag tgc aag gtc tcc aac aaa gcc ctc cca gcc ccc atc gag     1008
Glu Tyr Lys Cys Lys Val Ser Asn Lys Ala Leu Pro Ala Pro Ile Glu
                325                 330                 335 aaa acc atc tcc aaa gcc aaa ggg cag ccc cga gaa cca cag gtg tac     1056
Lys Thr Ile Ser Lys Ala Lys Gly Gln Pro Arg Glu Pro Gln Val Tyr
            340                 345                 350 acc ctg ccc cca tcc cgg gat gag ctg acc aag aac cag gtc agc ctg     1104
Thr Leu Pro Pro Ser Arg Asp Glu Leu Thr Lys Asn Gln Val Ser Leu
        355                 360                 365 acc tgc ctg gtc aaa ggc ttc tat ccc agc gac atc gcc gtg gag tgg     1152
Thr Cys Leu Val Lys Gly Phe Tyr Pro Ser Asp Ile Ala Val Glu Trp
    370                 375                 380 gag agc aat ggg cag ccg gag aac aac tac aag acc acg cct ccc gtg     1200
Glu Ser Asn Gly Gln Pro Glu Asn Asn Tyr Lys Thr Thr Pro Pro Val
385                 390                 395                 400 ctg gac tcc gac ggc tcc ttc ttc ctc tat agc aag ctc acc gtg gac     1248
Leu Asp Ser Asp Gly Ser Phe Phe Leu Tyr Ser Lys Leu Thr Val Asp
                405                 410                 415 aag agc agg tgg cag cag ggg aac gtc ttc tca tgc tcc gtg atg cat     1296
Lys Ser Arg Trp Gln Gln Gly Asn Val Phe Ser Cys Ser Val Met His
            420                 425                 430 gag gct ctg cac aac cac tac acg cag aag agc ctc tcc ctg tct ccg     1344
Glu Ala Leu His Asn His Tyr Thr Gln Lys Ser Leu Ser Leu Ser Pro
        435                 440                 445 ggt aaa                                                             1350
Gly Lys
    450

<210> SEQ ID NO 38
<211> LENGTH: 450
<212> TYPE: PRT
<213> ORGANISM: Artificial Sequence
<220> FEATURE:
<223> OTHER INFORMATION: Synthetic Construct

<400> SEQUENCE: 38

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Ala Met Ala Trp Val Arg Gln Ala Pro Gly Lys Gly Leu Glu Trp Val
        35                  40                  45

Ala Thr Ile Ile Tyr Asp Gly Ser Ser Thr Tyr Tyr Arg Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Thr Tyr Tyr Cys
                85                  90                  95
```

```
Ala Thr Gly Leu Gly Ile Ala Thr Asp Tyr Phe Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
            165                 170                 175
Leu Gln Ser Ser Gly Leu Tyr Ser Leu Ser Ser Val Val Thr Val Pro
        180                 185                 190
Ser Ser Ser Leu Gly Thr Gln Thr Tyr Ile Cys Asn Val Asn His Lys
    195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
            245                 250                 255
Ser Arg Thr Pro Glu Val Thr Cys Val Val Val Asp Val Ser His Glu
        260                 265                 270
Asp Pro Glu Val Lys Phe Asn Trp Tyr Val Asp Gly Val Glu Val His
    275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
            325                 330                 335
Lys Thr Ile Ser Lys Ala Lys Gly Gln Pro Arg Glu Pro Gln Val Tyr
        340                 345                 350
Thr Leu Pro Pro Ser Arg Asp Glu Leu Thr Lys Asn Gln Val Ser Leu
    355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
        420                 425                 430
Glu Ala Leu His Asn His Tyr Thr Gln Lys Ser Leu Ser Leu Ser Pro
    435                 440                 445
Gly Lys
    450

<210> SEQ ID NO 39
<211> LENGTH: 360
<212> TYPE: DNA
<213> ORGANISM: Artificial Sequence
<220> FEATURE:
<223> OTHER INFORMATION: Chimera
<220> FEATURE:
<221> NAME/KEY: CDS
<222> LOCATION: (1)..(360)
```

<400> SEQUENCE: 39

```
gaa gta cag ttg gtc gaa agt ggg ggg gga gtt gta caa cct gga cga      48
Glu Val Gln Leu Val Glu Ser Gly Gly Gly Val Val Gln Pro Gly Arg
1               5                   10                  15 tca ctt aga ctt tct tgc gct gca agc gga ttt aca ttt tca gat tac      96
Ser Leu Arg Leu Ser Cys Ala Ala Ser Gly Phe Thr Phe Ser Asp Tyr
            20                  25                  30 gcc atg gca tgg gtt cga caa gct cct ggg aaa gga ttg gaa tgg gta     144
Ala Met Ala Trp Val Arg Gln Ala Pro Gly Lys Gly Leu Glu Trp Val
        35                  40                  45 gca aca att att tac gat gga tct tca aca tat tat cgc gac tct gtc     192
Ala Thr Ile Ile Tyr Asp Gly Ser Ser Thr Tyr Tyr Arg Asp Ser Val
    50                  55                  60 aaa gga cga ttt aca atc tca cga gat aac gct aag aat acc ctt tac     240
Lys Gly Arg Phe Thr Ile Ser Arg Asp Asn Ala Lys Asn Thr Leu Tyr
65                  70                  75                  80 ctt caa atg aat tca ctg aga gca gaa gat acg gct aca tat tat tgt     288
Leu Gln Met Asn Ser Leu Arg Ala Glu Asp Thr Ala Thr Tyr Tyr Cys
                85                  90                  95 gca acc gga ctt gga att gcg act gat tat ttt gat tat tgg ggc cag     336
Ala Thr Gly Leu Gly Ile Ala Thr Asp Tyr Phe Asp Tyr Trp Gly Gln
            100                 105                 110 gga aca ttg gta acc gtc tct agt                                     360
Gly Thr Leu Val Thr Val Ser Ser
        115                 120
```

<210> SEQ ID NO 40
<211> LENGTH: 120
<212> TYPE: PRT
<213> ORGANISM: Artificial Sequence
<220> FEATURE:
<223> OTHER INFORMATION: Synthetic Construct

<400> SEQUENCE: 40

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Ala Met Ala Trp Val Arg Gln Ala Pro Gly Lys Gly Leu Glu Trp Val
        35                  40                  45

Ala Thr Ile Ile Tyr Asp Gly Ser Ser Thr Tyr Tyr Arg Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Thr Gly Leu Gly Ile Ala Thr Asp Tyr Phe Asp Tyr Trp Gly Gln
            100                 105                 110

Gly Thr Leu Val Thr Val Ser Ser
        115                 120
```

<210> SEQ ID NO 41
<211> LENGTH: 1338
<212> TYPE: DNA
<213> ORGANISM: Artificial Sequence
<220> FEATURE:
<223> OTHER INFORMATION: Chimera
<220> FEATURE:
<221> NAME/KEY: CDS
<222> LOCATION: (1)..(1338)

```
<400> SEQUENCE: 41 gaa gta cag ttg gtc gaa agt ggg ggg gga gtt gta caa cct gga cga      48
Glu Val Gln Leu Val Glu Ser Gly Gly Gly Val Val Gln Pro Gly Arg
1               5                   10                  15 tca ctt aga ctt tct tgc gct gca agc gga ttt aca ttt tca gat tac      96
Ser Leu Arg Leu Ser Cys Ala Ala Ser Gly Phe Thr Phe Ser Asp Tyr
            20                  25                  30 gcc atg gca tgg gtt cga caa gct cct ggg aaa gga ttg gaa tgg gta     144
Ala Met Ala Trp Val Arg Gln Ala Pro Gly Lys Gly Leu Glu Trp Val
        35                  40                  45 gca aca att att tac gat gga tct tca aca tat tat cgc gac tct gtc     192
Ala Thr Ile Ile Tyr Asp Gly Ser Ser Thr Tyr Tyr Arg Asp Ser Val
    50                  55                  60 aaa gga cga ttt aca atc tca cga gat aac tct aag aat acc ctt tac     240
Lys Gly Arg Phe Thr Ile Ser Arg Asp Asn Ser Lys Asn Thr Leu Tyr
65                  70                  75                  80 ctt caa atg aat tca ctg aga gca gaa gat acg gct gtt tat tat tgt     288
Leu Gln Met Asn Ser Leu Arg Ala Glu Asp Thr Ala Val Tyr Tyr Cys
                85                  90                  95 gca acc gga ctt gga att gcg act gat tat ttt gat tat tgg ggc cag     336
Ala Thr Gly Leu Gly Ile Ala Thr Asp Tyr Phe Asp Tyr Trp Gly Gln
            100                 105                 110 gga aca ttg gta acc gtc tct agt gcc tcc acc aag ggc cca tcg gtc     384
Gly Thr Leu Val Thr Val Ser Ser Ala Ser Thr Lys Gly Pro Ser Val
        115                 120                 125 ttc ccc ctg gcg ccc tgc tcc agg agc acc tcc gag agc aca gcg gcc     432
Phe Pro Leu Ala Pro Cys Ser Arg Ser Thr Ser Glu Ser Thr Ala Ala
    130                 135                 140 ctg ggc tgc ctg gtc aag gac tac ttc ccc gaa ccg gtg acg gtg tcg     480
Leu Gly Cys Leu Val Lys Asp Tyr Phe Pro Glu Pro Val Thr Val Ser
145                 150                 155                 160 tgg aac tca ggc gct ctg acc agc ggc gtg cac acc ttc cca gct gtc     528
Trp Asn Ser Gly Ala Leu Thr Ser Gly Val His Thr Phe Pro Ala Val
                165                 170                 175 cta cag tcc tca gga ctc tac tcc ctc agc agc gtg gtg acc gtg ccc     576
Leu Gln Ser Ser Gly Leu Tyr Ser Leu Ser Ser Val Val Thr Val Pro
            180                 185                 190 tcc agc aac ttc ggc acc cag acc tac acc tgc aac gta gat cac aag     624
Ser Ser Asn Phe Gly Thr Gln Thr Tyr Thr Cys Asn Val Asp His Lys
        195                 200                 205 ccc agc aac acc aag gtg gac aag aca gtt gag cgc aaa tgt tgt gtc     672
Pro Ser Asn Thr Lys Val Asp Lys Thr Val Glu Arg Lys Cys Cys Val
    210                 215                 220 gag tgc cca ccg tgc cca gca cca cct gtg gca gga ccg tca gtc ttc     720
Glu Cys Pro Pro Cys Pro Ala Pro Pro Val Ala Gly Pro Ser Val Phe
225                 230                 235                 240 ctc ttc ccc cca aaa ccc aag gac acc ctc atg atc tcc cgg acc cct     768
Leu Phe Pro Pro Lys Pro Lys Asp Thr Leu Met Ile Ser Arg Thr Pro
                245                 250                 255 gag gtc acg tgc gtg gtg gtg gac gtg agc cac gaa gac ccc gag gtc     816
Glu Val Thr Cys Val Val Val Asp Val Ser His Glu Asp Pro Glu Val
            260                 265                 270 cag ttc aac tgg tac gtg gac ggc gtg gag gtg cat aat gcc aag aca     864
Gln Phe Asn Trp Tyr Val Asp Gly Val Glu Val His Asn Ala Lys Thr
        275                 280                 285 aag cca cgg gag gag cag ttc aac agc acg ttc cgt gtg gtc agc gtc     912
Lys Pro Arg Glu Glu Gln Phe Asn Ser Thr Phe Arg Val Val Ser Val
    290                 295                 300 ctc acc gtt gtg cac cag gac tgg ctg aac ggc aag gag tac aag tgc     960
Leu Thr Val Val His Gln Asp Trp Leu Asn Gly Lys Glu Tyr Lys Cys
```

```
                305                 310                 315                 320
aag gtc tcc aac aaa ggc ctc cca gcc ccc atc gag aaa acc atc tcc       1008
Lys Val Ser Asn Lys Gly Leu Pro Ala Pro Ile Glu Lys Thr Ile Ser
                    325                 330                 335 aaa acc aaa ggg cag ccc cga gaa cca cag gtg tac acc ctg ccc cca       1056
Lys Thr Lys Gly Gln Pro Arg Glu Pro Gln Val Tyr Thr Leu Pro Pro
                340                 345                 350 tcc cgg gag gag atg acc aag aac cag gtc agc ctg acc tgc ctg gtc       1104
Ser Arg Glu Glu Met Thr Lys Asn Gln Val Ser Leu Thr Cys Leu Val
            355                 360                 365 aaa ggc ttc tac ccc agc gac atc gcc gtg gag tgg gag agc aat ggg       1152
Lys Gly Phe Tyr Pro Ser Asp Ile Ala Val Glu Trp Glu Ser Asn Gly
        370                 375                 380 cag ccg gag aac aac tac aag acc aca cct ccc atg ctg gac tcc gac       1200
Gln Pro Glu Asn Asn Tyr Lys Thr Thr Pro Pro Met Leu Asp Ser Asp
385                 390                 395                 400 ggc tcc ttc ttc ctc tac agc aag ctc acc gtg gac aag agc agg tgg       1248
Gly Ser Phe Phe Leu Tyr Ser Lys Leu Thr Val Asp Lys Ser Arg Trp
                405                 410                 415 cag cag ggg aac gtc ttc tca tgc tcc gtg atg cat gag gct ctg cac       1296
Gln Gln Gly Asn Val Phe Ser Cys Ser Val Met His Glu Ala Leu His
            420                 425                 430 aac cac tac acg cag aag agc ctc tcc ctg tct ccg ggt aaa               1338
Asn His Tyr Thr Gln Lys Ser Leu Ser Leu Ser Pro Gly Lys
        435                 440                 445

<210> SEQ ID NO 42
<211> LENGTH: 446
<212> TYPE: PRT
<213> ORGANISM: Artificial Sequence
<220> FEATURE:
<223> OTHER INFORMATION: Synthetic Construct

<400> SEQUENCE: 42

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asp Tyr
                20                  25                  30

Ala Met Ala Trp Val Arg Gln Ala Pro Gly Lys Gly Leu Glu Trp Val
            35                  40                  45

Ala Thr Ile Ile Tyr Asp Gly Ser Ser Thr Tyr Tyr Arg Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Gly Leu Gly Ile Ala Thr Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
210                 215                 220

Glu Cys Pro Pro Cys Pro Ala Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 43
<211> LENGTH: 360
<212> TYPE: DNA
<213> ORGANISM: Artificial Sequence
<220> FEATURE:
<223> OTHER INFORMATION: Chimera
<220> FEATURE:
<221> NAME/KEY: CDS
<222> LOCATION: (1)..(360)

<400> SEQUENCE: 43 gaa gta cag ttg gtc gaa agt ggg ggg gga gtt gta caa cct gga cga      48
Glu Val Gln Leu Val Glu Ser Gly Gly Gly Val Val Gln Pro Gly Arg
1               5                   10                  15 tca ctt aga ctt tct tgc gct gca agc gga ttt aca ttt tca gat tac      96
Ser Leu Arg Leu Ser Cys Ala Ala Ser Gly Phe Thr Phe Ser Asp Tyr
            20                  25                  30 gcc atg gca tgg gtt cga caa gct cct ggg aaa gga ttg gaa tgg gta     144
Ala Met Ala Trp Val Arg Gln Ala Pro Gly Lys Gly Leu Glu Trp Val
        35                  40                  45 gca aca att att tac gat gga tct tca aca tat tat cgc gac tct gtc     192
Ala Thr Ile Ile Tyr Asp Gly Ser Ser Thr Tyr Tyr Arg Asp Ser Val
    50                  55                  60 aaa gga cga ttt aca atc tca cga gat aac tct aag aat acc ctt tac     240
Lys Gly Arg Phe Thr Ile Ser Arg Asp Asn Ser Lys Asn Thr Leu Tyr
65                  70                  75                  80
```

```
ctt caa atg aat tca ctg aga gca gaa gat acg gct gtt tat tat tgt      288
Leu Gln Met Asn Ser Leu Arg Ala Glu Asp Thr Ala Val Tyr Tyr Cys
                85                  90                  95 gca acc gga ctt gga att gcg act gat tat ttt gat tat tgg ggc cag      336
Ala Thr Gly Leu Gly Ile Ala Thr Asp Tyr Phe Asp Tyr Trp Gly Gln
            100                 105                 110 gga aca ttg gta acc gtc tct agt                                      360
Gly Thr Leu Val Thr Val Ser Ser
        115                 120

<210> SEQ ID NO 44
<211> LENGTH: 120
<212> TYPE: PRT
<213> ORGANISM: Artificial Sequence
<220> FEATURE:
<223> OTHER INFORMATION: Synthetic Construct

<400> SEQUENCE: 44

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Ala Met Ala Trp Val Arg Gln Ala Pro Gly Lys Gly Leu Glu Trp Val
        35                  40                  45

Ala Thr Ile Ile Tyr Asp Gly Ser Ser Thr Tyr Tyr Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Gly Leu Gly Ile Ala Thr Asp Tyr Phe Asp Tyr Trp Gly Gln
            100                 105                 110

Gly Thr Leu Val Thr Val Ser Ser
        115                 120

<210> SEQ ID NO 45
<211> LENGTH: 1338
<212> TYPE: DNA
<213> ORGANISM: Artificial Sequence
<220> FEATURE:
<223> OTHER INFORMATION: Chimera
<220> FEATURE:
<221> NAME/KEY: CDS
<222> LOCATION: (1)..(1338)

<400> SEQUENCE: 45 gaa gta cag ttg gtc gaa agt ggg ggg gga gtt gta caa cct gga cga      48
Glu Val Gln Leu Val Glu Ser Gly Gly Gly Val Val Gln Pro Gly Arg
1               5                   10                  15 tca ctt aga ctt tct tgc gct gca agc gga ttt aca ttt tca gat tac      96
Ser Leu Arg Leu Ser Cys Ala Ala Ser Gly Phe Thr Phe Ser Asp Tyr
            20                  25                  30 gcc atg gca tgg gtt cga caa gct cct ggg aaa gga ttg gaa tgg ctg     144
Ala Met Ala Trp Val Arg Gln Ala Pro Gly Lys Gly Leu Glu Trp Leu
        35                  40                  45 gca aca att att tac gat gga tct tca aca tat tat cgc gac tct gtc     192
Ala Thr Ile Ile Tyr Asp Gly Ser Ser Thr Tyr Tyr Arg Asp Ser Val
    50                  55                  60 aaa gga cga ttt aca atc tca cga gat aac tct aag aat acc ctt tac     240
Lys Gly Arg Phe Thr Ile Ser Arg Asp Asn Ser Lys Asn Thr Leu Tyr
65                  70                  75                  80
```

```
ctt caa atg aat tca ctg aga gca gaa gat acg gct gtt tat tat tgt      288
Leu Gln Met Asn Ser Leu Arg Ala Glu Asp Thr Ala Val Tyr Tyr Cys
            85                  90                  95 gca acc gga ctt gga att gcg act gat tat ttt gat tat tgg ggc cag      336
Ala Thr Gly Leu Gly Ile Ala Thr Asp Tyr Phe Asp Tyr Trp Gly Gln
        100                 105                 110 gga aca ttg gta acc gtc tct agt gcc tcc acc aag ggc cca tcg gtc      384
Gly Thr Leu Val Thr Val Ser Ser Ala Ser Thr Lys Gly Pro Ser Val
    115                 120                 125 ttc ccc ctg gcg ccc tgc tcc agg agc acc tcc gag agc aca gcg gcc      432
Phe Pro Leu Ala Pro Cys Ser Arg Ser Thr Ser Glu Ser Thr Ala Ala
130                 135                 140 ctg ggc tgc ctg gtc aag gac tac ttc ccc gaa ccg gtg acg gtg tcg      480
Leu Gly Cys Leu Val Lys Asp Tyr Phe Pro Glu Pro Val Thr Val Ser
145                 150                 155                 160 tgg aac tca ggc gct ctg acc agc ggc gtg cac acc ttc cca gct gtc      528
Trp Asn Ser Gly Ala Leu Thr Ser Gly Val His Thr Phe Pro Ala Val
                165                 170                 175 cta cag tcc tca gga ctc tac tcc ctc agc agc gtg gtg acc gtg ccc      576
Leu Gln Ser Ser Gly Leu Tyr Ser Leu Ser Ser Val Val Thr Val Pro
            180                 185                 190 tcc agc aac ttc ggc acc cag acc tac acc tgc aac gta gat cac aag      624
Ser Ser Asn Phe Gly Thr Gln Thr Tyr Thr Cys Asn Val Asp His Lys
        195                 200                 205 ccc agc aac acc aag gtg gac aag aca gtt gag cgc aaa tgt tgt gtc      672
Pro Ser Asn Thr Lys Val Asp Lys Thr Val Glu Arg Lys Cys Cys Val
    210                 215                 220 gag tgc cca ccg tgc cca gca cca cct gtg gca gga ccg tca gtc ttc      720
Glu Cys Pro Pro Cys Pro Ala Pro Pro Val Ala Gly Pro Ser Val Phe
225                 230                 235                 240 ctc ttc ccc cca aaa ccc aag gac acc ctc atg atc tcc cgg acc cct      768
Leu Phe Pro Pro Lys Pro Lys Asp Thr Leu Met Ile Ser Arg Thr Pro
                245                 250                 255 gag gtc acg tgc gtg gtg gtg gac gtg agc cac gaa gac ccc gag gtc      816
Glu Val Thr Cys Val Val Val Asp Val Ser His Glu Asp Pro Glu Val
            260                 265                 270 cag ttc aac tgg tac gtg gac ggc gtg gag gtg cat aat gcc aag aca      864
Gln Phe Asn Trp Tyr Val Asp Gly Val Glu Val His Asn Ala Lys Thr
        275                 280                 285 aag cca cgg gag gag cag ttc aac agc acg ttc cgt gtg gtc agc gtc      912
Lys Pro Arg Glu Glu Gln Phe Asn Ser Thr Phe Arg Val Val Ser Val
    290                 295                 300 ctc acc gtt gtg cac cag gac tgg ctg aac ggc aag gag tac aag tgc      960
Leu Thr Val Val His Gln Asp Trp Leu Asn Gly Lys Glu Tyr Lys Cys
305                 310                 315                 320 aag gtc tcc aac aaa ggc ctc cca gcc ccc atc gag aaa acc atc tcc     1008
Lys Val Ser Asn Lys Gly Leu Pro Ala Pro Ile Glu Lys Thr Ile Ser
                325                 330                 335 aaa acc aaa ggg cag ccc cga gaa cca cag gtg tac acc ctg ccc cca     1056
Lys Thr Lys Gly Gln Pro Arg Glu Pro Gln Val Tyr Thr Leu Pro Pro
            340                 345                 350 tcc cgg gag gag atg acc aag aac cag gtc agc ctg acc tgc ctg gtc     1104
Ser Arg Glu Glu Met Thr Lys Asn Gln Val Ser Leu Thr Cys Leu Val
        355                 360                 365 aaa ggc ttc tac ccc agc gac atc gcc gtg gag tgg gag agc aat ggg     1152
Lys Gly Phe Tyr Pro Ser Asp Ile Ala Val Glu Trp Glu Ser Asn Gly
    370                 375                 380 cag ccg gag aac aac tac aag acc aca cct ccc atg ctg gac tcc gac     1200
Gln Pro Glu Asn Asn Tyr Lys Thr Thr Pro Pro Met Leu Asp Ser Asp
385                 390                 395                 400
```

-continued

```
ggc tcc ttc ttc ctc tac agc aag ctc acc gtg gac aag agc agg tgg      1248
Gly Ser Phe Phe Leu Tyr Ser Lys Leu Thr Val Asp Lys Ser Arg Trp
            405                 410                 415 cag cag ggg aac gtc ttc tca tgc tcc gtg atg cat gag gct ctg cac      1296
Gln Gln Gly Asn Val Phe Ser Cys Ser Val Met His Glu Ala Leu His
        420                 425                 430 aac cac tac acg cag aag agc ctc tcc ctg tct ccg ggt aaa              1338
Asn His Tyr Thr Gln Lys Ser Leu Ser Leu Ser Pro Gly Lys
            435                 440                 445

<210> SEQ ID NO 46
<211> LENGTH: 446
<212> TYPE: PRT
<213> ORGANISM: Artificial Sequence
<220> FEATURE:
<223> OTHER INFORMATION: Synthetic Construct

<400> SEQUENCE: 46

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Ala Met Ala Trp Val Arg Gln Ala Pro Gly Lys Gly Leu Glu Trp Leu
        35                  40                  45

Ala Thr Ile Ile Tyr Asp Gly Ser Ser Thr Tyr Tyr Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Gly Leu Gly Ile Ala Thr Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
```

```
                    305                 310                 315                 320
Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 47
<211> LENGTH: 360
<212> TYPE: DNA
<213> ORGANISM: Artificial Sequence
<220> FEATURE:
<223> OTHER INFORMATION: Chimera
<220> FEATURE:
<221> NAME/KEY: CDS
<222> LOCATION: (1)..(360)

<400> SEQUENCE: 47 gaa gta cag ttg gtc gaa agt ggg ggg gga gtt gta caa cct gga cga        48
Glu Val Gln Leu Val Glu Ser Gly Gly Gly Val Val Gln Pro Gly Arg
1               5                   10                  15 tca ctt aga ctt tct tgc gct gca agc gga ttt aca ttt tca gat tac        96
Ser Leu Arg Leu Ser Cys Ala Ala Ser Gly Phe Thr Phe Ser Asp Tyr
            20                  25                  30 gcc atg gca tgg gtt cga caa gct cct ggg aaa gga ttg gaa tgg ctg       144
Ala Met Ala Trp Val Arg Gln Ala Pro Gly Lys Gly Leu Glu Trp Leu
        35                  40                  45 gca aca att att tac gat gga tct tca aca tat tat cgc gac tct gtc       192
Ala Thr Ile Ile Tyr Asp Gly Ser Ser Thr Tyr Tyr Arg Asp Ser Val
    50                  55                  60 aaa gga cga ttt aca atc tca cga gat aac tct aag aat acc ctt tac       240
Lys Gly Arg Phe Thr Ile Ser Arg Asp Asn Ser Lys Asn Thr Leu Tyr
65                  70                  75                  80 ctt caa atg aat tca ctg aga gca gaa gat acg gct gtt tat tat tgt       288
Leu Gln Met Asn Ser Leu Arg Ala Glu Asp Thr Ala Val Tyr Tyr Cys
                85                  90                  95 gca acc gga ctt gga att gcg act gat tat ttt gat tat tgg ggc cag       336
Ala Thr Gly Leu Gly Ile Ala Thr Asp Tyr Phe Asp Tyr Trp Gly Gln
            100                 105                 110 gga aca ttg gta acc gtc tct agt                                        360
Gly Thr Leu Val Thr Val Ser Ser
        115                 120

<210> SEQ ID NO 48
<211> LENGTH: 120
<212> TYPE: PRT
<213> ORGANISM: Artificial Sequence
<220> FEATURE:
<223> OTHER INFORMATION: Synthetic Construct

<400> SEQUENCE: 48
```

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Ala Met Ala Trp Val Arg Gln Ala Pro Gly Lys Gly Leu Glu Trp Leu
        35                  40                  45

Ala Thr Ile Ile Tyr Asp Gly Ser Ser Thr Tyr Tyr Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Gly Leu Gly Ile Ala Thr Asp Tyr Phe Asp Tyr Trp Gly Gln
            100                 105                 110

Gly Thr Leu Val Thr Val Ser Ser
        115                 120

<210> SEQ ID NO 49
<211> LENGTH: 1338
<212> TYPE: DNA
<213> ORGANISM: Artificial Sequence
<220> FEATURE:
<223> OTHER INFORMATION: Chimera
<220> FEATURE:
<221> NAME/KEY: CDS
<222> LOCATION: (1)..(1338)

<400> SEQUENCE: 49 gaa gta cag ttg gtc gaa agt ggg ggg gga gtt gta caa cct gga cga     48
Glu Val Gln Leu Val Glu Ser Gly Gly Gly Val Val Gln Pro Gly Arg
1               5                   10                  15 tca ctt aga ctt tct tgc gct gca agc gga ttt aca ttt tca gat tac     96
Ser Leu Arg Leu Ser Cys Ala Ala Ser Gly Phe Thr Phe Ser Asp Tyr
            20                  25                  30 gcc atg gca tgg gtt cga caa tct cct aag aaa gga ttg gaa tgg ctg    144
Ala Met Ala Trp Val Arg Gln Ser Pro Lys Lys Gly Leu Glu Trp Leu
        35                  40                  45 gca aca att att tac gat gga tct tca aca tat tat cgc gac tct gtc    192
Ala Thr Ile Ile Tyr Asp Gly Ser Ser Thr Tyr Tyr Arg Asp Ser Val
    50                  55                  60 aaa gga cga ttt aca atc tca cga gat aac tct aag aat acc ctt tac    240
Lys Gly Arg Phe Thr Ile Ser Arg Asp Asn Ser Lys Asn Thr Leu Tyr
65                  70                  75                  80 ctt caa atg aat tca ctg aga gca gaa gat acg gct gtt tat tat tgt    288
Leu Gln Met Asn Ser Leu Arg Ala Glu Asp Thr Ala Val Tyr Tyr Cys
                85                  90                  95 gca acc gga ctt gga att gcg act gat tat ttt gat tat tgg ggc cag    336
Ala Thr Gly Leu Gly Ile Ala Thr Asp Tyr Phe Asp Tyr Trp Gly Gln
            100                 105                 110 gga aca ttg gta acc gtc tct agt gcc tcc acc aag ggc cca tcg gtc    384
Gly Thr Leu Val Thr Val Ser Ser Ala Ser Thr Lys Gly Pro Ser Val
        115                 120                 125 ttc ccc ctg gcg ccc tgc tcc agg agc acc tcc gag agc aca gcg gcc    432
Phe Pro Leu Ala Pro Cys Ser Arg Ser Thr Ser Glu Ser Thr Ala Ala
    130                 135                 140 ctg ggc tgc ctg gtc aag gac tac ttc ccc gaa ccg gtg acg gtg tcg    480
Leu Gly Cys Leu Val Lys Asp Tyr Phe Pro Glu Pro Val Thr Val Ser
145                 150                 155                 160 tgg aac tca ggc gct ctg acc agc ggc gtg cac acc ttc cca gct gtc    528
Trp Asn Ser Gly Ala Leu Thr Ser Gly Val His Thr Phe Pro Ala Val
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     |     |     | 165 |     |     |     |     | 170 |     |     |     |     | 175 |     |     |
| cta | cag | tcc | tca | gga | ctc | tac | tcc | ctc | agc | agc | gtg | gtg | acc | gtg | ccc | 576 |
| Leu | Gln | Ser | Ser | Gly | Leu | Tyr | Ser | Leu | Ser | Ser | Val | Val | Thr | Val | Pro |     |
|     |     |     | 180 |     |     |     |     | 185 |     |     |     |     | 190 |     |     |     |
| tcc | agc | aac | ttc | ggc | acc | cag | acc | tac | acc | tgc | aac | gta | gat | cac | aag | 624 |
| Ser | Ser | Asn | Phe | Gly | Thr | Gln | Thr | Tyr | Thr | Cys | Asn | Val | Asp | His | Lys |     |
|     |     | 195 |     |     |     |     | 200 |     |     |     |     | 205 |     |     |     |     |
| ccc | agc | aac | acc | aag | gtg | gac | aag | aca | gtt | gag | cgc | aaa | tgt | tgt | gtc | 672 |
| Pro | Ser | Asn | Thr | Lys | Val | Asp | Lys | Thr | Val | Glu | Arg | Lys | Cys | Cys | Val |     |
|     | 210 |     |     |     |     | 215 |     |     |     |     | 220 |     |     |     |     |     |
| gag | tgc | cca | ccg | tgc | cca | gca | cca | cct | gtg | gca | gga | ccg | tca | gtc | ttc | 720 |
| Glu | Cys | Pro | Pro | Cys | Pro | Ala | Pro | Pro | Val | Ala | Gly | Pro | Ser | Val | Phe |     |
| 225 |     |     |     |     | 230 |     |     |     |     | 235 |     |     |     |     | 240 |     |
| ctc | ttc | ccc | cca | aaa | ccc | aag | gac | acc | ctc | atg | atc | tcc | cgg | acc | cct | 768 |
| Leu | Phe | Pro | Pro | Lys | Pro | Lys | Asp | Thr | Leu | Met | Ile | Ser | Arg | Thr | Pro |     |
|     |     |     |     | 245 |     |     |     |     | 250 |     |     |     |     | 255 |     |     |
| gag | gtc | acg | tgc | gtg | gtg | gtg | gac | gtg | agc | cac | gaa | gac | ccc | gag | gtc | 816 |
| Glu | Val | Thr | Cys | Val | Val | Val | Asp | Val | Ser | His | Glu | Asp | Pro | Glu | Val |     |
|     |     |     | 260 |     |     |     |     | 265 |     |     |     |     | 270 |     |     |     |
| cag | ttc | aac | tgg | tac | gtg | gac | ggc | gtg | gag | gtg | cat | aat | gcc | aag | aca | 864 |
| Gln | Phe | Asn | Trp | Tyr | Val | Asp | Gly | Val | Glu | Val | His | Asn | Ala | Lys | Thr |     |
|     |     | 275 |     |     |     |     | 280 |     |     |     |     | 285 |     |     |     |     |
| aag | cca | cgg | gag | gag | cag | ttc | aac | agc | acg | ttc | cgt | gtg | gtc | agc | gtc | 912 |
| Lys | Pro | Arg | Glu | Glu | Gln | Phe | Asn | Ser | Thr | Phe | Arg | Val | Val | Ser | Val |     |
|     | 290 |     |     |     |     | 295 |     |     |     |     | 300 |     |     |     |     |     |
| ctc | acc | gtt | gtg | cac | cag | gac | tgg | ctg | aac | ggc | aag | gag | tac | aag | tgc | 960 |
| Leu | Thr | Val | Val | His | Gln | Asp | Trp | Leu | Asn | Gly | Lys | Glu | Tyr | Lys | Cys |     |
| 305 |     |     |     |     | 310 |     |     |     |     | 315 |     |     |     |     | 320 |     |
| aag | gtc | tcc | aac | aaa | ggc | ctc | cca | gcc | ccc | atc | gag | aaa | acc | atc | tcc | 1008 |
| Lys | Val | Ser | Asn | Lys | Gly | Leu | Pro | Ala | Pro | Ile | Glu | Lys | Thr | Ile | Ser |     |
|     |     |     |     | 325 |     |     |     |     | 330 |     |     |     |     | 335 |     |     |
| aaa | acc | aaa | ggg | cag | ccc | cga | gaa | cca | cag | gtg | tac | acc | ctg | ccc | cca | 1056 |
| Lys | Thr | Lys | Gly | Gln | Pro | Arg | Glu | Pro | Gln | Val | Tyr | Thr | Leu | Pro | Pro |     |
|     |     |     | 340 |     |     |     |     | 345 |     |     |     |     | 350 |     |     |     |
| tcc | cgg | gag | gag | atg | acc | aag | aac | cag | gtc | agc | ctg | acc | tgc | ctg | gtc | 1104 |
| Ser | Arg | Glu | Glu | Met | Thr | Lys | Asn | Gln | Val | Ser | Leu | Thr | Cys | Leu | Val |     |
|     |     | 355 |     |     |     |     | 360 |     |     |     |     | 365 |     |     |     |     |
| aaa | ggc | ttc | tac | ccc | agc | gac | atc | gcc | gtg | gag | tgg | gag | agc | aat | ggg | 1152 |
| Lys | Gly | Phe | Tyr | Pro | Ser | Asp | Ile | Ala | Val | Glu | Trp | Glu | Ser | Asn | Gly |     |
| 370 |     |     |     |     | 375 |     |     |     |     | 380 |     |     |     |     |     |     |
| cag | ccg | gag | aac | aac | tac | aag | acc | aca | cct | ccc | atg | ctg | gac | tcc | gac | 1200 |
| Gln | Pro | Glu | Asn | Asn | Tyr | Lys | Thr | Thr | Pro | Pro | Met | Leu | Asp | Ser | Asp |     |
| 385 |     |     |     | 390 |     |     |     |     | 395 |     |     |     |     | 400 |     |     |
| ggc | tcc | ttc | ttc | ctc | tac | agc | aag | ctc | acc | gtg | gac | aag | agc | agg | tgg | 1248 |
| Gly | Ser | Phe | Phe | Leu | Tyr | Ser | Lys | Leu | Thr | Val | Asp | Lys | Ser | Arg | Trp |     |
|     |     |     | 405 |     |     |     |     | 410 |     |     |     |     | 415 |     |     |     |
| cag | cag | ggg | aac | gtc | ttc | tca | tgc | tcc | gtg | atg | cat | gag | gct | ctg | cac | 1296 |
| Gln | Gln | Gly | Asn | Val | Phe | Ser | Cys | Ser | Val | Met | His | Glu | Ala | Leu | His |     |
|     |     | 420 |     |     |     |     | 425 |     |     |     |     | 430 |     |     |     |     |
| aac | cac | tac | acg | cag | aag | agc | ctc | tcc | ctg | tct | ccg | ggt | aaa |     |     | 1338 |
| Asn | His | Tyr | Thr | Gln | Lys | Ser | Leu | Ser | Leu | Ser | Pro | Gly | Lys |     |     |     |
|     | 435 |     |     |     |     | 440 |     |     |     |     | 445 |     |     |     |     |     |

<210> SEQ ID NO 50
<211> LENGTH: 446
<212> TYPE: PRT
<213> ORGANISM: Artificial Sequence
<220> FEATURE:
<223> OTHER INFORMATION: Synthetic Construct

<400> SEQUENCE: 50

-continued

```
Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asp Tyr
                20                  25                  30

Ala Met Ala Trp Val Arg Gln Ser Pro Lys Lys Gly Leu Glu Trp Leu
        35                  40                  45

Ala Thr Ile Ile Tyr Asp Gly Ser Ser Thr Tyr Tyr Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Gly Leu Gly Ile Ala Thr Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430
```

Asn His Tyr Thr Gln Lys Ser Leu Ser Leu Ser Pro Gly Lys
        435                 440                 445

<210> SEQ ID NO 51
<211> LENGTH: 360
<212> TYPE: DNA
<213> ORGANISM: Artificial Sequence
<220> FEATURE:
<223> OTHER INFORMATION: Chimera
<220> FEATURE:
<221> NAME/KEY: CDS
<222> LOCATION: (1)..(360)

<400> SEQUENCE: 51

```
gaa gta cag ttg gtc gaa agt ggg ggg gga gtt gta caa cct gga cga      48
Glu Val Gln Leu Val Glu Ser Gly Gly Gly Val Val Gln Pro Gly Arg
1               5                   10                  15 tca ctt aga ctt tct tgc gct gca agc gga ttt aca ttt tca gat tac      96
Ser Leu Arg Leu Ser Cys Ala Ala Ser Gly Phe Thr Phe Ser Asp Tyr
            20                  25                  30 gcc atg gca tgg gtt cga caa tct cct aag aaa gga ttg gaa tgg ctg     144
Ala Met Ala Trp Val Arg Gln Ser Pro Lys Lys Gly Leu Glu Trp Leu
        35                  40                  45 gca aca att att tac gat gga tct tca aca tat tat cgc gac tct gtc     192
Ala Thr Ile Ile Tyr Asp Gly Ser Ser Thr Tyr Tyr Arg Asp Ser Val
    50                  55                  60 aaa gga cga ttt aca atc tca cga gat aac tct aag aat acc ctt tac     240
Lys Gly Arg Phe Thr Ile Ser Arg Asp Asn Ser Lys Asn Thr Leu Tyr
65                  70                  75                  80 ctt caa atg aat tca ctg aga gca gaa gat acg gct gtt tat tat tgt     288
Leu Gln Met Asn Ser Leu Arg Ala Glu Asp Thr Ala Val Tyr Tyr Cys
                85                  90                  95 gca acc gga ctt gga att gcg act gat tat ttt gat tat tgg ggc cag     336
Ala Thr Gly Leu Gly Ile Ala Thr Asp Tyr Phe Asp Tyr Trp Gly Gln
            100                 105                 110 gga aca ttg gta acc gtc tct agt                                     360
Gly Thr Leu Val Thr Val Ser Ser
            115                 120
```

<210> SEQ ID NO 52
<211> LENGTH: 120
<212> TYPE: PRT
<213> ORGANISM: Artificial Sequence
<220> FEATURE:
<223> OTHER INFORMATION: Synthetic Construct

<400> SEQUENCE: 52

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Ala Met Ala Trp Val Arg Gln Ser Pro Lys Lys Gly Leu Glu Trp Leu
        35                  40                  45

Ala Thr Ile Ile Tyr Asp Gly Ser Ser Thr Tyr Tyr Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Gly Leu Gly Ile Ala Thr Asp Tyr Phe Asp Tyr Trp Gly Gln
            100                 105                 110

```
Gly Thr Leu Val Thr Val Ser Ser
        115                 120

<210> SEQ ID NO 53
<211> LENGTH: 1338
<212> TYPE: DNA
<213> ORGANISM: Artificial Sequence
<220> FEATURE:
<223> OTHER INFORMATION: Chimera
<220> FEATURE:
<221> NAME/KEY: CDS
<222> LOCATION: (1)..(1338)

<400> SEQUENCE: 53 gaa gta cag ttg gtc gaa agt ggg ggg gga ctt gta caa cct gca cga      48
Glu Val Gln Leu Val Glu Ser Gly Gly Gly Leu Val Gln Pro Ala Arg
1               5                   10                  15 tca ctt aga ctt tct tgc gct gca agc gga ttt aca ttt tca gat tac      96
Ser Leu Arg Leu Ser Cys Ala Ala Ser Gly Phe Thr Phe Ser Asp Tyr
            20                  25                  30 gcc atg gca tgg gtt cga caa tct cct aag aaa gga ttg gaa tgg tta     144
Ala Met Ala Trp Val Arg Gln Ser Pro Lys Lys Gly Leu Glu Trp Leu
        35                  40                  45 gca aca att att tac gat gga tct tca aca tat tat cgc gac tct gtc     192
Ala Thr Ile Ile Tyr Asp Gly Ser Ser Thr Tyr Tyr Arg Asp Ser Val
    50                  55                  60 aaa gga cga ttt aca atc tca cga gat aac gtt aag aat acc ctt tac     240
Lys Gly Arg Phe Thr Ile Ser Arg Asp Asn Val Lys Asn Thr Leu Tyr
65                  70                  75                  80 ctt caa atg gac tca ctg aga tcc gaa gat acg gct aca tat tat tgt     288
Leu Gln Met Asp Ser Leu Arg Ser Glu Asp Thr Ala Thr Tyr Tyr Cys
                85                  90                  95 gca aca gga ctt gga att gcg act gat tat ttt gat tat tgg ggc cag     336
Ala Thr Gly Leu Gly Ile Ala Thr Asp Tyr Phe Asp Tyr Trp Gly Gln
            100                 105                 110 gga aca ttg gta acc gtc tct agt gcc tcc acc aag ggc cca tcg gtc     384
Gly Thr Leu Val Thr Val Ser Ser Ala Ser Thr Lys Gly Pro Ser Val
        115                 120                 125 ttc ccc ctg gcg ccc tgc tcc agg agc acc tcc gag agc aca gcg gcc     432
Phe Pro Leu Ala Pro Cys Ser Arg Ser Thr Ser Glu Ser Thr Ala Ala
    130                 135                 140 ctg ggc tgc ctg gtc aag gac tac ttc ccc gaa ccg gtg acg gtg tcg     480
Leu Gly Cys Leu Val Lys Asp Tyr Phe Pro Glu Pro Val Thr Val Ser
145                 150                 155                 160 tgg aac tca ggc gct ctg acc agc ggc gtg cac acc ttc cca gct gtc     528
Trp Asn Ser Gly Ala Leu Thr Ser Gly Val His Thr Phe Pro Ala Val
                165                 170                 175 cta cag tcc tca gga ctc tac tcc ctc agc agc gtg gtg acc gtg ccc     576
Leu Gln Ser Ser Gly Leu Tyr Ser Leu Ser Ser Val Val Thr Val Pro
            180                 185                 190 tcc agc aac ttc ggc acc cag acc tac acc tgc aac gta gat cac aag     624
Ser Ser Asn Phe Gly Thr Gln Thr Tyr Thr Cys Asn Val Asp His Lys
        195                 200                 205 ccc agc aac acc aag gtg gac aag aca gtt gag cgc aaa tgt tgt gtc     672
Pro Ser Asn Thr Lys Val Asp Lys Thr Val Glu Arg Lys Cys Cys Val
    210                 215                 220 gag tgc cca ccg tgc cca gca cca cct gtg gca gga ccg tca gtc ttc     720
Glu Cys Pro Pro Cys Pro Ala Pro Pro Val Ala Gly Pro Ser Val Phe
225                 230                 235                 240 ctc ttc ccc cca aaa ccc aag gac acc ctc atg atc tcc cgg acc cct     768
Leu Phe Pro Pro Lys Pro Lys Asp Thr Leu Met Ile Ser Arg Thr Pro
                245                 250                 255
```

```
gag gtc acg tgc gtg gtg gtg gac gtg agc cac gaa gac ccc gag gtc        816
Glu Val Thr Cys Val Val Val Asp Val Ser His Glu Asp Pro Glu Val
        260                 265                 270 cag ttc aac tgg tac gtg gac ggc gtg gag gtg cat aat gcc aag aca        864
Gln Phe Asn Trp Tyr Val Asp Gly Val Glu Val His Asn Ala Lys Thr
    275                 280                 285 aag cca cgg gag gag cag ttc aac agc acg ttc cgt gtg gtc agc gtc        912
Lys Pro Arg Glu Glu Gln Phe Asn Ser Thr Phe Arg Val Val Ser Val
290                 295                 300 ctc acc gtt gtg cac cag gac tgg ctg aac ggc aag gag tac aag tgc        960
Leu Thr Val Val His Gln Asp Trp Leu Asn Gly Lys Glu Tyr Lys Cys
305                 310                 315                 320 aag gtc tcc aac aaa ggc ctc cca gcc ccc atc gag aaa acc atc tcc       1008
Lys Val Ser Asn Lys Gly Leu Pro Ala Pro Ile Glu Lys Thr Ile Ser
                325                 330                 335 aaa acc aaa ggg cag ccc cga gaa cca cag gtg tac acc ctg ccc cca       1056
Lys Thr Lys Gly Gln Pro Arg Glu Pro Gln Val Tyr Thr Leu Pro Pro
            340                 345                 350 tcc cgg gag gag atg acc aag aac cag gtc agc ctg acc tgc ctg gtc       1104
Ser Arg Glu Glu Met Thr Lys Asn Gln Val Ser Leu Thr Cys Leu Val
        355                 360                 365 aaa ggc ttc tac ccc agc gac atc gcc gtg gag tgg gag agc aat ggg       1152
Lys Gly Phe Tyr Pro Ser Asp Ile Ala Val Glu Trp Glu Ser Asn Gly
    370                 375                 380 cag ccg gag aac aac tac aag acc aca cct ccc atg ctg gac tcc gac       1200
Gln Pro Glu Asn Asn Tyr Lys Thr Thr Pro Pro Met Leu Asp Ser Asp
385                 390                 395                 400 ggc tcc ttc ttc ctc tac agc aag ctc acc gtg gac aag agc agg tgg       1248
Gly Ser Phe Phe Leu Tyr Ser Lys Leu Thr Val Asp Lys Ser Arg Trp
                405                 410                 415 cag cag ggg aac gtc ttc tca tgc tcc gtg atg cat gag gct ctg cac       1296
Gln Gln Gly Asn Val Phe Ser Cys Ser Val Met His Glu Ala Leu His
            420                 425                 430 aac cac tac acg cag aag agc ctc tcc ctg tct ccg ggt aaa              1338
Asn His Tyr Thr Gln Lys Ser Leu Ser Leu Ser Pro Gly Lys
        435                 440                 445

<210> SEQ ID NO 54
<211> LENGTH: 446
<212> TYPE: PRT
<213> ORGANISM: Artificial Sequence
<220> FEATURE:
<223> OTHER INFORMATION: Synthetic Construct

<400> SEQUENCE: 54

Glu Val Gln Leu Val Glu Ser Gly Gly Gly Leu Val Gln Pro Ala Arg
1               5                   10                  15

Ser Leu Arg Leu Ser Cys Ala Ala Ser Gly Phe Thr Phe Ser Asp Tyr
            20                  25                  30

Ala Met Ala Trp Val Arg Gln Ser Pro Lys Lys Gly Leu Glu Trp Leu
        35                  40                  45

Ala Thr Ile Ile Tyr Asp Gly Ser Ser Thr Tyr Tyr Arg Asp Ser Val
    50                  55                  60

Lys Gly Arg Phe Thr Ile Ser Arg Asp Asn Val Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Thr Gly Leu Gly Ile Ala Thr Asp Tyr Phe Asp Tyr Trp Gly Gln
            100                 105                 110

Gly Thr Leu Val Thr Val Ser Ser Ala Ser Thr Lys Gly Pro Ser Val
```

```
                 115                 120                 125
Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 55
<211> LENGTH: 360
<212> TYPE: DNA
<213> ORGANISM: Artificial Sequence
<220> FEATURE:
<223> OTHER INFORMATION: Chimera
<220> FEATURE:
<221> NAME/KEY: CDS
<222> LOCATION: (1)..(360)

<400> SEQUENCE: 55 gaa gta cag ttg gtc gaa agt ggg ggg gga ctt gta caa cct gca cga      48
Glu Val Gln Leu Val Glu Ser Gly Gly Gly Leu Val Gln Pro Ala Arg
1               5                   10                  15 tca ctt aga ctt tct tgc gct gca agc gga ttt aca ttt tca gat tac      96
```

-continued

```
              Ser Leu Arg Leu Ser Cys Ala Ala Ser Gly Phe Thr Phe Ser Asp Tyr
                          20                  25                  30 gcc atg gca tgg gtt cga caa tct cct aag aaa gga ttg gaa tgg tta      144
Ala Met Ala Trp Val Arg Gln Ser Pro Lys Lys Gly Leu Glu Trp Leu
         35                  40                  45 gca aca att att tac gat gga tct tca aca tat tat cgc gac tct gtc      192
Ala Thr Ile Ile Tyr Asp Gly Ser Ser Thr Tyr Tyr Arg Asp Ser Val
 50                  55                  60 aaa gga cga ttt aca atc tca cga gat aac gtt aag aat acc ctt tac      240
Lys Gly Arg Phe Thr Ile Ser Arg Asp Asn Val Lys Asn Thr Leu Tyr
 65                  70                  75                  80 ctt caa atg gac tca ctg aga tcc gaa gat acg gct aca tat tat tgt      288
Leu Gln Met Asp Ser Leu Arg Ser Glu Asp Thr Ala Thr Tyr Tyr Cys
                 85                  90                  95 gca aca gga ctt gga att gcg act gat tat ttt gat tat tgg ggc cag      336
Ala Thr Gly Leu Gly Ile Ala Thr Asp Tyr Phe Asp Tyr Trp Gly Gln
            100                 105                 110 gga aca ttg gta acc gtc tct agt                                      360
Gly Thr Leu Val Thr Val Ser Ser
        115                 120
```

<210> SEQ ID NO 56
<211> LENGTH: 120
<212> TYPE: PRT
<213> ORGANISM: Artificial Sequence
<220> FEATURE:
<223> OTHER INFORMATION: Synthetic Construct

<400> SEQUENCE: 56

```
Glu Val Gln Leu Val Glu Ser Gly Gly Gly Leu Val Gln Pro Ala Arg
 1               5                  10                  15

Ser Leu Arg Leu Ser Cys Ala Ala Ser Gly Phe Thr Phe Ser Asp Tyr
             20                  25                  30

Ala Met Ala Trp Val Arg Gln Ser Pro Lys Lys Gly Leu Glu Trp Leu
         35                  40                  45

Ala Thr Ile Ile Tyr Asp Gly Ser Ser Thr Tyr Tyr Arg Asp Ser Val
 50                  55                  60

Lys Gly Arg Phe Thr Ile Ser Arg Asp Asn Val Lys Asn Thr Leu Tyr
 65                  70                  75                  80

Leu Gln Met Asp Ser Leu Arg Ser Glu Asp Thr Ala Thr Tyr Tyr Cys
                 85                  90                  95

Ala Thr Gly Leu Gly Ile Ala Thr Asp Tyr Phe Asp Tyr Trp Gly Gln
            100                 105                 110

Gly Thr Leu Val Thr Val Ser Ser
        115                 120
```

<210> SEQ ID NO 57
<211> LENGTH: 1338
<212> TYPE: DNA
<213> ORGANISM: Artificial Sequence
<220> FEATURE:
<223> OTHER INFORMATION: Chimera
<220> FEATURE:
<221> NAME/KEY: CDS
<222> LOCATION: (1)..(1338)

<400> SEQUENCE: 57

```
gaa gta cag ttg gtc gaa agt ggg tgg gga ctt gta caa cct gca aac       48
Glu Val Gln Leu Val Glu Ser Gly Trp Gly Leu Val Gln Pro Ala Asn
 1               5                  10                  15 tca ctt aaa ctt tct tgc gct gca agc gga ttt aca ttt tca gat tac       96
Ser Leu Lys Leu Ser Cys Ala Ala Ser Gly Phe Thr Phe Ser Asp Tyr
             20                  25                  30
```

```
                20                  25                  30
gcc atg gca tgg gtt cga caa tct cct aag aaa gga ttg gaa tgg tta      144
Ala Met Ala Trp Val Arg Gln Ser Pro Lys Lys Gly Leu Glu Trp Leu
     35                  40                  45 gca aca att att tac gat gga tct tca aca tat tat cgc gac tct gtc      192
Ala Thr Ile Ile Tyr Asp Gly Ser Ser Thr Tyr Tyr Arg Asp Ser Val
 50                  55                  60 aaa gga cga ttt aca atc tca cga gat aac gtt aag aat acc ctt tac      240
Lys Gly Arg Phe Thr Ile Ser Arg Asp Asn Val Lys Asn Thr Leu Tyr
 65                  70                  75                  80 ctt caa atg gac tca ctg aga tcc gaa gat acg gct aca tat tat tgt      288
Leu Gln Met Asp Ser Leu Arg Ser Glu Asp Thr Ala Thr Tyr Tyr Cys
                 85                  90                  95 gca aca gga ctt gga att gcg act gat tat ttt gat tat tgg ggc cag      336
Ala Thr Gly Leu Gly Ile Ala Thr Asp Tyr Phe Asp Tyr Trp Gly Gln
            100                 105                 110 gga gtt ttg gta acc gtc tct agt gcc tcc acc aag ggc cca tcg gtc      384
Gly Val Leu Val Thr Val Ser Ser Ala Ser Thr Lys Gly Pro Ser Val
        115                 120                 125 ttc ccc ctg gcg ccc tgc tcc agg agc acc tcc gag agc aca gcg gcc      432
Phe Pro Leu Ala Pro Cys Ser Arg Ser Thr Ser Glu Ser Thr Ala Ala
130                 135                 140 ctg ggc tgc ctg gtc aag gac tac ttc ccc gaa ccg gtg acg gtg tcg      480
Leu Gly Cys Leu Val Lys Asp Tyr Phe Pro Glu Pro Val Thr Val Ser
145                 150                 155                 160 tgg aac tca ggc gct ctg acc agc ggc gtg cac acc ttc cca gct gtc      528
Trp Asn Ser Gly Ala Leu Thr Ser Gly Val His Thr Phe Pro Ala Val
                165                 170                 175 cta cag tcc tca gga ctc tac tcc ctc agc agc gtg gtg acc gtg ccc      576
Leu Gln Ser Ser Gly Leu Tyr Ser Leu Ser Ser Val Val Thr Val Pro
            180                 185                 190 tcc agc aac ttc ggc acc cag acc tac acc tgc aac gta gat cac aag      624
Ser Ser Asn Phe Gly Thr Gln Thr Tyr Thr Cys Asn Val Asp His Lys
        195                 200                 205 ccc agc aac acc aag gtg gac aag aca gtt gag cgc aaa tgt tgt gtc      672
Pro Ser Asn Thr Lys Val Asp Lys Thr Val Glu Arg Lys Cys Cys Val
210                 215                 220 gag tgc cca ccg tgc cca gca cca cct gtg gca gga ccg tca gtc ttc      720
Glu Cys Pro Pro Cys Pro Ala Pro Pro Val Ala Gly Pro Ser Val Phe
225                 230                 235                 240 ctc ttc ccc cca aaa ccc aag gac acc ctc atg atc tcc cgg acc cct      768
Leu Phe Pro Pro Lys Pro Lys Asp Thr Leu Met Ile Ser Arg Thr Pro
                245                 250                 255 gag gtc acg tgc gtg gtg gtg gac gtg agc cac gaa gac ccc gag gtc      816
Glu Val Thr Cys Val Val Val Asp Val Ser His Glu Asp Pro Glu Val
            260                 265                 270 cag ttc aac tgg tac gtg gac ggc gtg gag gtg cat aat gcc aag aca      864
Gln Phe Asn Trp Tyr Val Asp Gly Val Glu Val His Asn Ala Lys Thr
        275                 280                 285 aag cca cgg gag gag cag ttc aac agc acg ttc cgt gtg gtc agc gtc      912
Lys Pro Arg Glu Glu Gln Phe Asn Ser Thr Phe Arg Val Val Ser Val
    290                 295                 300 ctc acc gtt gtg cac cag gac tgg ctg aac ggc aag gag tac aag tgc      960
Leu Thr Val Val His Gln Asp Trp Leu Asn Gly Lys Glu Tyr Lys Cys
305                 310                 315                 320 aag gtc tcc aac aaa ggc ctc cca gcc ccc atc gag aaa acc atc tcc      1008
Lys Val Ser Asn Lys Gly Leu Pro Ala Pro Ile Glu Lys Thr Ile Ser
                325                 330                 335 aaa acc aaa ggg cag ccc cga gaa cca cag gtg tac acc ctg ccc cca      1056
Lys Thr Lys Gly Gln Pro Arg Glu Pro Gln Val Tyr Thr Leu Pro Pro
```

```
                340                 345                 350
tcc cgg gag gag atg acc aag aac cag gtc agc ctg acc tgc ctg gtc    1104
Ser Arg Glu Glu Met Thr Lys Asn Gln Val Ser Leu Thr Cys Leu Val
        355                 360                 365 aaa ggc ttc tac ccc agc gac atc gcc gtg gag tgg gag agc aat ggg    1152
Lys Gly Phe Tyr Pro Ser Asp Ile Ala Val Glu Trp Glu Ser Asn Gly
370                 375                 380 cag ccg gag aac aac tac aag acc aca cct ccc atg ctg gac tcc gac    1200
Gln Pro Glu Asn Asn Tyr Lys Thr Thr Pro Pro Met Leu Asp Ser Asp
385                 390                 395                 400 ggc tcc ttc ttc ctc tac agc aag ctc acc gtg gac aag agc agg tgg    1248
Gly Ser Phe Phe Leu Tyr Ser Lys Leu Thr Val Asp Lys Ser Arg Trp
        405                 410                 415 cag cag ggg aac gtc ttc tca tgc tcc gtg atg cat gag gct ctg cac    1296
Gln Gln Gly Asn Val Phe Ser Cys Ser Val Met His Glu Ala Leu His
        420                 425                 430 aac cac tac acg cag aag agc ctc tcc ctg tct ccg ggt aaa            1338
Asn His Tyr Thr Gln Lys Ser Leu Ser Leu Ser Pro Gly Lys
        435                 440                 445

<210> SEQ ID NO 58
<211> LENGTH: 446
<212> TYPE: PRT
<213> ORGANISM: Artificial Sequence
<220> FEATURE:
<223> OTHER INFORMATION: Synthetic Construct

<400> SEQUENCE: 58

Glu Val Gln Leu Val Glu Ser Gly Trp Gly Leu Val Gln Pro Ala Asn
1               5                   10                  15

Ser Leu Lys Leu Ser Cys Ala Ala Ser Gly Phe Thr Phe Ser Asp Tyr
            20                  25                  30

Ala Met Ala Trp Val Arg Gln Ser Pro Lys Lys Gly Leu Glu Trp Leu
        35                  40                  45

Ala Thr Ile Ile Tyr Asp Gly Ser Ser Thr Tyr Tyr Arg Asp Ser Val
    50                  55                  60

Lys Gly Arg Phe Thr Ile Ser Arg Asp Asn Val Lys Asn Thr Leu Tyr
65                  70                  75                  80

Leu Gln Met Asp Ser Leu Arg Ser Glu Asp Thr Ala Thr Tyr Tyr Cys
            85                  90                  95

Ala Thr Gly Leu Gly Ile Ala Thr Asp Tyr Phe Asp Tyr Trp Gly Gln
        100                 105                 110

Gly Val Leu Val Thr Val Ser Ser Ala Ser Thr Lys Gly Pro Ser Val
    115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Asn Phe Gly Thr Gln Thr Tyr Thr Cys Asn Val Asp His Lys
    195                 200                 205

Pro Ser Asn Thr Lys Val Asp Lys Thr Val Glu Arg Lys Cys Cys Val
210                 215                 220

Glu Cys Pro Pro Cys Pro Ala Pro Pro Val Ala Gly Pro Ser Val Phe
225                 230                 235                 240
```

```
Leu Phe Pro Pro Lys Pro Lys Asp Thr Leu Met Ile Ser Arg Thr Pro
                245                 250                 255

Glu Val Thr Cys Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 59
<211> LENGTH: 360
<212> TYPE: DNA
<213> ORGANISM: Artificial Sequence
<220> FEATURE:
<223> OTHER INFORMATION: Chimera
<220> FEATURE:
<221> NAME/KEY: CDS
<222> LOCATION: (1)..(360)

<400> SEQUENCE: 59 gaa gta cag ttg gtc gaa agt ggg tgg gga ctt gta caa cct gca aac      48
Glu Val Gln Leu Val Glu Ser Gly Trp Gly Leu Val Gln Pro Ala Asn
1               5                   10                  15 tca ctt aaa ctt tct tgc gct gca agc gga ttt aca ttt tca gat tac      96
Ser Leu Lys Leu Ser Cys Ala Ala Ser Gly Phe Thr Phe Ser Asp Tyr
            20                  25                  30 gcc atg gca tgg gtt cga caa tct cct aag aaa gga ttg gaa tgg tta     144
Ala Met Ala Trp Val Arg Gln Ser Pro Lys Lys Gly Leu Glu Trp Leu
        35                  40                  45 gca aca att att tac gat gga tct tca aca tat tat cgc gac tct gtc     192
Ala Thr Ile Ile Tyr Asp Gly Ser Ser Thr Tyr Tyr Arg Asp Ser Val
    50                  55                  60 aaa gga cga ttt aca atc tca cga gat aac gtt aag aat acc ctt tac     240
Lys Gly Arg Phe Thr Ile Ser Arg Asp Asn Val Lys Asn Thr Leu Tyr
65                  70                  75                  80 ctt caa atg gac tca ctg aga tcc gaa gat acg gct aca tat tat tgt     288
Leu Gln Met Asp Ser Leu Arg Ser Glu Asp Thr Ala Thr Tyr Tyr Cys
                85                  90                  95 gca aca gga ctt gga att gcg act gat tat ttt gat tat tgg ggc cag     336
Ala Thr Gly Leu Gly Ile Ala Thr Asp Tyr Phe Asp Tyr Trp Gly Gln
            100                 105                 110
```

```
gga gtt ttg gta acc gtc tct agt                                      360
Gly Val Leu Val Thr Val Ser Ser
        115                 120

<210> SEQ ID NO 60
<211> LENGTH: 120
<212> TYPE: PRT
<213> ORGANISM: Artificial Sequence
<220> FEATURE:
<223> OTHER INFORMATION: Synthetic Construct

<400> SEQUENCE: 60

Glu Val Gln Leu Val Glu Ser Gly Trp Gly Leu Val Gln Pro Ala Asn
1               5                   10                  15

Ser Leu Lys Leu Ser Cys Ala Ala Ser Gly Phe Thr Phe Ser Asp Tyr
            20                  25                  30

Ala Met Ala Trp Val Arg Gln Ser Pro Lys Lys Gly Leu Glu Trp Leu
        35                  40                  45

Ala Thr Ile Ile Tyr Asp Gly Ser Ser Thr Tyr Tyr Arg Asp Ser Val
    50                  55                  60

Lys Gly Arg Phe Thr Ile Ser Arg Asp Asn Val Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Thr Gly Leu Gly Ile Ala Thr Asp Tyr Phe Asp Tyr Trp Gly Gln
            100                 105                 110

Gly Val Leu Val Thr Val Ser Ser
        115                 120

<210> SEQ ID NO 61
<211> LENGTH: 1338
<212> TYPE: DNA
<213> ORGANISM: Artificial Sequence
<220> FEATURE:
<223> OTHER INFORMATION: Chimera
<220> FEATURE:
<221> NAME/KEY: CDS
<222> LOCATION: (1)..(1338)

<400> SEQUENCE: 61 gaa gta cag ttg gtc gaa agt ggg ggg gga ctt gta caa cct gca aac    48
Glu Val Gln Leu Val Glu Ser Gly Gly Gly Leu Val Gln Pro Ala Asn
1               5                   10                  15 tca ctt aga ctt tct tgc gct gca agc gga ttt aca ttt tca gat tac    96
Ser Leu Arg Leu Ser Cys Ala Ala Ser Gly Phe Thr Phe Ser Asp Tyr
            20                  25                  30 gcc atg gca tgg gtt cga caa tct cct aag aaa gga ttg gaa tgg gta   144
Ala Met Ala Trp Val Arg Gln Ser Pro Lys Lys Gly Leu Glu Trp Val
        35                  40                  45 gca aca att att tac gat gga tct tca aca tat tat cgc gac tct gtc   192
Ala Thr Ile Ile Tyr Asp Gly Ser Ser Thr Tyr Tyr Arg Asp Ser Val
    50                  55                  60 aaa gga cga ttt aca atc tca cga gat aac gct aag agc acc ctt tac   240
Lys Gly Arg Phe Thr Ile Ser Arg Asp Asn Ala Lys Ser Thr Leu Tyr
65                  70                  75                  80 ctt caa atg gac tca ctg aga gca gaa gat acg gct gtt tat tat tgt   288
Leu Gln Met Asp Ser Leu Arg Ala Glu Asp Thr Ala Val Tyr Tyr Cys
                85                  90                  95 gca aca gga ctt gga att gcg act gat tat ttt gat tat tgg ggc cag   336
Ala Thr Gly Leu Gly Ile Ala Thr Asp Tyr Phe Asp Tyr Trp Gly Gln
            100                 105                 110
```

```
gga gtt ttg gta acc gtc tct agt gcc tcc acc aag ggc cca tcg gtc      384
Gly Val Leu Val Thr Val Ser Ser Ala Ser Thr Lys Gly Pro Ser Val
            115                 120                 125 ttc ccc ctg gcg ccc tgc tcc agg agc acc tcc gag agc aca gcg gcc      432
Phe Pro Leu Ala Pro Cys Ser Arg Ser Thr Ser Glu Ser Thr Ala Ala
130                 135                 140 ctg ggc tgc ctg gtc aag gac tac ttc ccc gaa ccg gtg acg gtg tcg      480
Leu Gly Cys Leu Val Lys Asp Tyr Phe Pro Glu Pro Val Thr Val Ser
145                 150                 155                 160 tgg aac tca ggc gct ctg acc agc ggc gtg cac acc ttc cca gct gtc      528
Trp Asn Ser Gly Ala Leu Thr Ser Gly Val His Thr Phe Pro Ala Val
                165                 170                 175 cta cag tcc tca gga ctc tac tcc ctc agc agc gtg gtg acc gtg ccc      576
Leu Gln Ser Ser Gly Leu Tyr Ser Leu Ser Ser Val Val Thr Val Pro
            180                 185                 190 tcc agc aac ttc ggc acc cag acc tac acc tgc aac gta gat cac aag      624
Ser Ser Asn Phe Gly Thr Gln Thr Tyr Thr Cys Asn Val Asp His Lys
        195                 200                 205 ccc agc aac acc aag gtg gac aag aca gtt gag cgc aaa tgt tgt gtc      672
Pro Ser Asn Thr Lys Val Asp Lys Thr Val Glu Arg Lys Cys Cys Val
210                 215                 220 gag tgc cca ccg tgc cca gca cca cct gtg gca gga ccg tca gtc ttc      720
Glu Cys Pro Pro Cys Pro Ala Pro Pro Val Ala Gly Pro Ser Val Phe
225                 230                 235                 240 ctc ttc ccc cca aaa ccc aag gac acc ctc atg atc tcc cgg acc cct      768
Leu Phe Pro Pro Lys Pro Lys Asp Thr Leu Met Ile Ser Arg Thr Pro
                245                 250                 255 gag gtc acg tgc gtg gtg gtg gac gtg agc cac gaa gac ccc gag gtc      816
Glu Val Thr Cys Val Val Val Asp Val Ser His Glu Asp Pro Glu Val
            260                 265                 270 cag ttc aac tgg tac gtg gac ggc gtg gag gtg cat aat gcc aag aca      864
Gln Phe Asn Trp Tyr Val Asp Gly Val Glu Val His Asn Ala Lys Thr
        275                 280                 285 aag cca cgg gag gag cag ttc aac agc acg ttc cgt gtg gtc agc gtc      912
Lys Pro Arg Glu Glu Gln Phe Asn Ser Thr Phe Arg Val Val Ser Val
    290                 295                 300 ctc acc gtt gtg cac cag gac tgg ctg aac ggc aag gag tac aag tgc      960
Leu Thr Val Val His Gln Asp Trp Leu Asn Gly Lys Glu Tyr Lys Cys
305                 310                 315                 320 aag gtc tcc aac aaa ggc ctc cca gcc ccc atc gag aaa acc atc tcc     1008
Lys Val Ser Asn Lys Gly Leu Pro Ala Pro Ile Glu Lys Thr Ile Ser
                325                 330                 335 aaa acc aaa ggg cag ccc cga gaa cca cag gtg tac acc ctg ccc cca     1056
Lys Thr Lys Gly Gln Pro Arg Glu Pro Gln Val Tyr Thr Leu Pro Pro
            340                 345                 350 tcc cgg gag gag atg acc aag aac cag gtc agc ctg acc tgc ctg gtc     1104
Ser Arg Glu Glu Met Thr Lys Asn Gln Val Ser Leu Thr Cys Leu Val
        355                 360                 365 aaa ggc ttc tac ccc agc gac atc gcc gtg gag tgg gag agc aat ggg     1152
Lys Gly Phe Tyr Pro Ser Asp Ile Ala Val Glu Trp Glu Ser Asn Gly
    370                 375                 380 cag ccg gag aac aac tac aag acc aca cct ccc atg ctg gac tcc gac     1200
Gln Pro Glu Asn Asn Tyr Lys Thr Thr Pro Pro Met Leu Asp Ser Asp
385                 390                 395                 400 ggc tcc ttc ttc ctc tac agc aag ctc acc gtg gac aag agc agg tgg     1248
Gly Ser Phe Phe Leu Tyr Ser Lys Leu Thr Val Asp Lys Ser Arg Trp
                405                 410                 415 cag cag ggg aac gtc ttc tca tgc tcc gtg atg cat gag gct ctg cac     1296
Gln Gln Gly Asn Val Phe Ser Cys Ser Val Met His Glu Ala Leu His
            420                 425                 430
```

```
aac cac tac acg cag aag agc ctc tcc ctg tct ccg ggt aaa           1338
Asn His Tyr Thr Gln Lys Ser Leu Ser Leu Ser Pro Gly Lys
        435                 440                 445

<210> SEQ ID NO 62
<211> LENGTH: 446
<212> TYPE: PRT
<213> ORGANISM: Artificial Sequence
<220> FEATURE:
<223> OTHER INFORMATION: Synthetic Construct

<400> SEQUENCE: 62

Glu Val Gln Leu Val Glu Ser Gly Gly Gly Leu Val Gln Pro Ala Asn
1               5                   10                  15

Ser Leu Arg Leu Ser Cys Ala Ala Ser Gly Phe Thr Phe Ser Asp Tyr
            20                  25                  30

Ala Met Ala Trp Val Arg Gln Ser Pro Lys Lys Gly Leu Glu Trp Val
        35                  40                  45

Ala Thr Ile Ile Tyr Asp Gly Ser Ser Thr Tyr Tyr Arg Asp Ser Val
    50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ala Glu Asp Thr Ala Val Tyr Tyr Cys
                85                  90                  95

Ala Thr Gly Leu Gly Ile Ala Thr Asp Tyr Phe Asp Tyr Trp Gly Gln
            100                 105                 110

Gly Val Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350
```

```
Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 63
<211> LENGTH: 360
<212> TYPE: DNA
<213> ORGANISM: Artificial Sequence
<220> FEATURE:
<223> OTHER INFORMATION: Chimera
<220> FEATURE:
<221> NAME/KEY: CDS
<222> LOCATION: (1)..(360)

<400> SEQUENCE: 63 gaa gta cag ttg gtc gaa agt ggg ggg gga ctt gta caa cct gca aac       48
Glu Val Gln Leu Val Glu Ser Gly Gly Gly Leu Val Gln Pro Ala Asn
1               5                   10                  15 tca ctt aga ctt tct tgc gct gca agc gga ttt aca ttt tca gat tac       96
Ser Leu Arg Leu Ser Cys Ala Ala Ser Gly Phe Thr Phe Ser Asp Tyr
            20                  25                  30 gcc atg gca tgg gtt cga caa tct cct aag aaa gga ttg gaa tgg gta      144
Ala Met Ala Trp Val Arg Gln Ser Pro Lys Lys Gly Leu Glu Trp Val
        35                  40                  45 gca aca att att tac gat gga tct tca aca tat tat cgc gac tct gtc      192
Ala Thr Ile Ile Tyr Asp Gly Ser Ser Thr Tyr Tyr Arg Asp Ser Val
    50                  55                  60 aaa gga cga ttt aca atc tca cga gat aac gct aag agc acc ctt tac      240
Lys Gly Arg Phe Thr Ile Ser Arg Asp Asn Ala Lys Ser Thr Leu Tyr
65                  70                  75                  80 ctt caa atg gac tca ctg aga gca gaa gat acg gct gtt tat tat tgt      288
Leu Gln Met Asp Ser Leu Arg Ala Glu Asp Thr Ala Val Tyr Tyr Cys
                85                  90                  95 gca aca gga ctt gga att gcg act gat tat ttt gat tat tgg ggc cag      336
Ala Thr Gly Leu Gly Ile Ala Thr Asp Tyr Phe Asp Tyr Trp Gly Gln
            100                 105                 110 gga gtt ttg gta acc gtc tct agt                                      360
Gly Val Leu Val Thr Val Ser Ser
        115                 120

<210> SEQ ID NO 64
<211> LENGTH: 120
<212> TYPE: PRT
<213> ORGANISM: Artificial Sequence
<220> FEATURE:
<223> OTHER INFORMATION: Synthetic Construct

<400> SEQUENCE: 64

Glu Val Gln Leu Val Glu Ser Gly Gly Gly Leu Val Gln Pro Ala Asn
1               5                   10                  15

Ser Leu Arg Leu Ser Cys Ala Ala Ser Gly Phe Thr Phe Ser Asp Tyr
            20                  25                  30

Ala Met Ala Trp Val Arg Gln Ser Pro Lys Lys Gly Leu Glu Trp Val
```

```
                35                  40                  45
Ala Thr Ile Ile Tyr Asp Gly Ser Ser Thr Tyr Arg Asp Ser Val
 50                  55                  60
Lys Gly Arg Phe Thr Ile Ser Arg Asp Asn Ala Lys Ser Thr Leu Tyr
 65                  70                  75                  80
Leu Gln Met Asp Ser Leu Arg Ala Glu Asp Thr Ala Val Tyr Tyr Cys
                 85                  90                  95
Ala Thr Gly Leu Gly Ile Ala Thr Asp Tyr Phe Asp Tyr Trp Gly Gln
                100                 105                 110
Gly Val Leu Val Thr Val Ser Ser
            115                 120

<210> SEQ ID NO 65
<211> LENGTH: 1338
<212> TYPE: DNA
<213> ORGANISM: Artificial Sequence
<220> FEATURE:
<223> OTHER INFORMATION: Chimera
<220> FEATURE:
<221> NAME/KEY: CDS
<222> LOCATION: (1)..(1338)

<400> SEQUENCE: 65 gaa gta cag ttg gtc gaa agt ggg ggg gga ctt gta caa cct gga cga        48
Glu Val Gln Leu Val Glu Ser Gly Gly Gly Leu Val Gln Pro Gly Arg
 1               5                  10                  15 tca ctt aaa ctt tct tgc gct gca agc gga ttt aca ttt tca gat tac        96
Ser Leu Lys Leu Ser Cys Ala Ala Ser Gly Phe Thr Phe Ser Asp Tyr
                 20                  25                  30 gcc atg gca tgg gtt cga caa tct cct aag aaa gga ttg aaa tgg gta       144
Ala Met Ala Trp Val Arg Gln Ser Pro Lys Lys Gly Leu Lys Trp Val
             35                  40                  45 gca aca att att tac gat gga tct tca aca tat tat cgc gac tct gtc       192
Ala Thr Ile Ile Tyr Asp Gly Ser Ser Thr Tyr Tyr Arg Asp Ser Val
 50                  55                  60 aaa gga cga ttt aca atc tca cga aat aac gct aag aat acc ctt tac       240
Lys Gly Arg Phe Thr Ile Ser Arg Asn Asn Ala Lys Asn Thr Leu Tyr
 65                  70                  75                  80 ctt caa atg aat tca ctg aga tcc gaa gat acg gct gtt tat tat tgt       288
Leu Gln Met Asn Ser Leu Arg Ser Glu Asp Thr Ala Val Tyr Tyr Cys
                 85                  90                  95 gca aca gga ctt gga att gcg act gat tat ttt gat tat tgg ggc cag       336
Ala Thr Gly Leu Gly Ile Ala Thr Asp Tyr Phe Asp Tyr Trp Gly Gln
                100                 105                 110 gga gtt ttg gta acc gtc tct agt gcc tcc acc aag ggc cca tcg gtc       384
Gly Val Leu Val Thr Val Ser Ser Ala Ser Thr Lys Gly Pro Ser Val
            115                 120                 125 ttc ccc ctg gcg ccc tgc tcc agg agc acc tcc gag agc aca gcg gcc       432
Phe Pro Leu Ala Pro Cys Ser Arg Ser Thr Ser Glu Ser Thr Ala Ala
130                 135                 140 ctg ggc tgc ctg gtc aag gac tac ttc ccc gaa ccg gtg acg gtg tcg       480
Leu Gly Cys Leu Val Lys Asp Tyr Phe Pro Glu Pro Val Thr Val Ser
145                 150                 155                 160 tgg aac tca ggc gct ctg acc agc ggc gtg cac acc ttc cca gct gtc       528
Trp Asn Ser Gly Ala Leu Thr Ser Gly Val His Thr Phe Pro Ala Val
                165                 170                 175 cta cag tcc tca gga ctc tac tcc ctc agc agc gtg gtg acc gtg ccc       576
Leu Gln Ser Ser Gly Leu Tyr Ser Leu Ser Ser Val Val Thr Val Pro
            180                 185                 190 tcc agc aac ttc ggc acc cag acc tac acc tgc aac gta gat cac aag       624
Ser Ser Asn Phe Gly Thr Gln Thr Tyr Thr Cys Asn Val Asp His Lys
```

```
ccc agc aac acc aag gtg gac aag aca gtt gag cgc aaa tgt tgt gtc     672
Pro Ser Asn Thr Lys Val Asp Lys Thr Val Glu Arg Lys Cys Cys Val
210                 215                 220 gag tgc cca ccg tgc cca gca cca cct gtg gca gga ccg tca gtc ttc     720
Glu Cys Pro Pro Cys Pro Ala Pro Pro Val Ala Gly Pro Ser Val Phe
225                 230                 235                 240 ctc ttc ccc cca aaa ccc aag gac acc ctc atg atc tcc cgg acc cct     768
Leu Phe Pro Pro Lys Pro Lys Asp Thr Leu Met Ile Ser Arg Thr Pro
            245                 250                 255 gag gtc acg tgc gtg gtg gtg gac gtg agc cac gaa gac ccc gag gtc     816
Glu Val Thr Cys Val Val Val Asp Val Ser His Glu Asp Pro Glu Val
        260                 265                 270 cag ttc aac tgg tac gtg gac ggc gtg gag gtg cat aat gcc aag aca     864
Gln Phe Asn Trp Tyr Val Asp Gly Val Glu Val His Asn Ala Lys Thr
    275                 280                 285 aag cca cgg gag gag cag ttc aac agc acg ttc cgt gtg gtc agc gtc     912
Lys Pro Arg Glu Glu Gln Phe Asn Ser Thr Phe Arg Val Val Ser Val
290                 295                 300 ctc acc gtt gtg cac cag gac tgg ctg aac ggc aag gag tac aag tgc     960
Leu Thr Val Val His Gln Asp Trp Leu Asn Gly Lys Glu Tyr Lys Cys
305                 310                 315                 320 aag gtc tcc aac aaa ggc ctc cca gcc ccc atc gag aaa acc atc tcc    1008
Lys Val Ser Asn Lys Gly Leu Pro Ala Pro Ile Glu Lys Thr Ile Ser
            325                 330                 335 aaa acc aaa ggg cag ccc cga gaa cca cag gtg tac acc ctg ccc cca    1056
Lys Thr Lys Gly Gln Pro Arg Glu Pro Gln Val Tyr Thr Leu Pro Pro
        340                 345                 350 tcc cgg gag gag atg acc aag aac cag gtc agc ctg acc tgc ctg gtc    1104
Ser Arg Glu Glu Met Thr Lys Asn Gln Val Ser Leu Thr Cys Leu Val
    355                 360                 365 aaa ggc ttc tac ccc agc gac atc gcc gtg gag tgg gag agc aat ggg    1152
Lys Gly Phe Tyr Pro Ser Asp Ile Ala Val Glu Trp Glu Ser Asn Gly
370                 375                 380 cag ccg gag aac aac tac aag acc aca cct ccc atg ctg gac tcc gac    1200
Gln Pro Glu Asn Asn Tyr Lys Thr Thr Pro Pro Met Leu Asp Ser Asp
385                 390                 395                 400 ggc tcc ttc ttc ctc tac agc aag ctc acc gtg gac aag agc agg tgg    1248
Gly Ser Phe Phe Leu Tyr Ser Lys Leu Thr Val Asp Lys Ser Arg Trp
            405                 410                 415 cag cag ggg aac gtc ttc tca tgc tcc gtg atg cat gag gct ctg cac    1296
Gln Gln Gly Asn Val Phe Ser Cys Ser Val Met His Glu Ala Leu His
        420                 425                 430 aac cac tac acg cag aag agc ctc tcc ctg tct ccg ggt aaa            1338
Asn His Tyr Thr Gln Lys Ser Leu Ser Leu Ser Pro Gly Lys
    435                 440                 445

<210> SEQ ID NO 66
<211> LENGTH: 446
<212> TYPE: PRT
<213> ORGANISM: Artificial Sequence
<220> FEATURE:
<223> OTHER INFORMATION: Synthetic Construct

<400> SEQUENCE: 66

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asp Tyr
            20                  25                  30

Ala Met Ala Trp Val Arg Gln Ser Pro Lys Lys Gly Leu Lys Trp Val
        35                  40                  45
```

```
Ala Thr Ile Ile Tyr Asp Gly Ser Ser Thr Tyr Tyr Arg Asp Ser Val
 50                  55                  60

Lys Gly Arg Phe Thr Ile Ser Arg Asn Asn Ala Lys Asn Thr Leu Tyr
 65                  70                  75                  80

Leu Gln Met Asn Ser Leu Arg Ser Glu Asp Thr Ala Val Tyr Tyr Cys
             85                  90                  95

Ala Thr Gly Leu Gly Ile Ala Thr Asp Tyr Phe Asp Tyr Trp Gly Gln
            100                 105                 110

Gly Val Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Asn Phe Gly Thr Gln Thr Tyr Thr Cys Asn Val Asp His Lys
            195                 200                 205

Pro Ser Asn Thr Lys Val Asp Lys Thr Val Glu Arg Lys Cys Cys Val
210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Asp Val Ser His Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Phe Arg Val Val Ser Val
            290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 67
<211> LENGTH: 360
<212> TYPE: DNA
```

<213> ORGANISM: Artificial Sequence
<220> FEATURE:
<223> OTHER INFORMATION: Chimera
<220> FEATURE:
<221> NAME/KEY: CDS
<222> LOCATION: (1)..(360)

<400> SEQUENCE: 67

```
gaa gta cag ttg gtc gaa agt ggg ggg gga ctt gta caa cct gga cga    48
Glu Val Gln Leu Val Glu Ser Gly Gly Gly Leu Val Gln Pro Gly Arg
1               5                   10                  15 tca ctt aaa ctt tct tgc gct gca agc gga ttt aca ttt tca gat tac    96
Ser Leu Lys Leu Ser Cys Ala Ala Ser Gly Phe Thr Phe Ser Asp Tyr
            20                  25                  30 gcc atg gca tgg gtt cga caa tct cct aag aaa gga ttg aaa tgg gta   144
Ala Met Ala Trp Val Arg Gln Ser Pro Lys Lys Gly Leu Lys Trp Val
        35                  40                  45 gca aca att att tac gat gga tct tca aca tat tat cgc gac tct gtc   192
Ala Thr Ile Ile Tyr Asp Gly Ser Ser Thr Tyr Tyr Arg Asp Ser Val
    50                  55                  60 aaa gga cga ttt aca atc tca cga aat aac gct aag aat acc ctt tac   240
Lys Gly Arg Phe Thr Ile Ser Arg Asn Asn Ala Lys Asn Thr Leu Tyr
65                  70                  75                  80 ctt caa atg aat tca ctg aga tcc gaa gat acg gct gtt tat tat tgt   288
Leu Gln Met Asn Ser Leu Arg Ser Glu Asp Thr Ala Val Tyr Tyr Cys
                85                  90                  95 gca aca gga ctt gga att gcg act gat tat ttt gat tat tgg ggc cag   336
Ala Thr Gly Leu Gly Ile Ala Thr Asp Tyr Phe Asp Tyr Trp Gly Gln
            100                 105                 110 gga gtt ttg gta acc gtc tct agt                                    360
Gly Val Leu Val Thr Val Ser Ser
        115                 120
```

<210> SEQ ID NO 68
<211> LENGTH: 120
<212> TYPE: PRT
<213> ORGANISM: Artificial Sequence
<220> FEATURE:
<223> OTHER INFORMATION: Synthetic Construct

<400> SEQUENCE: 68

```
Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asp Tyr
            20                  25                  30

Ala Met Ala Trp Val Arg Gln Ser Pro Lys Lys Gly Leu Lys Trp Val
        35                  40                  45

Ala Thr Ile Ile Tyr Asp Gly Ser Ser Thr Tyr Tyr Arg Asp Ser Val
    50                  55                  60

Lys Gly Arg Phe Thr Ile Ser Arg Asn Asn Ala Lys Asn Thr Leu Tyr
65                  70                  75                  80

Leu Gln Met Asn Ser Leu Arg Ser Glu Asp Thr Ala Val Tyr Tyr Cys
                85                  90                  95

Ala Thr Gly Leu Gly Ile Ala Thr Asp Tyr Phe Asp Tyr Trp Gly Gln
            100                 105                 110

Gly Val Leu Val Thr Val Ser Ser
        115                 120
```

<210> SEQ ID NO 69
<211> LENGTH: 33
<212> TYPE: DNA
<213> ORGANISM: Rattus sp.

```
<220> FEATURE:
<221> NAME/KEY: CDS
<222> LOCATION: (1)..(33)

<400> SEQUENCE: 69 ctg gca tca gaa gac att tac agc gac ctt gca                            33
Leu Ala Ser Glu Asp Ile Tyr Ser Asp Leu Ala
1               5                   10

<210> SEQ ID NO 70
<211> LENGTH: 11
<212> TYPE: PRT
<213> ORGANISM: Rattus sp.

<400> SEQUENCE: 70

Leu Ala Ser Glu Asp Ile Tyr Ser Asp Leu Ala
1               5                   10

<210> SEQ ID NO 71
<211> LENGTH: 21
<212> TYPE: DNA
<213> ORGANISM: Rattus sp.
<220> FEATURE:
<221> NAME/KEY: CDS
<222> LOCATION: (1)..(21)

<400> SEQUENCE: 71 aac gcc aat agc ctc cag aac                                            21
Asn Ala Asn Ser Leu Gln Asn
1               5

<210> SEQ ID NO 72
<211> LENGTH: 7
<212> TYPE: PRT
<213> ORGANISM: Rattus sp.

<400> SEQUENCE: 72

Asn Ala Asn Ser Leu Gln Asn
1               5

<210> SEQ ID NO 73
<211> LENGTH: 27
<212> TYPE: DNA
<213> ORGANISM: Rattus sp.
<220> FEATURE:
<221> NAME/KEY: CDS
<222> LOCATION: (1)..(27)

<400> SEQUENCE: 73 caa caa tac aat aac tac ccc ccc aca                                    27
Gln Gln Tyr Asn Asn Tyr Pro Pro Thr
1               5

<210> SEQ ID NO 74
<211> LENGTH: 9
<212> TYPE: PRT
<213> ORGANISM: Rattus sp.

<400> SEQUENCE: 74

Gln Gln Tyr Asn Asn Tyr Pro Pro Thr
1               5

<210> SEQ ID NO 75
<211> LENGTH: 15
<212> TYPE: DNA
<213> ORGANISM: Rattus sp.
<220> FEATURE:
<221> NAME/KEY: CDS
```

```
<222> LOCATION: (1)..(15)

<400> SEQUENCE: 75 gat tac gcc atg gca                                              15
Asp Tyr Ala Met Ala
1               5

<210> SEQ ID NO 76
<211> LENGTH: 5
<212> TYPE: PRT
<213> ORGANISM: Rattus sp.

<400> SEQUENCE: 76

Asp Tyr Ala Met Ala
1               5

<210> SEQ ID NO 77
<211> LENGTH: 51
<212> TYPE: DNA
<213> ORGANISM: Rattus sp.
<220> FEATURE:
<221> NAME/KEY: CDS
<222> LOCATION: (1)..(51)

<400> SEQUENCE: 77 aca att att tac gat gga tct tca aca tat tat cgc gac tct gtc aaa  48
Thr Ile Ile Tyr Asp Gly Ser Ser Thr Tyr Tyr Arg Asp Ser Val Lys
1               5                   10                  15 gga                                                              51
Gly

<210> SEQ ID NO 78
<211> LENGTH: 17
<212> TYPE: PRT
<213> ORGANISM: Rattus sp.

<400> SEQUENCE: 78

Thr Ile Ile Tyr Asp Gly Ser Ser Thr Tyr Tyr Arg Asp Ser Val Lys
1               5                   10                  15

Gly

<210> SEQ ID NO 79
<211> LENGTH: 33
<212> TYPE: DNA
<213> ORGANISM: Rattus sp.
<220> FEATURE:
<221> NAME/KEY: CDS
<222> LOCATION: (1)..(33)

<400> SEQUENCE: 79 gga ctt gga att gcg act gat tat ttt gat tat                      33
Gly Leu Gly Ile Ala Thr Asp Tyr Phe Asp Tyr
1               5                   10

<210> SEQ ID NO 80
<211> LENGTH: 11
<212> TYPE: PRT
<213> ORGANISM: Rattus sp.

<400> SEQUENCE: 80

Gly Leu Gly Ile Ala Thr Asp Tyr Phe Asp Tyr
1               5                   10

<210> SEQ ID NO 81
<211> LENGTH: 642
<212> TYPE: DNA
```

```
<213> ORGANISM: Rattus sp.
<220> FEATURE:
<221> NAME/KEY: CDS
<222> LOCATION: (1)..(642)

<400> SEQUENCE: 81 gat atc cgg atg aca cag tct cca gct tcc ctg tct gca tct ctg gga      48
Asp Ile Arg Met Thr Gln Ser Pro Ala Ser Leu Ser Ala Ser Leu Gly
 1               5                  10                  15 gaa act gtc aac atc gaa tgt cta gca agt gag gac att tac agt gat      96
Glu Thr Val Asn Ile Glu Cys Leu Ala Ser Glu Asp Ile Tyr Ser Asp
                20                  25                  30 tta gca tgg tat cag cag aag cca ggg aaa tct cct cag ctc ctg atc     144
Leu Ala Trp Tyr Gln Gln Lys Pro Gly Lys Ser Pro Gln Leu Leu Ile
            35                  40                  45 tat aat gca aat agc ttg caa aat ggg gtc cct tca cgg ttt agt ggc     192
Tyr Asn Ala Asn Ser Leu Gln Asn Gly Val Pro Ser Arg Phe Ser Gly
    50                  55                  60 agt gga tct ggc aca cag tat tct cta aaa ata aac agc ctg caa tct     240
Ser Gly Ser Gly Thr Gln Tyr Ser Leu Lys Ile Asn Ser Leu Gln Ser
65                  70                  75                  80 gaa gat gtc gcg act tat ttc tgt caa caa tat aac aat tat cct ccg     288
Glu Asp Val Ala Thr Tyr Phe Cys Gln Gln Tyr Asn Asn Tyr Pro Pro
                85                  90                  95 acg ttc ggt gga ggc acc aag ctg gaa ttg aaa cgg gct gat gct gca     336
Thr Phe Gly Gly Gly Thr Lys Leu Glu Leu Lys Arg Ala Asp Ala Ala
               100                 105                 110 cca act gta tct atc ttc cca cca tcc acg gaa cag tta gca act gga     384
Pro Thr Val Ser Ile Phe Pro Pro Ser Thr Glu Gln Leu Ala Thr Gly
            115                 120                 125 ggt gcc tca gtc gtg tgc ctc atg aac aac ttc tat ccc aga gac atc     432
Gly Ala Ser Val Val Cys Leu Met Asn Asn Phe Tyr Pro Arg Asp Ile
   130                 135                 140 agt gtc aag tgg aag att gat ggc act gaa cga cga gat ggt gtc ctg     480
Ser Val Lys Trp Lys Ile Asp Gly Thr Glu Arg Arg Asp Gly Val Leu
145                 150                 155                 160 gac agt gtt act gat cag gac agc aaa gac agc acg tac agc atg agc     528
Asp Ser Val Thr Asp Gln Asp Ser Lys Asp Ser Thr Tyr Ser Met Ser
                165                 170                 175 agc acc ctc tcg ttg acc aag gct gac tat gaa agt cat aac ctc tat     576
Ser Thr Leu Ser Leu Thr Lys Ala Asp Tyr Glu Ser His Asn Leu Tyr
            180                 185                 190 acc tgt gag gtt gtt cat aag aca tca tcc tca ccc gtc gtc aag agc     624
Thr Cys Glu Val Val His Lys Thr Ser Ser Ser Pro Val Val Lys Ser
        195                 200                 205 ttc aac agg aat gag tgt                                             642
Phe Asn Arg Asn Glu Cys
    210

<210> SEQ ID NO 82
<211> LENGTH: 214
<212> TYPE: PRT
<213> ORGANISM: Rattus sp.

<400> SEQUENCE: 82

Asp Ile Arg Met Thr Gln Ser Pro Ala Ser Leu Ser Ala Ser Leu Gly
 1               5                  10                  15

Glu Thr Val Asn Ile Glu Cys Leu Ala Ser Glu Asp Ile Tyr Ser Asp
                20                  25                  30

Leu Ala Trp Tyr Gln Gln Lys Pro Gly Lys Ser Pro Gln Leu Leu Ile
            35                  40                  45
```

```
Tyr Asn Ala Asn Ser Leu Gln Asn Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Val Ala Thr Tyr Phe Cys Gln Gln Tyr Asn Asn Tyr Pro Pro
                85                  90                  95

Thr Phe Gly Gly Gly Thr Lys Leu Glu Leu Lys Arg Ala Asp Ala Ala
            100                 105                 110

Pro Thr Val Ser Ile Phe Pro Pro Ser Thr Glu Gln Leu Ala Thr Gly
        115                 120                 125

Gly Ala Ser Val Val Cys Leu Met Asn Asn Phe Tyr Pro Arg Asp Ile
    130                 135                 140

Ser Val Lys Trp Lys Ile Asp Gly Thr Glu Arg Arg Asp Gly Val Leu
145                 150                 155                 160

Asp Ser Val Thr Asp Gln Asp Ser Lys Asp Ser Thr Tyr Ser Met Ser
                165                 170                 175

Ser Thr Leu Ser Leu Thr Lys Ala Asp Tyr Glu Ser His Asn Leu Tyr
            180                 185                 190

Thr Cys Glu Val His Lys Thr Ser Ser Pro Val Val Lys Ser
        195                 200                 205

Phe Asn Arg Asn Glu Cys
    210

<210> SEQ ID NO 83
<211> LENGTH: 321
<212> TYPE: DNA
<213> ORGANISM: Rattus sp.
<220> FEATURE:
<221> NAME/KEY: CDS
<222> LOCATION: (1)..(321)

<400> SEQUENCE: 83 gat atc cgg atg aca cag tct cca gct tcc ctg tct gca tct ctg gga      48
Asp Ile Arg Met Thr Gln Ser Pro Ala Ser Leu Ser Ala Ser Leu Gly
1               5                   10                  15 gaa act gtc aac atc gaa tgt cta gca agt gag gac att tac agt gat      96
Glu Thr Val Asn Ile Glu Cys Leu Ala Ser Glu Asp Ile Tyr Ser Asp
                20                  25                  30 tta gca tgg tat cag cag aag cca ggg aaa tct cct cag ctc ctg atc     144
Leu Ala Trp Tyr Gln Gln Lys Pro Gly Lys Ser Pro Gln Leu Leu Ile
            35                  40                  45 tat aat gca aat agc ttg caa aat ggg gtc cct tca cgg ttt agt ggc     192
Tyr Asn Ala Asn Ser Leu Gln Asn Gly Val Pro Ser Arg Phe Ser Gly
    50                  55                  60 agt gga tct ggc aca cag tat tct cta aaa ata aac agc ctg caa tct     240
Ser Gly Ser Gly Thr Gln Tyr Ser Leu Lys Ile Asn Ser Leu Gln Ser
65                  70                  75                  80 gaa gat gtc gcg act tat ttc tgt caa caa tat aac aat tat cct ccg     288
Glu Asp Val Ala Thr Tyr Phe Cys Gln Gln Tyr Asn Asn Tyr Pro Pro
                85                  90                  95 acg ttc ggt gga ggc acc aag ctg gaa ttg aaa                         321
Thr Phe Gly Gly Gly Thr Lys Leu Glu Leu Lys
            100                 105

<210> SEQ ID NO 84
<211> LENGTH: 107
<212> TYPE: PRT
<213> ORGANISM: Rattus sp.

<400> SEQUENCE: 84
```

```
Asp Ile Arg Met Thr Gln Ser Pro Ala Ser Leu Ser Ala Ser Leu Gly
1               5                  10                  15

Glu Thr Val Asn Ile Glu Cys Leu Ala Ser Glu Asp Ile Tyr Ser Asp
                20                  25                  30

Leu Ala Trp Tyr Gln Gln Lys Pro Gly Lys Ser Pro Gln Leu Leu Ile
            35                  40                  45

Tyr Asn Ala Asn Ser Leu Gln Asn Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Val Ala Thr Tyr Phe Cys Gln Gln Tyr Asn Asn Tyr Pro Pro
                85                  90                  95

Thr Phe Gly Gly Gly Thr Lys Leu Glu Leu Lys
            100                 105
```

<210> SEQ ID NO 85
<211> LENGTH: 33
<212> TYPE: DNA
<213> ORGANISM: Rattus sp.

<400> SEQUENCE: 85
ctagcaagtg aggacattta cagtgattta gca                                33

<210> SEQ ID NO 86
<211> LENGTH: 21
<212> TYPE: DNA
<213> ORGANISM: Rattus sp.

<400> SEQUENCE: 86
aatgcaaata gcttgcaaaa t                                             21

<210> SEQ ID NO 87
<211> LENGTH: 27
<212> TYPE: DNA
<213> ORGANISM: Rattus sp.

<400> SEQUENCE: 87
caacaatata acaattatcc tccgacg                                       27

<210> SEQ ID NO 88
<211> LENGTH: 1338
<212> TYPE: DNA
<213> ORGANISM: Rattus sp.
<220> FEATURE:
<221> NAME/KEY: CDS
<222> LOCATION: (1)..(1338)

<400> SEQUENCE: 88

```
gag gta cag ctg gtg gag tct ggc gga gga ttg gta cag cct gca aac        48
Glu Val Gln Leu Val Glu Ser Gly Gly Gly Leu Val Gln Pro Ala Asn
1               5                  10                  15 tcc ctg aaa ctc tcc tgt gca gcc tca gga ttc act ttc agt gac tat        96
Ser Leu Lys Leu Ser Cys Ala Ala Ser Gly Phe Thr Phe Ser Asp Tyr
                20                  25                  30 gcc atg gcc tgg gtc cgc cag tct cca aag aag ggt ctg gag tgg gtc       144
Ala Met Ala Trp Val Arg Gln Ser Pro Lys Lys Gly Leu Glu Trp Val
            35                  40                  45 gca acc att att tat gat ggt agt agc act tac tat cga gac tcc gtg       192
Ala Thr Ile Ile Tyr Asp Gly Ser Ser Thr Tyr Tyr Arg Asp Ser Val
    50                  55                  60 aag ggc cga ttc act atc tcc aga gat aat gca aaa agc acc cta tac       240
Lys Gly Arg Phe Thr Ile Ser Arg Asp Asn Ala Lys Ser Thr Leu Tyr
```

-continued

```
             65                  70                  75                  80
ctg caa atg gac agt ctg agg tct gag gac acg gcc act tat tac tgt      288
Leu Gln Met Asp Ser Leu Arg Ser Glu Asp Thr Ala Thr Tyr Tyr Cys
             85                  90                  95 gca aca ggt ctg ggt ata gct acg gac tac ttt gat tac tgg ggc caa      336
Ala Thr Gly Leu Gly Ile Ala Thr Asp Tyr Phe Asp Tyr Trp Gly Gln
            100                 105                 110 gga gtc ctg gtc aca gtc tcc tca gct gaa aca aca gcc cca tct gtc      384
Gly Val Leu Val Thr Val Ser Ser Ala Glu Thr Thr Ala Pro Ser Val
            115                 120                 125 tat cca ctg gct cct gga act gct ctc aaa agt aac tcc atg gtg acc      432
Tyr Pro Leu Ala Pro Gly Thr Ala Leu Lys Ser Asn Ser Met Val Thr
            130                 135                 140 ctg gga tgc ctg gtc aag ggc tat ttc cct gag cca gtc acc gtg acc      480
Leu Gly Cys Leu Val Lys Gly Tyr Phe Pro Glu Pro Val Thr Val Thr
145                 150                 155                 160 tgg aac tct gga gcc ctg tcc agc ggt gtg cac acc ttc cca gct gtc      528
Trp Asn Ser Gly Ala Leu Ser Ser Gly Val His Thr Phe Pro Ala Val
                    165                 170                 175 ctg cag tct ggg ctc tac act ctc acc agc tca gtg act gta ccc tcc      576
Leu Gln Ser Gly Leu Tyr Thr Leu Thr Ser Ser Val Thr Val Pro Ser
            180                 185                 190 agc acc tgg ccc agc cag acc gtc acc tgc aac gta gcc cac ccg gcc      624
Ser Thr Trp Pro Ser Gln Thr Val Thr Cys Asn Val Ala His Pro Ala
            195                 200                 205 agc agc acc aag gtg gac aag aaa att gtg ccc aga aac tgt gga ggt      672
Ser Ser Thr Lys Val Asp Lys Lys Ile Val Pro Arg Asn Cys Gly Gly
            210                 215                 220 gat tgc aag cct tgt ata tgt aca ggc tca gaa gta tca tct gtc ttc      720
Asp Cys Lys Pro Cys Ile Cys Thr Gly Ser Glu Val Ser Ser Val Phe
225                 230                 235                 240 atc ttc ccc cca aag ccc aaa gat gtg ctc acc atc act ctg act cct      768
Ile Phe Pro Pro Lys Pro Lys Asp Val Leu Thr Ile Thr Leu Thr Pro
                    245                 250                 255 aag gtc acg tgt gtt gtg gta gac att agc cag gac gat ccc gag gtc      816
Lys Val Thr Cys Val Val Val Asp Ile Ser Gln Asp Asp Pro Glu Val
            260                 265                 270 cat ttc agc tgg ttt gta gat gac gtg gaa gtc cac aca gct cag act      864
His Phe Ser Trp Phe Val Asp Asp Val Glu Val His Thr Ala Gln Thr
            275                 280                 285 cga cca cca gag gag cag ttc aac agc act ttc cgc tca gtc agt gaa      912
Arg Pro Pro Glu Glu Gln Phe Asn Ser Thr Phe Arg Ser Val Ser Glu
            290                 295                 300 ctc ccc atc ctg cac cag gac tgg ctc aat ggc agg acg ttc aga tgc      960
Leu Pro Ile Leu His Gln Asp Trp Leu Asn Gly Arg Thr Phe Arg Cys
305                 310                 315                 320 aag gtc acc agt gca gct ttc cca tcc ccc atc gag aaa acc atc tcc     1008
Lys Val Thr Ser Ala Ala Phe Pro Ser Pro Ile Glu Lys Thr Ile Ser
                    325                 330                 335 aaa ccc gaa ggc aga aca caa gtt ccg cat gta tac acc atg tca cct     1056
Lys Pro Glu Gly Arg Thr Gln Val Pro His Val Tyr Thr Met Ser Pro
            340                 345                 350 acc aag gaa gag atg acc cag aat gaa gtc agt atc acc tgc atg gta     1104
Thr Lys Glu Glu Met Thr Gln Asn Glu Val Ser Ile Thr Cys Met Val
            355                 360                 365 aaa ggc ttc tat ccc cca gac att tat gtg gag tgg cag atg aac ggg     1152
Lys Gly Phe Tyr Pro Pro Asp Ile Tyr Val Glu Trp Gln Met Asn Gly
            370                 375                 380 cag cca cag gaa aac tac aag aac act cca cct acg atg gac aca gat     1200
Gln Pro Gln Glu Asn Tyr Lys Asn Thr Pro Pro Thr Met Asp Thr Asp
```

```
                   385                 390                 395                 400
ggg agt tac ttc ctc tac agc aag ctc aat gtg aag aag gaa aaa tgg              1248
Gly Ser Tyr Phe Leu Tyr Ser Lys Leu Asn Val Lys Lys Glu Lys Trp
            405                 410                 415 cag cag gga aac acg ttc acg tgt tct gtg ctg cat gaa ggc ctg cac              1296
Gln Gln Gly Asn Thr Phe Thr Cys Ser Val Leu His Glu Gly Leu His
        420                 425                 430 aac cac cat act gag aag agt ctc tcc cac tct ccg ggt aaa                      1338
Asn His His Thr Glu Lys Ser Leu Ser His Ser Pro Gly Lys
    435                 440                 445

<210> SEQ ID NO 89
<211> LENGTH: 446
<212> TYPE: PRT
<213> ORGANISM: Rattus sp.

<400> SEQUENCE: 89

Glu Val Gln Leu Val Glu Ser Gly Gly Gly Leu Val Gln Pro Ala Asn
1               5                   10                  15

Ser Leu Lys Leu Ser Cys Ala Ala Ser Gly Phe Thr Phe Ser Asp Tyr
            20                  25                  30

Ala Met Ala Trp Val Arg Gln Ser Pro Lys Lys Gly Leu Glu Trp Val
        35                  40                  45

Ala Thr Ile Ile Tyr Asp Gly Ser Ser Thr Tyr Tyr Arg Asp Ser Val
    50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Ala Thr Gly Leu Gly Ile Ala Thr Asp Tyr Phe Asp Tyr Trp Gly Gln
            100                 105                 110

Gly Val Leu Val Thr Val Ser Ser Ala Glu Thr Thr Ala Pro Ser Val
        115                 120                 125

Tyr Pro Leu Ala Pro Gly Thr Ala Leu Lys Ser Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ala Leu Ser Ser Gly Val His Thr Phe Pro Ala Val
                165                 170                 175

Leu Gln Ser Gly Leu Tyr Thr Leu Thr Ser Ser Val Thr Val Pro Ser
            180                 185                 190

Ser Thr Trp Pro Ser Gln Thr Val Thr Cys Asn Val Ala His Pro Ala
        195                 200                 205

Ser Ser Thr Lys Val Asp Lys Lys Ile Val Pro Arg Asn Cys Gly Gly
    210                 215                 220

Asp Cys Lys Pro Cys Ile Cys Thr Gly Ser Glu Val Ser Ser Val Phe
225                 230                 235                 240

Ile Phe Pro Pro Lys Pro Lys Asp Val Leu Thr Ile Thr Leu Thr Pro
                245                 250                 255

Lys Val Thr Cys Val Val Val Asp Ile Ser Gln Asp Asp Pro Glu Val
            260                 265                 270

His Phe Ser Trp Phe Val Asp Asp Val Glu Val His Thr Ala Gln Thr
        275                 280                 285

Arg Pro Pro Glu Glu Gln Phe Asn Ser Thr Phe Arg Ser Val Ser Glu
    290                 295                 300

Leu Pro Ile Leu His Gln Asp Trp Leu Asn Gly Arg Thr Phe Arg Cys
```

```
                    305                 310                 315                 320
Lys Val Thr Ser Ala Ala Phe Pro Ser Pro Ile Glu Lys Thr Ile Ser
                    325                 330                 335
Lys Pro Glu Gly Arg Thr Gln Val Pro His Val Tyr Thr Met Ser Pro
                    340                 345                 350
Thr Lys Glu Glu Met Thr Gln Asn Glu Val Ser Ile Thr Cys Met Val
                    355                 360                 365
Lys Gly Phe Tyr Pro Pro Asp Ile Tyr Val Glu Trp Gln Met Asn Gly
                    370                 375                 380
Gln Pro Gln Glu Asn Tyr Lys Asn Thr Pro Pro Thr Met Asp Thr Asp
385                 390                 395                 400
Gly Ser Tyr Phe Leu Tyr Ser Lys Leu Asn Val Lys Lys Glu Lys Trp
                    405                 410                 415
Gln Gln Gly Asn Thr Phe Thr Cys Ser Val Leu His Glu Gly Leu His
                    420                 425                 430
Asn His His Thr Glu Lys Ser Leu Ser His Ser Pro Gly Lys
                    435                 440                 445

<210> SEQ ID NO 90
<211> LENGTH: 360
<212> TYPE: DNA
<213> ORGANISM: Rattus sp.
<220> FEATURE:
<221> NAME/KEY: CDS
<222> LOCATION: (1)..(360)

<400> SEQUENCE: 90 gag gta cag ctg gtg gag tct ggc gga gga ttg gta cag cct gca aac        48
Glu Val Gln Leu Val Glu Ser Gly Gly Gly Leu Val Gln Pro Ala Asn
1               5                   10                  15 tcc ctg aaa ctc tcc tgt gca gcc tca gga ttc act ttc agt gac tat        96
Ser Leu Lys Leu Ser Cys Ala Ala Ser Gly Phe Thr Phe Ser Asp Tyr
                20                  25                  30 gcc atg gcc tgg gtc cgc cag tct cca aag aag ggt ctg gag tgg gtc       144
Ala Met Ala Trp Val Arg Gln Ser Pro Lys Lys Gly Leu Glu Trp Val
            35                  40                  45 gca acc att att tat gat ggt agt agc act tac tat cga gac tcc gtg       192
Ala Thr Ile Ile Tyr Asp Gly Ser Ser Thr Tyr Tyr Arg Asp Ser Val
        50                  55                  60 aag ggc cga ttc act atc tcc aga gat aat gca aaa agc acc cta tac       240
Lys Gly Arg Phe Thr Ile Ser Arg Asp Asn Ala Lys Ser Thr Leu Tyr
65                  70                  75                  80 ctg caa atg gac agt ctg agg tct gag gac acg gcc act tat tac tgt       288
Leu Gln Met Asp Ser Leu Arg Ser Glu Asp Thr Ala Thr Tyr Tyr Cys
                85                  90                  95 gca aca ggt ctg ggt ata gct acg gac tac ttt gat tac tgg ggc caa       336
Ala Thr Gly Leu Gly Ile Ala Thr Asp Tyr Phe Asp Tyr Trp Gly Gln
            100                 105                 110 gga gtc ctg gtc aca gtc tcc tca                                       360
Gly Val Leu Val Thr Val Ser Ser
        115                 120

<210> SEQ ID NO 91
<211> LENGTH: 120
<212> TYPE: PRT
<213> ORGANISM: Rattus sp.

<400> SEQUENCE: 91

Glu Val Gln Leu Val Glu Ser Gly Gly Gly Leu Val Gln Pro Ala Asn
1               5                   10                  15
```

```
Ser Leu Lys Leu Ser Cys Ala Ala Ser Gly Phe Thr Phe Ser Asp Tyr
            20              25                  30

Ala Met Ala Trp Val Arg Gln Ser Pro Lys Lys Gly Leu Glu Trp Val
        35              40                  45

Ala Thr Ile Ile Tyr Asp Gly Ser Ser Thr Tyr Tyr Arg Asp Ser Val
    50              55                  60

Lys Gly Arg Phe Thr Ile Ser Arg Asp Asn Ala Lys Ser Thr Leu Tyr
65              70                  75                  80

Leu Gln Met Asp Ser Leu Arg Ser Glu Asp Thr Ala Thr Tyr Tyr Cys
                85                  90                  95

Ala Thr Gly Leu Gly Ile Ala Thr Asp Tyr Phe Asp Tyr Trp Gly Gln
            100                 105                 110

Gly Val Leu Val Thr Val Ser Ser
        115                 120

<210> SEQ ID NO 92
<211> LENGTH: 15
<212> TYPE: DNA
<213> ORGANISM: Rattus sp.

<400> SEQUENCE: 92
gactatgcca tggcc                                                    15

<210> SEQ ID NO 93
<211> LENGTH: 51
<212> TYPE: DNA
<213> ORGANISM: Rattus sp.

<400> SEQUENCE: 93
accattattt atgatggtag tagcacttac tatcgagact ccgtgaaggg c             51

<210> SEQ ID NO 94
<211> LENGTH: 33
<212> TYPE: DNA
<213> ORGANISM: Rattus sp.

<400> SEQUENCE: 94
ggtctgggta tagctacgga ctactttgat tac                                33
```